(12) United States Patent
Harrison et al.

(10) Patent No.: US 9,296,725 B2
(45) Date of Patent: Mar. 29, 2016

(54) HETEROCYCLYL PYRIMIDINE ANALOGUES AS TYK2 INHIBITORS

(71) Applicant: Cellzome Limited, Brentford, Middlesex (GB)

(72) Inventors: Richard John Harrison, Cambridgeshire (GB); Nigel Ramsden, Hertfordshire (GB); Jeremy Major, Brentford (GB); Adeline Morel, Essex (GB); Laura Convery, Hertfordshire (GB); Mihiro Sunose, Cambridgeshire (GB); Rosemary Lynch, Cambridgeshire (GB); Rita Adrego, Suffolk (GB); Alison Jones, Cambridgeshire (GB)

(73) Assignee: Cellzome Limited, Brentford, Middlesex (GB)

( * ) Notice: Subject to any disclaimer, the term of this patent is extended or adjusted under 35 U.S.C. 154(b) by 0 days.

(21) Appl. No.: 14/402,194

(22) PCT Filed: May 23, 2013

(86) PCT No.: PCT/EP2013/060563
§ 371 (c)(1),
(2) Date: Nov. 19, 2014

(87) PCT Pub. No.: WO2013/174895
PCT Pub. Date: Nov. 28, 2013

(65) Prior Publication Data
US 2015/0166513 A1   Jun. 18, 2015

Related U.S. Application Data

(60) Provisional application No. 61/776,013, filed on Mar. 11, 2013.

(30) Foreign Application Priority Data

May 24, 2012   (EP) .................................. 12169254

(51) Int. Cl.
| | |
|---|---|
| *A61K 31/505* | (2006.01) |
| *C07D 403/12* | (2006.01) |
| *C07D 401/14* | (2006.01) |
| *C07D 405/14* | (2006.01) |
| *C07D 413/14* | (2006.01) |
| *A61K 31/506* | (2006.01) |
| *A61K 31/5377* | (2006.01) |
| *C07D 403/14* | (2006.01) |
| *C07D 407/14* | (2006.01) |
| *C07D 417/14* | (2006.01) |
| *C07D 471/08* | (2006.01) |
| *C07D 487/10* | (2006.01) |
| *C07D 491/048* | (2006.01) |
| *C07D 491/107* | (2006.01) |

(52) U.S. Cl.
CPC ............ *C07D 403/12* (2013.01); *A61K 31/505* (2013.01); *A61K 31/506* (2013.01); *A61K 31/5377* (2013.01); *C07D 401/14* (2013.01); *C07D 403/14* (2013.01); *C07D 405/14* (2013.01); *C07D 407/14* (2013.01); *C07D 413/14* (2013.01); *C07D 417/14* (2013.01); *C07D 471/08* (2013.01); *C07D 487/10* (2013.01); *C07D 491/048* (2013.01); *C07D 491/107* (2013.01)

(58) Field of Classification Search
CPC .. C07D 403/12; C07D 401/14; C07D 405/14; C07D 413/14; C07D 471/08; C07D 407/14; C07D 403/14; C07D 491/107; C07D 491/048; C07D 487/10; C07D 417/14; A61K 31/5377; A61K 31/505; A61K 31/506
See application file for complete search history.

(56) References Cited

FOREIGN PATENT DOCUMENTS

| WO | WO 0250066 A2 * | 6/2002 |
|---|---|---|
| WO | 2008/132502 A1 | 11/2008 |

(Continued)

OTHER PUBLICATIONS

T.A. Denison et al., Heterogeneity of Cancers and Its Implication for Targeted Drug Delivery in, Cancer Targeted Drug Delivery an Elusive Dream, 337-362 (Y.H. Bae et al., eds, 2013).*

(Continued)

*Primary Examiner* — Alexander R Pagano
(74) *Attorney, Agent, or Firm* — Robert Steve Thomas

(57) ABSTRACT

The present invention relates to compounds of formula (I)

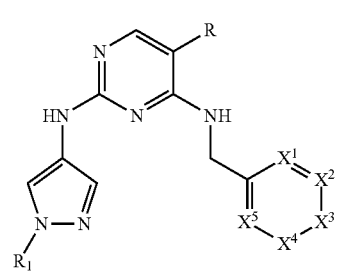

(I)

wherein R, $R^1$, $X^1$ to $X^5$ have the meaning as cited in the description and the claims. Said compounds are useful as TYK2 inhibitors for the treatment or prophylaxis of immunological, inflammatory, autoimmune, allergic disorders, and immunologically-mediated diseases. The invention also relates to pharmaceutical compositions including said compounds as well as their use as medicaments.

16 Claims, No Drawings

(56) References Cited

FOREIGN PATENT DOCUMENTS

| WO | WO 2008132502 A1 | * | 11/2008 |
| WO | 2010/129802 A1 | | 11/2010 |
| WO | WO 2010129802 A1 | * | 11/2010 |
| WO | 2012/062704 A1 | | 5/2012 |
| WO | WO 2012062704 A1 | * | 5/2012 |

OTHER PUBLICATIONS

U. McDermott et al., 27 Journal of Clinical Oncology, 5650-5659 (2009).*
D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 NATURE Reviews | Drug Discovery, 883-897 (2010).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
A. Ghigo et al., 32 BioEssays, 185-196 (2010).*
Z. Wang et al., 19 Drug Discovery Today, 145-150 (2014).*
U.K. Marelli et al., 3 Frontiers in Oncology, 1-12 (2013).*
Kinase Inhibitors Methods and Protocols (B. Kuster ed., 2012).*
J. Liang et al., 67 European Journal of Medicinal Chemistry, 175-187 (2013).*
J.P. Malerich et al., 20 Bioorganic & Medicinal Chemistry Letters, 7454-7457 (2010).*
R. Stupp et al., 25 Journal of Clinical Oncology, 1637-1638 (2007).*
A.M. Jubb et al., 6, Nature Reviews | Cancer 626-635 (2006).*

* cited by examiner

HETEROCYCLYL PYRIMIDINE ANALOGUES AS TYK2 INHIBITORS

CROSS-REFERENCE TO RELATED APPLICATIONS

This application is filed pursuant to 35 USC 371 as a United States National Phase Application of International Patent Application Serial No. PCT/EP2013/060563 filed on May 23, 2013, which claims priority from Ser. No. 12/169,254.5 filed on May 24, 2012 in Europe and 61/776,013 filed on Mar. 11, 2013 in the United States.

FIELD OF THE INVENTION

Background of the Invention

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate TYK2 activity, and signal transduction pathways relating to cellular activities as mentioned above. Furthermore, the present invention relates to pharmaceutical compositions comprising said compounds, for example for the treatment or prevention of an immunological, inflammatory, autoimmune, or allergic disorder or disease or a transplant rejection or a Graft-versus-host disease and processes for preparing said compounds.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues. The tyrosine kinases include membrane-spanning growth factor receptors such as the epidermal growth factor receptor (EGFR) and cytosolic non-receptor kinases such as Janus kinases (JAK).

Inappropriately high protein kinase activity is involved in many diseases including cancer, metabolic diseases, autoimmune or inflammatory disorders. This effect can be caused either directly or indirectly by the failure of control mechanisms due to mutation, overexpression or inappropriate activation of the enzyme. In all of these instances, selective inhibition of the kinase is expected to have a beneficial effect.

One group of kinases that has become a recent focus of drug discovery is the Janus kinase (JAK) family of non-receptor tyrosine kinases. In mammals, the family has four members, JAK1, JAK2, JAK3 and Tyrosine kinase 2 (TYK2). Each protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (Stat) family (Yamaoka et al., 2004. The Janus kinases (Jaks). Genome Biology 5(12): 253).

In mammals, JAK1, JAK2 and TYK2 are ubiquitously expressed. By contrast, the expression of JAK3 is predominantly in hematopoietic cells and it is highly regulated with cell development and activation (Musso et al., 1995. J. Exp. Med. 181(4):1425-31).

The study of JAK-deficient cell lines and gene-targeted mice has revealed the essential, nonredundant functions of JAKs in cytokine signalling. JAK1 knockout mice display a perinatal lethal phenotype, probably related to the neurological effects that prevent them from sucking (Rodig et al., 1998. Cell 93(3):373-83). Deletion of the JAK2 gene results in embryonic lethality at embryonic day 12.5 as a result of a defect in erythropoiesis (Neubauer et al., 1998. Cell 93(3): 397-409). Interestingly, JAK3 deficiency was first identified in humans with autosomal recessive severe combined immunodeficiency (SCID) (Macchi et al., 1995. Nature 377(6544): 65-68). JAK3 knockout mice too exhibit SCID but do not display non-immune defects, suggesting that an inhibitor of JAK3 as an immunosuppressant would have restricted effects in vivo and therefore presents a promising drug for immunosuppression (Papageorgiou and Wikman 2004, Trends in Pharmacological Sciences 25(11):558-62).

The role of TYK2 in the biological response to cytokines was first characterized using a mutant human cell line that was resistant to the effects of Type I interferons (IFNs) and the demonstration that IFNα responsiveness could be restored by genetic complementation of TYK2 (Velazquez et al, 1992. Cell 70, 313-322). Further in vitro studies implicated TYK2 in the signaling pathways of multiple other cytokines involved in both innate and adaptive immunity. Analysis of TYK-2$^{-/-}$ mice however revealed less profound immunological defects than were anticipated (Karaghiosoff et al., 2000. Immunity 13, 549-560; Shimoda et al., 2000. Immunity 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signaling with the absence of TYK2 resulting in defective STAT4 activation and the failure of T cells from these mice to differentiate into IFNγ-producing Th1 cells. Consistent with the involvement of TYK2 in mediating the biological effects of Type I IFNs and IL-12, TYK2−/− mice were more susceptible to viral and bacterial infections.

Thus far only a single patient with an autosomal recessive TYK2 deficiency has been described (Minegishi et al., 2006. Immunity 25, 745-755). The homozygous deletion of four base pairs (GCTT at nucleotide 550 in the TYK2 gene) and consequent frameshift mutation in the patient's coding DNA introduced a premature stop codon and resulted in the truncation of the TYK2 protein at amino acid 90. The phenotype of this null mutation in human cells was much more severe than predicted by the studies in murine cells lacking TYK2. The patient displayed clinical features reminiscent of the primary immunodeficiency hyper-IgE syndrome (HIES) including recurrent skin abscesses, atopic dermatitis, highly elevated serum IgE levels and susceptibility to multiple opportunistic infections. Contrary to reports in TYK2−/− mice, signaling by a wide variety of cytokines was found to be impaired thus highlighting non-redundant roles for human TYK2 in the function of Type I IFNs, IL-6, IL-10, IL-12 and IL-23. An imbalance in T helper cell differentiation was also observed, with the patient's T cells exhibiting an extreme skew towards the development of IL-4 producing Th2 cells and impaired Th1 differentiation. Indeed, these cytokine signaling defects could be responsible for many of the clinical manifestations described, for example atopic dermatitis and elevated IgE levels (enhanced Th2), increased incidence of viral infections (IFN defect), infection with intracellular bacteria (IL-12/Th1 defect) and extracellular bacteria (IL-6 and IL-23/Th17 defect).

Emerging evidence from genome-wide association studies suggests that single nucleotide polymorphisms (SNPs) in the TYK2 gene significantly influence autoimmune disease susceptibility. Less efficient TYK2 variants are associated with protection against systemic lupus erythematosus (SLE) (TYK2 rs2304256 and rs12720270, Sigurdsson et al., 2005. Am. J. Hum. Genet. 76, 528-537; Graham et al., 2007. Rheumatology 46, 927-930; Hellquist et al., 2009. J. Rheumatol. 36, 1631-1638; Jarvinen et al., 2010. Exp. Dermatol. 19, 123-131) and multiple sclerosis (MS) (rs34536443, Ban et al., 2009. Eur. J. Hum. Genet. 17, 1309-1313; Mero et al., 2009. Eur. J. Hum. Genet. 18, 502-504). Whereas predicted gain-of-function mutations increase susceptibility to inflammatory bowel disease (IBD) (rs280519 and rs2304256, Sato et al., 2009. J. Clin. Immunol. 29, 815-825). In support of the involvement of TYK2 in immunopathologic disease processes, it has been shown that B10.D1 mice harbouring a missense mutation in the pseudokinase domain of TYK2 that results in the absence of encoded TYK2 protein are resistant to both autoimmune arthritis (CIA) and experimental autoimmune encephalomyelitis (EAE) (Shaw et al., 2003. PNAS 100, 11594-11599; Spach et al., 2009. J. Immunol. 182, 7776-7783). Furthermore, a recent study showed that TYK2-/- mice were completely resistant to MOG-induced EAE (Oyamada et al., 2009. J. Immunol. 183, 7539-7546). In these mice resistance was accompanied by a lack of CD4 T cells infiltrating the spinal cord, a failure to signal through IL-12R and IL-23R and hence the inability to upregulate encephalitogenic levels of IFNγ and IL-17.

The non-receptor tyrosine kinase TYK2 plays essential roles in both innate and adaptive immunity. A lack of TYK2 expression manifests in the attenuated signaling of multiple pro-inflammatory cytokines and a profound imbalance in T helper cell differentiation. Furthermore, evidence from genetic association studies supports that TYK2 is a shared autoimmune disease susceptibility gene. Taken together, these reasons suggest TYK2 as a target for the treatment of inflammatory and auto-immune diseases.

Several JAK family inhibitors have been reported in the literature which may be useful in the medical field (Ghoreschi et al., 2009. Immunol Rev, 228:273-287). It is expected that a selective TYK2 inhibitor that inhibits TYK2 with greater potency than JAK2 may have advantageous therapeutic properties, because inhibition of JAK2 can cause anemia (Ghoreschi et al., 2009. Nature Immunol. 4, 356-360).

Pyrimidine derivatives exhibiting JAK3 and JAK2 kinase inhibiting activities are described in WO-A 2008/009458. Pyrimidine compounds in the treatment of conditions in which modulation of the JAK pathway or inhibition of JAK kinases, particularly JAK3 are described in WO-A 2008/118822 and WO-A 2008/118823.

Fluoro substituted pyrimidine compounds as JAK3 inhibitors are described in WO-A 2010/118986. Heterocyclyl pyrazolopyrimidine analogues as JAK inhibitors WO-A 2011/048082.

WO-A 2008/129380 relates to sulfonyl amide derivatives for the treatment of abnormal cell growth.

TYK2 inhibitors are described in WO-A 2012/000970 and WO-A 2012062704.

TYK2 inhibitors are also known from DE-A 102009001438, DE-A 102009015070, WO-A 2011/113802, WO-A 2012/035039 and WO-A 2012/000970.

Accordingly, compounds that inhibit the activity of TYK2 are beneficial, especially with selectivity over JAK2. Such compounds may deliver a pharmacological response that favourably treats one or more of the conditions outlined herein without undue side-effects associated with inhibition of JAK2.

Even though TYK2 inhibitors are known in the art there is a need for providing additional inhibitors having at least partially more effective pharmaceutically relevant properties, like activity, selectivity especially over JAK2 kinase, and ADMET properties.

Thus, an object of the present invention is to provide a new class of compounds as TYK2 inhibitors which preferably show selectivity over JAK2 and may be effective in the treatment or prophylaxis of disorders associated with TYK2.

SUMMARY OF THE INVENTION

Accordingly, the present invention provides compounds of formula (I)

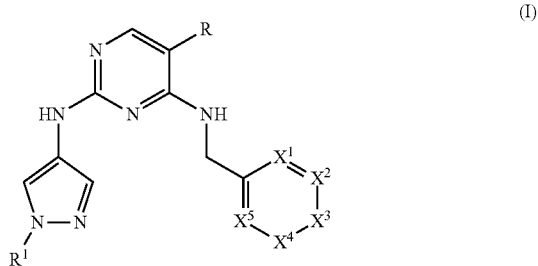

or a pharmaceutically acceptable salt or isotopic derivative thereof, wherein

R is H; F; Cl; Br; or unsubstituted $C_{1-3}$ alkyl;

$R^1$ is H; $C(O)OR^2$; $C(O)R^2$; $C(O)N(R^2R^{2a})$; $S(O)_2N(R^2R^{2a})$; $S(O)N(R^2R^{2a})$; $S(O)_2R^2$; $S(O)R^2$; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^2$, $R^{2a}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $NO_2$; $OC(O)R^4$; $N(R^4)C(O)R^{4a}$; $N(R^4)S(O)_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^1$;

$R^4$, $R^{4a}$, $R^{4b}$ independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^5$, which are the same or different;

$R^5$ is halogen; CN; $C(O)OR^6$; $OR^6$; $C(O)R^6$; $C(O)N(R^6R^{6a})$; $S(O)_2N(R^6R^{6a})$; $S(O)N(R^6R^{6a})$; $S(O)_2R^6$; $S(O)R^6$; $N(R^6)S(O)_2N(R^{6a}R^{6b})$; $N(R^6)S(O)N(R^{6a}R^{6b})$; $SR^6$; $N(R^6R^{6a})$; $NO_2$; $OC(O)R^6$; $N(R^6)C(O)R^{6a}$; $N(R^6)S(O)_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$; or $T^1$;

$R^6$, $R^{6a}$, $R^{6b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^1$ is phenyl, $C_{3-7}$ cycloalkyl; 4 to 7 membered heterocyclyl; or 7 to 11 membered heterobicyclyl, wherein $T^1$ is optionally substituted with one or more $R^7$, which are the same or different;

$R^7$ is halogen; CN; $C(O)OR^8$; $OR^8$; oxo (=O), where the ring is at least partially saturated; $C(O)R^8$; $C(O)N(R^8R^{8a})$; $S(O)_2N(R^8R^{8a})$; $S(O)N(R^8R^{8a})$; $S(O)_2R^8$; $S(O)R^8$; $N(R^8)S(O)_2N(R^{8a}R^{8b})$; $N(R^8)S(O)N(R^{8a}R^{8b})$; $SR^8$; $N(R^8R^{8a})$; $NO_2$; $OC(O)R^8$; $N(R^8)C(O)R^{8a}$; $N(R^8)S(O)_2R^{8a}$; $N(R^8)S(O)R^{8a}$; $N(R^8)C(O)N(R^{8a}R^{8b})$; $N(R^8)C(O)OR^{8a}$; $OC(O)N(R^8R^{8a})$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^9$ is halogen; CN; $C(O)OR^{10}$; $OR^{10}$; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $S(O)R^{10}$; $N(R^{10})S(O)_2N(R^{10a}R^{10b})$; $N(R^{10})S(O)N(R^{10a}R^{10b})$; $SR^{10}$; $N(R^{10}R^{10a})$; $NO_2$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; or $OC(O)N(R^{10}R^{10a})$;

$R^{10}$, $R^{10a}$; $R^{10b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$X^1$ is $C(R^{11a})$ or N; $X^2$ is $C(R^{11b})$ or N; $X^3$ is $C(R^{11c})$ or N; $X^4$ is $C(R^{11d})$ or N; $X^5$ is $C(R^{11e})$ or N, provided that at most two of $X^1$, $X^2$, $X^3$, $X^4$, $X^5$ are N;

$R^{11a}$, $R^{11c}$, $R^{11e}$ are independently selected from the group consisting of H; halogen; CN; $C(O)OR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $N(R^{12})S(O)N(R^{12a}R^{12b})$; $SR^{12}$; $N(R^{12}R^{12a})$; $NO_2$; $OC(O)R^{12}$; $N(R^{12})C(O)R^{12a}$; $N(R^{12})C(O)N(R^{12a}R^{12b})$; $N(R^{12})C(O)OR^{12a}$; $OC(O)N(R^{12}R^{12a})$; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{13}$, which are the same or different;

$R^{11b}$, $R^{11d}$ are independently selected from the group consisting of H; halogen; CN; $C(O)OR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $N(R^{12})S(O)N(R^{12a}R^{12b})$; $SR^{12}$; $N(R^{12}R^{12a})$; $NO_2$; $OC(O)R^{12}$; $N(R^{12})C(O)R^{12a}$; $N(R^{12})C(O)N(R^{12a}R^{12b})$; $N(R^{12})C(O)OR^{12a}$; $OC(O)N(R^{12}R^{12a})$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{13}$, which are the same or different;

$R^{12}$; $R^{12a}$; $R^{12b}$ are independently selected from the group consisting of H; $T^2$; and $C_{1-6}$ alkyl, wherein $C_{1-6}$ alkyl; is optionally substituted with one or more $R^{13}$, which are the same or different;

$R^{13}$ is halogen; CN; $C(O)OR^{14}$; $OR^{14}$; $C(O)R^{14}$; $C(O)N(R^{14}R^{14a})$; $S(O)_2N(R^{14}R^{14a})$; $S(O)N(R^{14}R^{14a})$; $S(O)_2R^{14}$; $S(O)R^{14}$; $N(R^{14})S(O)_2N(R^{14a}R^{14b})$; $N(R^{14})S(O)N(R^{14a}R^{14b})$; $SR^{14}$; $N(R^{14}R^{14a})$; $NO_2$; $OC(O)R^{14}$; $N(R^{14})C(O)R^{14a}$; $N(R^{14})S(O)_2R^{14a}$; $N(R^{14})S(O)R^{14a}$; $N(R^{14})C(O)N(R^{14a}R^{14b})$; $N(R^{14})C(O)OR^{14a}$; $OC(O)N(R^{14}R^{14a})$; or $T^2$;

$R^{14}$, $R^{14a}$, $R^{14b}$ are independently selected from the group consisting of H; $T^2$; or $C_{1-6}$ alkyl, wherein $C_{1-6}$ alkyl is optionally substituted with one or more $R^{15}$, which are the same or different;

$R^{15}$ is halogen; CN; $C(O)OR^{16}$; $OR^{16}$; $C(O)R^{16}$; $C(O)N(R^{16}R^{16a})$; $S(O)_2N(R^{16}R^{16a})$; $S(O)N(R^{16}R^{16a})$; $S(O)_2R^{16}$; $S(O)R^{16}$; $N(R^{16})S(O)_2N(R^{16a}R^{16b})$; $N(R^{16})S(O)N(R^{16a}R^{16b})$; $SR^{16}$; $N(R^{16}R^{16a})$; $NO_2$; $OC(O)R^{16}$; $N(R^{16})C(O)R^{16a}$; $N(R^{16})S(O)_2R^{16a}$; $N(R^{16})S(O)R^{16a}$; $N(R^{16})C(O)N(R^{16a}R^{16b})$; $N(R^{16})C(O)OR^{16a}$; $OC(O)N(R^{16}R^{16a})$; or $T^2$;

$R^{16}$; $R^{16a}$; $R^{16b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^2$ is phenyl; naphthyl; indenyl; indanyl; $C_{3-7}$ cycloalkyl; 4 to 7 membered heterocyclyl; or 7 to 11 membered heterobicyclyl, wherein $T^2$ is optionally substituted with one or more $R^{17}$, which are the same or different;

$R^{17}$ is halogen; CN; $C(O)OR^{18}$; $OR^{18}$; oxo (=O), where the ring is at least partially saturated; $C(O)R^{18}$; $C(O)N(R^{18}R^{18a})$; $S(O)_2N(R^{18}R^{18a})$; $S(O)N(R^{18}R^{18a})$; $S(O)_2R^{18}$; $S(O)R^{18}$; $N(R^{18})S(O)_2N(R^{18a}R^{18b})$; $N(R^{18})S(O)N(R^{18a}R^{18b})$; $SR^{18}$; $N(R^{18}R^{18a})$; $NO_2$; $OC(O)R^{18}$; $N(R^{18})C(O)R^{18a}$; $N(R^{18})S(O)_2R^{18a}$; $N(R^{18})S(O)R^{18a}$; $N(R^{18})C(O)N(R^{18a}R^{18b})$; $N(R^{18})C(O)OR^{18a}$; $OC(O)N(R^{18}R^{18a})$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{19}$, which are the same or different;

$R^{18}$, $R^{18a}$, $R^{18b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{19}$, which are the same or different;

$R^{19}$ is halogen; CN; $C(O)OR^{20}$; $OR^{20}$; $C(O)R^{20}$; $C(O)N(R^{20}R^{20a})$; $S(O)_2N(R^{20}R^{20a})$; $S(O)N(R^{20a}R^{20a})$; $S(O)_2R^{20}$; $S(O)R^{20}$; $N(R^{20})S(O)_2N(R^{20a}R^{20b})$; $N(R^{20})S(O)N(R^{20a}R^{20b})$; $SR^{20}$; $N(R^{20}R^{20a})$; $NO_2$; $OC(O)R^{20}$; $N(R^{20})C(O)R^{20a}$; $N(R^{20})S(O)_2R^{20a}$; $N(R^{20})S(O)R^{20a}$; $N(R^{20})C(O)N(R^{20a}R^{20b})$; $N(R^{20})C(O)OR^{20a}$; or $OC(O)N(R^{20}R^{20a})$;

$R^{20}$, $R^{20a}$, $R^{20b}$ are independently selected from the group consisting of h; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different.

DETAILED DESCRIPTION

In case a variable or substituent can be selected from a group of different variants and such variable or substituent occurs more than once the respective variants can be the same or different.

Within the meaning of the present invention the terms are used as follows:

The term "optionally substituted" means unsubstituted or substituted. Generally—but not limited to-, "one or more substituents" means one, two or three, preferably one or two and more preferably one. Generally these substituents can be the same or different.

"Alkyl" means a straight-chain or branched hydrocarbon chain. Each hydrogen of an alkyl carbon may be replaced by a substituent as further specified herein.

"Alkenyl" means a straight-chain or branched hydrocarbon chain that contains at least one carbon-carbon double bond. Each hydrogen of an alkenyl carbon may be replaced by a substituent as further specified herein.

"Alkynyl" means a straight-chain or branched hydrocarbon chain that contains at least one carbon-carbon triple bond. Each hydrogen of an alkynyl carbon may be replaced by a substituent as further specified herein.

"$C_{1-3}$ alkyl" means an alkyl chain having 1-3 carbon atoms, e.g. if present at the end of a molecule: methyl, ethyl, n-propyl, isopropyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-3}$ alkyl carbon may be replaced by a substituent as further specified herein.

"$C_{1-4}$ alkyl" means an alkyl chain having 1-4 carbon atoms, e.g. if present at the end of a molecule: $C_{1-3}$ alkyl, methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent as further specified herein.

"$C_{1-6}$ alkyl" means an alkyl chain having 1-6 carbon atoms, e.g. if present at the end of a molecule: $C_{1-3}$ alkyl, $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent as further specified herein.

"$C_{2-6}$ alkenyl" means an alkenyl chain having 2 to 6 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-6}$ alkenyl carbon may be replaced by a substituent as further specified herein.

"$C_{2-6}$ alkynyl" means an alkynyl chain having 2 to 6 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-6}$ alkynyl carbon may be replaced by a substituent as further specified herein.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cyloalkyl refers to cyclopropyl, cyclobutyl, cyclopentyl, cyclohexyl, or cycloheptyl. Each hydrogen of a cycloalkyl carbon may be replaced by a substituent as further specified herein. The term "$C_{3-5}$ cycloalkyl" or "$C_{3-5}$ cycloalkyl ring" is defined accordingly.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples of a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly.

"Saturated 4 to 7 membered heterocyclyl" or "saturated 4 to 7 membered heterocycle" means fully saturated "4 to 7 membered heterocyclyl" or "4 to 7 membered heterocycle".

"5 membered aromatic heterocyclyl" or "5 membered aromatic heterocycle" means a heterocycle derived from cyclopentadienyl, where at least one carbon atom is replaced by a heteoatom selected from the group consisting of sulfur (including —S(O)—, —$S(O)_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples of a 7 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydro quinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 11 membered heterobicycle also includes spiro structures of two rings like 1,4-dioxa-8-azaspiro[4.5]decane 2-oxa-6-azaspiro[3.3]heptan-6-yl or 2,6-diazaspiro[3.3]heptan-6-yl or bridged heterocycles like 8-aza-bicyclo[3.2.1]octane or 2,5-diazabicyclo[2.2.2]octan-2-yl.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning Hence, one or more of these substituents can have the preferred or more preferred meanings given below.

Preferably, $R^1$ is unsubstituted $C_{1-4}$ alkyl; or $C_{1-4}$ alkyl, substituted with one or more $R^3$, which are the same or different. More preferably, $R^1$ is $C_{1-4}$ alkyl substituted with one or two $R^3$.

Preferably, $R^1$ is H; or $CH_3$.

Preferably, $R^3$ is halogen, $OR^4$; $C(O)N(R^4R^{4a})$; $C(O)T^1$; or $T^1$. More preferably, $R^3$ is $C(O)N(R^4R^{4a})$; $C(O)T^1$; or $T^1$.

Preferably, $R^4$, $R^{4a}$ are independently selected from the group consisting of H; $T^1$; and $C_{1-4}$ alkyl optionally substituted with $OR^6$. More preferably, $R^4$ is iso-propyl optionally substituted by OH; or cyclopropyl.

Preferably $T^1$ is morpholinyl; pyrrolidinyl; piperidinyl; tetrahydrofuranyl; cyclobutyl; or cyclopropyl. More preferably, $T^1$ is morpholinyl; pyrrolidinyl; tetrahydrofuranyl; or cyclopropyl.

Preferably, $R^1$ is $CH_2C(O)NHCH(CH_3)_2$; $CH_2C(O)NHCH(CH_3)CH_2OH$; $CH_2C(O)NH(morpholin-4-yl)$; $CH_2C(O)NH(cyclopropyl)$; or $CH_2CH_2(morpholin-4-yl)$.

Preferably, R is H; F; Cl; or CH₃; More preferably, R is H; or F; Even more preferably, R is H.

Preferably, the groups $R^{11a}$, $R^{11b}$, $R^{11c}$, $R^{11d}$, $R^{11e}$ are selected from the group consisting of H; halogen; CN; $OR^{12}$; $C(O)R^{12}$; $C(O)N(R^{12}R^{12a})$; $S(O)_2N(R^{12}R^{12a})$; $S(O)_2R^{12}$; or $C_{1-6}$ alkyl optionally substituted with one or more halogen. More preferably, the groups $R^{11a}$, $R^{11b}$, $R^{11c}$, $R^{11d}$, $R^{11e}$ are selected from the group consisting of H; F; Cl; CN; OCH₃; OCHF₂; C(O)NH₂; SO₂NH₂; CH₃; or CF₃.

Preferably, $R^{11a}$, $R^{11b}$ are independently F; or Cl.

Preferably both $R^{11a}$ and $R^{11e}$ are Cl.

Preferred combinations of substituents are defined by formula (Ia):

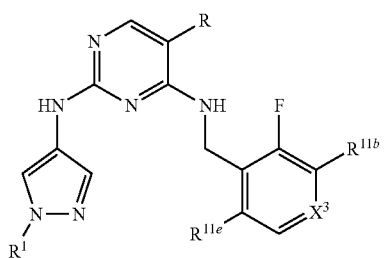

(Ia)

wherein, R is H or F;
$X^3$ is N; or $C(R^{11c})$;
$R^{11b}$ is H; F; Cl; CH₃; CN; or OCH₃;
$R^{11c}$ is H; F; Cl; CH₃; CN; OCH₃; SO₂NH₂; or $C(O)N(R^{12}R^{12a})$;
$R^{11e}$ is F; Cl; or CH₃;
and wherein $R^1$, $R^{12}$, $R^{12a}$ have the meanings as indicated above;
provided that at least one or both of $R^{11b}$, $R^{11c}$ are H.

Preferably $X^1$, $X^2$, $X^4$, $X^5$ are other than N.

Preferably, R is H.

Compounds of formula (I) in which some or all of the above-mentioned groups have the preferred meanings are also an object of the present invention.

Further preferred compounds of the present invention are selected from the group consisting of:

2-(4-((4-((4-cyano-2,6-difluorobenzyl)amino)pyrimidin-2-yl)amino)-1H-pyrazol-1-yl)-N-isopropylacetamide;
(S)-2-(4-((4-((2,6-dichlorobenzyl)amino)pyrimidin-2-yl)amino)-1H-pyrazol-1-yl)-N-(1-hydroxypropan-2-yl)acetamide;
N-cyclopropyl-2-(4-((5-fluoro-4-((2,4,6-trifluorobenzyl)amino)pyrimidin-2-yl)amino)-1H-pyrazol-1-yl)acetamide;
N-(1-cyanoethyl)-2-(4-((4-((2,4,6-trifluorobenzyl)amino)pyrimidin-2-yl)amino)-1H-pyrazol-1-yl)acetamide;
N-ethyl-2-(4-((4-((2,4,6-trifluorobenzyl)amino)pyrimidin-2-yl)amino)-1H-pyrazol-1-yl)acetamide;
3,5-difluoro-N,N-dimethyl-4-(((2-((1-methyl-1H-pyrazol-4-yl)amino)pyrimidin-4-yl)amino)methyl)benzamide;
4-(((2-((1-(2-hydroxyethyl)-1H-pyrazol-4-yl)amino)-5-methylpyrimidin-4-yl)amino)methyl)benzenesulfonamide;
4-(((5-fluoro-2-((1-(2-hydroxyethyl)-1H-pyrazol-4-yl)amino)pyrimidin-4-yl)amino)methyl)benzenesulfonamide;
2-(4-((5-chloro-4-((4-sulfamoylbenzyl)amino)pyrimidin-2-yl)amino)-1H-pyrazol-1-yl)-N-cyclopropylacetamide;
4-(((5-fluoro-2-((1-(2-morpholino-2-oxoethyl)-1H-pyrazol-4-yl)amino)pyrimidin-4-yl)amino)methyl)benzenesulfonamide;
2-(4-((4-((2,6-difluoro-3-methoxybenzyl)amino)-5-fluoropyrimidin-2-yl)amino)-1H-pyrazol-1-yl)-N-methylacetamide;
2-(4-((4-((2,6-difluoro-3-methoxybenzyl)amino)-5-fluoropyrimidin-2-yl)amino)-1H-pyrazol-1-yl)-N,N-dimethylacetamide;
2-(4-((4-((3-(difluoromethoxy)benzyl)amino)-5-fluoropyrimidin-2-yl)amino)-1H-pyrazol-1-yl)-N,N-dimethylacetamide;
2-(4-((5-chloro-4-((2,4,6-trifluorobenzyl)amino)pyrimidin-2-yl)amino)-1H-pyrazol-1-yl)ethanol;
2-(4-((5-chloro-4-((2,4,6-trifluorobenzyl)amino)pyrimidin-2-yl)amino)-1H-pyrazol-1-yl)-N,N-dimethylacetamide;
2-(4-((5-fluoro-4-((2,4,6-trifluorobenzyl)amino)pyrimidin-2-yl)amino)-1H-pyrazol-1-yl)ethanol;
2-(4-((5-fluoro-4-((2,4,6-trifluorobenzyl)amino)pyrimidin-2-yl)amino)-1H-pyrazol-1-yl)-N,N-dimethylacetamide;
N,N-dimethyl-2-(4-((5-methyl-4-((2,4,6-trifluorobenzyl)amino)pyrimidin-2-yl)amino)-1H-pyrazol-1-yl)acetamide;
2-(4-((4-((2,6-difluoro-3-methoxybenzyl)amino)-5-methylpyrimidin-2-yl)amino)-1H-pyrazol-1-yl)-N,N-dimethylacetamide;
2-(4-((5-methyl-4-((2,4,6-trifluorobenzyl)amino)pyrimidin-2-yl)amino)-1H-pyrazol-1-yl)-1-morpholinoethanone;
2-(4-((4-((2,6-difluoro-3-methoxybenzyl)amino)-5-methylpyrimidin-2-yl)amino)-1H-pyrazol-1-yl)-1-morpholinoethanone;
2-(4-((4-((3-(difluoromethoxy)benzyl)amino)-5-methylpyrimidin-2-yl)amino)-1H-pyrazol-1-yl)-1-morpholinoethanone;
2-(4-((4-((2,6-difluoro-3-methoxybenzyl)amino)-5-fluoropyrimidin-2-yl)amino)-1H-pyrazol-1-yl)-1-morpholinoethanone;
2-(4-((4-((3-bromo-2-fluorobenzyl)amino)-5-chloropyrimidin-2-yl)amino)-1H-pyrazol-1-yl)ethanol;
2-(4-((5-fluoro-4-((2,4,6-trifluorobenzyl)amino)pyrimidin-2-yl)amino)-1H-pyrazol-1-yl)-1-morpholinoethanone;
1-morpholino-2-(4-((4-((2,4,6-trifluorobenzyl)amino)pyrimidin-2-yl)amino)-1H-pyrazol-1-yl)ethanone;
2-(4-((4-((2,6-difluorobenzyl)amino)pyrimidin-2-yl)amino)-1H-pyrazol-1-yl)-1-morpholinoethanone;
2-(4-((4-((2,6-difluoro-4-methoxybenzyl)amino)-5-methylpyrimidin-2-yl)amino)-1H-pyrazol-1-yl)-1-morpholinoethanone;
4-(((5-fluoro-2-((1-(2-oxo-2-(piperidin-1-yl)ethyl)-1H-pyrazol-4-yl)amino)pyrimidin-4-yl)amino)methyl)benzenesulfonamide;
3,5-difluoro-4-(((5-fluoro-2-((1-(2-oxo-2-(piperidin-1-yl)ethyl)-1H-pyrazol-4-yl)amino)pyrimidin-4-yl)amino)methyl)benzenesulfonamide;
N-isopropyl-2-(4-((5-methyl-4-((2,4,6-trifluorobenzyl)amino)pyrimidin-2-yl)amino)-1H-pyrazol-1-yl)acetamide;
N-cyclobutyl-2-(4-((5-methyl-4-((2,4,6-trifluorobenzyl)amino)pyrimidin-2-yl)amino)-1H-pyrazol-1-yl)acetamide;
1-(2,2-dimethylmorpholino)-2-(4-((5-methyl-4-((2,4,6-trifluorobenzyl)amino)pyrimidin-2-yl)amino)-1H-pyrazol-1-yl)ethanone;
(R)—N-(1-hydroxypropan-2-yl)-2-(4-((5-methyl-4-((2,4,6-trifluorobenzyl)amino)pyrimidin-2-yl)amino)-1H-pyrazol-1-yl)acetamide;
(S)—N-(1-hydroxypropan-2-yl)-2-(4-((5-methyl-4-((2,4,6-trifluorobenzyl)amino)pyrimidin-2-yl)amino)-1H-pyrazol-1-yl)acetamide;

2-(4-((5-methyl-4-((2,4,6-trifluorobenzyl)amino)pyrimidin-2-yl)amino)-1H-pyrazol-1-yl)-N-(tetrahydrofuran-3-yl)acetamide;

2-(4-((5-fluoro-4-((2,4,6-trifluorobenzyl)amino)pyrimidin-2-yl)amino)-1H-pyrazol-1-yl)-N-isopropylacetamide;

1-(2,2-dimethylmorpholino)-2-(4-((5-fluoro-4-((2,4,6-trifluorobenzyl)amino)pyrimidin-2-yl)amino)-1H-pyrazol-1-yl)ethanone;

(R)-2-(4-((5-fluoro-4-((2,4,6-trifluorobenzyl)amino)pyrimidin-2-yl)amino)-1H-pyrazol-1-yl)-1-(3-methylmorpholino)ethanone;

(R)-2-(4-((5-fluoro-4-((2,4,6-trifluorobenzyl)amino)pyrimidin-2-yl)amino)-1H-pyrazol-1-yl)-N-(1-hydroxypropan-2-yl)acetamide;

(S)-2-(4-((5-fluoro-4-((2,4,6-trifluorobenzyl)amino)pyrimidin-2-yl)amino)-1H-pyrazol-1-yl)-N-(1-hydroxypropan-2-yl)acetamide;

3,5-difluoro-4-(((5-methyl-2-((1-methyl-1H-pyrazol-4-yl)amino)pyrimidin-4-yl)amino)methyl)benzenesulfonamide;

2-(4-((4-((3-(difluoromethoxy)benzyl)amino)-5-fluoropyrimidin-2-yl)amino)-1H-pyrazol-1-yl)-1-morpholinoethanone;

2-(4-((4-((3-(difluoromethoxy)benzyl)amino)-5-fluoropyrimidin-2-yl)amino)-1H-pyrazol-1-yl)-N-isopropylacetamide;

N-cyclopropyl-2-(4-((4-((3-(difluoromethoxy)benzyl)amino)-5-fluoropyrimidin-2-yl)amino)-1H-pyrazol-1-yl)acetamide;

isopropyl 2-(4-((4-((2,6-difluoro-3-methoxybenzyl)amino)-5-fluoropyrimidin-2-yl)amino)-1H-pyrazol-1-yl)acetate;

2-(4-((4-((2,6-difluoro-3-methoxybenzyl)amino)-5-fluoropyrimidin-2-yl)amino)-1H-pyrazol-1-yl)-N-isopropylacetamide;

2-(4-((4-((2,6-dichlorobenzyl)amino)-5-fluoropyrimidin-2-yl)amino)-1H-pyrazol-1-yl)-1-morpholinoethanone;

N-isopropyl-2-(4-((4-((2,4,6-trifluorobenzyl)amino)pyrimidin-2-yl)amino)-1H-pyrazol-1-yl)acetamide;

N-(tert-butyl)-2-(4-((4-((2,4,6-trifluorobenzyl)amino)pyrimidin-2-yl)amino)-1H-pyrazol-1-yl)acetamide;

(S)-1-(3-methylmorpholino)-2-(4-((4-((2,4,6-trifluorobenzyl)amino)pyrimidin-2-yl)amino)-1H-pyrazol-1-yl)ethanone;

ethyl 2-(4-((4-((2,6-difluoro-3-methoxybenzyl)amino)-5-fluoropyrimidin-2-yl)amino)-1H-pyrazol-1-yl)acetate;

ethyl 2-(4-((5-fluoro-4-((2,4,6-trifluorobenzyl)amino)pyrimidin-2-yl)amino)-1H-pyrazol-1-yl)acetate;

N4-(2-chloro-6-fluorobenzyl)-N2-(1-methyl-1H-pyrazol-4-yl)pyrimidine-2,4-diamine;

2-(4-((4-((3-(difluoromethoxy)benzyl)amino)-5-fluoropyrimidin-2-yl)amino)-1H-pyrazol-1-yl)-N-isopropyl-N-methylacetamide;

2-(4-((4-((2,6-difluoro-3-methoxybenzyl)amino)-5-fluoropyrimidin-2-yl)amino)-1H-pyrazol-1-yl)-N-isopropyl-N-methylacetamide;

2-(4-((5-fluoro-4-((2,4,6-trifluorobenzyl)amino)pyrimidin-2-yl)amino)-1H-pyrazol-1-yl)-N-(pentan-3-yl)acetamide;

2-(4-((5-fluoro-4-((2,4,6-trifluorobenzyl)amino)pyrimidin-2-yl)amino)-1H-pyrazol-1-yl)-N-isopropyl-N-methylacetamide;

N4-(3,6-dichloro-2-fluorobenzyl)-N2-(1-methyl-1H-pyrazol-4-yl)pyrimidine-2,4-diamine;

N4-(6-chloro-2-fluoro-3-methoxybenzyl)-N2-(1-methyl-1H-pyrazol-4-yl)pyrimidine-2,4-diamine;

2-(4-((4-((2,6-difluorobenzyl)amino)pyrimidin-2-yl)amino)-1H-pyrazol-1-yl)-N-isopropylacetamide;

N-isopropyl-2-(4-((4-((2,3,6-trifluorobenzyl)amino)pyrimidin-2-yl)amino)-1H-pyrazol-1-yl)acetamide;

2-(4-((4-((2,6-difluoro-4-methoxybenzyl)amino)pyrimidin-2-yl)amino)-1H-pyrazol-1-yl)-N-isopropylacetamide;

2-(4-((4-((2,6-difluoro-3-methoxybenzyl)amino)pyrimidin-2-yl)amino)-1H-pyrazol-1-yl)-N-isopropylacetamide;

2-(4-((4-((2,6-difluorobenzyl)amino)-5-fluoropyrimidin-2-yl)amino)-1H-pyrazol-1-yl)-N-isopropylacetamide;

2-(4-((4-((3-(difluoromethoxy)benzyl)amino)pyrimidin-2-yl)amino)-1H-pyrazol-1-yl)-N-isopropylacetamide;

N4-(6-chloro-2,3-difluorobenzyl)-N2-(1-methyl-1H-pyrazol-4-yl)pyrimidine-2,4-diamine;

3,5-difluoro-4-(((2-((1-methyl-1H-pyrazol-4-yl)amino)pyrimidin-4-yl)amino)methyl)benzamide;

2-(4-((4-((2,6-difluoro-4-methoxybenzyl)amino)-5-fluoropyrimidin-2-yl)amino)-1H-pyrazol-1-yl)-N-isopropylacetamide;

(S)-2-(4-((5-fluoro-4-((2,4,6-trifluorobenzyl)amino)pyrimidin-2-yl)amino)-1H-pyrazol-1-yl)-N-(1-methoxypropan-2-yl)acetamide;

5-chloro-N4-(5-fluoro-2-(methylsulfonyl)benzyl)-N2-(1H-pyrazol-4-yl)pyrimidine-2,4-diamine;

(S)-2-(4-((5-fluoro-4-((2,4,6-trifluorobenzyl)amino)pyrimidin-2-yl)amino)-1H-pyrazol-1-yl)-1-(3-methylmorpholino)ethanone;

2-(4-((5-chloro-4-((5-fluoro-2-(methylsulfonyl)benzyl)amino)pyrimidin-2-yl)amino)-1H-pyrazol-1-yl)-N-cyclopropylacetamide;

(S)—N-(1-hydroxypropan-2-yl)-2-(4-((4-((2,4,6-trifluorobenzyl)amino)pyrimidin-2-yl)amino)-1H-pyrazol-1-yl)acetamide;

2-(4-((4-((2,6-dichlorobenzyl)amino)pyrimidin-2-yl)amino)-1H-pyrazol-1-yl)-N-isopropylacetamide;

2-(4-((4-((2-chloro-6-fluorobenzyl)amino)pyrimidin-2-yl)amino)-1H-pyrazol-1-yl)-N-isopropylacetamide;

2-(4-((4-((3,6-dichloro-2-fluorobenzyl)amino)pyrimidin-2-yl)amino)-1H-pyrazol-1-yl)-N-isopropylacetamide;

2-(4-((4-((6-chloro-2-fluoro-3-methoxybenzyl)amino)pyrimidin-2-yl)amino)-1H-pyrazol-1-yl)-N-isopropylacetamide;

N-cyclopropyl-2-(4-((4-((2,4,6-trifluorobenzyl)amino)pyrimidin-2-yl)amino)-1H-pyrazol-1-yl)acetamide;

2-(4-((4-((6-chloro-2-fluoro-3-methoxybenzyl)amino)-5-fluoropyrimidin-2-yl)amino)-1H-pyrazol-1-yl)-1-morpholinoethanone;

2-(4-((4-((3,6-dichloro-2-fluorobenzyl)amino)-5-fluoropyrimidin-2-yl)amino)-1H-pyrazol-1-yl)-N-isopropylacetamide;

2-(4-((4-((3,6-dichloro-2-fluorobenzyl)amino)-5-fluoropyrimidin-2-yl)amino)-1H-pyrazol-1-yl)-1-morpholinoethanone;

2-(4-((4-((6-chloro-2-fluoro-3-methoxybenzyl)amino)-5-fluoropyrimidin-2-yl)amino)-1H-pyrazol-1-yl)-N-isopropylacetamide;

N4-(6-chloro-2-fluoro-3-methoxybenzyl)-5-fluoro-N2-(1-methyl-1H-pyrazol-4-yl)pyrimidine-2,4-diamine;

2-(4-((4-((2,4,6-trifluorobenzyl)amino)pyrimidin-2-yl)amino)-1H-pyrazol-1-yl)-N-(2,2,2-trifluoroethyl)acetamide;

N2-(1-(2,2-difluoroethyl)-1H-pyrazol-4-yl)-5-methyl-N4-(2,3,6-trifluorobenzyl)pyrimidine-2,4-diamine;

2-(4-((5-fluoro-4-((2-methoxy-5-(methylsulfonyl)benzyl)amino)pyrimidin-2-yl)amino)-1H-pyrazol-1-yl)ethanol;

N-(2-hydroxyethyl)-2-(4-((4-((2,4,6-trifluorobenzyl)amino)pyrimidin-2-yl)amino)-1H-pyrazol-1-yl)acetamide;

N-(2-fluoroethyl)-2-(4-((4-((2,4,6-trifluorobenzyl)amino)pyrimidin-2-yl)amino)-1H-pyrazol-1-yl)acetamide;

N-(2,2-difluorocyclopropyl)-2-(4-((4-((2,4,6-trifluorobenzyl)amino)pyrimidin-2-yl)amino)-1H-pyrazol-1-yl)acetamide;

N-(2,2-difluoroethyl)-2-(4-((4-((2,4,6-trifluorobenzyl)amino)pyrimidin-2-yl)amino)-1H-pyrazol-1-yl)acetamide;

2-(4-((4-((6-chloro-2,3-difluorobenzyl)amino)pyrimidin-2-yl)amino)-1H-pyrazol-1-yl)-N-isopropylacetamide;

2-(4-((4-((2-chloro-4,6-difluorobenzyl)amino)pyrimidin-2-yl)amino)-1H-pyrazol-1-yl)-N-isopropylacetamide;

N-(tetrahydrofuran-3-yl)-2-(4-((4-((2,4,6-trifluorobenzyl)amino)pyrimidin-2-yl)amino)-1H-pyrazol-1-yl)acetamide;

N4-(3,5-difluoro-2-methoxybenzyl)-5-methyl-N2-(1-methyl-1H-pyrazol-4-yl)pyrimidine-2,4-diamine;

2-(4-((5-fluoro-4-((5-fluoro-2-(methylsulfonyl)benzyl)amino)pyrimidin-2-yl)amino)-1H-pyrazol-1-yl)-N-methylacetamide;

5-chloro-N4-(2-fluoro-5-(methylsulfonyl)benzyl)-N2-(1H-pyrazol-4-yl)pyrimidine-2,4-diamine;

5-chloro-N4-(2-fluoro-5-(methylsulfonyl)benzyl)-N2-(l-methyl-1H-pyrazol-4-yl)pyrimidine-2,4-diamine;

2-(4-((5-chloro-4-((2-fluoro-5-(methylsulfonyl)benzyl)amino)pyrimidin-2-yl)amino)-1H-pyrazol-1-yl)acetamide;

N-cyclopropyl-2-(4-((5-methyl-4-((2,3,5-trifluorobenzyl)amino)pyrimidin-2-yl)amino)-1H-pyrazol-1-yl)acetamide;

N-((1R,2S)-2-fluorocyclopropyl)-2-(4-((4-((2,4,6-trifluorobenzyl)amino)pyrimidin-2-yl)amino)-1H-pyrazol-1-yl)acetamide;

N2-(1-(2,2-difluoroethyl)-1H-pyrazol-4-yl)-5-methyl-N4-(2,3,5-trifluorobenzyl)pyrimidine-2,4-diamine;

N4-(2,5-difluorobenzyl)-N2-(1-(2,2-difluoroethyl)-1H-pyrazol-4-yl)-5-methylpyrimidine-2,4-diamine;

N-(1-(tetrahydrofuran-3-yl)ethyl)-2-(4-((4-((2,4,6-trifluorobenzyl)amino)pyrimidin-2-yl)amino)-1H-pyrazol-1-yl)acetamide;

(R)-2-(4-((4-((2-chloro-6-fluorobenzyl)amino)pyrimidin-2-yl)amino)-1H-pyrazol-1-yl)-N-(1-hydroxypropan-2-yl)acetamide;

N2-(1-(2,2-difluoroethyl)-1H-pyrazol-4-yl)-N4-(2-methoxy-5-(methylsulfonyl)benzyl)-5-methylpyrimidine-2,4-diamine;

2-(((5-chloro-2-((1-(2,2-difluoroethyl)-1H-pyrazol-4-yl)amino)pyrimidin-4-yl)amino)methyl)-N-methylbenzenesulfonamide;

2-(((5-chloro-2-((1-(2,2-difluoroethyl)-1H-pyrazol-4-yl)amino)pyrimidin-4-yl)amino)methyl)-N,N-dimethylbenzenesulfonamide;

N-(cyanomethyl)-2-(4-((4-((2,4,6-trifluorobenzyl)amino)pyrimidin-2-yl)amino)-1H-pyrazol-1-yl)acetamide;

1-(2-(4-((4-((2,4,6-trifluorobenzyl)amino)pyrimidin-2-yl)amino)-1H-pyrazol-1-yl)ethyl)pyrrolidin-2-one;

N2-(1-(2-morpholinoethyl)-1H-pyrazol-4-yl)-N4-(2,4,6-trifluorobenzyl)pyrimidine-2,4-diamine;

2-(4-((4-((3,5-difluoro-2-methoxybenzyl)amino)-5-methylpyrimidin-2-yl)amino)-1H-pyrazol-1-yl)-N-methylacetamide;

5-fluoro-N4-(2-fluoro-5-(methylsulfonyl)benzyl)-N2-(1H-pyrazol-4-yl)pyrimidine-2,4-diamine;

2-(4-((5-fluoro-4-((2-fluoro-5-(methylsulfonyl)benzyl)amino)pyrimidin-2-yl)amino)-1H-pyrazol-1-yl)ethanol;

2-(4-((5-fluoro-4-((2-fluoro-5-(methylsulfonyl)benzyl)amino)pyrimidin-2-yl)amino)-1H-pyrazol-1-yl)acetamide;

2-(4-((4-((2,6-difluoro-3-methoxybenzyl)amino)pyrimidin-2-yl)amino)-1H-pyrazol-1-yl)-1-morpholinoethanone;

5-chloro-N4-(2-fluoro-6-(trifluoromethyl)benzyl)-N2-(1-methyl-1H-pyrazol-4-yl)pyrimidine-2,4-diamine;

2-(4-((4-((2,6-dichloro-3-fluorobenzyl)amino)pyrimidin-2-yl)amino)-1H-pyrazol-1-yl)-N-isopropylacetamide;

(S)-2-(4-((4-((2-chloro-6-fluorobenzyl)amino)pyrimidin-2-yl)amino)-1H-pyrazol-1-yl)-N-(1-hydroxypropan-2-yl)acetamide;

(S)-2-(4-((4-((3,6-dichloro-2-fluorobenzyl)amino)pyrimidin-2-yl)amino)-1H-pyrazol-1-yl)-N-(1-hydroxypropan-2-yl)acetamide;

(S)-2-(4-((4-((6-chloro-2-fluoro-3-methoxybenzyl)amino)pyrimidin-2-yl)amino)-1H-pyrazol-1-yl)-N-(1-hydroxypropan-2-yl)acetamide;

(R)-2-(4-((4-((6-chloro-2-fluoro-3-methoxybenzyl)amino)pyrimidin-2-yl)amino)-1H-pyrazol-1-yl)-N-(1-hydroxypropan-2-yl)acetamide;

(R)-2-(4-((4-((2,6-difluoro-3-methoxybenzyl)amino)pyrimidin-2-yl)amino)-1H-pyrazol-1-yl)-N-(1-hydroxypropan-2-yl)acetamide;

N-cyclopropyl-2-(4-((4-((2,6-difluoro-3-methoxybenzyl)amino)pyrimidin-2-yl)amino)-1H-pyrazol-1-yl)acetamide;

2-(4-((4-((2,6-difluoro-3-methoxybenzyl)amino)pyrimidin-2-yl)amino)-1H-pyrazol-1-yl)-N-(2-fluoroethyl)acetamide;

2-(4-((4-((2,6-difluoro-3-methoxybenzyl)amino)pyrimidin-2-yl)amino)-1H-pyrazol-1-yl)-N-(2,2-difluoroethyl)acetamide;

2-(4-((4-((2,6-difluoro-3-methoxybenzyl)amino)pyrimidin-2-yl)amino)-1H-pyrazol-1-yl)-N-((1R,2S)-2-fluorocyclopropyl)acetamide;

2-(4-((4-((2-chloro-6-fluorobenzyl)amino)pyrimidin-2-yl)amino)-1H-pyrazol-1-yl)-1-morpholinoethanone;

(S)-2-(4-((4-((2,6-difluoro-3-methylbenzyl)amino)pyrimidin-2-yl)amino)-1H-pyrazol-1-yl)-N-(1-hydroxypropan-2-yl)acetamide;

(R)-2-(4-((4-((3,6-dichloro-2-fluorobenzyl)amino)pyrimidin-2-yl)amino)-1H-pyrazol-1-yl)-N-(1-hydroxypropan-2-yl)acetamide;

(S)-2-(4-((4-((2-chloro-4,6-difluorobenzyl)amino)pyrimidin-2-yl)amino)-1H-pyrazol-1-yl)-N-(1-hydroxypropan-2-yl)acetamide;

(S)-2-(4-((4-((2,6-difluoro-3-methoxybenzyl)amino)pyrimidin-2-yl)amino)-1H-pyrazol-1-yl)-N-(1-hydroxypropan-2-yl)acetamide;

2-(4-((4-((3-cyano-2,6-difluorobenzyl)amino)pyrimidin-2-yl)amino)-1H-pyrazol-1-yl)-N-isopropylacetamide;

2,4-difluoro-3-(((2-((1-methyl-1H-pyrazol-4-yl)amino)pyrimidin-4-yl)amino)methyl)benzonitrile;

5-chloro-N4-(3-fluoro-2-(trifluoromethyl)benzyl)-N2-(1H-pyrazol-4-yl)pyrimidine-2,4-diamine;

(R)—N-(tetrahydrofuran-3-yl)-2-(4-((4-((2,4,6-trifluorobenzyl)amino)pyrimidin-2-yl)amino)-1 H-pyrazol-1-yl) acetamide;

(S)—N-(tetrahydrofuran-3-yl)-2-(4-((4-((2,4,6-trifluorobenzyl)amino)pyrimidin-2-yl)amino)-1 H-pyrazol-1-yl) acetamide;

2-(4-((4-((2-chloro-6-fluorobenzyl)amino)pyrimidin-2-yl)amino)-1H-pyrazol-1-yl)-N-cyclopropylacetamide;

2-(4-((4-((2-chloro-6-fluorobenzyl)amino)pyrimidin-2-yl)amino)-1H-pyrazol-1-yl)-N-(2-fluoroethyl)acetamide;

2-(4-((4-((2-chloro-6-fluorobenzyl)amino)pyrimidin-2-yl)amino)-1H-pyrazol-1-yl)-N-(2,2-difluoroethyl)acetamide;

2-(4-((4-((2-chloro-6-fluorobenzyl)amino)pyrimidin-2-yl)
amino)-1H-pyrazol-1-yl)-N-((1R,2S)-2-fluorocyclopro-
pyl)acetamide;

(R)—N-(1-hydroxypropan-2-yl)-2-(4-((4-((2,3,6-trifluo-
robenzyl)amino)pyrimidin-2-yl)amino)-1 H-pyrazol-1-
yl)acetamide;

N-cyclopropyl-2-(4-((4-((2,3,6-trifluorobenzyl)amino)pyri-
midin-2-yl)amino)-1H-pyrazol-1-yl)acetamide;

2-(4-((4-(((3,5-difluoropyridin-4-yl)methyl)amino)pyrimi-
din-2-yl)amino)-1H-pyrazol-1-yl)-N-isopropylaceta-
mide;

(S)-2-(4-((4-(((3,5-difluoropyridin-4-yl)methyl)amino)pyri-
midin-2-yl)amino)-1H-pyrazol-1-yl)-N-(1-hydroxypro-
pan-2-yl)acetamide;

(R)-2-(4-((4-(((3,5-difluoropyridin-4-yl)methyl)amino)pyri-
midin-2-yl)amino)-1H-pyrazol-1-yl)-N-(1-hydroxypro-
pan-2-yl)acetamide;

N4-((3,5-difluoropyridin-4-yl)methyl)-N2-(1-methyl-1H-
pyrazol-4-yl)pyrimidine-2,4-diamine;

N-(1,1-difluoropropan-2-yl)-2-(4-((4-((2,4,6-trifluoroben-
zyl)amino)pyrimidin-2-yl)amino)-1H-pyrazol-1-yl)
acetamide;

N-(2-(4-((5-fluoro-4-((2,4,6-trifluorobenzyl)amino)pyrimi-
din-2-yl)amino)-1H-pyrazol-1-yl)ethyl)acetamide;

(S)-2-(4-((4-((2,6-difluorobenzyl)amino)pyrimidin-2-yl)
amino)-1H-pyrazol-1-yl)-N-(1-hydroxypropan-2-yl)ac-
etamide;

N-cyclopropyl-2-(4-((4-((2,6-difluorobenzyl)amino)pyrimi-
din-2-yl)amino)-1H-pyrazol-1-yl)acetamide;

(S)-2-(4-((4-((3-cyano-2,6-difluorobenzyl)amino)pyrimi-
din-2-yl)amino)-1H-pyrazol-1-yl)-N-(1-hydroxypropan-
2-yl)acetamide;

(R)-2-(4-((4-((3-cyano-2,6-difluorobenzyl)amino)pyrimi-
din-2-yl)amino)-1H-pyrazol-1-yl)-N-(1-hydroxypropan-
2-yl)acetamide;

2-(4-((4-((2-fluoro-6-methylbenzyl)amino)pyrimidin-2-yl)
amino)-1H-pyrazol-1-yl)-N-isopropylacetamide;

(S)-2-(4-((4-((2-fluoro-6-methylbenzyl)amino)pyrimidin-2-
yl)amino)-1H-pyrazol-1-yl)-N-(1-hydroxypropan-2-yl)
acetamide; and 2-(4-((5-fluoro-4-((2,4,6-trifluorobenzyl)amino)pyrimidin-
2-yl)amino)-1H-pyrazol-1-yl)acetamide.

Further preferred compounds of the present invention are
selected from the group consisting of:

$N^4$-benzyl-5-chloro-$N^2$-(1-methyl-1H-pyrazol-4-yl)pyrimi-
dine-2,4-diamine;

3-(((5-chloro-2-((1-methyl-1H-pyrazol-4-yl)amino)pyrimi-
din-4-yl)amino)methyl)benzonitrile;

2-(4-((4-(benzylamino)-5-chloropyrimidin-2-yl)amino)-1H-
pyrazol-1-yl)-1-morpholinoethanone;

2-(4-((5-chloro-4-((2,6-difluorobenzyl)amino)pyrimidin-2-
yl)amino)-1H-pyrazol-1-yl)-1-morpholinoethanone;

2-(4-((5-chloro-4-((3,5-difluorobenzyl)amino)pyrimidin-2-
yl)amino)-1H-pyrazol-1-yl)-1-morpholinoethanone;

$N^4$-(3-bromobenzyl)-5-chloro-$N^2$-(1-methyl-1H-pyrazol-4-
yl)pyrimidine-2,4-diamine;

2-(4-((4-((5-bromo-2-fluorobenzyl)amino)-5-chloropyrimi-
din-2-yl)amino)-1H-pyrazol-1-yl)ethanol;

2-(4-((5-chloro-4-((2,6-difluorobenzyl)amino)pyrimidin-2-
yl)amino)-1H-pyrazol-1-yl)acetic acid;

5-chloro-$N^4$-(3-fluoro-5-(trifluoromethyl)benzyl)-$N^2$-(1-
methyl-1H-pyrazol-4-yl)pyrimidine-2,4-diamine;

3-(((5-fluoro-2-((1-(2-hydroxyethyl)-1H-pyrazol-4-yl)
amino)pyrimidin-4-yl)amino)methyl)benzonitrile;

2-(4-((5-chloro-4-((3,5-difluorobenzyl)amino)pyrimidin-2-
yl)amino)-1H-pyrazol-1-yl)acetic acid;

2-(4-((4-(benzylamino)-5-methylpyrimidin-2-yl)amino)-
1H-pyrazol-1-yl)ethano 1;

2-(4-((4-((2,3-difluorobenzyl)amino)-5-fluoropyrimidin-2-
yl)amino)-1H-pyrazol-1-yl)ethano 1;

2-(4-((5-chloro-4-((3-fluorobenzyl)amino)pyrimidin-2-yl)
amino)-1H-pyrazol-1-yl)ethano 1;

3-(((5-chloro-2-((1-(2-morpholino-2-oxoethyl)-1H-pyrazol-
4-yl)amino)pyrimidin-4-yl)amino)methyl)benzonitrile;

5-chloro-$N^4$-(2-fluorobenzyl)-$N^2$-(1-methyl-1H-pyrazol-4-
yl)pyrimidine-2,4-diamine;

2-(4-((5-chloro-4-((2-fluorobenzyl)amino)pyrimidin-2-yl)
amino)-1H-pyrazol-1-yl)ethano 1;

5-chloro-$N^4$-(2,6-difluorobenzyl)-$N^2$-(1-methyl-1H-pyra-
zol-4-yl)pyrimidine-2,4-diamine;

5-chloro-$N^4$-(3,5-difluorobenzyl)-$N^2$-(1-methyl-1H-pyra-
zol-4-yl)pyrimidine-2,4-diamine;

$N^4$-(2,3-difluorobenzyl)-5-fluoro-$N^2$-(1-methyl-1H-pyra-
zol-4-yl)pyrimidine-2,4-diamine;

2-(4-((5-chloro-4-((2,3-difluorobenzyl)amino)pyrimidin-2-
yl)amino)-1H-pyrazol-1-yl)-1-morpholinoethanone;

5-chloro-$N^4$-(2,3-difluorobenzyl)-$N^2$-(1-methyl-1H-pyra-
zol-4-yl)pyrimidine-2,4-diamine;

2-(4-((5-chloro-4-((2,3-difluorobenzyl)amino)pyrimidin-2-
yl)amino)-1H-pyrazol-1-yl)ethano 1;

2-(4-((5-chloro-4-((3-fluoro-5-(trifluoromethyl)benzyl)
amino)pyrimidin-2-yl)amino)-1H-pyrazol-1-yl)ethanol;

3-(((5-chloro-2-((1-(2-hydroxyethyl)-1H-pyrazol-4-yl)
amino)pyrimidin-4-yl)amino)methyl)benzonitrile;

3-(((5-fluoro-2-((1-methyl-1H-pyrazol-4-yl)amino)pyrimi-
din-4-yl)amino)methyl)benzonitrile;

3-(((5-chloro-2-((1-(2-hydroxypropyl)-1H-pyrazol-4-yl)
amino)pyrimidin-4-yl)amino)methyl)-4-fluorobenzene-
sulfonamide;

2-(4-((5-chloro-4-((2-methoxybenzyl)amino)pyrimidin-2-
yl)amino)-1H-pyrazol-1-yl)ethanol;

2-(4-((5-chloro-4-((3-methoxybenzyl)amino)pyrimidin-2-
yl)amino)-1H-pyrazol-1-yl)ethanol;

2-(4-((4-(benzylamino)-5-chloropyrimidin-2-yl)amino)-1H-
pyrazol-1-yl)-1-(piperazin-1-yl)ethanone;

2-(4-((4-(benzylamino)-5-chloropyrimidin-2-yl)amino)-1H-
pyrazol-1-yl)-1-(tetrahydro-1H-furo[3,4-c]pyrrol-5 (3H)-
yl)ethanone;

2-(4-((5-chloro-4-((3-fluoro-5-(trifluoromethyl)benzyl)
amino)pyrimidin-2-yl)amino)-1H-pyrazol-1-yl)-N-me-
thylacetamide;

2-(4-((5-chloro-4-((3,5-difluorobenzyl)amino)pyrimidin-2-
yl)amino)-1H-pyrazol-1-yl)-N-methylacetamide;

2-(4-((5-chloro-4-((2-(trifluoromethyl)benzyl)amino)pyri-
midin-2-yl)amino)-1H-pyrazol-1-yl)ethanol;

2-(4-((4-(benzylamino)-5-chloropyrimidin-2-yl)amino)-1H-
pyrazol-1-yl)ethanol;

2-(4-((4-(benzylamino)-5-fluoropyrimidin-2-yl)amino)-1H-
pyrazol-1-yl)ethanol;

2-(4-((4-(benzylamino)-5-chloropyrimidin-2-yl)amino)-1H-
pyrazol-1-yl)-1-(2,5-diazabicyclo[2.2.2]octan-2-yl)etha-
none;

2-(4-((4-(benzylamino)-5-chloropyrimidin-2-yl)amino)-1H-
pyrazol-1-yl)-N-methylacetamide;

2-(3-((4-(benzylamino)-5-chloropyrimidin-2-yl)amino)-1H-
pyrazol-1-yl)ethanol;

tert-butyl 5-(2-(4-((4-(benzylamino)-5-chloropyrimidin-2-
yl)amino)-1H-pyrazol-1-yl)acetyl)-2,5-diazabicyclo
[2.2.2]octane-2-carboxylate;

3-(((5-chloro-2-((1-methyl-1H-pyrazol-4-yl)amino)pyrimi-
din-4-yl)amino)methyl)benzenesulfonamide;

3-(((5-chloro-2-((1-(2-hydroxyethyl)-1H-pyrazol-4-yl)amino)pyrimidin-4-yl)amino)methyl)benzenesulfonamide;
3-(((5-chloro-2-((1-methyl-1H-pyrazol-4-yl)amino)pyrimidin-4-yl)amino)methyl)-N-methylbenzenesulfonamide;
$N^4$-benzyl-5-chloro-$N^2$-(1H-pyrazol-4-yl)pyrimidine-2,4-diamine;
2-(4-((5-fluoro-4-((2,3,6-trifluorobenzyl)amino)pyrimidin-2-yl)amino)-1H-pyrazol-1-yl)ethanol;
2-(4-((4-((2,5-difluorobenzyl)amino)-5-fluoropyrimidin-2-yl)amino)-1H-pyrazol-1-yl)ethanol;
2-(4-((4-((2,6-difluorobenzyl)amino)-5-fluoropyrimidin-2-yl)amino)-1H-pyrazol-1-yl)ethanol;
2-(4-((5-fluoro-4-((2-fluorobenzyl)amino)pyrimidin-2-yl)amino)-1H-pyrazol-1-yl)ethanol;
2-(4-((4-(benzylamino)-5-chloropyrimidin-2-yl)amino)-1H-pyrazol-1-yl)acetamide;
tert-butyl 4-(2-(4-((4-(benzylamino)-5-chloropyrimidin-2-yl)amino)-1H-pyrazol-1-yl)acetyl)piperazine-1-carboxylate;
2-(4-((5-chloro-4-((2,3-difluorobenzyl)amino)pyrimidin-2-yl)amino)-1H-pyrazol-1-yl)-N-methylacetamide;
1-(4-((5-chloro-4-((2,6-difluorobenzyl)amino)pyrimidin-2-yl)amino)-1H-pyrazol-1-yl)propan-2-ol;
2-(4-((5-fluoro-4-((3-fluorobenzyl)amino)pyrimidin-2-yl)amino)-1H-pyrazol-1-yl)ethano 1;
2-(4-((5-chloro-4-((2-fluorobenzyl)amino)pyrimidin-2-yl)amino)-1H-pyrazol-1-yl)-N-methylacetamide;
2-(4-((5-chloro-4-((3-fluorobenzyl)amino)pyrimidin-2-yl)amino)-1H-pyrazol-1-yl)-N-methylacetamide;
1-(4-((5-chloro-4-((2-fluorobenzyl)amino)pyrimidin-2-yl)amino)-1H-pyrazol-1-yl)propan-2-ol;
1-(4-((5-chloro-4-((3-fluorobenzyl)amino)pyrimidin-2-yl)amino)-1H-pyrazol-1-yl)propan-2-ol;
1-(4-((5-chloro-4-((2,3-difluorobenzyl)amino)pyrimidin-2-yl)amino)-1H-pyrazol-1-yl)propan-2-ol;
1-(4-((4-(benzylamino)-5-chloropyrimidin-2-yl)amino)-1H-pyrazol-1-yl)propan-2-ol;
2-(4-((4-(benzylamino)-5-chloropyrimidin-2-yl)amino)-1H-pyrazol-1-yl)-N,N-dimethylacetamide;
$N^4$-(5-bromo-2-fluorobenzyl)-5-chloro-$N^2$-(1-methyl-1H-pyrazol-4-yl)pyrimidine-2,4-diamine;
4-(((5-chloro-2-((1-(2-hydroxyethyl)-1H-pyrazol-4-yl)amino)pyrimidin-4-yl)amino)methyl)phenol;
tert-butyl 6-(2-(4-((4-(benzylamino)-5-chloropyrimidin-2-yl)amino)-1H-pyrazol-1-yl)acetyl)-2,6-diazaspiro[3.3]heptane-2-carboxylate;
2-(4-((4-(benzylamino)-5-chloropyrimidin-2-yl)amino)-1H-pyrazol-1-yl)-N-(2-(dimethylamino)ethyl)acetamide;
2-(4-((4-(benzylamino)-5-chloropyrimidin-2-yl)amino)-1H-pyrazol-1-yl)acetic acid;
5-chloro-$N^4$-(2,5-difluorobenzyl)-$N^2$-(1-(difluoromethyl)-1H-pyrazol-4-yl)pyrimidine-2,4-diamine;
5-chloro-$N^4$-(2,6-difluorobenzyl)-$N^2$-(1-(difluoromethyl)-1H-pyrazol-4-yl)pyrimidine-2,4-diamine;
ethyl 2-(4-((4-(benzylamino)-5-chloropyrimidin-2-yl)amino)-1H-pyrazol-1-yl)acetate;
3-(((5-chloro-2-((1-(2-hydroxyethyl)-1H-pyrazol-4-yl)amino)pyrimidin-4-yl)amino)methyl)-4-fluorobenzenesulfonamide;
3-(((5-chloro-2-((1-methyl-1H-pyrazol-4-yl)amino)pyrimidin-4-yl)amino)methyl)-4-fluorobenzenesulfonamide;
5-chloro-$N^4$-(2-methoxybenzyl)-$N^2$-(1-methyl-1H-pyrazol-4-yl)pyrimidine-2,4-diamine;
2-(4-((5-chloro-4-((2,6-difluorobenzyl)amino)pyrimidin-2-yl)amino)-1H-pyrazol-1-yl)-N-methylacetamide;
2-(4-((5-chloro-4-((3-cyanobenzyl)amino)pyrimidin-2-yl)amino)-1H-pyrazol-1-yl)-N-methylacetamide;
2-(4-((4-(benzylamino)-5-chloropyrimidin-2-yl)amino)-1H-pyrazol-1-yl) 1,1,2,2-d4-ethanol;
2-(4-((5-chloro-4-((3-fluorobenzyl)amino)pyrimidin-2-yl)amino)-1H-pyrazol-1-yl)1,1,2,2-d4-ethanol;
2-(4-((5-chloro-4-((2,3-difluorobenzyl)amino)pyrimidin-2-yl)amino)-1H-pyrazol-1-yl) 1,1,2,2-d4-ethanol;
2-(4-((5-chloro-4-((2,6-difluorobenzyl)amino)pyrimidin-2-yl)amino)-1H-pyrazol-1-yl) 1,1,2,2-d4-ethanol;
2-(4-((5-chloro-4-((3-methoxybenzyl)amino)pyrimidin-2-yl)amino)-1H-pyrazol-1-yl) 1,1,2,2-d4-ethanol;
2-(4-((4-(benzylamino)-5-chloropyrimidin-2-yl)amino)-1H-pyrazol-1-yl)-1-(2-oxa-6-azaspiro[3.3]heptan-6-yl)ethanone;
1-(2-(4-((4-(benzylamino)-5-chloropyrimidin-2-yl)amino)-1H-pyrazol-1-yl)acetyl)pyrrolidine-2-carbonitrile;
2-(4-((4-(benzylamino)-5-chloropyrimidin-2-yl)amino)-1H-pyrazol-1-yl)-N-(cyanomethyl)-N-methylacetamide;
2-(4-((4-(benzylamino)-5-chloropyrimidin-2-yl)amino)-1H-pyrazol-1-yl)-1-(2-oxa-7-azaspiro[3.5]nonan-7-yl)ethanone;
2-(4-((5-chloro-4-((2,6-difluorobenzyl)amino)pyrimidin-2-yl)amino)-1H-pyrazol-1-yl)acetamide;
3-(((5-chloro-2-((1-(2-hydroxyethyl)-1H-pyrazol-4-yl)amino)pyrimidin-4-yl)amino)methyl)-N-ethylbenzamide;
3-(((5-chloro-2-((1-(2-hydroxyethyl)-1H-pyrazol-4-yl)amino)pyrimidin-4-yl)amino)methyl)-N-(cyanomethyl)benzamide;
2-(4-((5-chloro-4-((3-methoxybenzyl)amino)pyrimidin-2-yl)amino)-1H-pyrazol-1-yl)-N-methylacetamide;
2-(4-((5-chloro-4-((3-methoxybenzyl)amino)pyrimidin-2-yl)amino)-1H-pyrazol-1-yl)-N,N-dimethylacetamide;
2-(4-((5-chloro-4-((2-fluoro-4-(trifluoromethyl)benzyl)amino)pyrimidin-2-yl)amino)-1H-pyrazol-1-yl)ethanol;
4-(((5-chloro-2-((1-(2-hydroxyethyl)-1H-pyrazol-4-yl)amino)pyrimidin-4-yl)amino)methyl)benzenesulfonamide;
2-(4-((5-chloro-4-((pyridin-2-ylmethyl)amino)pyrimidin-2-yl)amino)-1H-pyrazol-1-yl)ethanol;
$N^4$-benzyl-5-chloro-$N^2$-(1-((1-methyl-1H-imidazol-2-yl)methyl)-1H-pyrazol-4-yl)pyrimidine-2,4-diamine;
$N^4$-benzyl-5-chloro-$N^2$-(1-(oxazol-2-ylmethyl)-1H-pyrazol-4-yl)pyrimidine-2,4-diamine;
$N^4$-benzyl-5-chloro-$N^2$-(1-((1-methyl-1H-1,2,4-triazol-5-yl)methyl)-1H-pyrazol-4-yl)pyrimidine-2,4-diamine;
2-(4-((4-((2,6-dichlorobenzyl)amino)-5-fluoropyrimidin-2-yl)amino)-1H-pyrazol-1-yl)-N,N-dimethylacetamide;
2-(4-((5-fluoro-4-((2,4,6-trifluorobenzyl)amino)pyrimidin-2-yl)amino)-1H-pyrazol-1-yl)-N-(2,2,2-trifluoroethyl)acetamide;
3-(4-((4-(benzylamino)-5-chloropyrimidin-2-yl)amino)-1H-pyrazol-1-yl)-1-methylpyrrolidin-2-one;
$N^4$-benzyl-5-chloro-$N^2$-(1-((methylsulfonyl)methyl)-1H-pyrazol-4-yl)pyrimidine-2,4-diamine;
2-(4-((5-chloro-4-((pyridin-3-ylmethyl)amino)pyrimidin-2-yl)amino)-1H-pyrazol-1-yl)ethanol;
(R)-1-(4-((5-chloro-4-((2-fluorobenzyl)amino)pyrimidin-2-yl)amino)-1H-pyrazol-1-yl)propan-2-ol;
(S)-1-(4-((5-chloro-4-((2-fluorobenzyl)amino)pyrimidin-2-yl)amino)-1H-pyrazol-1-yl)propan-2-ol;
5-chloro-$N^4$-((5-fluoropyridin-3-yl)methyl)-$N^2$-(1-methyl-1H-pyrazol-4-yl)pyrimidine-2,4-diamine;
2-(4-((5-chloro-4-(((3-fluoropyridin-2-yl)methyl)amino)pyrimidin-2-yl)amino)-1H-pyrazol-1-yl)ethanol;
5-chloro-$N^4$-((3-fluoropyridin-2-yl)methyl)-$N^2$-(l-methyl-1H-pyrazol-4-yl)pyrimidine-2,4-diamine;

2-(4-((4-((5-bromo-2,3-difluorobenzyl)amino)-5-chloropyrimidin-2-yl)amino)-1H-pyrazol-1-yl)acetamide;
2-(4-((4-((5-bromo-2,3-difluorobenzyl)amino)-5-chloropyrimidin-2-yl)amino)-1H-pyrazol-1-yl)-N-methylacetamide;
2-(4-((4-((5-bromo-2,3-difluorobenzyl)amino)-5-chloropyrimidin-2-yl)amino)-1H-pyrazol-1-yl)-N,N-dimethylacetamide;
2-(4-((4-((5-bromo-2,3-difluorobenzyl)amino)-5-chloropyrimidin-2-yl)amino)-1H-pyrazol-1-yl)ethanol;
2-(4-((5-chloro-4-((2-fluoro-6-(1H-pyrazol-4-yl)benzyl)amino)pyrimidin-2-yl)amino)-1H-pyrazol-1-yl)ethanol;
2-(4-((5-chloro-4-((2-(methylsulfonyl)benzyl)amino)pyrimidin-2-yl)amino)-1H-pyrazol-1-yl)ethanol;
2-(4-((5-chloro-4-((3-ethoxy-2,6-difluorobenzyl)amino)pyrimidin-2-yl)amino)-1H-pyrazol-1-yl)acetamide;
2-(4-((5-chloro-4-((3-ethoxy-2,6-difluorobenzyl)amino)pyrimidin-2-yl)amino)-1H-pyrazol-1-yl)-N,N-dimethylacetamide;
2-(4-((5-chloro-4-((3-ethoxy-2,6-difluorobenzyl)amino)pyrimidin-2-yl)amino)-1H-pyrazol-1-yl)-N-methylacetamide;
(S)-1-(2-(4-((4-(benzylamino)-5-chloropyrimidin-2-yl)amino)-1H-pyrazol-1-yl)acetyl)pyrrolidine-3-carbonitrile;
(R)-1-(2-(4-((4-(benzylamino)-5-chloropyrimidin-2-yl)amino)-1H-pyrazol-1-yl)acetyl)pyrrolidine-3-carbonitrile;
(S)-1-(2-(4-((4-(benzylamino)-5-chloropyrimidin-2-yl)amino)-1H-pyrazol-1-yl)acetyl)pyrrolidine-2-carbonitrile;
2-(4-((4-(benzylamino)-5-chloropyrimidin-2-yl)amino)-1H-pyrazol-1-yl)-N-(2-methoxyethyl)acetamide;
1-(2-(4-((4-(benzylamino)-5-chloropyrimidin-2-yl)amino)-1H-pyrazol-1-yl)acetyl)azetidine-3-carbonitrile;
2-(4-((5-chloro-4-((3-fluoro-5-(trifluoromethyl)benzyl)amino)pyrimidin-2-yl)amino)-1H-pyrazol-1-yl)acetic acid;
5-chloro-$N^4$-(3,5-difluoro-2-methoxybenzyl)-$N^2$-(1-methyl-1H-pyrazol-4-yl)pyrimidine-2,4-diamine;
5-chloro-$N^4$-(2-fluoro-5-(trifluoromethyl)benzyl)-$N^2$-(1-methyl-1H-pyrazol-4-yl)pyrimidine-2,4-diamine;
5-chloro-$N^4$-(2-chloro-5-(trifluoromethyl)benzyl)-$N^2$-(1-methyl-1H-pyrazol-4-yl)pyrimidine-2,4-diamine;
2-(4-((5-chloro-4-((2-fluoro-5-(trifluoromethyl)benzyl)amino)pyrimidin-2-yl)amino)-1H-pyrazol-1-yl)-N-methylacetamide;
2-(4-((5-chloro-4-((2-chloro-5-(trifluoromethyl)benzyl)amino)pyrimidin-2-yl)amino)-1H-pyrazol-1-yl)-N-methylacetamide;
2-(4-((5-chloro-4-((2-fluoro-5-(trifluoromethyl)benzyl)amino)pyrimidin-2-yl)amino)-1H-pyrazol-1-yl)ethanol;
2-(4-((5-chloro-4-((2,6-difluoro-3-methylbenzyl)amino)pyrimidin-2-yl)amino)-1H-pyrazol-1-yl)acetamide;
2-(4-((5-chloro-4-((2,6-difluoro-3-methylbenzyl)amino)pyrimidin-2-yl)amino)-1H-pyrazol-1-yl)-N,N-dimethylacetamide;
2-(4-((5-chloro-4-((2,6-difluoro-3-methylbenzyl)amino)pyrimidin-2-yl)amino)-1H-pyrazol-1-yl)-N-methylacetamide;
2-(4-((4-(benzylamino)-5-chloropyrimidin-2-yl)amino)-1H-pyrazol-1-yl)propanamide;
2-(4-((5-chloro-4-((2-cyano-3-fluorobenzyl)amino)pyrimidin-2-yl)amino)-1H-pyrazol-1-yl)acetamide;
2-(((5-chloro-2-((1-(2-hydroxyethyl)-1H-pyrazol-4-yl)amino)pyrimidin-4-yl)amino)methyl)-6-fluorobenzonitrile;
2-(4-((5-chloro-4-((2-(hydroxymethyl)benzyl)amino)pyrimidin-2-yl)amino)-1H-pyrazol-1-yl)acetamide;
$N^4$-benzyl-5-chloro-$N^2$-(1-(2-(methylsulfonyl)ethyl)-1H-pyrazol-4-yl)pyrimidine-2,4-diamine;
(R)-2-(4-((4-(benzylamino)-5-chloropyrimidin-2-yl)amino)-1H-pyrazol-1-yl)propanamide;
(S)-2-(4-((4-(benzylamino)-5-chloropyrimidin-2-yl)amino)-1H-pyrazol-1-yl)propanamide;
1-(4-((5-chloro-4-((2,5-difluorobenzyl)amino)pyrimidin-2-yl)amino)-1H-pyrazol-1-yl)-2-methylpropan-2-ol;
2-(4-((5-chloro-4-((3-(difluoromethyl)benzyl)amino)pyrimidin-2-yl)amino)-1H-pyrazol-1-yl)ethanol;
2-(4-((5-chloro-4-((3-ethoxybenzyl)amino)pyrimidin-2-yl)amino)-1H-pyrazol-1-yl)ethanol;
2-(4-((5-chloro-4-((2,6-difluoro-3-methoxybenzyl)amino)pyrimidin-2-yl)amino)-1H-pyrazol-1-yl)acetic acid;
2-(4-((4-(benzylamino)-5-methylpyrimidin-2-yl)amino)-1H-pyrazol-1-yl)-1-morpholinoethanone;
N-cyclobutyl-2-(4-((4-((2,4,6-trifluorobenzyl)amino)pyrimidin-2-yl)amino)-1H-pyrazol-1-yl)acetamide;
2-(4-((4-((2,6-difluorobenzyl)amino)-5-methylpyrimidin-2-yl)amino)-1H-pyrazol-1-yl)ethanol;
2-(4-((4-((2,6-difluorobenzyl)amino)-5-methylpyrimidin-2-yl)amino)-1H-pyrazol-1-yl)-N,N-dimethylacetamide;
2-(4-((4-(benzylamino)-5-methylpyrimidin-2-yl)amino)-1H-pyrazol-1-yl)-N,N-dimethylacetamide;
5-methyl-$N^2$-(1-methyl-1H-pyrazol-4-yl)-$N^4$-(2,4,6-trifluorobenzyl)pyrimidine-2,4-diamine;
$N^4$-(2,6-difluoro-3-methoxybenzyl)-5-methyl-$N^2$-(1-methyl-1H-pyrazol-4-yl)pyrimidine-2,4-diamine;
2-(4-((5-methyl-4-((2,4,6-trifluorobenzyl)amino)pyrimidin-2-yl)amino)-1H-pyrazol-1-yl)ethanol;
2-(4-((4-((2,6-difluoro-3-methoxybenzyl)amino)-5-methylpyrimidin-2-yl)amino)-1H-pyrazol-1-yl)ethanol;
2-(4-((4-((2,6-difluorobenzyl)amino)-5-methylpyrimidin-2-yl)amino)-1H-pyrazol-1-yl)-1-morpholinoethanone;
2-(4-((5-methyl-4-((2,4,6-trifluorobenzyl)amino)pyrimidin-2-yl)amino)-1H-pyrazol-1-yl)acetic acid;
2-(4-((5-fluoro-4-((2,4,6-trifluorobenzyl)amino)pyrimidin-2-yl)amino)-1H-pyrazol-1-yl)acetic acid;
N-cyclobutyl-2-(4-((5-fluoro-4-((2,4,6-trifluorobenzyl)amino)pyrimidin-2-yl)amino)-1H-pyrazol-1-yl)acetamide;
1-(3,3-dimethylmorpholino)-2-(4-((5-fluoro-4-((2,4,6-trifluorobenzyl)amino)pyrimidin-2-yl)amino)-1H-pyrazol-1-yl)ethanone;
$N^2$-(1-methyl-1H-pyrazol-4-yl)-$N^4$-(2,4,6-trifluorobenzyl)pyrimidine-2,4-diamine;
2-(4-((4-((2,4,6-trifluorobenzyl)amino)pyrimidin-2-yl)amino)-1H-pyrazol-1-yl)acetamide;
$N^4$-(2,6-difluorobenzyl)-$N^2$-(1-methyl-1H-pyrazol-4-yl)pyrimidine-2,4-diamine;
2-(4-((4-((2,6-difluorobenzyl)amino)pyrimidin-2-yl)amino)-1H-pyrazol-1-yl)acetamide;
$N^4$-(2,6-difluoro-4-methoxybenzyl)-5-methyl-$N^2$-(1-methyl-1H-pyrazol-4-yl)pyrimidine-2,4-diamine;
2-(4-((4-((2,6-difluoro-4-methoxybenzyl)amino)-5-methylpyrimidin-2-yl)amino)-1H-pyrazol-1-yl)acetamide;
2-(4-((5-methyl-4-((2,4,6-trifluorobenzyl)amino)pyrimidin-2-yl)amino)-1H-pyrazol-1-yl)acetamide;
N-isopropyl-N-methyl-2-(4-((4-((2,4,6-trifluorobenzyl)amino)pyrimidin-2-yl)amino)-1H-pyrazol-1-yl)acetamide;
N-(tert-butyl)-N-methyl-2-(4-((4-((2,4,6-trifluorobenzyl)amino)pyrimidin-2-yl)amino)-1H-pyrazol-1-yl)acetamide;

5-chloro-$N^4$-(2,6-difluoro-3-methoxybenzyl)-$N^2$-(1-methyl-1H-pyrazol-4-yl)pyrimidine-2,4-diamine;
2-(4-((5-chloro-4-((2,6-difluoro-3-methoxybenzyl)amino)pyrimidin-2-yl)amino)-1H-pyrazol-1-yl)ethanol;
2-(4-((5-chloro-4-((2-methoxybenzyl)amino)pyrimidin-2-yl)amino)-1H-pyrazol-1-yl)acetamide;
2-(4-((5-chloro-4-((3-(difluoromethoxy)benzyl)amino)pyrimidin-2-yl)amino)-1H-pyrazol-1-yl)ethanol;
2-(4-((5-chloro-4-((2,6-dichlorobenzyl)amino)pyrimidin-2-yl)amino)-1H-pyrazol-1-yl)ethanol;
2-(4-((5-chloro-4-((2,6-dichlorobenzyl)amino)pyrimidin-2-yl)amino)-1H-pyrazol-1-yl)acetamide;
2-(4-((5-chloro-4-((2,6-dichlorobenzyl)amino)pyrimidin-2-yl)amino)-1H-pyrazol-1-yl)-N-methylacetamide;
2-(4-((5-chloro-4-((2,6-dichlorobenzyl)amino)pyrimidin-2-yl)amino)-1H-pyrazol-1-yl)-N,N-dimethylacetamide;
2-(4-((4-((2,6-dichlorobenzyl)amino)-5-fluoropyrimidin-2-yl)amino)-1H-pyrazol-1-yl)ethanol;
2-(4-((4-((2,6-dichlorobenzyl)amino)-5-fluoropyrimidin-2-yl)amino)-1H-pyrazol-1-yl)acetamide;
2-(4-((4-((2,6-dichlorobenzyl)amino)-5-fluoropyrimidin-2-yl)amino)-1H-pyrazol-1-yl)-N-methylacetamide;
2-(4-((4-((3-fluoro-5-(trifluoromethyl)benzyl)amino)-5-methylpyrimidin-2-yl)amino)-1H-pyrazol-1-yl)-N,N-dimethylacetamide;
2-(4-((5-fluoro-4-((3-fluoro-5-(trifluoromethyl)benzyl)amino)pyrimidin-2-yl)amino)-1H-pyrazol-1-yl)-N,N-dimethylacetamide;
2-(4-((5-fluoro-4-((3-fluoro-5-(trifluoromethyl)benzyl)amino)pyrimidin-2-yl)amino)-1H-pyrazol-1-yl)-1-morpholinoethanone;
2-(4-((5-chloro-4-((3-fluoro-2-(trifluoromethyl)benzyl)amino)pyrimidin-2-yl)amino)-1H-pyrazol-1-yl)ethanol;
2-(4-((5-chloro-4-((3-isopropoxybenzyl)amino)pyrimidin-2-yl)amino)-1H-pyrazol-1-yl)ethanol;
2-(4-((5-chloro-4-((2,3,6-trifluorobenzyl)amino)pyrimidin-2-yl)amino)-1H-pyrazol-1-yl)-N-cyclopropylacetamide;
5-chloro-$N^2$-(1-(2,2-difluoroethyl)-1H-pyrazol-4-yl)-$N^4$-(2,3,6-trifluorobenzyl)pyrimidine-2,4-diamine;
2-(4-((5-chloro-4-((pyridin-3-ylmethyl)amino)pyrimidin-2-yl)amino)-1H-pyrazol-1-yl)-1-morpholinoethanone;
2-(4-((5-chloro-4-((pyridin-2-ylmethyl)amino)pyrimidin-2-yl)amino)-1H-pyrazol-1-yl)-1-morpholinoethanone;
2-(4-((5-chloro-4-(((5-fluoropyridin-3-yl)methyl)amino)pyrimidin-2-yl)amino)-1H-pyrazol-1-yl)-1-morpholinoethanone;
5-chloro-$N^2$-(1-methyl-1H-pyrazol-4-yl)-$N^4$-(2,3,6-trifluorobenzyl)pyrimidine-2,4-diamine;
N-cyclopropyl-2-(4-((4-((2,3-difluorobenzyl)amino)-5-methylpyrimidin-2-yl)amino)-1H-pyrazol-1-yl)acetamide;
5-methyl-$N^2$-(1-methyl-1H-pyrazol-4-yl)-$N^4$-(2,3,5-trifluorobenzyl)pyrimidine-2,4-diamine;
$N^4$-(3,5-difluorobenzyl)-5-methyl-$N^2$-(1-methyl-1H-pyrazol-4-yl)pyrimidine-2,4-diamine;
N-cyclopropyl-2-(4-((4-((3,5-difluorobenzyl)amino)-5-methylpyrimidin-2-yl)amino)-1H-pyrazol-1-yl)acetamide;
N-cyclopropyl-2-(4-((4-((3,5-difluoro-2-methoxybenzyl)amino)-5-methylpyrimidin-2-yl)amino)-1H-pyrazol-1-yl)acetamide;
N-cyclopropyl-2-(4-((4-((2,5-difluorobenzyl)amino)-5-methylpyrimidin-2-yl)amino)-1H-pyrazol-1-yl)acetamide;
$N^4$-(2,3-difluorobenzyl)-$N^2$-(1-(2,2-difluoroethyl)-1H-pyrazol-4-yl)-5-methylpyrimidine-2,4-diamine;
2-(4-((4-((3,5-difluorobenzyl)amino)-5-methylpyrimidin-2-yl)amino)-1H-pyrazol-1-yl)-1-morpholinoethanone;
$N^4$-(3,5-difluoro-2-methoxybenzyl)-$N^2$-(1-(2,2-difluoroethyl)-1H-pyrazol-4-yl)-5-methylpyrimidine-2,4-diamine;
$N^4$-(3,5-difluorobenzyl)-5-methyl-$N^2$-(1-(2,2,2-trifluoroethyl)-1H-pyrazol-4-yl)pyrimidine-2,4-diamine;
5-methyl-$N^4$-(2,3,5-trifluorobenzyl)-$N^2$-(1-(2,2,2-trifluoroethyl)-1H-pyrazol-4-yl)pyrimidine-2,4-diamine;
$N^4$-(3,5-difluoro-2-methoxybenzyl)-5-methyl-$N^2$-(1-(2,2,2-trifluoroethyl)-1H-pyrazol-4-yl)pyrimidine-2,4-diamine;
$N^4$-(2,5-difluorobenzyl)-5-methyl-$N^2$-(1-(2,2,2-trifluoroethyl)-1H-pyrazol-4-yl)pyrimidine-2,4-diamine;
2-(4-((4-((3,5-difluorobenzyl)amino)-5-methylpyrimidin-2-yl)amino)-1H-pyrazol-1-yl)-N-methylacetamide;
2-(4-((5-chloro-4-((2-(N-methylsulfamoyl)benzyl)amino)pyrimidin-2-yl)amino)-1H-pyrazol-1-yl)-N-methylacetamide;
2-(4-((5-chloro-4-((2-(N,N-dimethylsulfamoyl)benzyl)amino)pyrimidin-2-yl)amino)-1H-pyrazol-1-yl)-N-methylacetamide;
2-(4-((5-chloro-4-((2-(hydroxymethyl)benzyl)amino)pyrimidin-2-yl)amino)-1H-pyrazol-1-yl)ethanol;
2-(4-((5-chloro-4-((3-ethoxy-2,6-difluorobenzyl)amino)pyrimidin-2-yl)amino)-1H-pyrazol-1-yl)ethanol;
2-(4-((5-chloro-4-((2,3,6-trifluorobenzyl)amino)pyrimidin-2-yl)amino)-1H-pyrazol-1-yl)-N-methylacetamide;
2-(4-((5-chloro-4-((2,3,6-trifluorobenzyl)amino)pyrimidin-2-yl)amino)-1H-pyrazol-1-yl)-N,N-dimethylacetamide;
2-(4-((4-(benzylamino)-5-chloropyrimidin-2-yl)amino)-1H-pyrazol-1-yl)propan-1-ol;
2-(4-((5-chloro-4-((3-(cyanomethoxy)benzyl)amino)pyrimidin-2-yl)amino)-1H-pyrazol-1-yl)acetamide;
2-(4-((5-chloro-4-((3-(methylsulfonyl)benzyl)amino)pyrimidin-2-yl)amino)-1H-pyrazol-1-yl)ethanol;
2-(4-((5-chloro-4-((3-(cyanomethoxy)benzyl)amino)pyrimidin-2-yl)amino)-1H-pyrazol-1-yl)-N-methylacetamide;
2-(4-((5-chloro-4-((3-(cyanomethoxy)benzyl)amino)pyrimidin-2-yl)amino)-1H-pyrazol-1-yl)-N,N-dimethylacetamide;
2-(3-(((5-chloro-2-((1-(2-morpholino-2-oxoethyl)-1H-pyrazol-4-yl)amino)pyrimidin-4-yl)amino)methyl)phenoxy)acetonitrile;
2-(4-((5-chloro-4-((3-(cyanomethoxy)benzyl)amino)pyrimidin-2-yl)amino)-1H-pyrazol-1-yl)-N-(2-(dimethylamino)ethyl)acetamide;
5-chloro-$N^4$-(3-ethoxy-2,6-difluorobenzyl)-$N^2$-(1H-pyrazol-4-yl)pyrimidine-2,4-diamine;
5-chloro-$N^4$-(2-fluorobenzyl)-$N^2$-(1H-pyrazol-4-yl)pyrimidine-2,4-diamine;
5-chloro-$N^4$-(3-fluorobenzyl)-$N^2$-(1H-pyrazol-4-yl)pyrimidine-2,4-diamine;
5-chloro-$N^4$-(2,6-difluoro-3-methylbenzyl)-$N^2$-(1H-pyrazol-4-yl)pyrimidine-2,4-diamine;
5-chloro-$N^2$-(1H-pyrazol-4-yl)-$N^4$-(2,4,6-trifluorobenzyl)pyrimidine-2,4-diamine;
2-(4-((5-chloro-4-((2,3,6-trifluorobenzyl)amino)pyrimidin-2-yl)amino)-1H-pyrazol-1-yl)ethanol;
5-fluoro-$N^2$-(1-methyl-1H-pyrazol-4-yl)-$N^4$-(2,4,6-trifluorobenzyl)pyrimidine-2,4-diamine;
2-(4-((5-chloro-4-((2,6-difluoro-3-methoxybenzyl)amino)pyrimidin-2-yl)amino)-1H-pyrazol-1-yl)acetamide;
2-(4-((5-chloro-4-((2,6-difluoro-3-methoxybenzyl)amino)pyrimidin-2-yl)amino)-1H-pyrazol-1-yl)-N,N-dimethylacetamide;
2-(4-((5-chloro-4-((2,6-difluoro-3-methoxybenzyl)amino)pyrimidin-2-yl)amino)-1H-pyrazol-1-yl)-1-morpholinoethanone;
3,5-difluoro-4-(((5-methyl-2-((1-(2-morpholino-2-oxoethyl)-1H-pyrazol-4-yl)amino)pyrimidin-4-yl)amino)methyl)benzenesulfonamide;

3,5-difluoro-4-(((5-fluoro-2-((1-methyl-1H-pyrazol-4-yl)amino)pyrimidin-4-yl)amino)methyl)benzenesulfonamide;

2-(4-((4-((2,6-difluorobenzyl)amino)-5-fluoropyrimidin-2-yl)amino)-1H-pyrazol-1-yl)acetamide;

2-(4-((4-((2,6-difluorobenzyl)amino)-5-fluoropyrimidin-2-yl)amino)-1H-pyrazol-1-yl)-N-methylacetamide;

2-(4-((4-((2,6-difluorobenzyl)amino)-5-fluoropyrimidin-2-yl)amino)-1H-pyrazol-1-yl)-N,N-dimethylacetamide;

$N^4$-(2,6-difluoro-3-methoxybenzyl)-5-fluoro-$N^2$-(1-methyl-H-pyrazol-4-yl)pyrimidine-2,4-diamine;

2-(4-((4-((2,6-difluoro-3-methoxybenzyl)amino)-5-fluoropyrimidin-2-yl)amino)-1H-pyrazol-1-yl)acetamide;

5-chloro-$N^2$-(1-methyl-1H-pyrazol-4-yl)-$N^4$-(2,4,6-trifluorobenzyl)pyrimidine-2,4-diamine;

2-(4-((5-chloro-4-((2,4,6-trifluorobenzyl)amino)pyrimidin-2-yl)amino)-1H-pyrazol-1-yl)ethano 1;

2-(4-((5-chloro-4-((2,4,6-trifluorobenzyl)amino)pyrimidin-2-yl)amino)-1H-pyrazol-1-yl)acetamide;

2-(4-((5-chloro-4-((2,4,6-trifluorobenzyl)amino)pyrimidin-2-yl)amino)-1H-pyrazol-1-yl)-N-methylacetamide;

2-(4-((5-chloro-4-((2,4,6-trifluorobenzyl)amino)pyrimidin-2-yl)amino)-1H-pyrazol-1-yl)-N,N-dimethylacetamide;

3-(((5-chloro-2-((1-(2-(dimethylamino)-2-oxoethyl)-1H-pyrazol-4-yl)amino)pyrimidin-4-yl)amino)methyl)benzamide;

2-(4-((5-chloro-4-((3-(difluoromethoxy)benzyl)amino)pyrimidin-2-yl)amino)-1H-pyrazol-1-yl)-N-isopropylacetamide;

2-(4-((5-chloro-4-((3-(difluoromethoxy)benzyl)amino)pyrimidin-2-yl)amino)-1H-pyrazol-1-yl)-N-isobutylacetamide;

2-(4-((5-chloro-4-((2,4,6-trifluorobenzyl)amino)pyrimidin-2-yl)amino)-1H-pyrazol-1-yl)-N-isopropylacetamide;

$N^4$-(2,6-difluoro-3-methoxybenzyl)-5-fluoro-$N^2$-(1-(2-isopropoxyethyl)-1H-pyrazol-4-yl)pyrimidine-2,4-diamine;

5-fluoro-$N^2$-(1-(2-isopropoxyethyl)-1H-pyrazol-4-yl)-$N^4$-(2,4,6-trifluorobenzyl)pyrimidine-2,4-diamine;

N-(3-(((5-chloro-2-((1-(2-morpholino-2-oxoethyl)-1H-pyrazol-4-yl)amino)pyrimidin-4-yl)amino)methyl)benzyl)methanesulfonamide;

2-(4-((5-chloro-4-((3-(methylsulfonamidomethyl)benzyl)amino)pyrimidin-2-yl)amino)-1H-pyrazol-1-yl)acetamide;

N-(3-(((5-chloro-2-((1-(2-hydroxyethyl)-1H-pyrazol-4-yl)amino)pyrimidin-4-yl)amino)methyl)benzyl)-N-methylmethanesulfonamide;

(R)—N-(3-(((5-chloro-2-((1-(2-(2-cyanopyrrolidin-1-yl)-2-oxoethyl)-1H-pyrazol-4-yl)amino)pyrimidin-4-yl)amino)methyl)benzyl)methanesulfonamide;

(S)—N-(3-(((5-chloro-2-((1-(2-(2-cyanopyrrolidin-1-yl)-2-oxoethyl)-1H-pyrazol-4-yl)amino)pyrimidin-4-yl)amino)methyl)benzyl)methanesulfonamide;

N-(3-(((5-chloro-2-((1-(2-morpholino-2-oxoethyl)-1H-pyrazol-4-yl)amino)pyrimidin-4-yl)amino)methyl)benzyl)-N-methylmethanesulfonamide;

N-(3-(((5-methyl-2-((1-methyl-1H-pyrazol-4-yl)amino)pyrimidin-4-yl)amino)methyl)benzyl)methanesulfonamide;

2-(4-((5-chloro-4-((3-fluoro-2-methoxybenzyl)amino)pyrimidin-2-yl)amino)-1H-pyrazol-1-yl)acetic acid;

2-(4-((5-chloro-4-((3-fluoro-2-methoxybenzyl)amino)pyrimidin-2-yl)amino)-1H-pyrazol-1-yl)acetamide;

2-(4-((5-chloro-4-(((2-hydroxypyridin-3-yl)methyl)amino)pyrimidin-2-yl)amino)-1H-pyrazol-1-yl)acetamide;

5-chloro-$N^4$-((2-fluoropyridin-3-yl)methyl)-$N^2$-(1-methyl-1H-pyrazol-4-yl)pyrimidine-2,4-diamine;

2-(4-((4-((3-(difluoromethoxy)benzyl)amino)-5-fluoropyrimidin-2-yl)amino)-1H-pyrazol-1-yl)ethano 1;

2-(4-((4-((3-(difluoromethoxy)benzyl)amino)-5-fluoropyrimidin-2-yl)amino)-1H-pyrazol-1-yl)-N-methylacetamide;

2-(4-((5-fluoro-4-((2,3,6-trifluorobenzyl)amino)pyrimidin-2-yl)amino)-1H-pyrazol-1-yl)acetamide;

2-(4-((5-fluoro-4-((2,3,6-trifluorobenzyl)amino)pyrimidin-2-yl)amino)-1H-pyrazol-1-yl)-N-methylacetamide;

2-(4-((5-fluoro-4-((2,3,6-trifluorobenzyl)amino)pyrimidin-2-yl)amino)-1H-pyrazol-1-yl)-N,N-dimethylacetamide;

5-chloro-$N^4$-(5-(difluoromethoxy)-2-fluorobenzyl)-$N^2$-(1-methyl-1H-pyrazol-4-yl)pyrimidine-2,4-diamine;

2-(4-((5-chloro-4-((5-(difluoromethoxy)-2-fluorobenzyl)amino)pyrimidin-2-yl)amino)-1H-pyrazol-1-yl)ethanol;

2-(4-((5-chloro-4-((5-(difluoromethoxy)-2-fluorobenzyl)amino)pyrimidin-2-yl)amino)-1H-pyrazol-1-yl)-N,N-dimethylacetamide;

N-(3-(((5-fluoro-2-((1-(2-hydroxyethyl)-1H-pyrazol-4-yl)amino)pyrimidin-4-yl)amino)methyl)benzyl)methanesulfonamide;

2-(4-((5-chloro-4-((3-(methylsulfonamidomethyl)benzyl)amino)pyrimidin-2-yl)amino)-1H-pyrazol-1-yl)-N,N-dimethylacetamide;

N-(3-(((5-chloro-2-((1-(2-hydroxyethyl)-1H-pyrazol-4-yl)amino)pyrimidin-4-yl)amino)methyl)benzyl)methanesulfonamide;

$N^4$-(2,6-difluorobenzyl)-5-methyl-$N^2$-(1-methyl-1H-pyrazol-4-yl)pyrimidine-2,4-diamine;

2-(4-((4-((2,6-difluorobenzyl)amino)-5-methylpyrimidin-2-yl)amino)-1H-pyrazol-1-yl)-N-methylacetamide;

5-methyl-$N^2$-(1-methyl-1H-pyrazol-4-yl)-$N^4$-(2,3,6-trifluorobenzyl)pyrimidine-2,4-diamine;

N-methyl-2-(4-((5-methyl-4-((2,3,6-trifluorobenzyl)amino)pyrimidin-2-yl)amino)-1H-pyrazol-1-yl)acetamide;

N,N-dimethyl-2-(4-((5-methyl-4-((2,3,6-trifluorobenzyl)amino)pyrimidin-2-yl)amino)-1H-pyrazol-1-yl)acetamide;

2-(4-((5-methyl-4-((2,3,6-trifluorobenzyl)amino)pyrimidin-2-yl)amino)-1H-pyrazol-1-yl)-1-morpholinoethanone;

2-(4-((5-methyl-4-((2,3,6-trifluorobenzyl)amino)pyrimidin-2-yl)amino)-1H-pyrazol-1-yl)acetic acid;

2-(4-((3-(difluoromethoxy)benzyl)amino)-5-fluoropyrimidin-2-yl)amino)-1H-pyrazol-1-yl)acetic acid;

2-(4-((4-((2,6-difluoro-3-methoxybenzyl)amino)-5-fluoropyrimidin-2-yl)amino)-1H-pyrazol-1-yl)acetic acid;

2-(4-((5-chloro-4-((2,6-difluoro-3-methoxybenzyl)amino)pyrimidin-2-yl)amino)-1H-pyrazol-1-yl)-N-isopropylacetamide;

2-(4-((5-chloro-4-((2,6-difluoro-3-methoxybenzyl)amino)pyrimidin-2-yl)amino)-1H-pyrazol-1-yl)-N-isobutylacetamide;

N-(tert-butyl)-2-(4-((5-fluoro-4-((2,4,6-trifluorobenzyl)amino)pyrimidin-2-yl)amino)-1H-pyrazol-1-yl)acetamide;

N-(1-fluoro-2-methylpropan-2-yl)-2-(4-((4-((2,4,6-trifluorobenzyl)amino)pyrimidin-2-yl)amino)-1H-pyrazol-1-yl)acetamide;

N-(1-(tetrahydrofuran-2-yl)ethyl)-2-(4-((4-((2,4,6-trifluorobenzyl)amino)pyrimidin-2-yl)amino)-1H-pyrazol-1-yl)acetamide;

N-((1,4-dioxan-2-yl)methyl)-2-(4-((4-((2,4,6-trifluorobenzyl)amino)pyrimidin-2-yl)amino)-1H-pyrazol-1-yl)acetamide;

2-(4-((5-methyl-4-((2-(methylsulfonyl)benzyl)amino)pyrimidin-2-yl)amino)-1H-pyrazol-1-yl)ethanol;

2-(4-((5-methyl-4-((2-(methylsulfonyl)benzyl)amino)pyrimidin-2-yl)amino)-1H-pyrazol-1-yl)acetamide;

2-(4-((5-fluoro-4-((2-(methylsulfonyl)benzyl)amino)pyrimidin-2-yl)amino)-1H-pyrazol-1-yl)ethanol;

2-(4-((5-fluoro-4-((2-(methylsulfonyl)benzyl)amino)pyrimidin-2-yl)amino)-1H-pyrazol-1-yl)acetamide;

$N^4$-(2-fluoro-6-methylbenzyl)-$N^2$-(1-methyl-1H-pyrazol-4-yl)pyrimidine-2,4-diamine;

2-(4-((5-chloro-4-((5-fluoro-2-(methylsulfonyl)benzyl)amino)pyrimidin-2-yl)amino)-1H-pyrazol-1-yl)-N-methylacetamide;

2-(4-((5-chloro-4-((3-(methylsulfonyl)benzyl)amino)pyrimidin-2-yl)amino)-1H-pyrazol-1-yl)acetamide;

2-(4-((5-chloro-4-((3-(methylsulfonyl)benzyl)amino)pyrimidin-2-yl)amino)-1H-pyrazol-1-yl)-N-cyclopropylacetamide;

2-(4-((5-chloro-4-((3-(methylsulfonyl)benzyl)amino)pyrimidin-2-yl)amino)-1H-pyrazol-1-yl)-N-(2-hydroxyethyl)acetamide;

5-chloro-$N^2$-(1-methyl-1H-pyrazol-4-yl)-$N^4$-(3-((methylsulfonyl)methyl)benzyl)pyrimidine-2,4-diamine;

2-(4-((5-chloro-4-((3-((methylsulfonyl)methyl)benzyl)amino)pyrimidin-2-yl)amino)-1H-pyrazol-1-yl)acetamide;

2-(4-((5-chloro-4-((2-methoxy-5-(methylsulfonyl)benzyl)amino)pyrimidin-2-yl)amino)-1H-pyrazol-1-yl)-N-methylacetamide;

2-(4-((5-chloro-4-((3-((methylsulfonyl)methyl)benzyl)amino)pyrimidin-2-yl)amino)-1H-pyrazol-1-yl)-N-methylacetamide;

5-fluoro-$N^4$-(2-methoxy-5-(methylsulfonyl)benzyl)-$N^2$-(1-methyl-1H-pyrazol-4-yl)pyrimidine-2,4-diamine;

2-(4-((5-fluoro-4-((2-methoxy-5-(methylsulfonyl)benzyl)amino)pyrimidin-2-yl)amino)-1H-pyrazol-1-yl)ethanol;

2-(4-((5-fluoro-4-((2-methoxy-5-(methylsulfonyl)benzyl)amino)pyrimidin-2-yl)amino)-1H-pyrazol-1-yl)-N-methylacetamide;

5-chloro-$N^4$-(2-methoxy-5-(methylsulfonyl)benzyl)-$N^2$-(1-methyl-1H-pyrazol-4-yl)pyrimidine-2,4-diamine;

2-(4-((5-chloro-4-((2-(methylsulfonyl)benzyl)amino)pyrimidin-2-yl)amino)-1H-pyrazol-1-yl)acetamide;

2-(4-((5-chloro-4-((2-(methylsulfonyl)benzyl)amino)pyrimidin-2-yl)amino)-1H-pyrazol-1-yl)-N-methylacetamide;

2-(4-((5-chloro-4-((2-(methylsulfonyl)benzyl)amino)pyrimidin-2-yl)amino)-1H-pyrazol-1-yl)-N,N-dimethylacetamide;

2-(4-((5-chloro-4-((2-(methylsulfonyl)benzyl)amino)pyrimidin-2-yl)amino)-1H-pyrazol-1-yl)-1-morpholinoethanone;

N-((1S,2R)-2-fluorocyclopropyl)-2-(4-((4-((2,4,6-trifluorobenzyl)amino)pyrimidin-2-yl)amino)-1H-pyrazol-1-yl)acetamide;

2-(4-((5-fluoro-4-((2,3,6-trifluorobenzyl)amino)pyrimidin-2-yl)amino)-1H-pyrazol-1-yl)-N-isopropylacetamide;

(R)—N-(1-hydroxypropan-2-yl)-2-(4-((4-((2,4,6-trifluorobenzyl)amino)pyrimidin-2-yl)amino)-1 H-pyrazol-1-yl)acetamide;

$N^4$-(3,6-dichloro-2-fluorobenzyl)-5-fluoro-$N^2$-(1-methyl-1H-pyrazol-4-yl)pyrimidine-2,4-diamine;

1-(3,3-dimethylazetidin-1-yl)-2-(4-((4-((2,4,6-trifluorobenzyl)amino)pyrimidin-2-yl)amino)-1 H-pyrazol-1-yl)ethanone;

1-(3,3-dimethylmorpholino)-2-(4-((4-((2,4,6-trifluorobenzyl)amino)pyrimidin-2-yl)amino)-1 H-pyrazol-1-yl)ethanone;

N-(1-hydroxy-2-methylpropan-2-yl)-2-(4-((4-((2,4,6-trifluorobenzyl)amino)pyrimidin-2-yl)amino)-1H-pyrazol-1-yl)acetamide;

$N^4$-benzyl-5-chloro-$N^2$-(1-(2-fluoroethyl)-1H-pyrazol-4-yl)pyrimidine-2,4-diamine;

5-fluoro-$N^2$-(1-methyl-1H-pyrazol-4-yl)-$N^4$-(2,3,5,6-tetrafluorobenzyl)pyrimidine-2,4-diamine;

$N^4$-(3,5-difluorobenzyl)-5-methyl-$N^2$-(1-(3,3,3-trifluoropropyl)-1H-pyrazol-4-yl)pyrimidine-2,4-diamine;

$N^2$-(1-(2,2-difluoroethyl)-1H-pyrazol-4-yl)-5-fluoro-$N^4$-(2,4,6-trifluorobenzyl)pyrimidine-2,4-diamine;

4-(((2-((1-(2,2-difluoroethyl)-1H-pyrazol-4-yl)amino)-5-methylpyrimidin-4-yl)amino)methyl)benzenesulfonamide;

$N^2$-(1-(2,2-difluoroethyl)-1H-pyrazol-4-yl)-5-methyl-$N^4$-(3-(methylsulfonyl)benzyl)pyrimidine-2,4-diamine;

5-chloro-$N^2$-(1-(2,2-difluoroethyl)-1H-pyrazol-4-yl)-$N^4$-(3-(methylsulfonyl)benzyl)pyrimidine-2,4-diamine;

5-chloro-$N^2$-(1-(2,2-difluoroethyl)-1H-pyrazol-4-yl)-$N^4$-(2,3,5-trifluorobenzyl)pyrimidine-2,4-diamine;

5-chloro-$N^4$-(2,6-difluorobenzyl)-$N^2$-(1-(2,2-difluoroethyl)-1H-pyrazol-4-yl)pyrimidine-2,4-diamine;

5-chloro-$N^4$-(3,5-difluorobenzyl)-$N^2$-(1-(2,2-difluoroethyl)-1H-pyrazol-4-yl)pyrimidine-2,4-diamine;

5-chloro-$N^2$-(1-(2,2-difluoroethyl)-1H-pyrazol-4-yl)-$N^4$-(2-(methylsulfonyl)benzyl)pyrimidine-2,4-diamine;

2-(((5-chloro-2-((1-(2-hydroxyethyl)-1H-pyrazol-4-yl)amino)pyrimidin-4-yl)amino)methyl)-N-methylbenzenesulfonamide;

2-(((5-chloro-2-((1-methyl-1H-pyrazol-4-yl)amino)pyrimidin-4-yl)amino)methyl)-N-methylbenzenesulfonamide;

2-(((5-chloro-2-((1-methyl-1H-pyrazol-4-yl)amino)pyrimidin-4-yl)amino)methyl)-N,N-dimethylbenzenesulfonamide;

5-chloro-$N^4$-(2-(methylsulfonyl)benzyl)-$N^2$-(1-(2,2,2-trifluoroethyl)-1H-pyrazol-4-yl)pyrimidine-2,4-diamine;

5-chloro-$N^2$-(1-(cyclopropylmethyl)-1H-pyrazol-4-yl)-$N^4$-(2-(methylsulfonyl)benzyl)pyrimidine-2,4-diamine;

$N^2$-(1-(2,2-difluoroethyl)-1H-pyrazol-4-yl)-5-fluoro-$N^4$-(2-(methylsulfonyl)benzyl)pyrimidine-2,4-diamine;

$N^2$-(1-(2,2-difluoroethyl)-1H-pyrazol-4-yl)-5-methyl-$N^4$-(2-(methylsulfonyl)benzyl)pyrimidine-2,4-diamine;

2-(4-((4-((3-bromo-4-fluorobenzyl)amino)-5-methylpyrimidin-2-yl)amino)-1H-pyrazol-1-yl)-1-morpholinoethanone;

$N^2$-(1-(2,2-difluoroethyl)-1H-pyrazol-4-yl)-5-fluoro-$N^4$-(2-methoxy-5-(methylsulfonyl)benzyl)pyrimidine-2,4-diamine;

5-chloro-$N^4$-(2,6-difluorobenzyl)-$N^2$-(1-(oxazol-2-ylmethyl)-1H-pyrazol-4-yl)pyrimidine-2,4-diamine;

5-chloro-$N^4$-(2,6-difluorobenzyl)-$N^2$-(1-((1-methyl-1H-pyrazol-4-yl)methyl)-1H-pyrazol-4-yl)pyrimidine-2,4-diamine;

5-chloro-$N^4$-(2,6-difluorobenzyl)-$N^2$-(1-((3-methyl-1,2,4-oxadiazol-5-yl)methyl)-1H-pyrazol-4-yl)pyrimidine-2,4-diamine;

5-chloro-$N^4$-(2,6-difluorobenzyl)-$N^2$-(1-((5-methylthiazol-4-yl)methyl)-1H-pyrazol-4-yl)pyrimidine-2,4-diamine;

5-fluoro-$N^4$-(2-fluoro-5-(methylsulfonyl)benzyl)-$N^2$-(1-methyl-1H-pyrazol-4-yl)pyrimidine-2,4-diamine;

5-fluoro-$N^4$-(5-fluoro-2-(methylsulfonyl)benzyl)-$N^2$-(1H-pyrazol-4-yl)pyrimidine-2,4-diamine;

5-fluoro-$N^4$-(5-fluoro-2-(methylsulfonyl)benzyl)-$N^2$-(1-methyl-1H-pyrazol-4-yl)pyrimidine-2,4-diamine;

2-(4-((5-fluoro-4-((5-fluoro-2-(methylsulfonyl)benzyl)amino)pyrimidin-2-yl)amino)-1H-pyrazol-1-yl)ethanol;

2-(4-((5-fluoro-4-((5-fluoro-2-(methylsulfonyl)benzyl) amino)pyrimidin-2-yl)amino)-1H-pyrazol-1-yl)acetamide; and (R)-2-(4-((4-((2,6-difluorobenzyl)amino)pyrimidin-2-yl) amino)-1H-pyrazol-1-yl)-N-(1-hydroxypropan-2-yl)acetamide.

Where tautomerism, e.g. keto-enol tautomerism, of compounds of general formula (I) may occur, the individual forms, e.g. the keto and enol form, are comprised separately and together as mixtures in any ratio. The same applies for stereoisomers, e.g. enantiomers, cis/trans isomers, conformers and the like.

Isotopic labeled compounds ("isotopic derivatives") of formula (I) are also within the scope of the present invention. Methods for isotope labeling are known in the art. Preferred isotopes are those of the elements H, C, N, O and S.

If desired, isomers can be separated by methods well known in the art, e.g. by liquid chromatography. The same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

According to the present invention "JAK" comprises all members of the JAK family (e.g. JAK1, JAK2, JAK3, and TYK2).

According to the present invention, the expression "JAK1" or "JAK1 kinase" means "Janus kinase 1". The human gene encoding JAK1 is located on chromosome 1p31.3.

According to the present invention, the expression "JAK2" or "JAK2 kinase" means "Janus kinase 2". The human gene encoding JAK2 is located on chromosome 9p24.

According to the present invention, the expression "JAK3" or "JAK3 kinase" means "Janus kinase 3". The gene encoding JAK3 is located on human chromosome 19p13.1 and it is predominantly in hematopoietic cells.

According to the present invention, the expression "TYK2" or "TYK2 kinase" means "Protein-Tyrosine kinase 2". The JAK3 and TYK2 genes are clustered on chromosome 19p13.1 and 19p13.2, respectively.

As shown in the examples, compounds of the invention were tested for their selectivity for TYK2 over JAK2 kinases. As shown, all tested compounds bind TYK2 more selectively than, JAK2 (see table 13 below).

Consequently, the compounds of the present invention as mentioned above are considered to be useful for the prevention or treatment of diseases and disorders associated with TYK2, for example immunological, inflammatory, autoimmune, or allergic disorders, transplant rejection, or Graft-versus-Host-Disease.

In a preferred embodiment, the compounds of the present invention are selective TYK2 inhibitors.

The compounds of the present invention may be further characterized by determining whether they have an effect on TYK2, for example on its kinase activity (Fridman et al 2010. J. Immunology 2010 184(9):5298-307).

A cell-based assay was described to assess the inhibitory activity of small molecule drugs toward TYK2-dependent signal transduction (Bacon et al 1995. PNAS 92, 7307-7311; WO2009155551).

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or other JAK inhibitors. Further bioactive compounds may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying antirheumatic drugs (DMARDs) such as methotrexate, sulphasalazine, cyclosporin A, hydroxychoroquine, auranofin, aurothioglucose, gold sodium thiomalate and penicillamine.

Further combination treatments are described in WO-A 2007/107318, incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament as mentioned above.

A preferred aspect of the present invention is a compound of the present invention or a pharmaceutically acceptable salt thereof for use in a method of treating or preventing a disease or disorder associated with TYK2 as mentioned above.

In the context of the present invention, a disease or disorder associated with TYK2 is defined as a disease or disorder where TYK2 is involved.

In a preferred embodiment, wherein the diseases or disorder is associated with TYK2 is an immunological, inflammatory, autoimmune, or allergic disorder or disease of a transplant rejection or a Graft-versus-host disease.

Consequently, another aspect of the present invention is a compound or a pharmaceutically acceptable salt thereof of the present invention for use in a method of treating or preventing an immunological, inflammatory, autoimmune, or allergic disorder or disease of a transplant rejection or a Graft-versus-host disease.

Inflammation of tissues and organs occurs in a wide range of disorders and diseases and in certain variations, results from activation of the cytokine family of receptors. Exemplary inflammatory disorders associated with activation of TYK2 include, in a non-limiting manner, skin inflammation due to radiation exposure, asthma, allergic inflammation and chronic inflammation.

In a preferred embodiment, the inflammatory disease is an eye disease.

Dry eye syndrome (DES, also known as keratoconjunctivitis sicca) is one of the most common problems treated by eye physicians. Sometimes DES is referred to as dysfunctional tear syndrome (Jackson, 2009. Canadian Journal Ophthalmology 44(4), 385-394). DES affects up to 10% of the population between the ages of 20 to 45 years, with this percentage increasing with age. Although a wide variety of artificial tear products are available, these products provide only transitory relief of symptoms. As such, there is a need for agents, compositions and therapeutic methods to treat dry eye.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolality of the tear film and inflammation of the ocular surface." (Lemp, 2007. "The Definition and Classification of Dry Eye Disease: Report of the Definition and Classification Subcommittee of the International Dry Eye Workshop", The Ocular Surface, 5(2), 75-92). Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

Uveitis is the most common form of intraocular inflammation and remains a significant cause of visual loss. Current treatments for uveitis employs systemic medications that have severe side effects and are globally immunosuppressive. Clinically, chronic progressive or relapsing forms of non-infectious uveitis are treated with topical and/or systemic corticosteroids. In addition, macrolides such as cyclosporine and rapamycin are used, and in some cases cytotoxic agents such as cyclophosphamide and chlorambucil, and antimetabolites such as azathioprine, methotrexate, and leflunomide (Srivastava et al., 2010. Uveitis: Mechanisms and recent advances in therapy. Clinica Chimica Acta, doi:10.1016/j.cca.2010.04.017).

Further eye diseases, combination treatments and route of administration are described for example in WO-A 2010/039939, which is hereby incorporated herein by reference.

According to the present invention, an autoimmune disease is a disease which is at least partially provoked by an immune reaction of the body against own components, for example proteins, lipids or DNA. Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis. Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting beta-cells of the islets of Langerhans.

In a preferred embodiment, the autoimmune disease is selected from the group consisting of rheumatoid arthritis (RA), inflammatory bowel disease (IBD; Crohns's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361). Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has been considered as an autoimmune disorder mediated by CD4+ type 1 T helper cells, but recent studies indicated a role of other immune cells (Hemmer et al., 2002, Nat. Rev. Neuroscience 3, 291-301).

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

Graft-versus-host disease (GVDH) is a major complication in allogeneic bone marrow transplantation (BMT). GVDH is caused by donor T cells that recognize and react to recipient differences in the histocompatibility complex system, resulting in significant morbidity and mortality.

Yet another aspect of the present invention is the use of a compound of the present invention or a pharmaceutically acceptable salt thereof for the manufacture of a medicament for the treatment or prophylaxis of diseases and disorders associated with TYK2.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus-host disease.

In the context of these uses of the invention, diseases and disorders associated with TYK2 are as defined above.

Yet another aspect of the present invention is a method for treating, controlling, delaying or preventing in a mammalian patient in need thereof one or more conditions selected from the group consisting of diseases and disorders associated with TYK2, wherein the method comprises the administration to said patient a therapeutically effective amount of a compound according to the present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus-host disease, wherein the method comprises the administration to said patient a therapeutically effective amount of a compound according to the present invention or a pharmaceutically acceptable salt thereof.

In the context of these methods of the invention, diseases and disorders associated with TYK2 are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

Exemplary routes for the preparation of compounds of the present invention are described below. It is clear to a practitioner in the art to combine or adjust such routes especially in combination with the introduction of activating or protective chemical groups.

Compounds of formula (I) were prepared by reacting a compound of formula (II) with a compound of formula (III). Optionally, a solvent was employed, in particular a protic or polar aprotic solvent such as alcohols, dioxane, DMF or THF. Optionally, the procedure was conducted in the presence of an organic or mineral acid such as a sulfonic acid or hydrogen chloride. Alternatively, the procedure could be conducted in the presence of an organic or inorganic base such as an amine base, metal carbonate, metal hydrogen carbonate or metal hydroxide wherein the metal is often an alkali earth metal such as sodium, potassium or cesium. Many amine bases are known to those skilled in the art including triethylamine, DIPEA, DBU and DMAP. The reactions were performed at a temperature between −78 and 200° C. For temperatures in excess of room temperature, heating could be by conventional means or by the use of microwave irradiation. Conceivably, the chloride leaving group in (II) could be replaced by another leaving group known to those skilled in the art, such as another halogen, a sulfide or sulfone.

In one embodiment, compounds of formula (I) were prepared by reacting a compound of formula (II) with a compound of formula (III) in a polar aprotic solvent such as DMF, dioxane or THF, optionally in the presence of a sulfonic acid, such as methanesulfonic acid or toluenesulfonic acid; at a temperature between −20 and 100° C. A preferred embodiment is described by Procedure A.

Alternatively, compounds of formula (I) were prepared by reacting a compound of formula (IV) with a compound of formula (V). Optionally, a solvent was employed, in particular a protic or polar aprotic solvent such as an alcohol, dioxane, DMF, THF, acetonitrile or DMSO.

Optionally, the procedure was conducted in the presence of an organic or mineral acid such as a sulfonic acid or hydrogen chloride. Alternatively, the reactions were conducted in the presence of a base, such as a metal carbonate or metal alkoxide, together with a palladium catalyst and optionally a phosphine ligand. The reactions were performed at a temperature between 20 and 200° C. For temperatures in excess of room temperature, heating could be by conventional means or by the use of microwave irradiation. Conceivably, the chloride leaving group in (IV) could be replaced by another leaving group known to those skilled in the art, such as another halogen, triflate, a sulfide or sulfone.

In one such embodiment, compounds of formula (I) were prepared by reacting a compound of formula (IV) with a compound of formula (V) in either ethanol, IPA, butanol, dioxane or THF; in the presence of toluenesulfonic acid or hydrogen chloride which could be in catalytic or stoichiometirc amounts; at a temperature between 80 and 160° C. In another such embodiment, compounds of formula I were prepared by reacting a compound of formula (IV) with a compound of formula V in either acetonitrile, DMF, dioxane or THF; in the presence of a base such as a alkali metal carbonate or alkali metal alkoxide; in the presence of a palladium catalyst such as palladium acetate, $Pd_2dba_3$, $Pd(Ph_3)_4$; optionally in the presence of a phosphine ligand such as Xantphos or BINAP; at a temperature between 80 and 160° C. A preferred embodiment is described by Procedure B. Another preferred embodiment is described by Procedure C.

Scheme 1

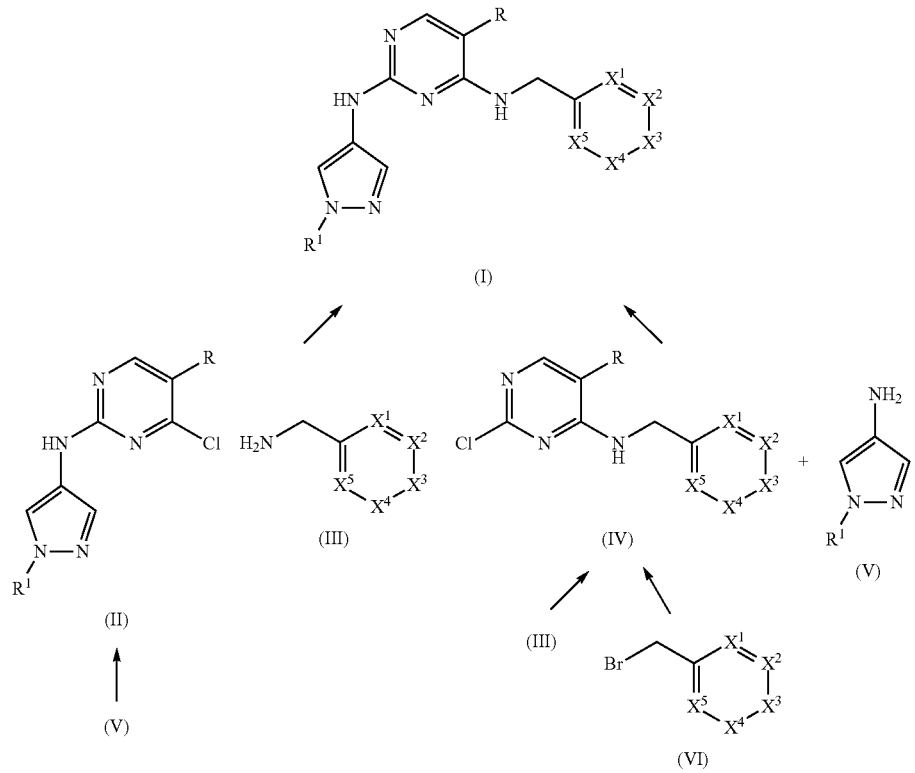

EXAMPLES

Analytical Methods

NMR spectra were obtained on a Brucker dpx400. LC-MS (methods A, B, G and H) was carried out on an Agilent 1100. Solvents used were water and acetonitrile or methanol (0.1% formic acid-low pH, 0.1% ammonia-high pH) with an injection volume of 3 µL.

Wavelengths were 254 and 210 nm. LC-MS methods C, D, E, F was carried out on a Waters uPLC-SQD. Photodiode array detection was between 210 and 400 nm.

Method A

Column: Waters Novapak C18, 3.9×150 mm, 4 µm.

Flow rate: 1.0 mL/min.

Water contains 0.07% TFA.

TABLE 1

| Time (min) | Methanol (%) | Water (%) |
|---|---|---|
| 0 | 20.0 | 80.0 |
| 5 | 20.0 | 80.0 |
| 8 | 65.0 | 35.0 |
| 10 | 95.0 | 5.0 |
| 14 | 95.0 | 5.0 |
| 17 | 95.0 | 5.0 |

Method B

Column: Phenomenex Gemini-C18, 4.6×150 mm, 5 µm.

Flow rate: 1.0 mL/min.

Solvents contain 0.1% formic acid.

TABLE 2

| Time (min) | Water (%) | ACN (%) |
|---|---|---|
| 0.00 | 95.0 | 5.0 |
| 11.00 | 5.0 | 95.0 |
| 13.00 | 5.0 | 95.0 |
| 13.01 | 95.0 | 5.0 |
| 16.00 | 95.0 | 5.0 |

Method C

Column: Waters Acquity UPLC BEH C18, 2.1×30 mm, 1.7 µm.

Flow rate: 0.5 mL/min.

Solvents contain 0.1% ammonia.

TABLE 3

| Time (min) | Water (%) | ACN (%) |
|---|---|---|
| 0.00 | 95.0 | 5.0 |
| 0.20 | 95.0 | 5.0 |
| 1.00 | 5.0 | 95.0 |
| 1.50 | 5.0 | 95.0 |
| 1.70 | 95.0 | 5.0 |
| 2.70 | 95.0 | 5.0 |
| 3.00 | 95.0 | 5.0 |

Method D

As for method C except solvents contain 0.1% formic acid.

Method E

Column: Waters Acquity UPLC BEH C18, 2.1×50 mm, 1.7 µm.

Flow rate: 1.2 mL/min.

Solvents contain 0.1% ammonia.

TABLE 4

| Time (min) | Water (%) | ACN (%) |
|---|---|---|
| 0.00 | 95.0 | 5.0 |
| 0.20 | 95.0 | 5.0 |
| 4.20 | 5.0 | 95.0 |
| 4.70 | 5.0 | 95.0 |
| 4.75 | 95.0 | 5.0 |
| 6.00 | 95.0 | 5.0 |

Method F

As for method E except solvents contain 0.1% formic acid.

Method G

Column: Waters Novapak C18, 3.9×150 mm, 4 µm.

Flow rate: 1.0 mL/min.

Water contains 0.07% TFA.

TABLE 5

| Time (min) | MeOH (%) | Water (%) |
|---|---|---|
| 0 | 5 | 95 |
| 2 | 5 | 95 |
| 5 | 12 | 88 |
| 6 | 40 | 60 |
| 7 | 95 | 5 |
| 10 | 95 | 5 |
| 12 | 60 | 40 |
| 13 | 5 | 95 |
| 15 | 5 | 95 |

Method H

Column: Phenomenex Gemini-NX C18, 3.0×30 mm, 3 µm.

Flow rate: 1.2 mL/min.

Solvents contain 0.1% formic acid.

TABLE 6

| Time (min) | Water (%) | ACN (%) |
|---|---|---|
| 0.00 | 95.0 | 5.0 |
| 3.00 | 5.0 | 95.0 |
| 4.50 | 5.0 | 95.0 |
| 4.60 | 95.0 | 5.0 |
| 6.00 | 95.0 | 5.0 |

TABLE 7

| Abbreviations | |
|---|---|
| ACN | Acetonitrile |
| Ar | Aryl |
| aq | Aqueous |
| BINAP | 2,2'-Bis(diphenylphosphino)-1,1'-binaphthyl |
| Boc | Tert-Butoxycarbonyl |
| Bu | Butyl |
| BuLi | Butyllithium |
| Conc. | Concentrated |
| dba | Dibenzyledene acetone |
| DBU | 1,8-Diazabicyclo[5.4.0]undec-7-ene |
| DCM | Dichloromethane |

TABLE 7-continued

Abbreviations

| | |
|---|---|
| DIPEA | Diisopropylethylamine |
| DMAP | 4-Dimethylaminopyridine |
| DMF | N,N-Dimethylformamide |
| DMSO | N,N-dimethylsulfoxide |
| DP | Drug pulldown |
| EDTA | Ethylenediaminetetraacetic acid |
| ES+ | Electrospray positive ionisation |
| Et | Ethyl |
| Ether | Diethyl ether |
| eq | Equivalents |
| h | Hour |
| HATU | 2-(1H-7-Azabenzotriazol-1-yl)--1,1,3,3-tetramethyl uronium hexafluorophosphate methanaminium |
| HOBt | 1-Hydroxybenzotriazole |
| HPLC | High performance liquid chromatography |
| $IC_{50}$ | 50% inhibition concentration |
| IPA | Isopropyl alcohol |
| iPr | Isopropyl |
| LC-MS | Liquid chromatography - mass spectroscopy |
| Me | Methyl |
| Mesyl | Methanesulfonyl chloride |
| min | Minutes |
| mol % | Molar percent |
| m/z | Mass to charge ratio |
| NMR | Nuclear magnetic resonance |
| PBS | Phosphate buffered saline |
| Petrol | Petroleum Ether 40-60 |
| Ph | Phenyl |
| prep. | Preparative |
| rpm | Revolutions per minute |
| rt | Room temperature |
| RT | Retention time |
| sat. | Saturated |
| tert | Tertiary |
| TFA | Trifluoroacetic acid |
| TFFH | Tetramethylfluoroformamidinium hexafluorophosphate |
| THF | Tetrahydrofuran |
| TLC | Thin layer chromatography |
| Ts | Toluenesulfonyl |
| UPLC | Ultra performance liquid chromatography |
| Xantphos | 4,5-Bis(diphenylphosphino)-9,9-dimethylxanthene |

Procedures A-L describe how representative compounds of formula (I) were synthesized and act as general procedures by which all the examples were synthesized. A person skilled in the art would recognize that each example could be synthesized by combining these procedures in one or more ways. Compounds of formula (I) were prepared by reacting intermediates (II) with amines of formula (III) by Procedure A, particularly when intermediates II-1 and II-2 provided the requisite R and $R^1$. Further compounds of formula (I) were prepared by reacting intermediates of formula (IV) with aminopyrazole derivatives of formula (V) by either Procedure B or C.

Intermediates of formula (II) were prepared by Procedure D. Amine derivatives of formula (III) were either commercially available or made by Procedure E. Intermediates of formula (IV) were made by Procedures F1-F3. Aminopyrazole compounds of formula (V) were either commercially available or made by Procedures G1-G3. Bromides of formula (VI) were either commercially available or made by Procedure H.

Compounds of formula (I) could themselves be used as intermediates to synthesise further examples of formula (I). Examples I-81 and I-2 were converted to amides with formula (I) by Procedures I, J1, J2 and K.

Procedure A: Synthesis of Example I-1

2-(4-((4-((4-cyano-2,6-difluorobenzyl)amino)pyrimidin-2-yl)amino)-1H-pyrazol-1-yl)-N-Isopropylacetamide I-1

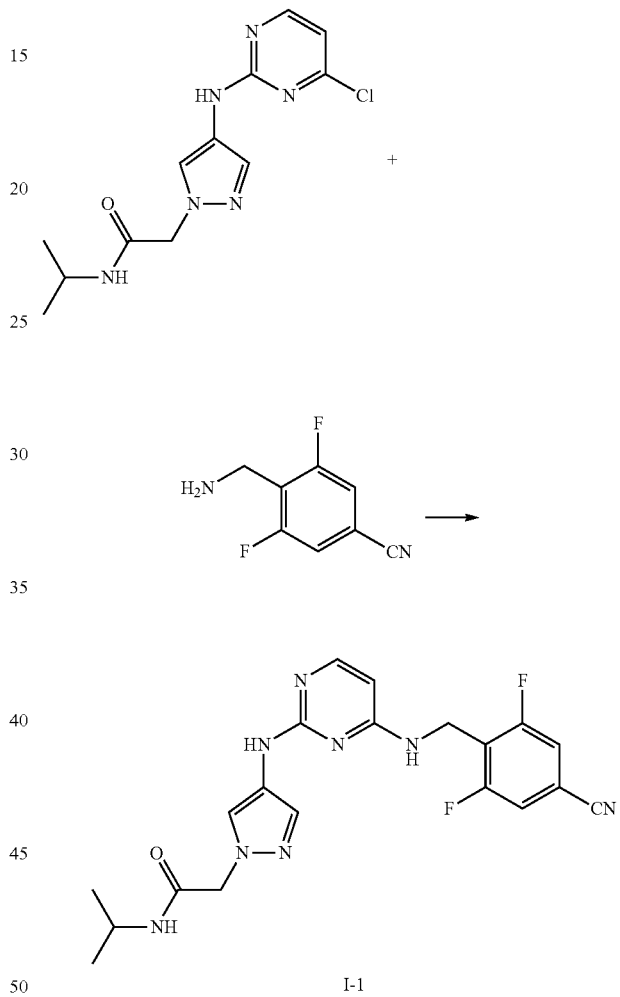

A solution of 2-(4-(4-chloropyrimidin-2-ylamino)-1H-pyrazol-1-yl)-N-isopropylacetamide (120 mg, 0.41 mmol) (II-1, prepared by Procedure D), 4-(aminomethyl)-3,5-difluorobenzonitrile (68 mg, 0.41 mmol) (III-1, prepared by Procedure E) and TsOH (56 mg, 0.33 mmol) in dioxane (2 mL) was heated to 160° C. for 2 h then concentrated in vacuo. The residue was dissolved in ethyl acetate, washed with $Na_2CO_3$(aq), dried ($Na_2SO_4$), concentrated in vacuo and purified by prep. TLC (5-10% v/v MeOH/DCM) to afford 2-(4-((4-((4-cyano-2,6-difluorobenzyl)amino)pyrimidin-2-yl)amino)-1H-pyrazol-1-yl)-N-isopropylacetamide I-1 (50 mg, 29%) as a white solid. LC-MS (Method A), RT=8.02 min. (ES+) 427.

Procedure B: Synthesis of Example I-2

2-(4-((4-((2,4,6-trifluorbenzyl)amino)pyrimidin-2-yl)amino)-1-pyrazol-1-yl)acetic acid I-2

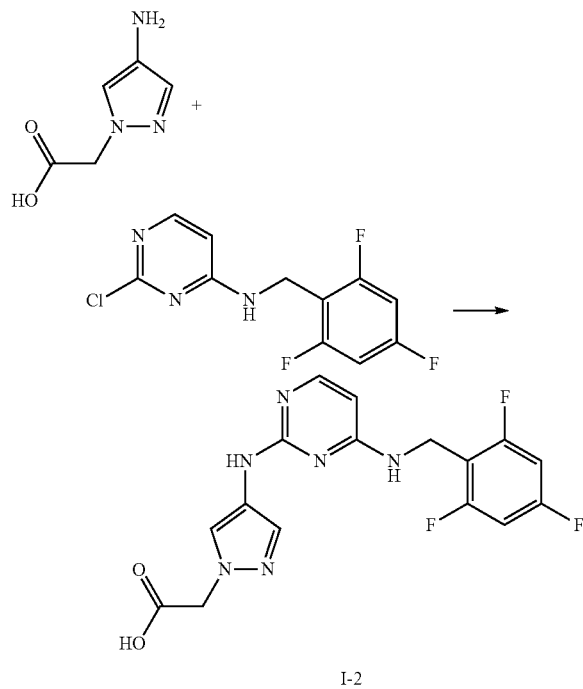

I-2

A solution of 2-chloro-N-(2,4,6-trifluorobenzyl)pyrimidin-4-amine IV-1 (0.5 g, 1.8 mmol, prepared by Procedure F1), 2-(4-amino-1H-pyrazol-1-yl)acetic acid dihydrochloride (0.45 g, 2 mmol) and TsOH (0.38 g, 2 mmol) in anhydrous dioxane was stirred under reflux for 3 h.

The reaction mixture was concentrated in vacuo and slurried with water. The resulting precipitate was filtered and purified using reverse phase column chromatography to afford 2-(4-((4-((2,4,6-trifluorobenzyl)amino)pyrimidin-2-yl)amino)-1H-pyrazol-1-yl)acetic acid I-2 (0.3 g, 0.8 mmol) as a white solid. LC-MS (Method D), RT=0.75 min. (ES$^+$) 379.

Procedure C: Synthesis of Example I-3

(S)-2-(4-((4-((2,6-dichlorobenzyl)amino)pyrimidin-2-yl)amino)-1H-pyrazol-1-yl)-N-(1-hydroxypropan-2-yl)acetamide I-3

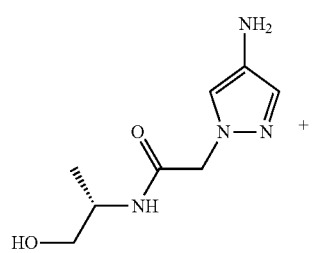

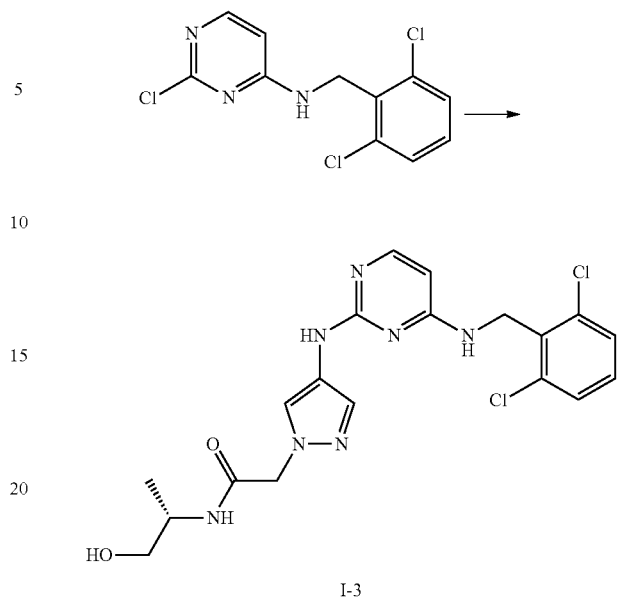

I-3

A mixture of 2-chloro-N-(2,6-dichlorobenzyl)pyrimidin-4-amine (120 mg, 0.41 mmol), (S)-2-(4-amino-1H-pyrazol-1-yl)-N-(1-hydroxypropan-2-yl)acetamide V-1 (110 mg, 0.54 mmol, prepared by Procedure G1), Xantphos (47 mg, 0.08 mmol), Pd$_2$dba$_3$ (37 mg, 0.04 mmol) and cesium carbonate (333 mg, 1.02 mmol) in dioxane (40 mL) was heated to reflux under nitrogen. Upon completion, the reaction was concentrated in vacuo, diluted with aqueous sodium carbonate solution then extracted with ethyl acetate. The organic layer was dried (Na$_2$SO$_4$), concentrated in vacuo and purified by column chromatography (0-10% v/v [10% NH$_3$ in MeOH]/DCM) to afford (S)-2-(4-((4-((2,6-dichlorobenzyl)amino)pyrimidin-2-yl)amino)-1H-pyrazol-1-yl)-N-(1-hydroxypropan-2-yl)acetamide I-3 (60 mg, 25%). LC-MS (Method A), RT=8.32 min. (ES$^+$) 450.

Procedure D: Synthesis of Intermediates of Formula (II)

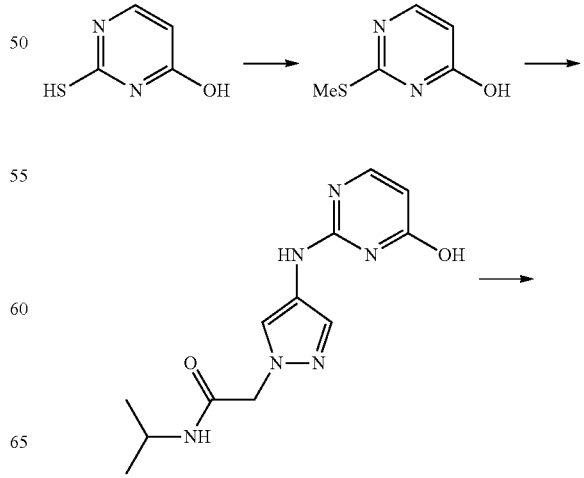

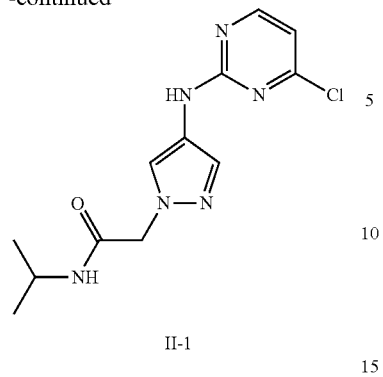

II-1

Step (i) 2-(methylthio)pyrimidin-4-ol

A mixture of methyl iodide (66 g, 0.47 mol) and 2-mercaptopyrimin-4-ol (50 g, 0.39 mol) in water (500 mL) was stirred at room temperature for 24 h then acetic acid was added to acidify the reaction mixture. The resultant precipitate was collected by filtration, washed with water and dried in vacuo to afford 2-(methylthio)pyrimidin-4-ol (40 g, 72% yield) as a white solid.

Step (ii) 2-(4-(4-hydroxypyrimidin-2-ylamino)-1H-pyrazol-1-yl)-N-isopropylacetamide A mixture of 2-(methylthio)pyrimin-4-ol (8.0 g, 56 mmol), 2-(4-amino-1H-pyrazol-1-yl)-N-isopropylacetamide V-3 (10.3 g, 56.5 mmol, prepared by Procedure G2) and triethylamine (11.4 g, 110 mmol) in diglyme (100 mL) was heated at 160° C. for 24 h then concentrated in vacuo. The residue was slurried with water and the solid collected by filtration and dried to give a first crop of 2-(4-(4-hydroxypyrimidin-2-ylamino)-1H-pyrazol-1-yl)-N-isopropylacetamide. The filtrate was adjusted to pH 7 then extracted with n-butanol and concentrated in vacuo. The residue was washed with ethyl acetate and dried to afford a second crop (total yield 10 g, 64%).

Step (iii) 2-(4-(4-chloropyrimidin-2-ylamino)-1H-pyrazol-1-yl)-N-isopropylacetamide II-1

To a mixture of 2-(4-(4-hydroxypyrimidin-2-ylamino)-1H-pyrazol-1-yl)-N-isopropylacetamide (6.0 g, 22 mmol) in acetonitrile (300 mL) was added 4M HCl in dioxane (12 mL, 48 mmol) then $POCl_3$ (10 g). The mixture was heated to reflux for 0.5 h then concentrated in vacuo. The residue was slurried with water and adjusted to pH 9 with aqueous sodium hydrogen carbonate. The remaining solid was collected by filtration and purified by column chromatography (50% v/v DCM/ethyl acetate) to afford 2-(4-(4-chloropyrimidin-2-ylamino)-1H-pyrazol-1-yl)-N-isopropylacetamide II-1 (2.30 g, 36%) as a white solid. LC-MS (Method A), RT=8.28 min. (ES+) 295.

By this procedure, two intermediates were synthesized as shown in Table 8.

TABLE 8

Intermediates of formula (II) made by Procedure D

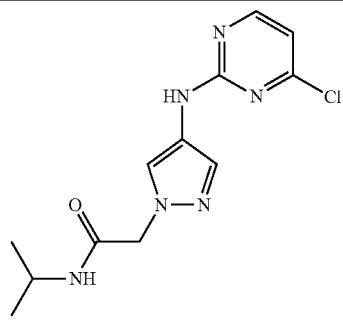

II-1

II-2

Procedure E: Synthesis of Methylamine Derivatives of Formula (III)

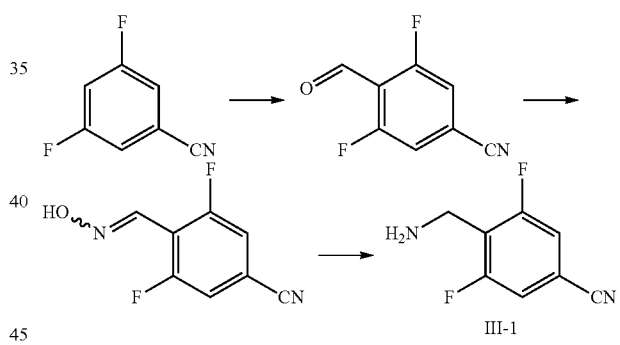

III-1

Step (i) 3,5-difluoro-4-formylbenzonitrile n-BuLi (2.5 M, 4.4 mL) was added to a stirred solution of DIPEA (1.1, 11 mmol) in dry THF (100 mL) at −78° C. under a nitrogen atmosphere then warmed to at 0° C. and stirred for 1 h. The solution was cooled to −78° C. and 3,5-difluorobenzonitrile (1.39 g, 10 mmol) was added. The mixture was stirred at −78° C. for 1 h then DMF (877 mg, 12 mmol) was added and the reaction continued for a further 0.5 h before addition of 10% v/v aqueous acetic acid (20 mL).

The mixture was warmed to room temperature, extracted with ethyl acetate and then concentrated in vacuo to afford 3,5-difluoro-4-formylbenzonitrile (1.29 g, 77%) as a yellow solid.

Step (ii) 3,5-difluoro-4-((hydroxyimino)methyl)benzonitrile

A mixture of 3,5-difluoro-4-formylbenzonitrile (500 mg, 3.0 mmol), hydroxylamine hydrochloride (207 mg, 3.0 mmol) and potassium acetate (586 mg, 6.0 mmol) in methanol (10 mL) was heated to 60° C. for 1 h then concentrated in vacuo and purified by column chromatography (eluent: DCM) to afford 3,5-difluoro-4-((hydroxyimino)methyl)benzonitrile (130 mg, 0.7 mmol) as a white solid.

Step (iii) 4-(aminomethyl)-3,5-difluorobenzonitrile

An excess of zinc powder was added to a stirred mixture of 3,5-difluoro-4-((hydroxyimino)methyl)benzonitrile (130 mg, 0.7 mmol) in acetic acid (10 mL) then heated to 60° C. for 2 h. The mixture was made basic by addition of aqueous ammonia and extracted with ethyl acetate. The organic layer was washed with brine, dried (Na$_2$SO$_4$) and concentrated in vacuo to afford 4-(aminomethyl)-3,5-difluorobenzonitrile (100 mg, 0.6 mmol) as a colourless oil.

By this method, intermediates with formula (III) were synthesized as shown in Table 9.

TABLE 9

Intermediates of formula (III) made by Procedure E

III-1
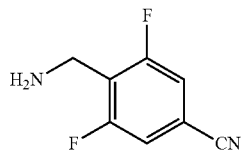 [SMILES: N#Cc1cc(F)c(CN)c(F)c1]

III-2
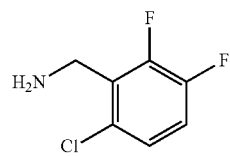 [SMILES: NCc1c(Cl)ccc(F)c1F]

III-3
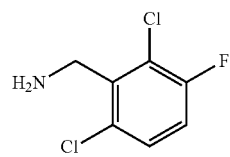 [SMILES: NCc1c(Cl)ccc(F)c1Cl]

III-4
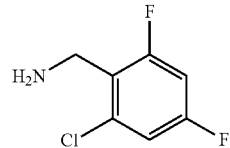 [SMILES: NCc1c(F)cc(F)cc1Cl]

III-5
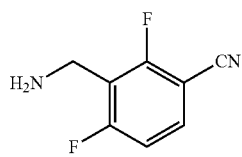 [SMILES: N#Cc1ccc(F)c(CN)c1F]

TABLE 9-continued

Intermediates of formula (III) made by Procedure E

III-6
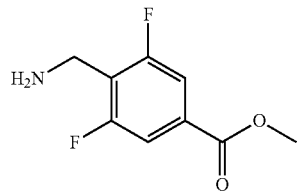

III-7
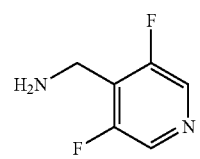

III-8
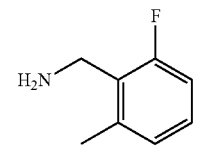

Procedure F1: Synthesis of Intermediates of Formula (IV) from Compounds of Formula (III)

2-chloro-N-(2,4,6-trifluorobenzyl)pyrimidin-4-amine
IV-1

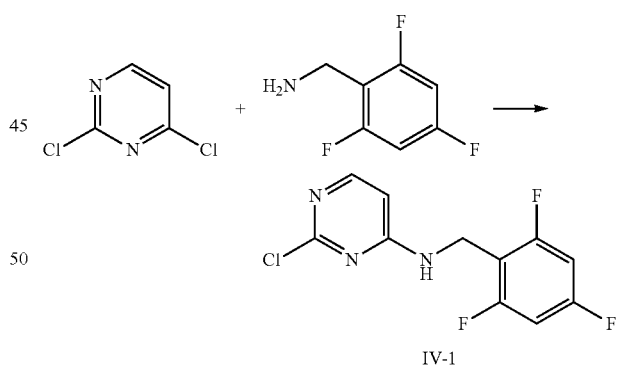

2,4,6-trifluorobenzylamine (5 g, 31 mmol) was added dropwise to a stirred suspension of 2,4-dichloropyrimidine (4.6 g, 31 mmol) and DIPEA (5.4 mL, 62 mmol) in IPA (100 mL) at 0° C. then the reaction mixture was warmed to room temperature and stirred overnight. The precipitate was collected and washed with diethyl ether to afford the first crop of 2-chloro-N-(2,4,6-trifluorobenzyl)pyrimidin-4-amine IV-1. The filtrate was concentrated and purified by column chromatography (0-30% v/v ethyl acetate/petrol) to afford a second crop (total yield 5.3 g, 62%). LC-MS (Method F), RT=2.27 min. (ES$^+$) 274.

By this method, all required intermediates of formula IV were made except IV-2 and IV-3 which were made by Procedures F2 and F3 respectively.

Procedure F2: Synthesis of Intermediates of Formula IV from Compounds of Formula VI 2-chloro-N-(2-methoxy-5-(methylsulfonyl)benzyl)-5-methylpyrimidin-4-amine

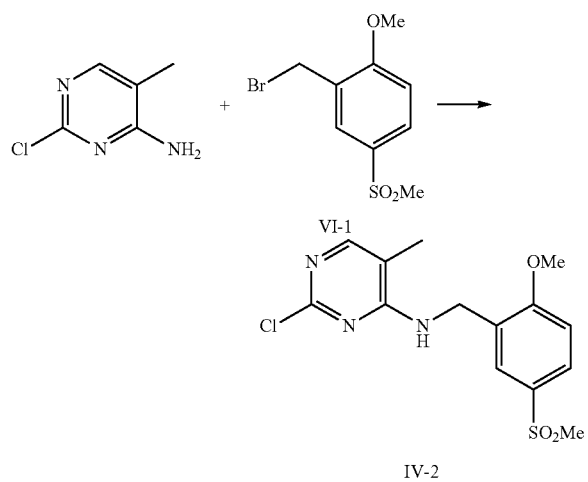

2-(Bromomethyl)-1-methoxy-4-(methylsulfonyl)benzene VI-1 (1 g, 3.6 mmol, prepared by Procedure H) was added to a stirred solution of 2-chloro-5-methylpyrimidin-4-amine (1 g, 6.9 mmol) and K₂CO₃ (1 g, 7.2 mmol) in acetonitrile (10 mL) and heated overnight at 100° C. The mixture was filtered, concentrated in vacuo and purified by flash chromatography (ethyl acetate/petrol) to afford 2-chloro-N-(2-methoxy-5-(methylsulfonyl)benzyl)-5-methylpyrimidin-4-amine as a yellow solid. LC-MS (Method C) RT=0.93 min (ES⁺) 342.

Procedure F3: Synthesis of Intermediate IV-3

4-(((2-chloro-5-methylpyrimidin-4-yl)amino)methyl)-3,5-difluorobenzenesulfonamide III-9

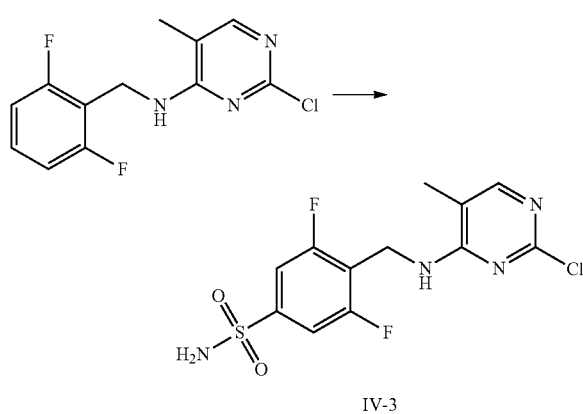

A solution of 2-chloro-N-(2,6-difluorobenzyl)-5-methylpyrimidin-4-amine (393 mg, 1.5 mmol, prepared by Procedure F1) in chlorosulfonic acid (2 mL) was stirred at 100° C. for 5 h then cooled to room temperature and poured over ice. The resultant precipitate was collected by filtration and stirred with ammonia (28% aqueous, 5 mL) at room temperature for 2 h. The mixture was concentrated in vacuo and the residue purified by reverse phase column chromatography (acetonitrile/water, high pH) to afford 4-(((2-chloro-5-methylpyrimidin-4-yl)amino)methyl)-3,5-difluorobenzenesulfonamide IV-3 as a pale pink gum (43 mg, 8.5%). LC-MS (Method C) RT=3.0 mins (ES⁺) 349.

Procedure G1: Synthesis of Aminopyrazole Intermediates of Formula (V)

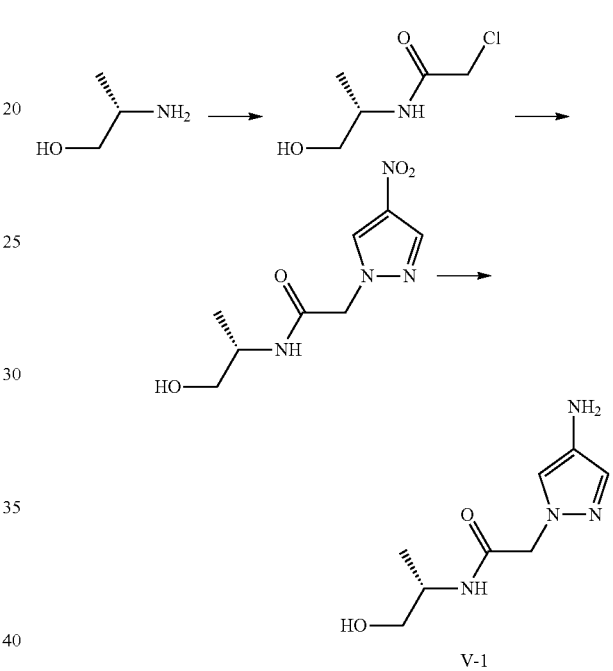

Step (i) (S)-2-chloro-N-(1-hydroxypropan-2-yl)acetamide

To a stirred solution of (S)-2-aminopropan-1-ol (10 g, 0.13 mol) in water at 0° C. was added simultaneously a solution of chloroacetyl chloride (18 g, 0.16 mol) in dichloromethane (50 mL) and 1.6M aqueous sodium hydroxide (100 mL) dropwise over 1 h. The dichloromethane was removed under reduced pressure then the aqueous layer was extracted with ethyl acetate. The separated organic layer was dried (Na₂SO₄) and concentrated to afford (S)-2-chloro-N-(1-hydroxypropan-2-yl)acetamide (16.2 g, 83%) as a colourless oil which was used in the next step without further purification.

Step (ii) (S)—N-(1-hydroxypropan-2-yl)-2-(4-nitro-1H-pyrazol-1-yl)acetamide

2-Chloro-N—((S)-1-hydroxypropan-2-yl)acetamide (700 mg, 4.64 mmol), potassium iodide (960 mg, 5.8 mmol) and cesium carbonate (1.9 g, 5.8 mmol) were added to a solution of 4-nitropyrazole (436 mg, 3.86 mmol) in acetonitrile (10 mL) then the mixture was heated to 160° C. for 30 min in a microwave reactor. The reaction mixture was combined with those from 13 other identical reactions, diluted with water then extracted four times with ethyl acetate. The combined organic layers were dried, concentrated in vacuo and purified by column chromatography (3% v/v MeOH/DCM) to afford (S)—N-(1-hydroxypropan-2-yl)-2-(4-nitro-1H-pyrazol-1-yl)acetamide (7.9 g, 64%) as a white solid.

Step (iii) (S)-2-(4-amino-1H-pyrazol-1-yl)-N-(1-hydroxypropan-2-yl)acetamide V-1

A mixture of N—((S)-1-hydroxypropan-2-yl)-2-(4-nitro-1H-pyrazol-1-yl)acetamide (4 g, 17.5 mmol) and 10% Pd/C (500 mg) in THF (50 mL) was stirred overnight at room temperature under a hydrogen atmosphere. The Pd/C was removed through filtration and the filtrate was concentrated in vacuo to afford (S)-2-(4-amino-1H-pyrazol-1-yl)-N-(1-hydroxypropan-2-yl)acetamide V-1 (3.5 g, 100%) as a grey solid which was used without further purification.

$^1$H NMR (400 MHz, d$^6$-DMSO) δ 7.70 (d, J=8.0 Hz, 1H), 7.01 (s, 1H), 6.91 (s, 1H), 4.76 (t, J=5.4 Hz, 1H), 4.54 (s, 2H), 3.83 (s, 2H), 3.74 (m, 1H), 3.35-3.30 (m, 1H), 3.27-3.19 (m, 1H), 1.02 (d, J=6.6 Hz, 3H).

Procedure G2: Synthesis of Aminopyrazole Intermediates of Formula V

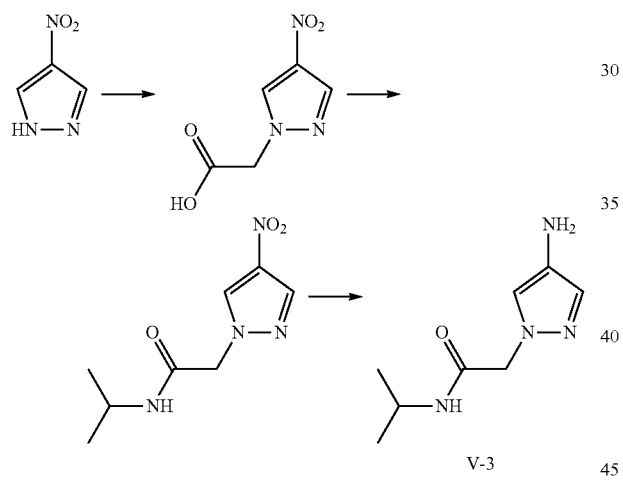

Step (i) 2-(4-nitro-1H-pyrazol-1-yl)acetic acid

A solution of potassium hydroxide (32.7 g, 0.58 mol) in water (100 mL) was added to a stirred mixture of 4-nitro-1H-pyrazole (30 g, 0.27 mol) in acetone (500 mL) at room temperature. After 30 min, a solution of 2-bromoacetic acid (38.7 g, 0.27 mol) in acetone (100 mL) was added and the reaction was stirred overnight. The solvent was removed in vacuo, the residue was diluted with water then extracted three times with ethyl acetate and the combined organic layer was concentrated in vacuo. The residue was further extracted with dichloromethane and methanol and the combined organic layer was concentrated in vacuo to afford 2-(4-nitro-1H-pyrazol-1-yl) acetic acid (40 g, 88%).

Step (ii) N-isopropyl-2-(4-nitro-1H-pyrazol-1-yl) acetamide

Oxalyl chloride (29.6 g, 234 mmol) and DMF (several drops) were added to a stirred mixture of 2-(4-nitro-1H-pyrazol-1-yl)acetic acid (20 g, 117 mmol) in dichloromethane (200 mL) and stirred at room temperature for 5 h. The solvent was then removed in vacuo and the residue was diluted with THF (100 mL). This solution was added to a stirred solution of triethylamine (23.7 g, 234 mmol) and iso-propylamine (10.4 g, 176 mmol) in THF (200 mL) and the reaction was stirred at room temperature overnight. The solvent was removed in vacuo and the residue diluted with 1M hydrochloric acid to pH <4. The solid was filtered, washed with 1M hydrochloric acid and dried in a vacuum oven to afford N-isopropyl-2-(4-nitro-1H-pyrazol-1-yl)acetamide as a yellow solid (18 g, 84.8 mmol).

Step (iii) 2-(4-amino-1H-pyrazol-1-yl)-N-isopropylacetamide V-3

A mixture of N-isopropyl-2-(4-nitro-1H-pyrazol-1-yl)acetamide (12 g, 56.5 mmol) and Pd/C (1 g) in THF (100 mL) was stirred at room temperature under an atmosphere of hydrogen for 5 h then filtered over Celite. The filtrate was concentrated in vacuo to afford 2-(4-amino-1H-pyrazol-1-yl)-N-isopropylacetamide V-3 (10.3 g, 100%). LC-MS (Method A), RT=1.42 min. (ES$^+$) 183.

Procedure G3: Synthesis of Aminopyrazole Intermediates of Formula (V)

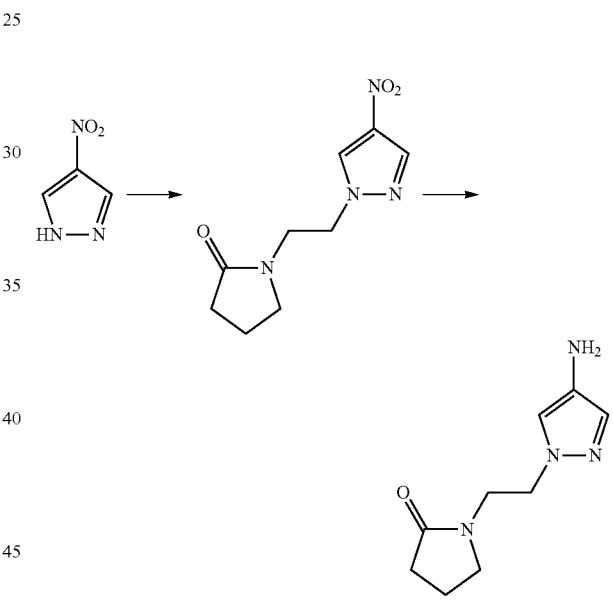

Step (i) 1-(2-(4-nitro-1H-pyrazol-1-yl)ethyl)pyrrolidin-2-one 1-(2-Chloroethyl)pyrrolidin-2-one (0.72 g, 4.8 mmol) was added to a solution of potassium carbonate (1.2 g, 8.7 mmol), 4-nitro-1H-pyrazole (0.5 g, 4.4 mmol) in dry acetonitrile (4 mL) and the reaction was stirred at 60° C. overnight. The solvent was concentrated in vacuo, then the residue was slurried in water, collected by filtration and dried in vacuo to afford 1-(2-(4-nitro-1H-pyrazol-1-yl)ethyl)pyrrolidin-2-one (0.21 g, 0.9 mmol). LC-MS (Method H), RT=1.23 min. (ES$^+$) 225.

Step (ii) 1-(2-(4-amino-1H-pyrazol-1-yl)ethyl)pyrrolidin-2-one V-5

A mixture of 1-(2-(4-nitro-1H-pyrazol-1-yl)ethyl)pyrrolidin-2-one (0.21 g, 0.9 mmol) and Pd/C (50 mg) in ethanol (20 mL) was stirred overnight at room temperature under an atmosphere of hydrogen then filtered over Celite. The filtrate was concentrated in vacuo to afford 1-(2-(4-amino-1H-pyrazol-1-yl)ethyl)pyrrolidin-2-one V-5 (0.19 g, 100%) as a purple oil. LC-MS (Method C), RT=0.38 min. (ES$^+$) 195.

By these methods, intermediates of formula (V) were synthesized as shown in Table 10.

TABLE 10

Intermediates of formula (V) made by Procedures G1-G3

| | Structure | Procedure |
|---|---|---|
| V-1 | 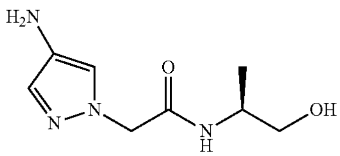 | G1 |
| V-2 | 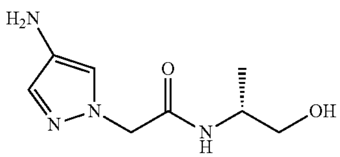 | G1 |
| V-3 | 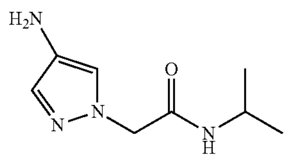 | G2 |
| V-4 | 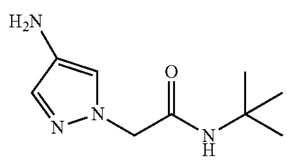 | G2 |
| V-5 | 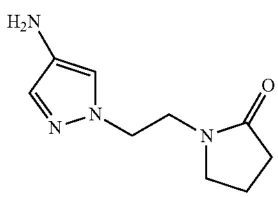 [SMILES: Nc1cnn(CCN2CCCC2=O)c1] | G3 |
| V-6 | 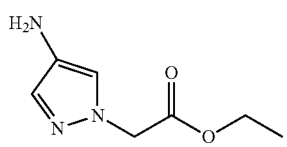 | G3 |
| V-7 | 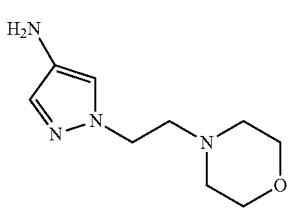 [SMILES: Nc1cnn(CCN2CCOCC2)c1] | G3 |
| V-8 | 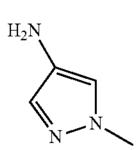 | G3 |

Procedure H: Synthesis of Benzyl Bromide Intermediates of Formula (VI)

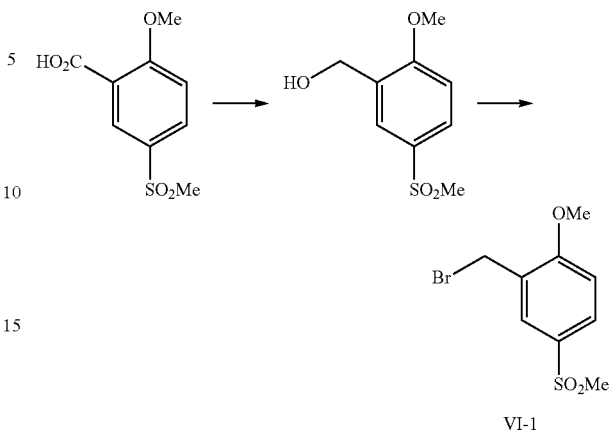

Step (i)
2-methoxy-5-(methylsulfonyl)phenyl)methanol

1M BH$_3$-THF (44 mL, 2 eq) was added to a stirred solution of 2-methoxy-5-(methyl sulfonyl)benzoic acid (5 g, 1 eq) in anhydrous THF (10 mL) at 0° C. After 16 h the reaction was quenched with saturated ammonium chloride solution and extracted twice with DCM, then the combined organic layer was concentrated in vacuo to afford 2-methoxy-5-(methylsulfonyl)phenyl)methanol as a white solid (4.9 g). LC-MS (Method D) RT=0.75 min. (ES$^-$) 214.

Step (ii) 2-(bromomethyl)-1-methoxy-4-(methylsulfonyl)benzene VI-1

Phosphourous tribromide (1.4 mL, 1 eq) was added to a stirred solution of (2-methoxy-5-(methylsulfonyl)phenyl) methanol (3.3 g, 15.3 mmol, 1 eq) in DCM (10 mL) at 0° C. and the reaction was stirred for 18 h at room temperature. The mixture was cooled to 0° C., quenched with saturated sodium hydrogen carbonate solution then extracted twice with DCM. The separated organic layer was filtered through Celite and concentrated in vacuo to afford 2-(bromomethyl)-1-methoxy-4-(methylsulfonyl)benzene VI-1 (3.1 g) as an off-white solid. LC-MS (Method D), RT=0.98 min. (ES$^+$) 296.

Procedure I: Interconversion of Compounds of Formula I: Example I-4

N-cyclopropyl-2-(4-((5-fluoro-4-((2,4,6-trifluorobenzyl)amino)pyrimidin-2-yl)amino)-1H-pyrazol-1-yl)acetamide

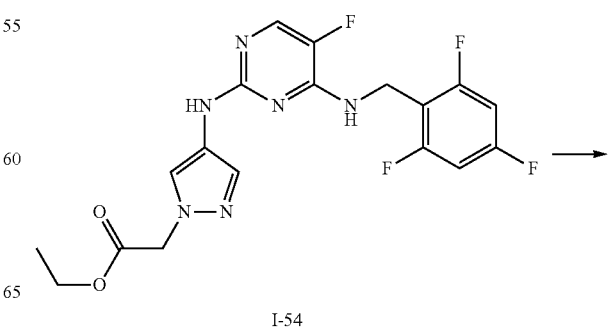

I-54

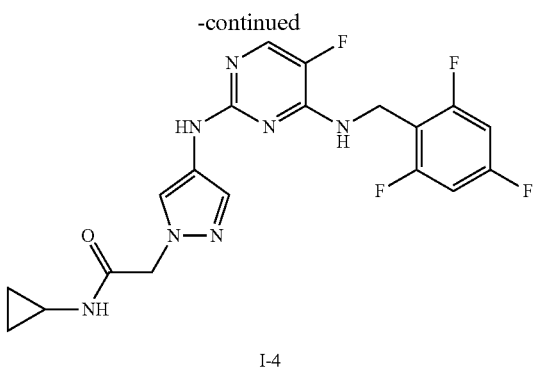

I-4

Ethyl 2-(4-((5-fluoro-4-((2,4,6-trifluorobenzyl)amino)pyrimidin-2-yl)amino)-1H-pyrazol-1-yl)acetate I-54 (97 mg, 0.23 mmol, prepared by Procedure B), cyclopropylamine (0.5 mL, 7.2 mmol) and conc. hydrochloric acid (2 drops) were mixed in a vessel and then heated in a microwave reactor at 140° C. for 30 min. The resulting precipitate was collected, triturated in ethyl acetate, filtered, washed with ether and methanol to afford N-cyclopropyl-2-(4-((5-fluoro-4-((2,4,6-trifluorobenzyl)amino)pyrimidin-2-yl)amino)-1H-pyrazol-1-yl)acetamide I-4 (24 mg, 0.05 mmol) as a white solid. LC-MS (Method B), RT=5.88 min. (ES⁺) 436.

Procedure J1: Interconversion of Compounds of Formula I: Example I-5

N-(1-cyanoethyl)-2-(4-((4-((2,4,6-trifluorobenzyl)amino)pyrimidin-2-yl)amino)-1H-pyrazol-1-yl)acetamide I-5

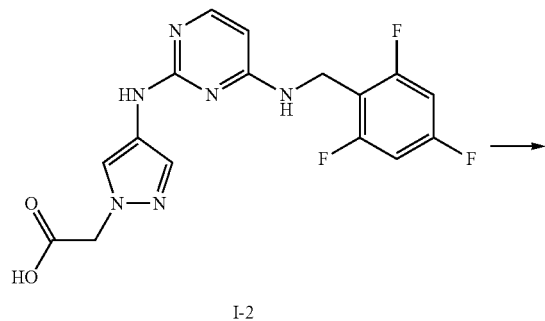

I-2

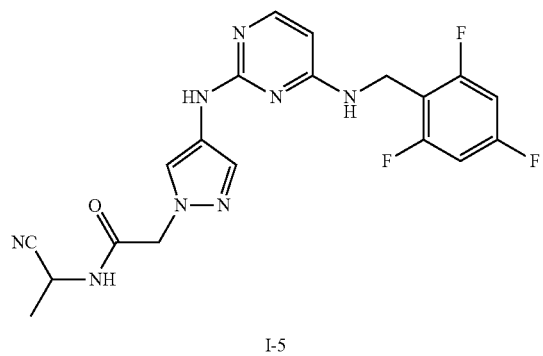

I-5

A solution of 2-(4-((4-((2,4,6-trifluorobenzyl)amino)pyrimidin-2-yl)amino)-1H-pyrazol-1-yl)acetic acid I-2 (0.1 g, 0.26 mmol, prepared by Procedure B), DIPEA (0.15 mL, 0.8 mmol), 2-aminopropanenitrile hydrochloride (34 mg, 0.3 mmol), propylphosphonic anhydride solution (50% in DMF) (0.17 g, 0.5 mmol) in DMF was stirred overnight at room temperature then extracted into water and washed with DCM. The aqueous layer was neutralised with aqueous sodium bicarbonate and extracted with three times with DCM. The combined organic layer was concentrated in vacuo and purified by prep. HPLC to afford N-(1-cyanoethyl)-2-(4-((4-((2,4,6-trifluorobenzyl)amino)pyrimidin-2-yl)amino)-1H-pyrazol-1-yl)acetamide I-5 (80 mg, 0.18 mmol). LC-MS (Method B), RT=5.15 min. (ES⁺) 431.

Procedure J2: Interconversion of Compounds of Formula I: Example I-6

N-ethyl-2-(4-((4-((2,4,6-trifluorobenzyl)amino)pyrimidin-2-yl)amino)-1H-pyrazol-1-yl)acetamide I-6

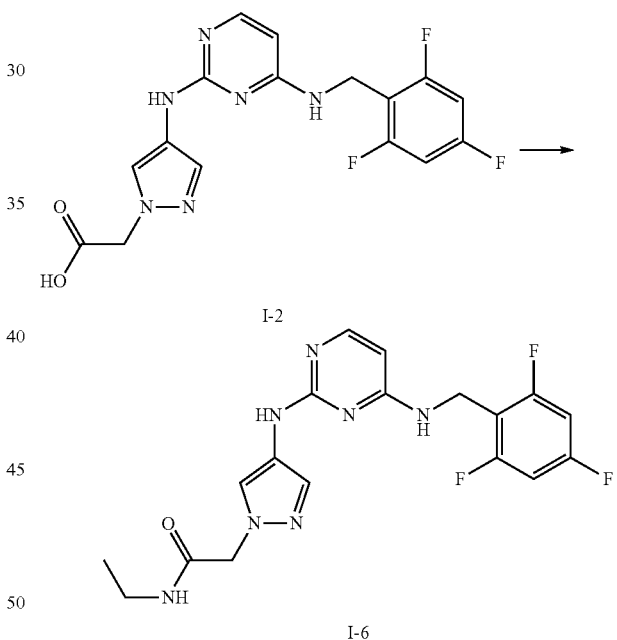

A mixture of 2-(4-((4-((2,4,6-trifluorobenzyl)amino)pyrimidin-2-yl)amino)-1H-pyrazol-1-yl)acetic acid I-2 (80 mg, 0.21 mmol, prepared by Procedure B), DIPEA (187 µL, 1.06 mmol) and TFFH (61 mg, 0.23 mmol) in dioxane (4 mL) was stirred for 10 min at room temperature. Ethylamine (2M in THF, 529 µL, 1.06 mmol) was added and the reaction was stirred for 2 h, then diluted with water and extracted with DCM. The organic layer was concentrated in vacuo and purified by prep. HPLC to afford N-ethyl-2-(4-((4-((2,4,6-trifluorobenzyl)amino)pyrimidin-2-yl)amino)-1H-pyrazol-1-yl)acetamide I-6 (8.8 mg, 0.02 mmol). LC-MS (Method B), RT=5.23 min. (ES⁺) 406.

Procedure K: Interconversion of Compounds of Formula I: Example I-7

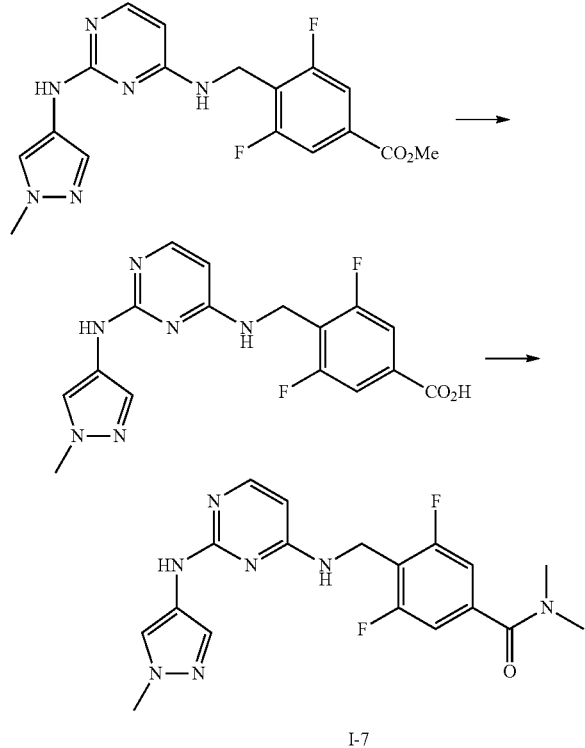

I-7

Step (i) 3,5-difluoro-4-(((2-((1-methyl-1H-pyrazol-4-yl)amino)pyrimidin-4-yl)amino)methyl)benzoic acid 2M NaOH(aq) (2 mL, 4 mmol) was added to a stirred mixture of methyl 3,5-difluoro-4-(((2-((1-methyl-1H-pyrazol-4-yl)amino)pyrimidin-4-yl)amino)methyl)benzoate (370 mg, 1 mmol, prepared by Procedure A) in 3:1 v/v THF/MeOH (40 mL) and the reaction was stirred at room temperature overnight. The mixture was neutralized with 1M hydrochloric acid and concentrated in vacuo to afford 3,5-difluoro-4-(((2-((1-methyl-1H-pyrazol-4-yl)amino)pyrimidin-4-yl)amino)methyl)benzoic acid (theoretically 360 mg) which was used in the next step without purification.

Step (ii) 3,5-difluoro-4-(((2-((1-methyl-1H-pyrazol-4-yl)amino)pyrimidin-4-yl)amino)methyl)-N,N-dimethylbenzamide I-7

A mixture of 3,5-difluoro-4-(((2-((1-methyl-1H-pyrazol-4-yl)amino)pyrimidin-4-yl)amino)methyl)benzoic acid (crude from step i, theoretical 60 mg, 0.17 mmol), HATU (82 mg, 0.22 mmol), DIPEA (43 mg, 0.33 mmol) and dimethylamine (excess) in acetonitrile (10 mL) was stirred at room temperature overnight then further DMF, HATU, DIPEA and dimethylamine were added to push the reaction to completion. After 5 h the reaction was diluted with water and extracted with ethyl acetate. The organic layer was washed with brine, concentrated in vacuo and purified by prep. TLC (10% v/v MeOH/DCM) to afford 3,5-difluoro-4-(((2-((1-methyl-1H-pyrazol-4-yl)amino)pyrimidin-4-yl)amino)methyl)-N,N-dimethylbenzamide I-7 (30 mg, 0.07 mmol) as a white solid. LC-MS (Method A), RT=7.79 min. (ES$^+$) 388.

Using these Procedures, further Examples could be prepared as shown in Table 11.

TABLE 11

Table of Examples

| Example | Structure | Analytical Method | RT (min) | m/z ES$^+$ |
|---|---|---|---|---|
| I-8 | 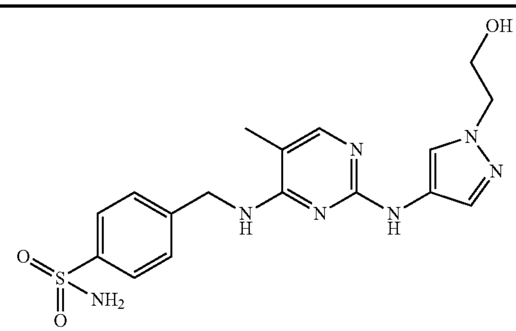 | C | 0.69 | 404 |
| I-9 | 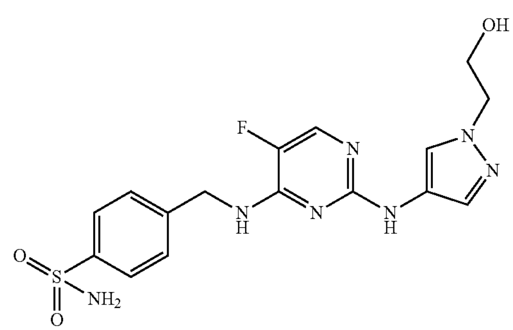 [SMILES: NS(=O)(=O)c1ccc(CNc2nc(Nc3cnn(CCO)c3)ncc2F)cc1] | C | 0.67 | 408 |

TABLE 11-continued

Table of Examples

| Example | Structure | Analytical Method | RT (min) | m/z ES+ |
|---------|-----------|-------------------|----------|---------|
| I-10 | 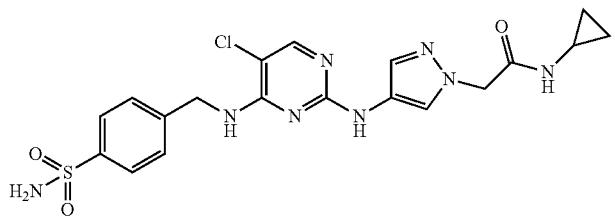 [SMILES: NS(=O)(=O)c1ccc(CNc2nc(Nc3cnn(CC(=O)NC4CC4)c3)ncc2Cl)cc1] | C | 0.73 | 477 |
| I-11 | 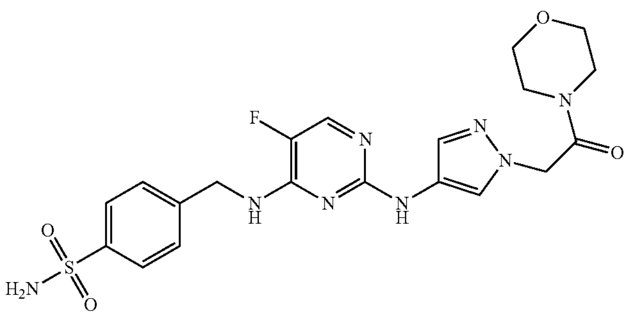 [SMILES: NS(=O)(=O)c1ccc(CNc2nc(Nc3cnn(CC(=O)N4CCOCC4)c3)ncc2F)cc1] | B | 5.78 | 491 |
| I-12 | 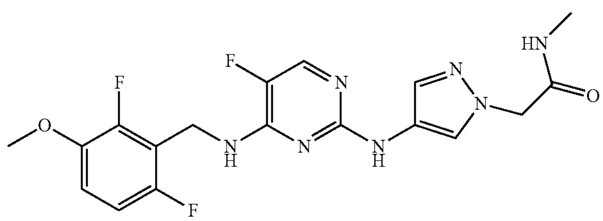 [SMILES: CNC(=O)Cn1cc(Nc2ncc(F)c(NCc3c(F)ccc(OC)c3F)n2)cn1] | B | 5.02 | 422 |
| I-13 | 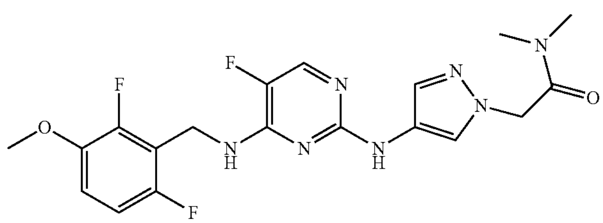 [SMILES: COc1ccc(F)c(CNc2nc(Nc3cnn(CC(=O)N(C)C)c3)ncc2F)c1F] | B | 5.20 | 436 |
| I-14 | 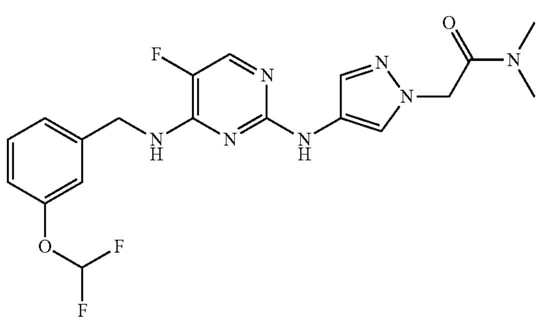 [SMILES: CN(C)C(=O)Cn1cc(Nc2ncc(F)c(NCc3cccc(OC(F)F)c3)n2)cn1] | B | 5.57 | 436 |
| I-15 | 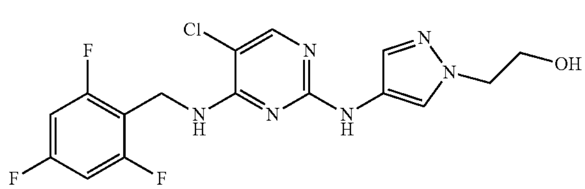 [SMILES: OCCn1cc(Nc2ncc(Cl)c(NCc3c(F)cc(F)cc3F)n2)cn1] | B | 5.63 | 399 |

TABLE 11-continued

Table of Examples

| Example | Structure | Analytical Method | RT (min) | m/z ES+ |
|---------|-----------|-------------------|----------|---------|
| I-16 | 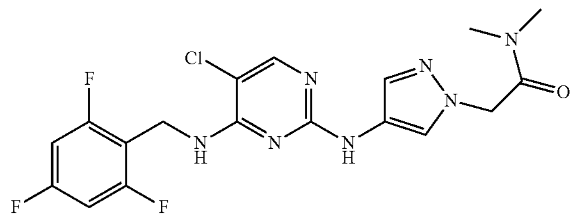 [SMILES: CN(C)C(=O)Cn1cc(Nc2ncc(Cl)c(NCc3c(F)cc(F)cc3F)n2)cn1] | F | 5.83 | 440 |
| I-17 | 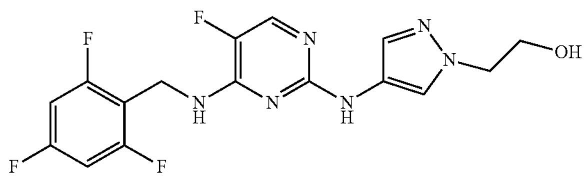 [SMILES: OCCn1cc(Nc2ncc(F)c(NCc3c(F)cc(F)cc3F)n2)cn1] | F | 4.89 | 383 |
| I-18 | 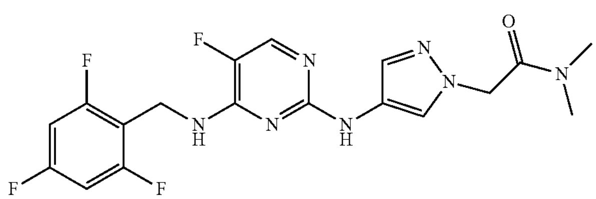 [SMILES: CN(C)C(=O)Cn1cc(Nc2ncc(F)c(NCc3c(F)cc(F)cc3F)n2)cn1] | F | 5.17 | 424 |
| I-19 | 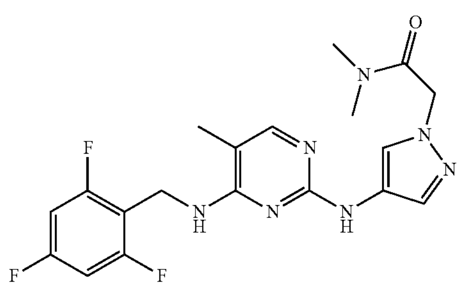 [SMILES: Cc1cnc(Nc2cnn(CC(=O)N(C)C)c2)nc1NCc1c(F)cc(F)cc1F] | C | 0.96 | 420 |
| I-20 | 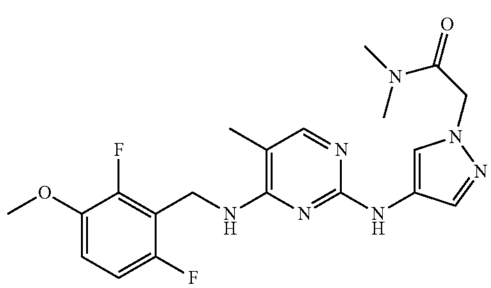 [SMILES: COc1ccc(F)c(CNc2nc(Nc3cnn(CC(=O)N(C)C)c3)ncc2C)c1F] | C | 0.94 | 432 |
| I-21 | 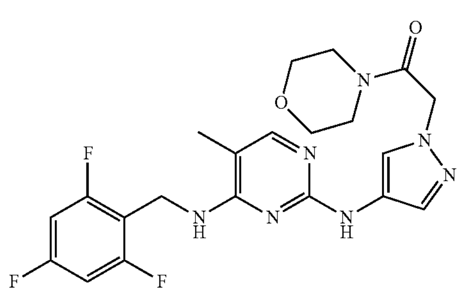 [SMILES: Cc1cnc(Nc2cnn(CC(=O)N3CCOCC3)c2)nc1NCc1c(F)cc(F)cc1F] | C | 0.96 | 462 |

TABLE 11-continued

Table of Examples

| Example | Structure | Analytical Method | RT (min) | m/z ES+ |
|---|---|---|---|---|
| I-22 | 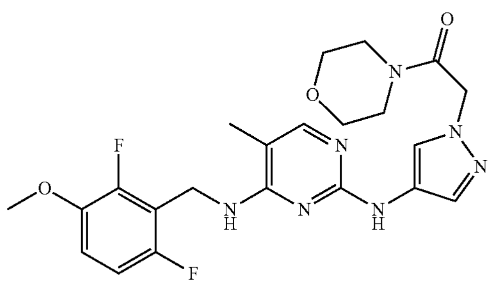 [SMILES: COc1ccc(F)c(CNc2nc(Nc3cnn(CC(=O)N4CCOCC4)c3)ncc2C)c1F] | C | 0.94 | 474 |
| I-23 | 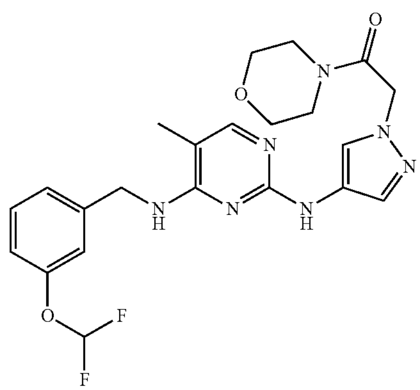 [SMILES: Cc1cnc(Nc2cnn(CC(=O)N3CCOCC3)c2)nc1NCc1cccc(OC(F)F)c1] | C | 0.78 | 474 |
| I-24 | 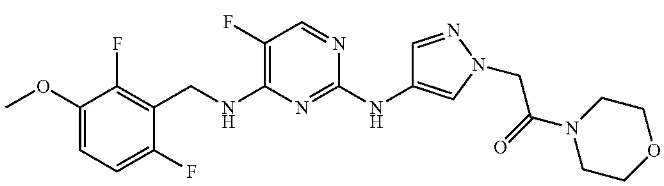 [SMILES: COc1ccc(F)c(CNc2nc(Nc3cnn(CC(=O)N4CCOCC4)c3)ncc2F)c1F] | F | 5.03 | 478 |
| I-25 | 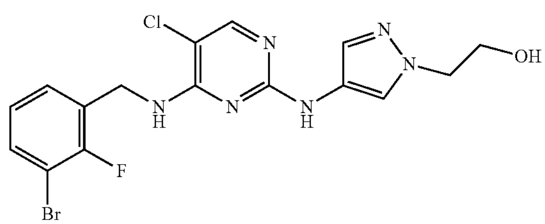 [SMILES: OCCn1cc(Nc2ncc(Cl)c(NCc3cccc(Br)c3F)n2)cn1] | B | 6.11 | 441 |
| I-26 | 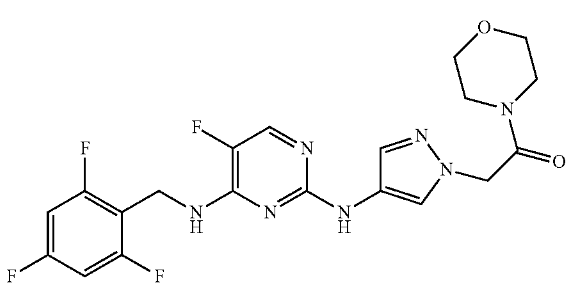 [SMILES: O=C(Cn1cc(Nc2ncc(F)c(NCc3c(F)cc(F)cc3F)n2)cn1)N1CCOCC1] | B | 4.83 | 466 |

TABLE 11-continued

Table of Examples

| Example | Structure | Analytical Method | RT (min) | m/z ES+ |
|---------|-----------|-------------------|----------|---------|
| I-27 | 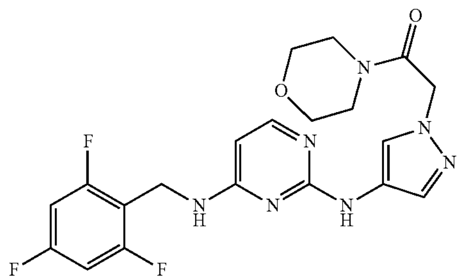 [SMILES: O=C(Cn1cc(Nc2nccc(NCc3c(F)cc(F)cc3F)n2)cn1)N1CCOCC1] | E | 2.04 | 448 |
| I-28 | 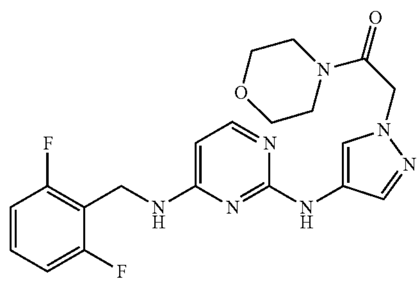 [SMILES: O=C(Cn1cc(Nc2nccc(NCc3c(F)cccc3F)n2)cn1)N1CCOCC1] | C | 0.91 | 430 |
| I-29 | 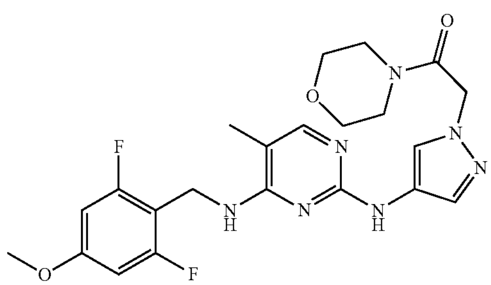 [SMILES: COc1cc(F)c(CNc2nc(Nc3cnn(CC(=O)N4CCOCC4)c3)ncc2C)c(F)c1] | C | 0.96 | 474 |
| I-30 | 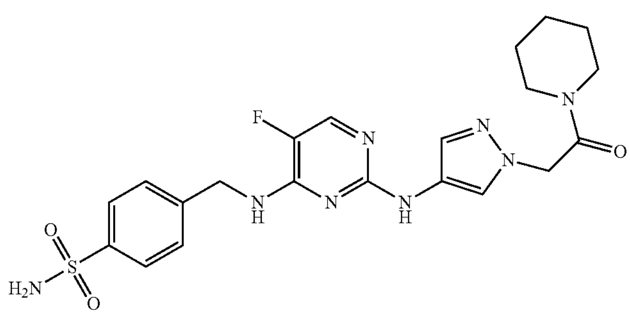 [SMILES: NS(=O)(=O)c1ccc(CNc2nc(Nc3cnn(CC(=O)N4CCCCC4)c3)ncc2F)cc1] | F | 3.63 | 489 |
| I-31 | 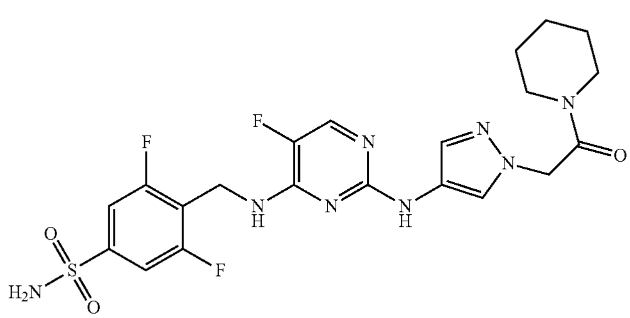 [SMILES: NS(=O)(=O)c1cc(F)c(CNc2nc(Nc3cnn(CC(=O)N4CCCCC4)c3)ncc2F)c(F)c1] | F | 3.98 | 525 |

TABLE 11-continued

Table of Examples

| Example | Structure | Analytical Method | RT (min) | m/z ES+ |
|---------|-----------|-------------------|----------|---------|
| I-32 | 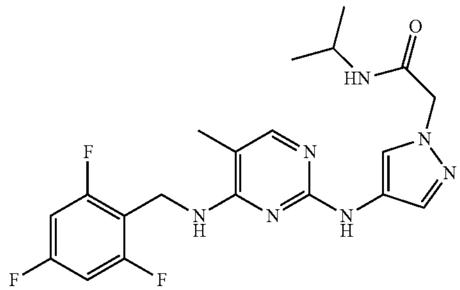 [SMILES: Cc1cnc(Nc2cnn(CC(=O)NC(C)C)c2)nc1NCc1c(F)cc(F)cc1F] | C | 1.00 | 434 |
| I-33 | 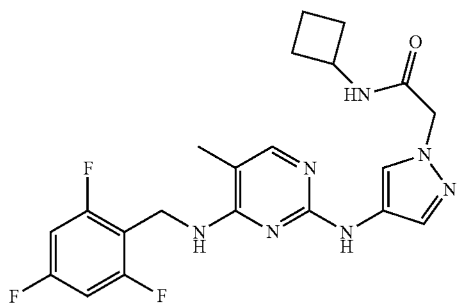 [SMILES: Cc1cnc(Nc2cnn(CC(=O)NC3CCC3)c2)nc1NCc1c(F)cc(F)cc1F] | C | 1.03 | 446 |
| I-34 | 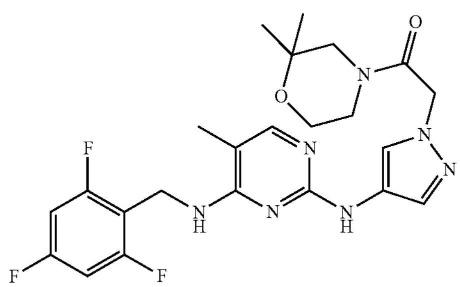 [SMILES: Cc1cnc(Nc2cnn(CC(=O)N3CCOC(C)(C)C3)c2)nc1NCc1c(F)cc(F)cc1F] | C | 1.01 | 490 |
| I-35 | 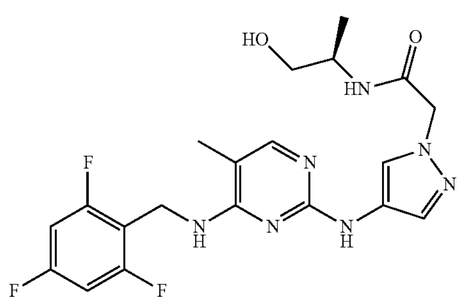 [SMILES: Cc1cnc(Nc2cnn(CC(=O)N[C@H](C)CO)c2)nc1NCc1c(F)cc(F)cc1F] | C | 0.93 | 450 |
| I-36 | 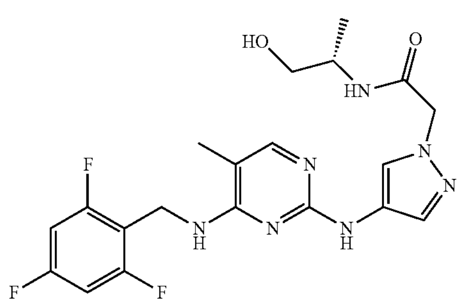 [SMILES: Cc1cnc(Nc2cnn(CC(=O)N[C@@H](C)CO)c2)nc1NCc1c(F)cc(F)cc1F] | C | 0.93 | 450 |

TABLE 11-continued

Table of Examples

| Example | Structure | Analytical Method | RT (min) | m/z ES+ |
|---|---|---|---|---|
| I-37 | 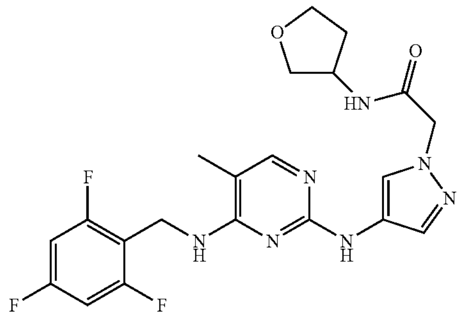 [SMILES: Cc1cnc(Nc2cnn(CC(=O)NC3CCOC3)c2)nc1NCc1c(F)cc(F)cc1F] | C | 0.96 | 462 |
| I-38 | 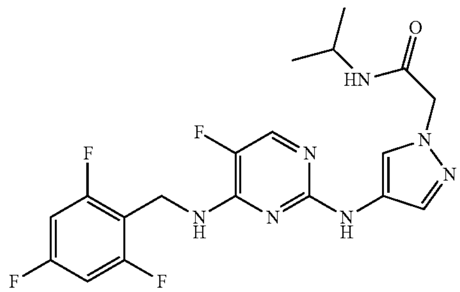 [SMILES: CC(C)NC(=O)Cn1cc(Nc2ncc(F)c(NCc3c(F)cc(F)cc3F)n2)cn1] | B | 5.67 | 438 |
| I-39 | 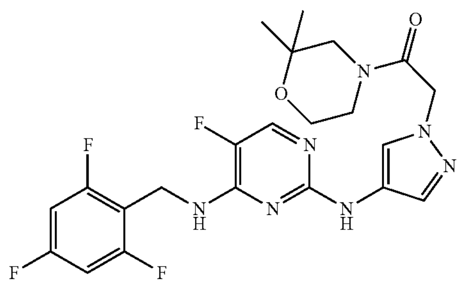 [SMILES: CC1(C)CN(C(=O)Cn2cc(Nc3ncc(F)c(NCc4c(F)cc(F)cc4F)n3)cn2)CCO1] | B | 5.81 | 494 |
| I-40 | 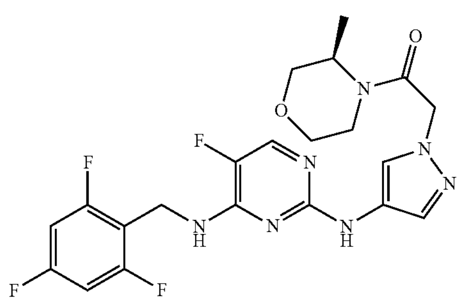 [SMILES: C[C@@H]1COCCN1C(=O)Cn1cc(Nc2ncc(F)c(NCc3c(F)cc(F)cc3F)n2)cn1] | C | 0.99 | 480 |
| I-41 | 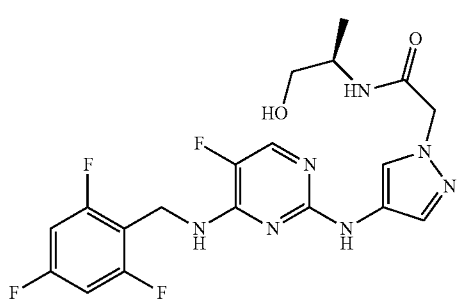 [SMILES: C[C@H](CO)NC(=O)Cn1cc(Nc2ncc(F)c(NCc3c(F)cc(F)cc3F)n2)cn1] | C | 0.93 | 454 |

TABLE 11-continued

Table of Examples

| Example | Structure | Analytical Method | RT (min) | m/z ES+ |
|---|---|---|---|---|
| I-42 | 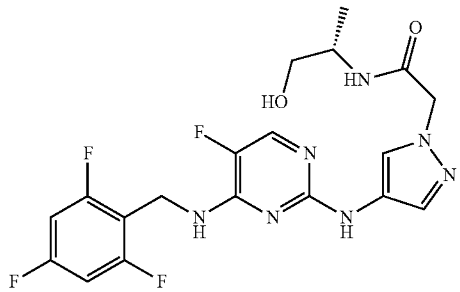 [SMILES: C[C@@H](CO)NC(=O)Cn1cc(Nc2ncc(F)c(NCc3c(F)cc(F)cc3F)n2)cn1] | C | 0.93 | 454 |
| I-43 | 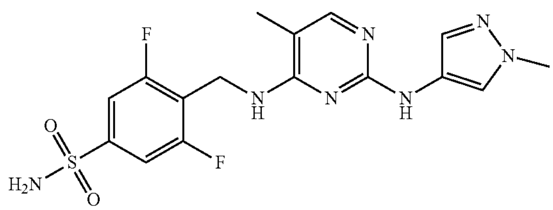 [SMILES: Cc1cnc(Nc2cnn(C)c2)nc1NCc1c(F)cc(S(N)(=O)=O)cc1F] | F | 4.32 | 410 |
| I-44 | 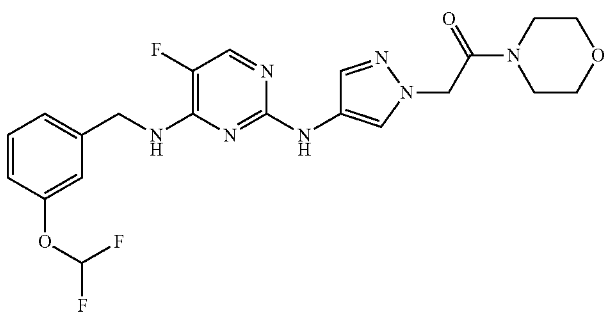 [SMILES: O=C(Cn1cc(Nc2ncc(F)c(NCc3cccc(OC(F)F)c3)n2)cn1)N1CCOCC1] | B | 5.37 | 478 |
| I-45 | 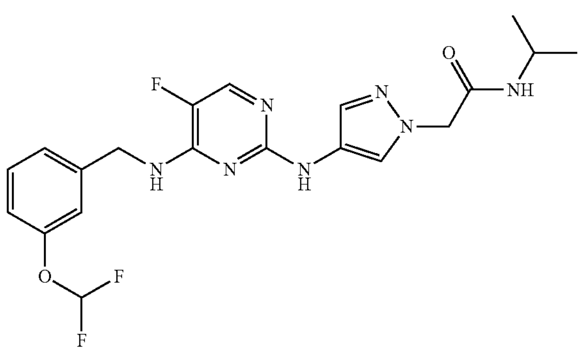 [SMILES: CC(C)NC(=O)Cn1cc(Nc2ncc(F)c(NCc3cccc(OC(F)F)c3)n2)cn1] | E | 2.34 | 450 |
| I-46 | 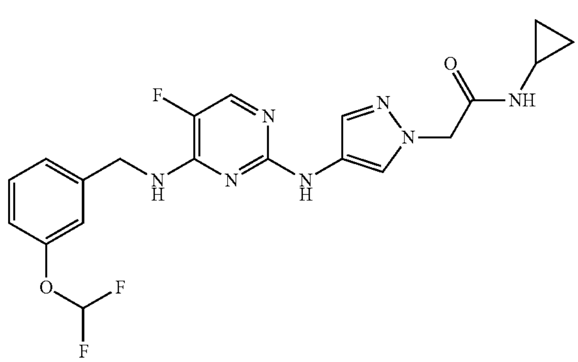 [SMILES: O=C(Cn1cc(Nc2ncc(F)c(NCc3cccc(OC(F)F)c3)n2)cn1)NC1CC1] | B | 5.60 | 448 |

TABLE 11-continued

Table of Examples

| Example | Structure | Analytical Method | RT (min) | m/z ES+ |
|---|---|---|---|---|
| I-47 | 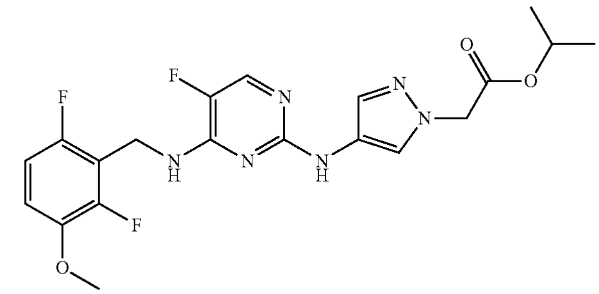 [SMILES: COc1ccc(F)c(CNc2nc(Nc3cnn(CC(=O)OC(C)C)c3)ncc2F)c1F] | E | 2.63 | 451 |
| I-48 | 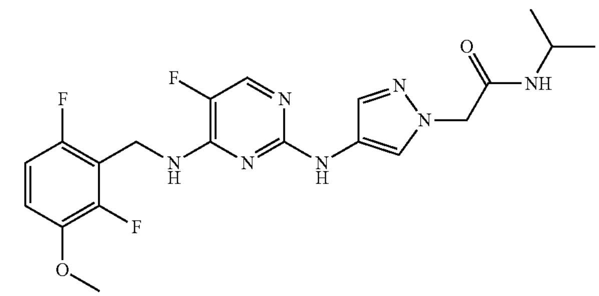 [SMILES: COc1ccc(F)c(CNc2nc(Nc3cnn(CC(=O)NC(C)C)c3)ncc2F)c1F] | B | 5.72 | 450 |
| I-49 | 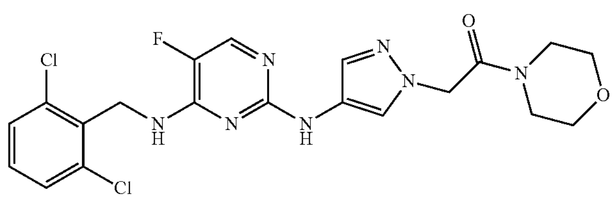 [SMILES: O=C(Cn1cc(Nc2ncc(F)c(NCc3c(Cl)cccc3Cl)n2)cn1)N1CCOCC1] | F | 0.97 | 480 |
| I-50 | 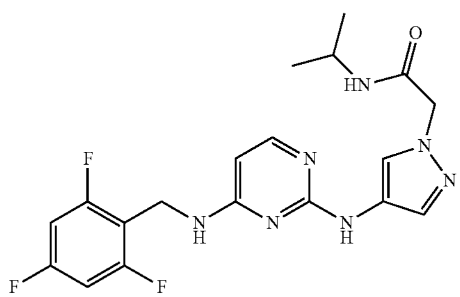 [SMILES: CC(C)NC(=O)Cn1cc(Nc2nccc(NCc3c(F)cc(F)cc3F)n2)cn1] | C | 0.96 | 420 |
| I-51 | 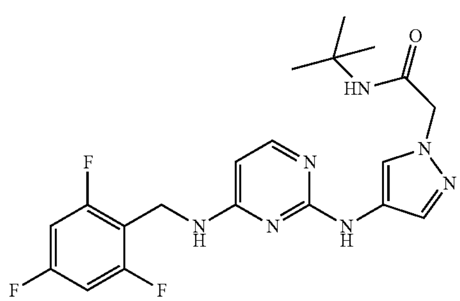 [SMILES: CC(C)(C)NC(=O)Cn1cc(Nc2nccc(NCc3c(F)cc(F)cc3F)n2)cn1] | B | 5.95 | 434 |

TABLE 11-continued

Table of Examples

| Example | Structure | Analytical Method | RT (min) | m/z ES+ |
|---|---|---|---|---|
| I-52 | 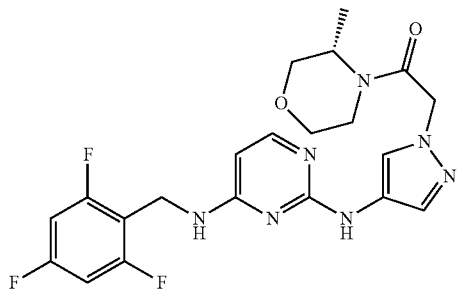 [SMILES: C[C@H]1COCCN1C(=O)Cn1cc(Nc2nccc(NCc3c(F)cc(F)cc3F)n2)cn1] | B | 5.46 | 462 |
| I-53 | 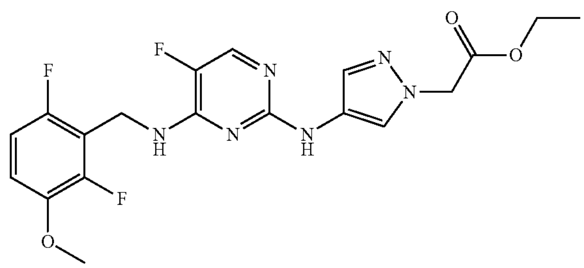 [SMILES: CCOC(=O)Cn1cc(Nc2ncc(F)c(NCc3c(F)ccc(OC)c3F)n2)cn1] | B | 6.09 | 437 |
| I-54 | 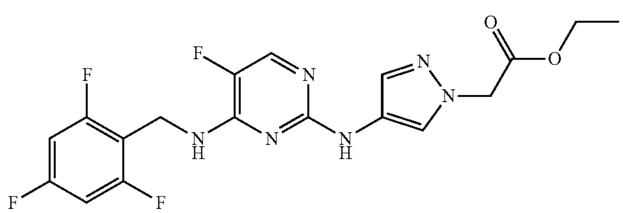 [SMILES: CCOC(=O)Cn1cc(Nc2ncc(F)c(NCc3c(F)cc(F)cc3F)n2)cn1] | B | 6.31 | 425 |
| I-55 | 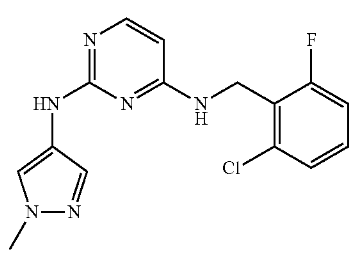 [SMILES: Cn1cc(Nc2nccc(NCc3c(F)cccc3Cl)n2)cn1] | A | 8.38 | 333 |
| I-56 | 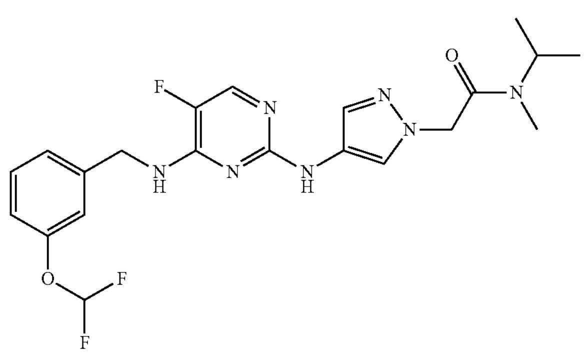 [SMILES: CC(C)N(C)C(=O)Cn1cc(Nc2ncc(F)c(NCc3cccc(OC(F)F)c3)n2)cn1] | B | 6.07 | 464 |

TABLE 11-continued

Table of Examples

| Example | Structure | Analytical Method | RT (min) | m/z ES+ |
|---------|-----------|-------------------|----------|---------|
| I-57 | 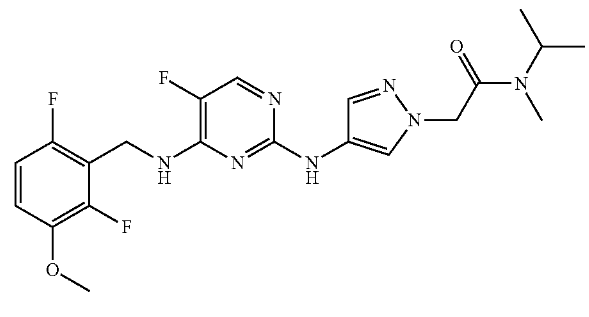 [SMILES: COc1ccc(F)c(CNc2nc(Nc3cnn(CC(=O)N(C)C(C)C)c3)ncc2F)c1F] | B | 5.71 | 464 |
| I-58 | 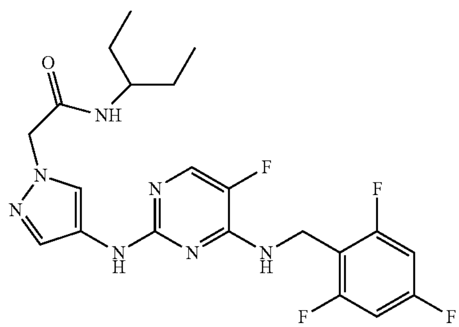 [SMILES: CCC(CC)NC(=O)Cn1cc(Nc2ncc(F)c(NCc3c(F)cc(F)cc3F)n2)cn1] | C | 1.05 | 466 |
| I-59 | 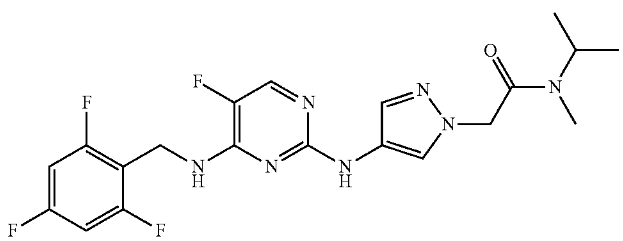 [SMILES: CC(C)N(C)C(=O)Cn1cc(Nc2ncc(F)c(NCc3c(F)cc(F)cc3F)n2)cn1] | B | 6.05 | 452 |
| I-60 | 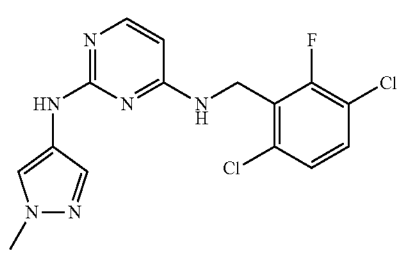 [SMILES: Cn1cc(Nc2nccc(NCc3c(Cl)ccc(Cl)c3F)n2)cn1] | A | 8.61 | 367 |
| I-61 | 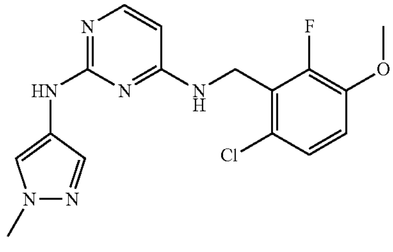 | A | 8.41 | 363 |

TABLE 11-continued

Table of Examples

| Example | Structure | Analytical Method | RT (min) | m/z ES+ |
|---|---|---|---|---|
| I-62 | 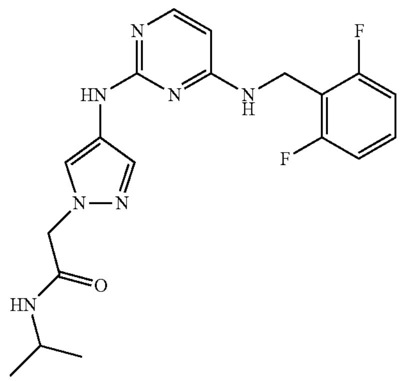 | B | 5.38 | 402 |
| I-63 | 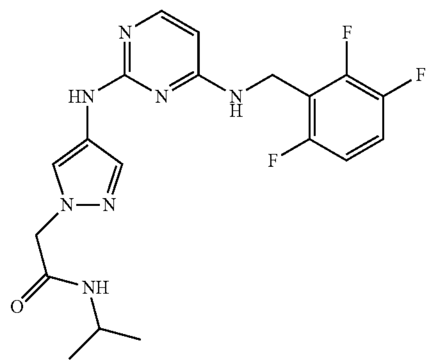 [SMILES: CC(C)NC(=O)Cn1cc(Nc2nccc(NCc3c(F)ccc(F)c3F)n2)cn1] | B | 5.31 | 420 |
| I-64 | 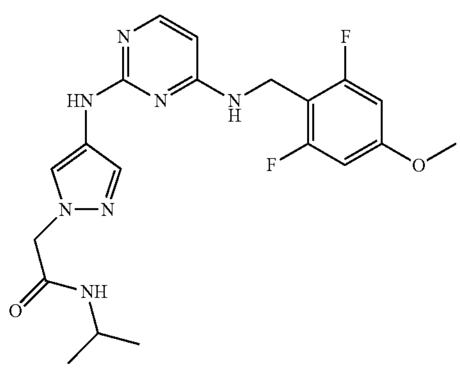 [SMILES: COc1cc(F)c(CNc2ccnc(Nc3cnn(CC(=O)NC(C)C)c3)n2)c(F)c1] | B | 5.55 | 432 |
| I-65 | 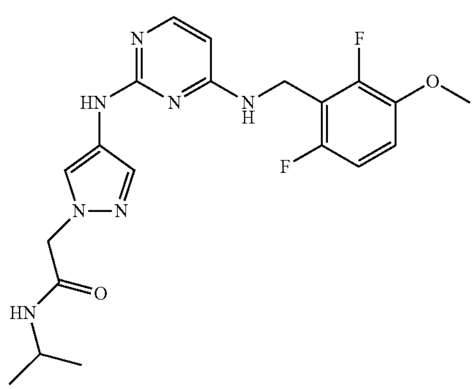 [SMILES: COc1ccc(F)c(CNc2ccnc(Nc3cnn(CC(=O)NC(C)C)c3)n2)c1F] | B | 5.43 | 432 |

TABLE 11-continued

Table of Examples

| Example | Structure | Analytical Method | RT (min) | m/z ES+ |
|---|---|---|---|---|
| I-66 | 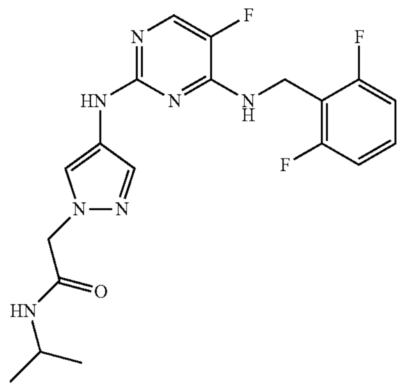 [SMILES: CC(C)NC(=O)Cn1cc(Nc2ncc(F)c(NCc3c(F)cccc3F)n2)cn1] | B | 5.56 | 420 |
| I-67 | 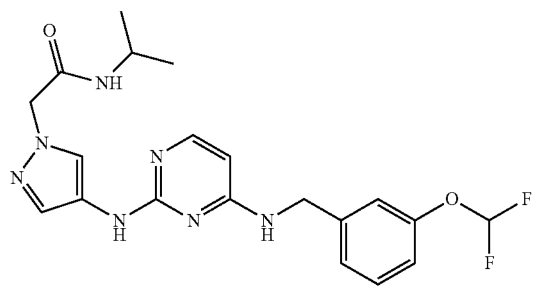 [SMILES: CC(C)NC(=O)Cn1cc(Nc2nccc(NCc3cccc(OC(F)F)c3)n2)cn1] | B | 5.64 | 432 |
| I-68 | 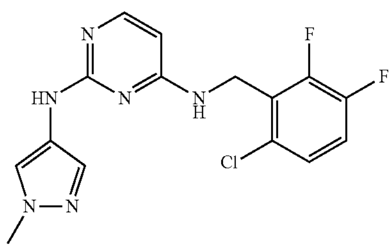 [SMILES: Cn1cc(Nc2nccc(NCc3c(Cl)ccc(F)c3F)n2)cn1] | A | 8.40 | 351 |
| I-69 | 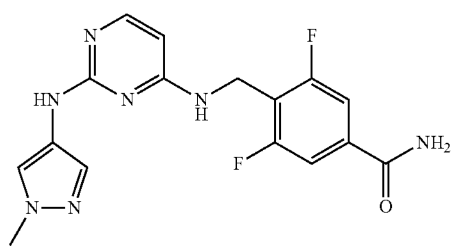 [SMILES: Cn1cc(Nc2nccc(NCc3c(F)cc(C(N)=O)cc3F)n2)cn1] | A | 7.30 | 360 |
| I-70 | 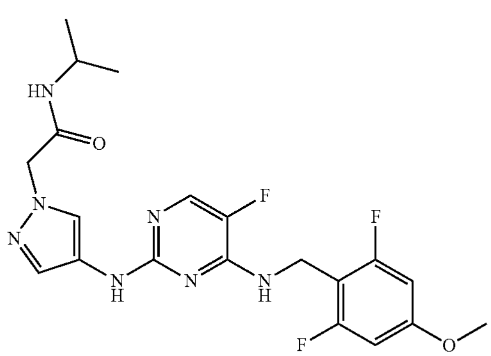 [SMILES: COc1cc(F)c(CNc2nc(Nc3cnn(CC(=O)NC(C)C)c3)ncc2F)c(F)c1] | B | 5.62 | 450 |

TABLE 11-continued

Table of Examples

| Example | Structure | Analytical Method | RT (min) | m/z ES+ |
|---|---|---|---|---|
| I-71 | 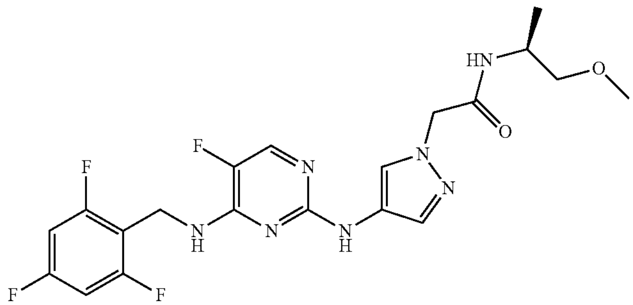 [SMILES: COC[C@H](C)NC(=O)Cn1cc(Nc2ncc(F)c(NCc3c(F)cc(F)cc3F)n2)cn1] | C | 0.97 | 468 |
| I-72 | 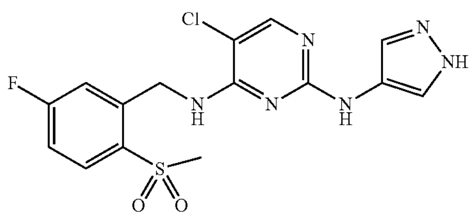 [SMILES: CS(=O)(=O)c1ccc(F)cc1CNc1nc(Nc2cn[nH]c2)ncc1Cl] | C | 0.94 | 397 |
| I-73 | 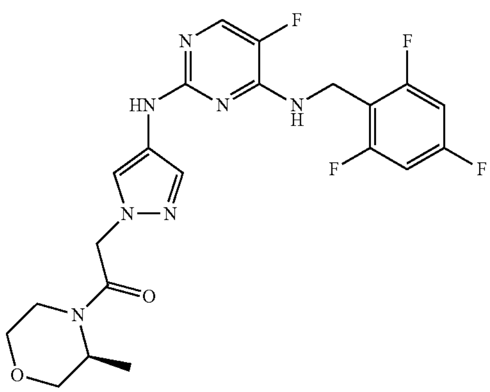 [SMILES: C[C@H]1COCCN1C(=O)Cn1cc(Nc2ncc(F)c(NCc3c(F)cc(F)cc3F)n2)cn1] | B | 5.65 | 480 |
| I-74 | 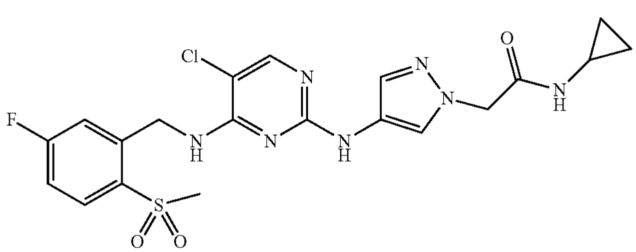 [SMILES: CS(=O)(=O)c1ccc(F)cc1CNc1nc(Nc2cnn(CC(=O)NC3CC3)c2)ncc1Cl] | C | 0.92 | 494 |

TABLE 11-continued

Table of Examples

| Example | Structure | Analytical Method | RT (min) | m/z ES+ |
|---------|-----------|-------------------|----------|---------|
| I-75 | 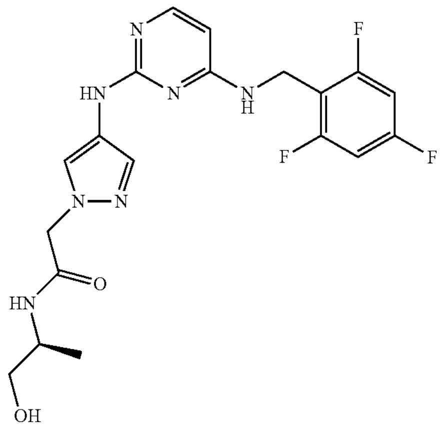 [SMILES: C[C@@H](CO)NC(=O)Cn1cc(Nc2nccc(NCc3c(F)cc(F)cc3F)n2)cn1] | B | 4.97 | 436 |
| I-76 | 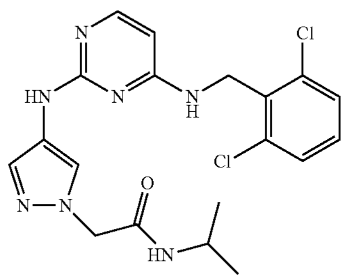 [SMILES: CC(C)NC(=O)Cn1cc(Nc2nccc(NCc3c(Cl)cccc3Cl)n2)cn1] | A | 8.57 | 434 |
| I-77 | 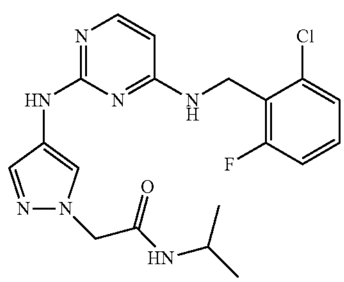 [SMILES: CC(C)NC(=O)Cn1cc(Nc2nccc(NCc3c(F)cccc3Cl)n2)cn1] | A | 8.43 | 418 |
| I-78 | 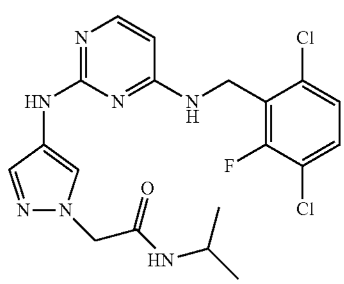 [SMILES: CC(C)NC(=O)Cn1cc(Nc2nccc(NCc3c(Cl)ccc(Cl)c3F)n2)cn1] | A | 8.66 | 452 |
| I-79 | 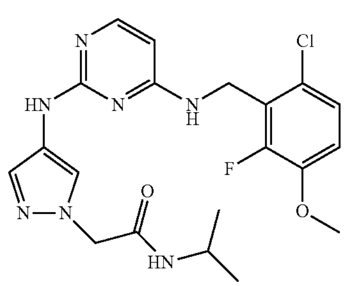 [SMILES: COc1ccc(Cl)c(CNc2ccnc(Nc3cnn(CC(=O)NC(C)C)c3)n2)c1F] | A | 8.44 | 448 |

TABLE 11-continued

Table of Examples

| Example | Structure | Analytical Method | RT (min) | m/z ES+ |
|---|---|---|---|---|
| I-80 | 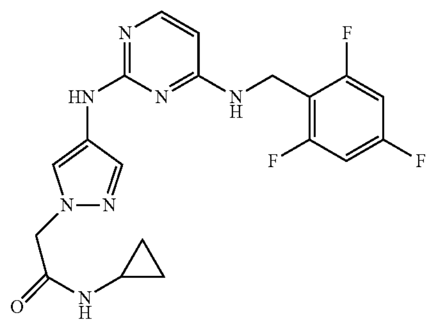 [SMILES: O=C(Cn1cc(Nc2nccc(NCc3c(F)cc(F)cc3F)n2)cn1)NC1CC1] | B | 5.13 | 418 |
| I-81 | 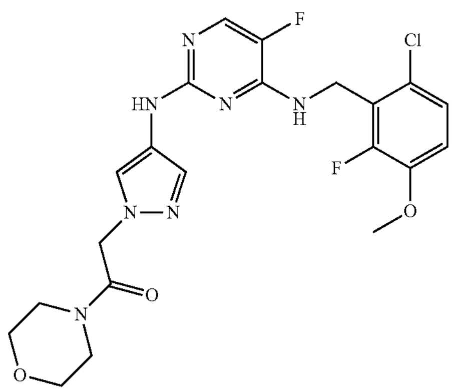 [SMILES: COc1ccc(Cl)c(CNc2nc(Nc3cnn(CC(=O)N4CCOCC4)c3)ncc2F)c1F] | B | 5.47 | 494 |
| I-82 | 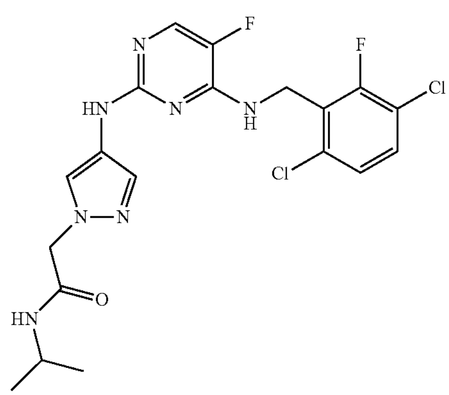 [SMILES: CC(C)NC(=O)Cn1cc(Nc2ncc(F)c(NCc3c(Cl)ccc(Cl)c3F)n2)cn1] | B | 6.34 | 470 |
| I-83 | 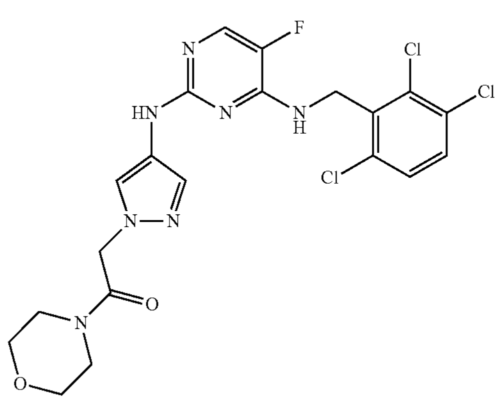 [SMILES: O=C(Cn1cc(Nc2ncc(F)c(NCc3c(Cl)ccc(Cl)c3Cl)n2)cn1)N1CCOCC1] | B | 5.88 | 498 |

TABLE 11-continued

Table of Examples

| Example | Structure | Analytical Method | RT (min) | m/z ES+ |
|---|---|---|---|---|
| I-84 | 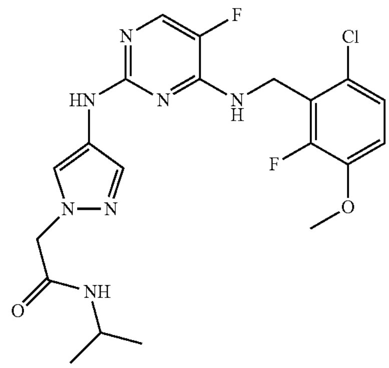 [SMILES: COc1ccc(Cl)c(CNc2nc(Nc3cnn(CC(=O)NC(C)C)c3)ncc2F)c1F] | B | 5.80 | 466 |
| I-85 | 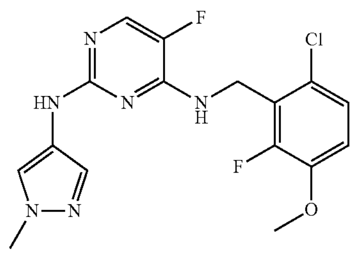 [SMILES: COc1ccc(Cl)c(CNc2nc(Nc3cnn(C)c3)ncc2F)c1F] | B | 5.90 | 381 |
| I-86 | 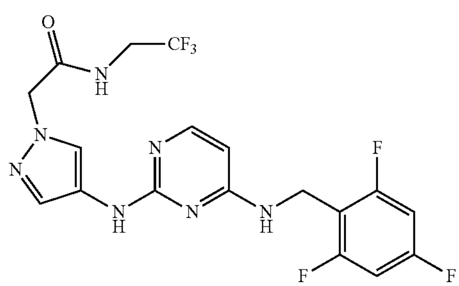 [SMILES: O=C(Cn1cc(Nc2nccc(NCc3c(F)cc(F)cc3F)n2)cn1)NCC(F)(F)F] | F | 1.69 | 460 |
| I-87 | 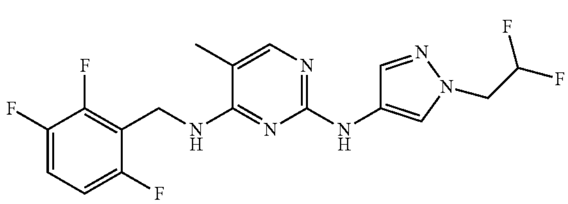 [SMILES: Cc1cnc(Nc2cnn(CC(F)F)c2)nc1NCc1c(F)ccc(F)c1F] | B | 5.89 | 399 |
| I-88 | 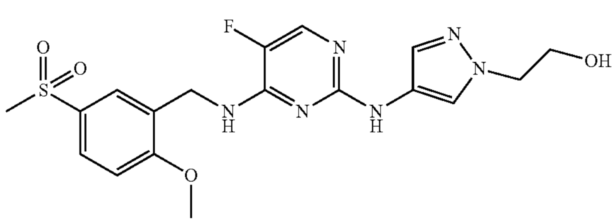 [SMILES: COc1ccc(S(C)(=O)=O)cc1CNc1nc(Nc2cnn(CCO)c2)ncc1F] | C | 0.82 | 437 |

TABLE 11-continued

Table of Examples

| Example | Structure | Analytical Method | RT (min) | m/z ES+ |
|---------|-----------|-------------------|----------|---------|
| I-89 | 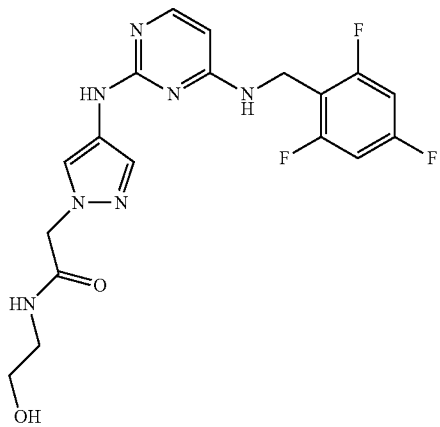 [SMILES: O=C(Cn1cc(Nc2nccc(NCc3c(F)cc(F)cc3F)n2)cn1)NCCO] | B | 4.74 | 422 |
| I-90 | 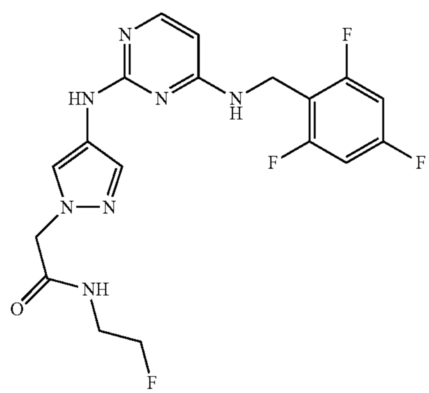 [SMILES: O=C(Cn1cc(Nc2nccc(NCc3c(F)cc(F)cc3F)n2)cn1)NCCF] | B | 5.07 | 424 |
| I-91 | 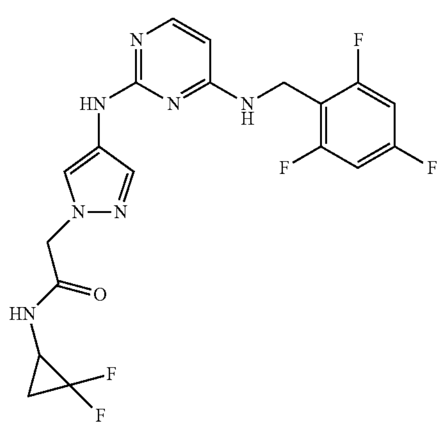 [SMILES: O=C(Cn1cc(Nc2nccc(NCc3c(F)cc(F)cc3F)n2)cn1)NC1CC1(F)F] | B | 5.48 | 454 |

TABLE 11-continued
Table of Examples
| Example | Structure | Analytical Method | RT (min) | m/z ES+ |
|---|---|---|---|---|
| I-92 | 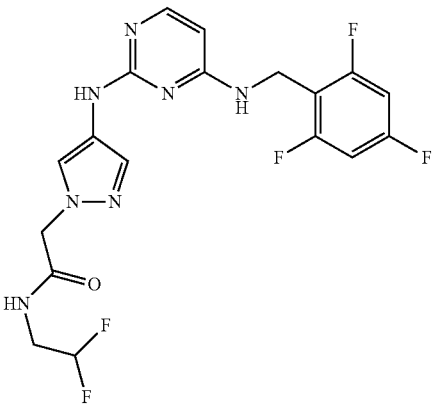 [SMILES: O=C(Cn1cc(Nc2nccc(NCc3c(F)cc(F)cc3F)n2)cn1)NCC(F)F] | B | 5.30 | 442 |
| I-93 | 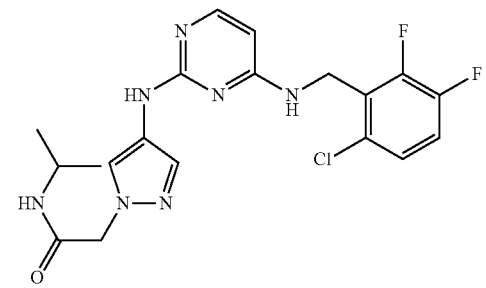 [SMILES: CC(C)NC(=O)Cn1cc(Nc2nccc(NCc3c(Cl)ccc(F)c3F)n2)cn1] | A | 8.45 | 436 |
| I-94 | 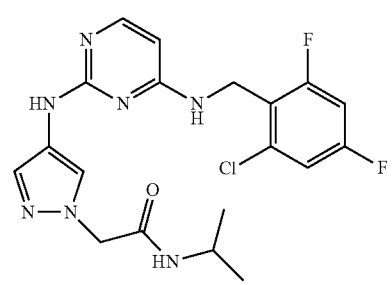 [SMILES: CC(C)NC(=O)Cn1cc(Nc2nccc(NCc3c(F)cc(F)cc3Cl)n2)cn1] | A | 8.53 | 436 |
| I-95 | 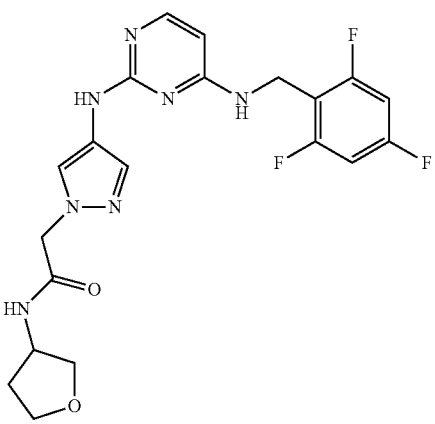 [SMILES: O=C(Cn1cc(Nc2nccc(NCc3c(F)cc(F)cc3F)n2)cn1)NC1CCOC1] | B | 5.20 | 448 |

TABLE 11-continued

Table of Examples

| Example | Structure | Analytical Method | RT (min) | m/z ES+ |
|---|---|---|---|---|
| I-96 | 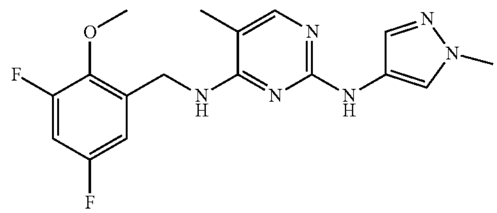 [SMILES: COc1c(F)cc(F)cc1CNc1nc(Nc2cnn(C)c2)ncc1C] | B | 5.65 | 361 |
| I-97 | 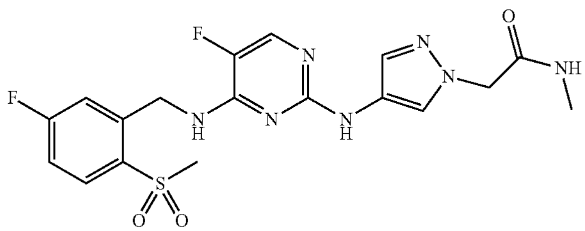 [SMILES: CNC(=O)Cn1cc(Nc2ncc(F)c(NCc3cc(F)ccc3S(C)(=O)=O)n2)cn1] | C | 0.84 | 452 |
| I-98 | 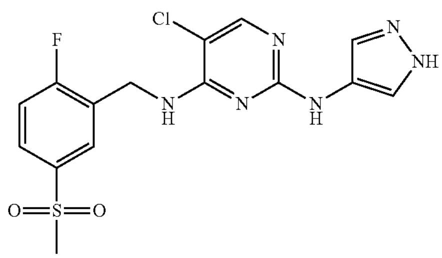 [SMILES: CS(=O)(=O)c1ccc(F)c(CNc2nc(Nc3cn[nH]c3)ncc2Cl)c1] | C | 0.87 | 397 |
| I-99 | 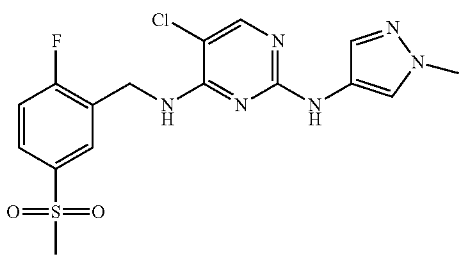 [SMILES: Cn1cc(Nc2ncc(Cl)c(NCc3cc(S(C)(=O)=O)ccc3F)n2)cn1] | C | 0.91 | 411 |
| I-100 | 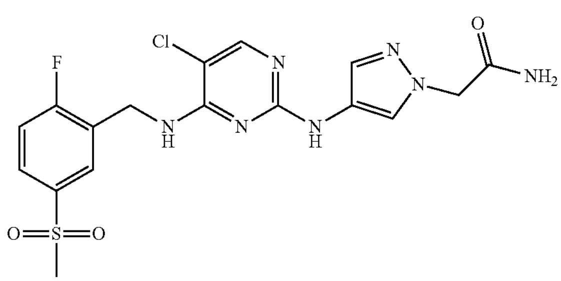 [SMILES: CS(=O)(=O)c1ccc(F)c(CNc2nc(Nc3cnn(CC(N)=O)c3)ncc2Cl)c1] | C | 0.83 | 454 |
| I-101 | 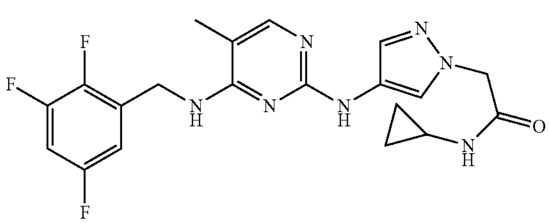 [SMILES: Cc1cnc(Nc2cnn(CC(=O)NC3CC3)c2)nc1NCc1cc(F)cc(F)c1F] | B | 5.80 | 432 |

TABLE 11-continued

Table of Examples

| Example | Structure | Analytical Method | RT (min) | m/z ES+ |
|---------|-----------|-------------------|----------|---------|
| I-102 | 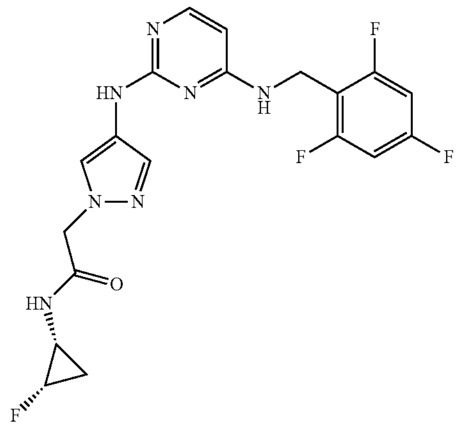 [SMILES: O=C(Cn1cc(Nc2nccc(NCc3c(F)cc(F)cc3F)n2)cn1)N[C@@H]1C[C@@H]1F] | B | 5.14 | 436 |
| I-103 | 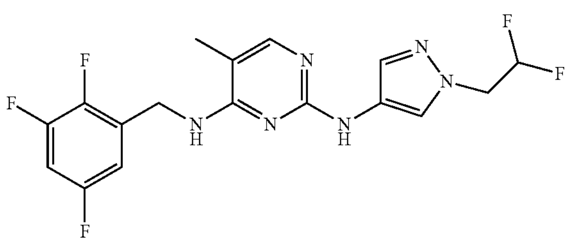 [SMILES: Cc1cnc(Nc2cnn(CC(F)F)c2)nc1NCc1cc(F)cc(F)c1F] | B | 5.96 | 399 |
| I-104 | 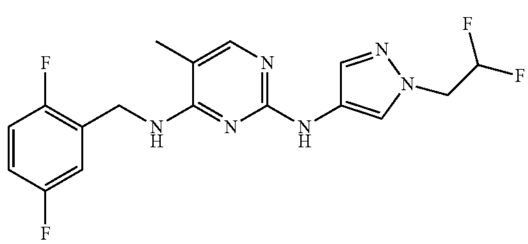 [SMILES: Cc1cnc(Nc2cnn(CC(F)F)c2)nc1NCc1cc(F)ccc1F] | B | 5.70 | 381 |
| I-105 | 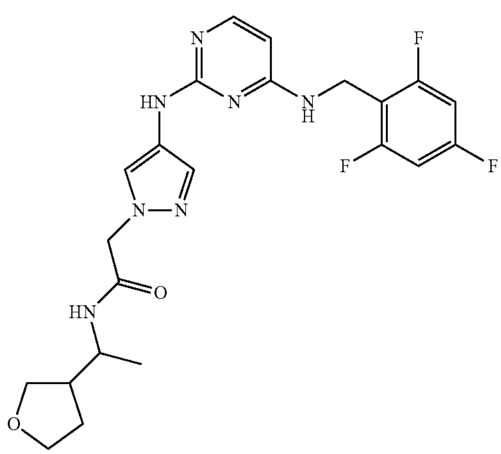 [SMILES: CC(NC(=O)Cn1cc(Nc2nccc(NCc3c(F)cc(F)cc3F)n2)cn1)C1CCOC1] | B | 5.40 | 476 |

TABLE 11-continued

Table of Examples

| Example | Structure | Analytical Method | RT (min) | m/z ES+ |
|---|---|---|---|---|
| I-106 | 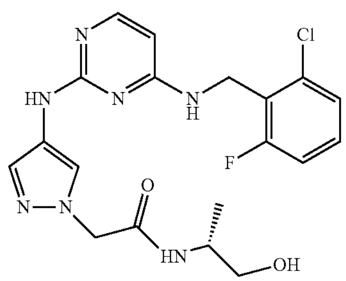 [SMILES: C[C@H](CO)NC(=O)Cn1cc(Nc2nccc(NCc3c(F)cccc3Cl)n2)cn1] | A | 8.11 | 434 |
| I-107 | 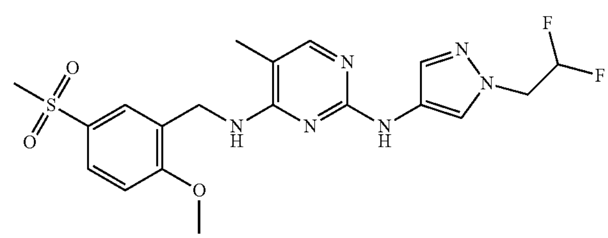 [SMILES: COc1ccc(S(C)(=O)=O)cc1CNc1nc(Nc2cnn(CC(F)F)c2)ncc1C] | B | 4.95 | 453 |
| I-108 | 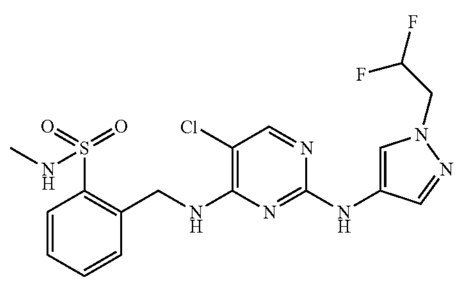 [SMILES: CNS(=O)(=O)c1ccccc1CNc1nc(Nc2cnn(CC(F)F)c2)ncc1Cl] | C | 0.99 | 458 |
| I-109 | 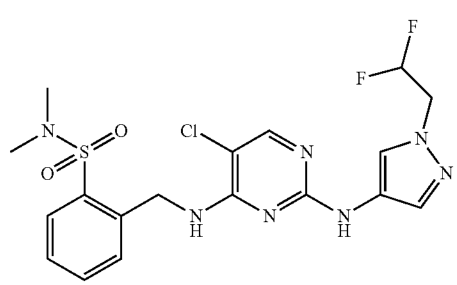 [SMILES: CN(C)S(=O)(=O)c1ccccc1CNc1nc(Nc2cnn(CC(F)F)c2)ncc1Cl] | C | 1.04 | 472 |
| I-110 | 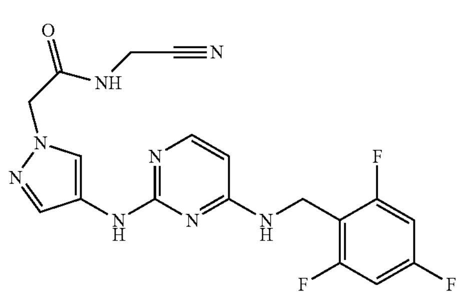 [SMILES: N#CCNC(=O)Cn1cc(Nc2nccc(NCc3c(F)cc(F)cc3F)n2)cn1] | B | 5.19 | 417 |

TABLE 11-continued

Table of Examples

| Example | Structure | Analytical Method | RT (min) | m/z ES+ |
|---------|-----------|-------------------|----------|---------|
| I-111 | 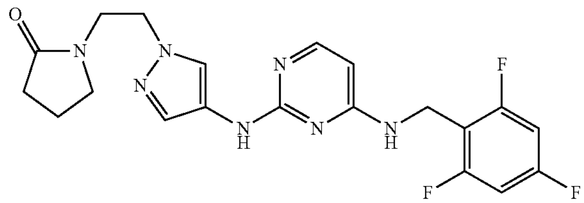 [SMILES: O=C1CCCN1CCn1cc(Nc2nccc(NCc3c(F)cc(F)cc3F)n2)cn1] | B | 5.22 | 432 |
| I-112 | 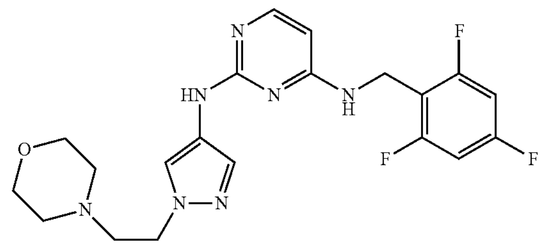 [SMILES: Fc1cc(F)c(CNc2ccnc(Nc3cnn(CCN4CCOCC4)c3)n2)c(F)c1] | B | 3.86 | 434 |
| I-113 | 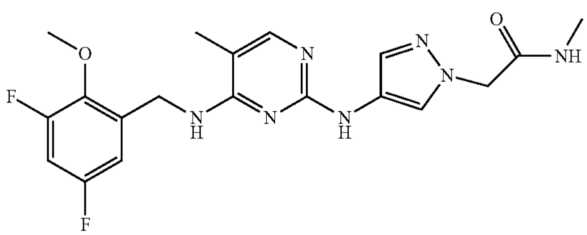 [SMILES: CNC(=O)Cn1cc(Nc2ncc(C)c(NCc3cc(F)cc(F)c3OC)n2)cn1] | B | 5.33 | 418 |
| I-114 | 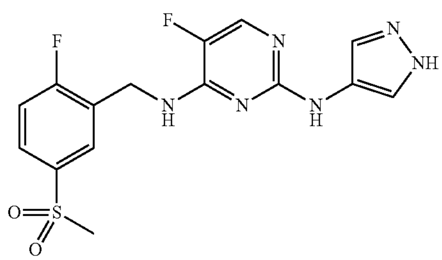 [SMILES: CS(=O)(=O)c1ccc(F)c(CNc2nc(Nc3cn[nH]c3)ncc2F)c1] | C | 0.83 | 381 |
| I-115 | 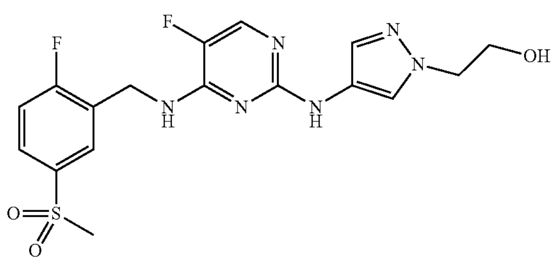 [SMILES: CS(=O)(=O)c1ccc(F)c(CNc2nc(Nc3cnn(CCO)c3)ncc2F)c1] | C | 0.82 | 425 |
| I-116 | 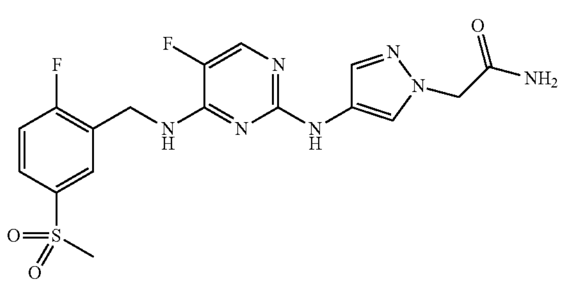 [SMILES: CS(=O)(=O)c1ccc(F)c(CNc2nc(Nc3cnn(CC(N)=O)c3)ncc2F)c1] | C | 0.79 | 438 |

TABLE 11-continued

Table of Examples

| Example | Structure | Analytical Method | RT (min) | m/z ES+ |
|---|---|---|---|---|
| I-117 | 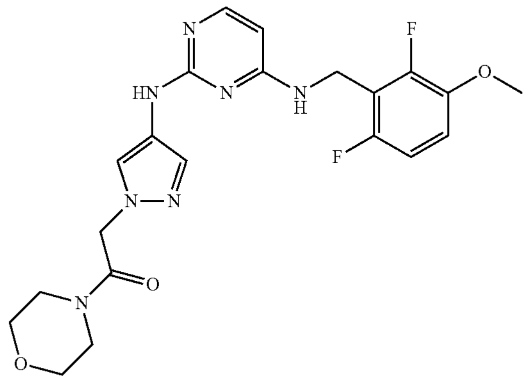 [SMILES: COc1ccc(F)c(CNc2ccnc(Nc3cnn(CC(=O)N4CCOCC4)c3)n2)c1F] | B | 4.88 | 460 |
| I-118 | 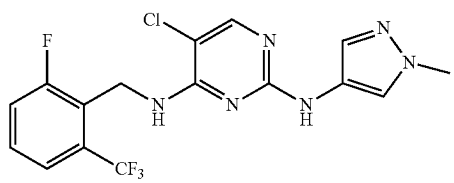 [SMILES: Cn1cc(Nc2ncc(Cl)c(NCc3c(F)cccc3C(F)(F)F)n2)cn1] | E | 1.39 | 401 |
| I-119 | 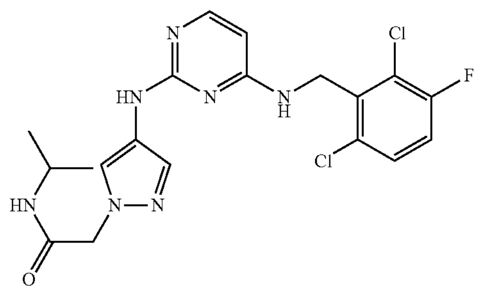 [SMILES: CC(C)NC(=O)Cn1cc(Nc2nccc(NCc3c(Cl)ccc(F)c3Cl)n2)cn1] | A | 8.58 | 452 |
| I-120 | 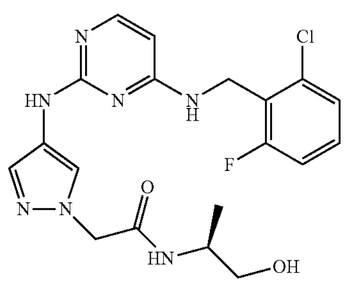 [SMILES: C[C@@H](CO)NC(=O)Cn1cc(Nc2nccc(NCc3c(F)cccc3Cl)n2)cn1] | A | 8.11 | 434 |
| I-121 | 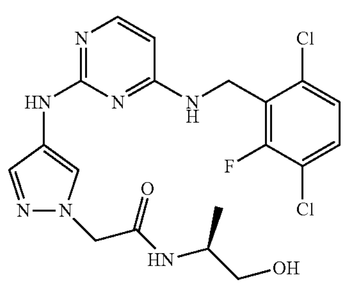 [SMILES: C[C@@H](CO)NC(=O)Cn1cc(Nc2nccc(NCc3c(Cl)ccc(Cl)c3F)n2)cn1] | A | 8.39 | 468 |

TABLE 11-continued

Table of Examples

| Example | Structure | Analytical Method | RT (min) | m/z ES+ |
|---|---|---|---|---|
| I-122 | 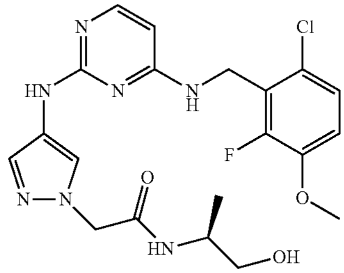 [SMILES: COc1ccc(Cl)c(CNc2ccnc(Nc3cnn(CC(=O)N[C@@H](C)CO)c3)n2)c1F] | A | 8.16 | 464 |
| I-123 | 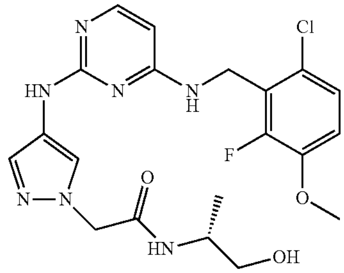 [SMILES: COc1ccc(Cl)c(CNc2ccnc(Nc3cnn(CC(=O)N[C@H](C)CO)c3)n2)c1F] | A | 8.14 | 464 |
| I-124 | 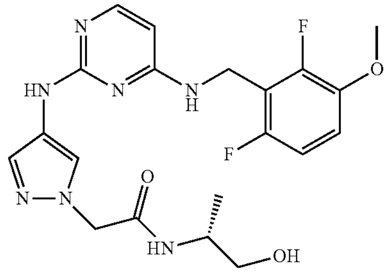 [SMILES: COc1ccc(F)c(CNc2ccnc(Nc3cnn(CC(=O)N[C@H](C)CO)c3)n2)c1F] | A | 7.88 | 448 |
| I-125 | 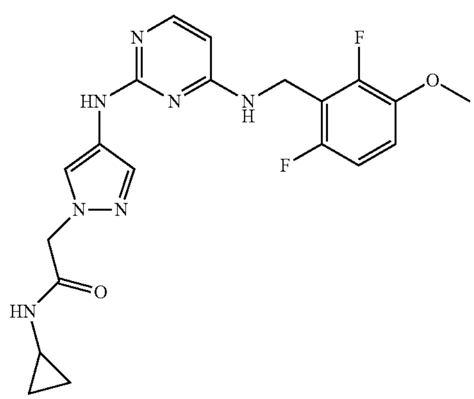 [SMILES: COc1ccc(F)c(CNc2ccnc(Nc3cnn(CC(=O)NC4CC4)c3)n2)c1F] | B | 5.12 | 430 |
| I-126 | 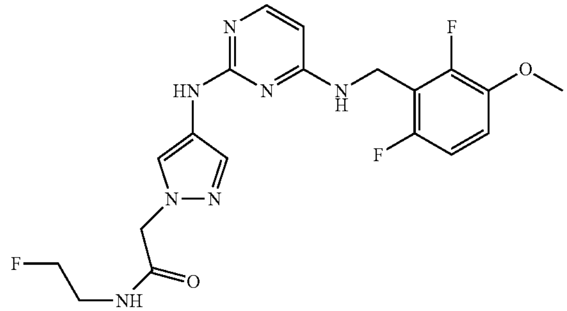 [SMILES: COc1ccc(F)c(CNc2ccnc(Nc3cnn(CC(=O)NCCF)c3)n2)c1F] | B | 4.98 | 436 |

TABLE 11-continued

Table of Examples

| Example | Structure | Analytical Method | RT (min) | m/z ES+ |
|---|---|---|---|---|
| I-127 | 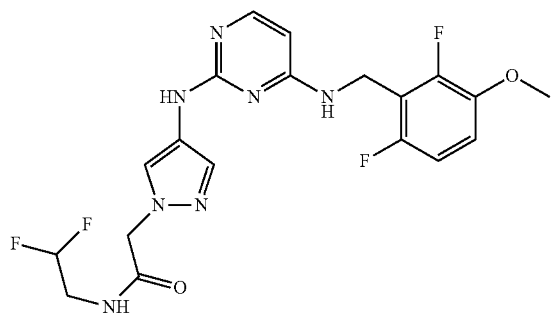 [SMILES: COc1ccc(F)c(CNc2ccnc(Nc3cnn(CC(=O)NCC(F)F)c3)n2)c1F] | B | 5.17 | 454 |
| I-128 | 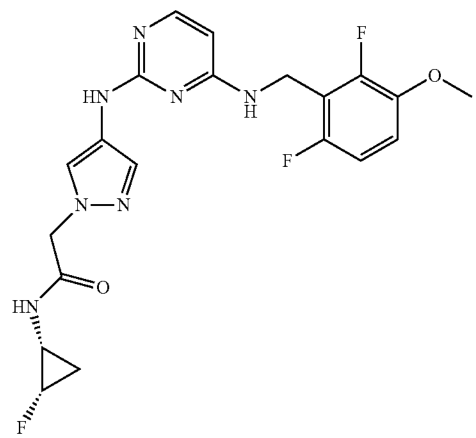 [SMILES: COc1ccc(F)c(CNc2ccnc(Nc3cnn(CC(=O)N[C@@H]4C[C@@H]4F)c3)n2)c1F] | B | 5.05 | 448 |
| I-129 | 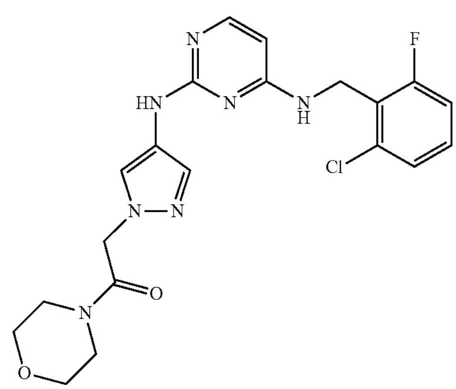 [SMILES: O=C(Cn1cc(Nc2nccc(NCc3c(F)cccc3Cl)n2)cn1)N1CCOCC1] | B | 5.12 | 446 |
| I-130 | 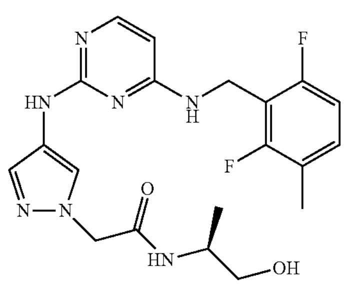 [SMILES: Cc1ccc(F)c(CNc2ccnc(Nc3cnn(CC(=O)N[C@@H](C)CO)c3)n2)c1F] | A | 8.24 | 432 |

TABLE 11-continued

Table of Examples

| Example | Structure | Analytical Method | RT (min) | m/z ES+ |
|---------|-----------|-------------------|----------|---------|
| I-131 | 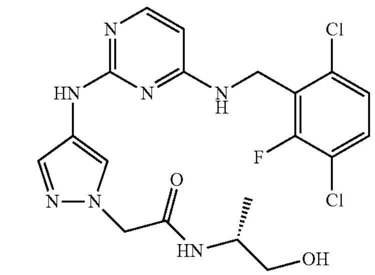 [SMILES: C[C@H](CO)NC(=O)Cn1cc(Nc2nccc(NCc3c(Cl)ccc(Cl)c3F)n2)cn1] | A | 8.39 | 468 |
| I-132 | 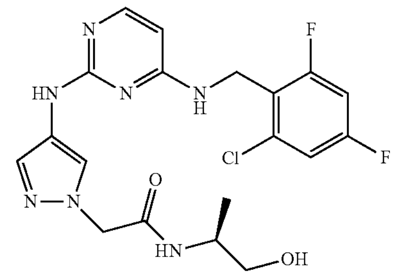 [SMILES: C[C@@H](CO)NC(=O)Cn1cc(Nc2nccc(NCc3c(F)cc(F)cc3Cl)n2)cn1] | A | 8.23 | 452 |
| I-133 | 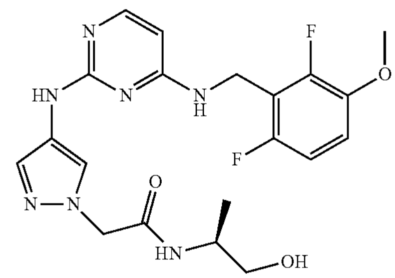 [SMILES: COc1ccc(F)c(CNc2ccnc(Nc3cnn(CC(=O)N[C@@H](C)CO)c3)n2)c1F] | A | 7.91 | 448 |
| I-134 | 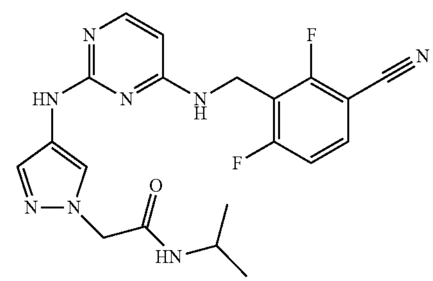 [SMILES: CC(C)NC(=O)Cn1cc(Nc2nccc(NCc3c(F)ccc(C#N)c3F)n2)cn1] | A | 7.97 | 427 |
| I-135 | 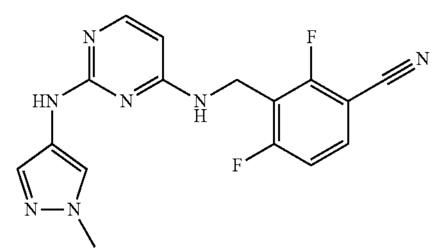 [SMILES: Cn1cc(Nc2nccc(NCc3c(F)ccc(C#N)c3F)n2)cn1] | A | 7.76 | 342 |
| I-136 | 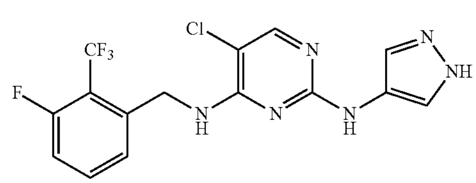 [SMILES: Fc1cccc(CNc2nc(Nc3cn[nH]c3)ncc2Cl)c1C(F)(F)F] | D | 0.89 | 387 |

TABLE 11-continued

Table of Examples

| Example | Structure | Analytical Method | RT (min) | m/z ES+ |
|---|---|---|---|---|
| I-137 | 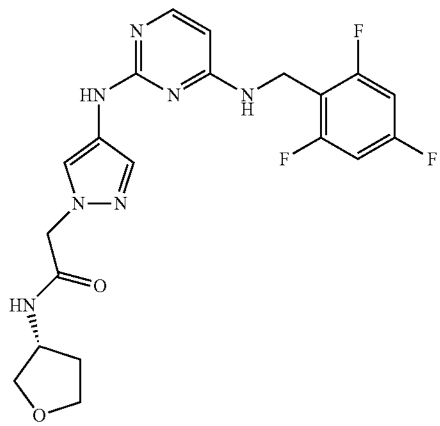 [SMILES: O=C(Cn1cc(Nc2nccc(NCc3c(F)cc(F)cc3F)n2)cn1)N[C@@H]1CCOC1] | B | 5.77 | 448 |
| I-138 | 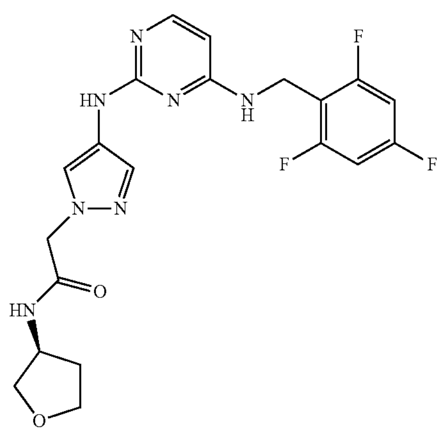 [SMILES: O=C(Cn1cc(Nc2nccc(NCc3c(F)cc(F)cc3F)n2)cn1)N[C@H]1CCOC1] | B | 5.53 | 448 |
| I-139 | 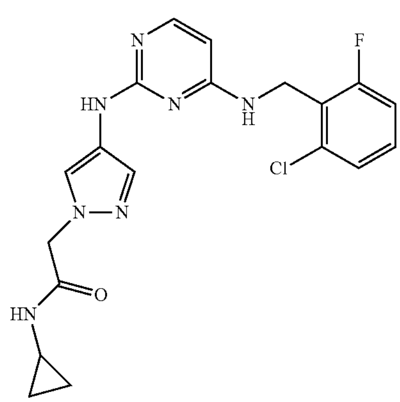 [SMILES: O=C(Cn1cc(Nc2nccc(NCc3c(F)cccc3Cl)n2)cn1)NC1CC1] | B | 5.76 | 416 |

TABLE 11-continued

Table of Examples

| Example | Structure | Analytical Method | RT (min) | m/z ES+ |
|---|---|---|---|---|
| I-140 | 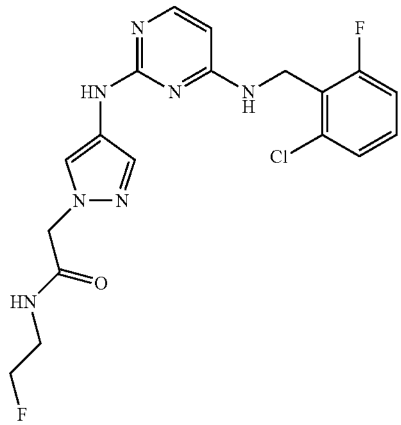 [SMILES: O=C(Cn1cc(Nc2nccc(NCc3c(F)cccc3Cl)n2)cn1)NCCF] | B | 5.39 | 422 |
| I-141 | 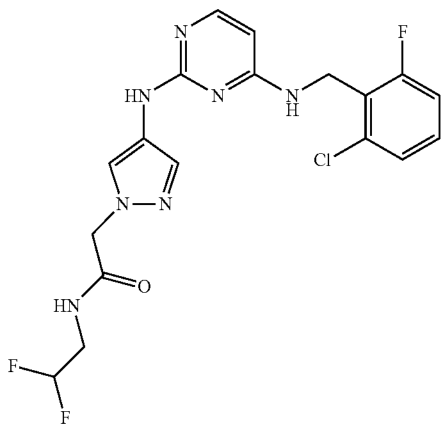 [SMILES: O=C(Cn1cc(Nc2nccc(NCc3c(F)cccc3Cl)n2)cn1)NCC(F)F] | B | 5.64 | 440 |
| I-142 | 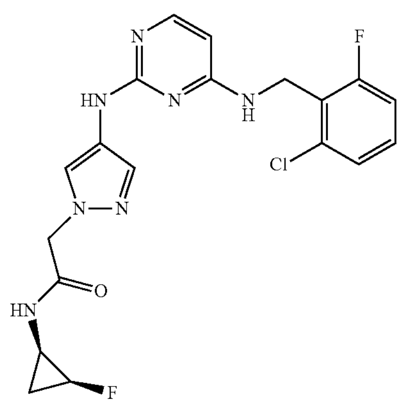 [SMILES: O=C(Cn1cc(Nc2nccc(NCc3c(F)cccc3Cl)n2)cn1)N[C@@H]1C[C@@H]1F] | B | 5.51 | 434 |
| I-143 | 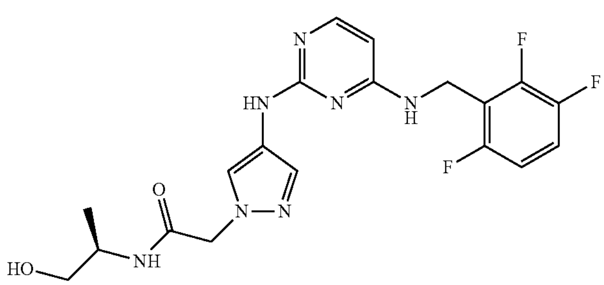 [SMILES: C[C@H](CO)NC(=O)Cn1cc(Nc2nccc(NCc3c(F)ccc(F)c3F)n2)cn1] | B | 4.85 | 436 |

TABLE 11-continued

Table of Examples

| Example | Structure | Analytical Method | RT (min) | m/z ES+ |
|---------|-----------|-------------------|----------|---------|
| I-144 | 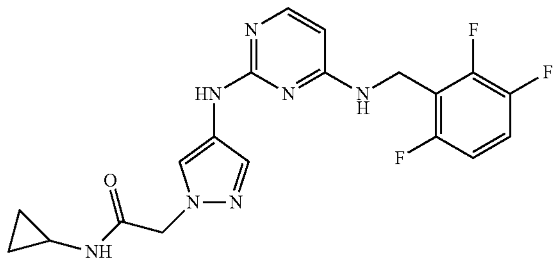 [SMILES: O=C(Cn1cc(Nc2nccc(NCc3c(F)ccc(F)c3F)n2)cn1)NC1CC1] | B | 5.21 | 418 |
| I-145 | 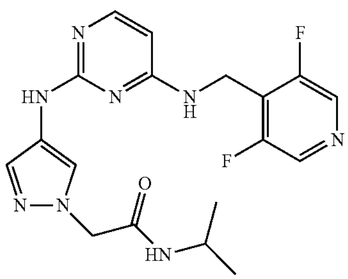 [SMILES: CC(C)NC(=O)Cn1cc(Nc2nccc(NCc3c(F)cncc3F)n2)cn1] | A | 7.44 | 403 |
| I-146 | 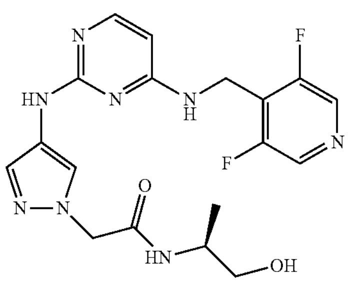 [SMILES: C[C@@H](CO)NC(=O)Cn1cc(Nc2nccc(NCc3c(F)cncc3F)n2)cn1] | G | 9.65 | 419 |
| I-147 | 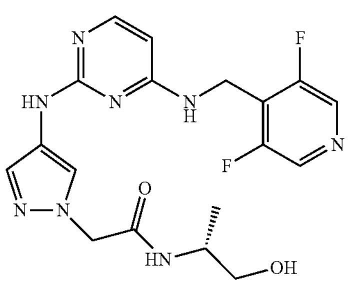 [SMILES: C[C@H](CO)NC(=O)Cn1cc(Nc2nccc(NCc3c(F)cncc3F)n2)cn1] | G | 9.64 | 419 |
| I-148 | 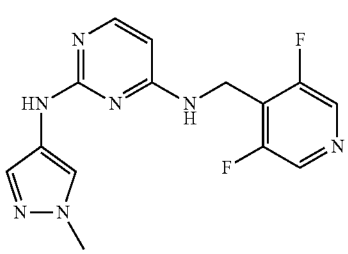 [SMILES: Cn1cc(Nc2nccc(NCc3c(F)cncc3F)n2)cn1] | G | 9.78 | 318 |

TABLE 11-continued

Table of Examples

| Example | Structure | Analytical Method | RT (min) | m/z ES+ |
|---------|-----------|-------------------|----------|---------|
| I-149 | 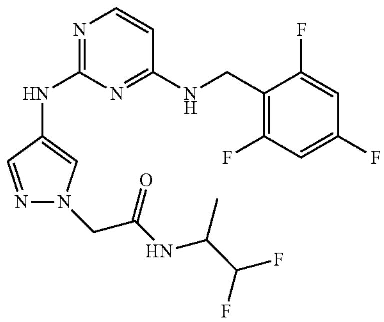 [SMILES: CC(NC(=O)Cn1cc(Nc2nccc(NCc3c(F)cc(F)cc3F)n2)cn1)C(F)F] | B | 5.42 | 456 |
| I-150 | 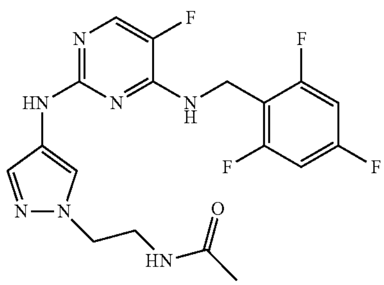 [SMILES: CC(=O)NCCn1cc(Nc2ncc(F)c(NCc3c(F)cc(F)cc3F)n2)cn1] | B | 5.00 | 424 |
| I-151 | 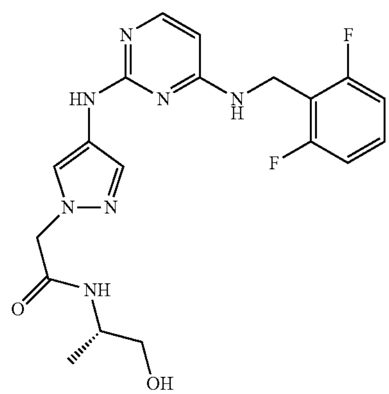 [SMILES: C[C@@H](CO)NC(=O)Cn1cc(Nc2nccc(NCc3c(F)cccc3F)n2)cn1] | B | 4.85 | 418 |
| I-152 | 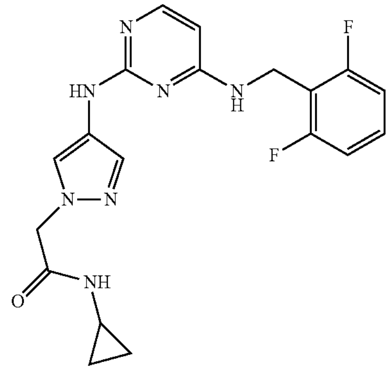 [SMILES: O=C(Cn1cc(Nc2nccc(NCc3c(F)cccc3F)n2)cn1)NC1CC1] | B | 4.84 | 400 |

TABLE 11-continued

Table of Examples

| Example | Structure | Analytical Method | RT (min) | m/z ES+ |
|---------|-----------|-------------------|----------|---------|
| I-153 | 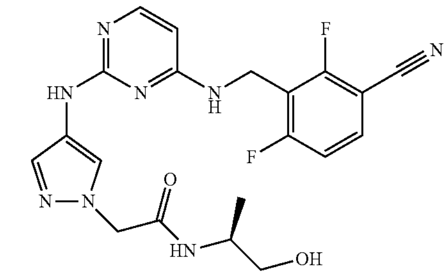 [SMILES: C[C@@H](CO)NC(=O)Cn1cc(Nc2nccc(NCc3c(F)ccc(C#N)c3F)n2)cn1] | A | 7.32 | 443 |
| I-154 | 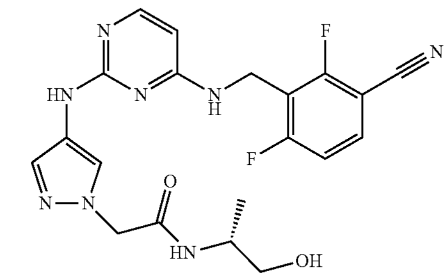 [SMILES: C[C@H](CO)NC(=O)Cn1cc(Nc2nccc(NCc3c(F)ccc(C#N)c3F)n2)cn1] | A | 7.28 | 443 |
| I-155 | 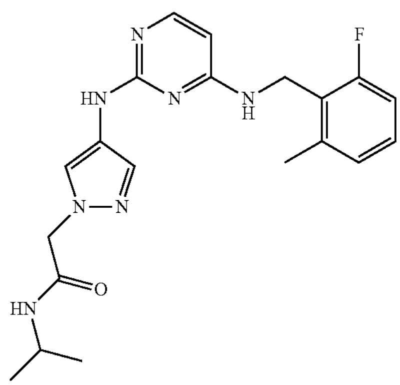 [SMILES: Cc1cccc(F)c1CNc1ccnc(Nc2cnn(CC(=O)NC(C)C)c2)n1] | B | 5.48 | 398 |
| I-156 | 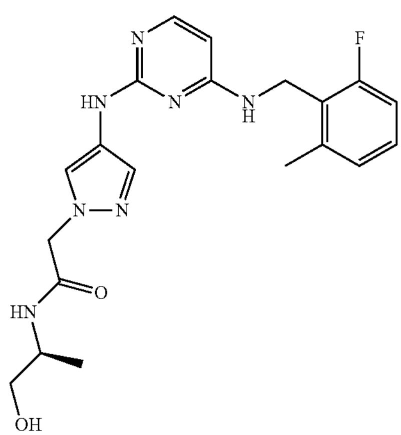 [SMILES: Cc1cccc(F)c1CNc1ccnc(Nc2cnn(CC(=O)N[C@@H](C)CO)c2)n1] | B | 4.99 | 414 |
| I-157 | 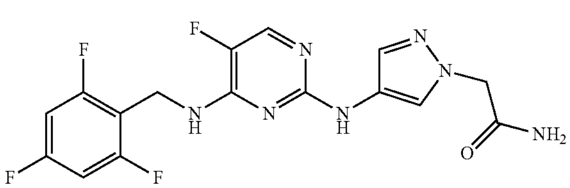 [SMILES: NC(=O)Cn1cc(Nc2ncc(F)c(NCc3c(F)cc(F)cc3F)n2)cn1] | B | 4.69 | 396 |

TABLE 11-continued

Table of Examples

| Example | Structure | Analytical Method | RT (min) | m/z ES+ |
|---------|-----------|-------------------|----------|---------|
| I-158 | (structure) | C | 1.73 | 315 |
| I-159 | (structure) | A | 0.82 | 340 |
| I-160 | (structure) | B | 0.95 | 428 |
| I-161 | (structure) | B | 0.98 | 464 |
| I-162 | (structure) | B | 0.98 | 464 |
| I-163 | (structure) | C | 1.92 | 394 |

TABLE 11-continued

Table of Examples

| Example | Structure | Analytical Method | RT (min) | m/z ES+ |
|---|---|---|---|---|
| I-164 | 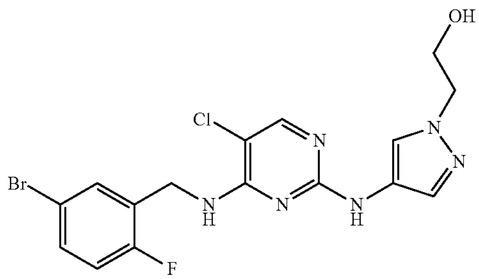 [SMILES: OCCn1cc(Nc2ncc(Cl)c(NCc3cc(Br)ccc3F)n2)cn1] | C | 1.82 | 442 |
| I-165 | 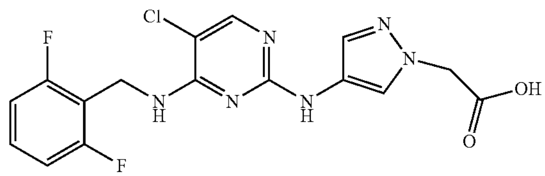 [SMILES: O=C(O)Cn1cc(Nc2ncc(Cl)c(NCc3c(F)cccc3F)n2)cn1] | A | 0.82 | 395 |
| I-166 | 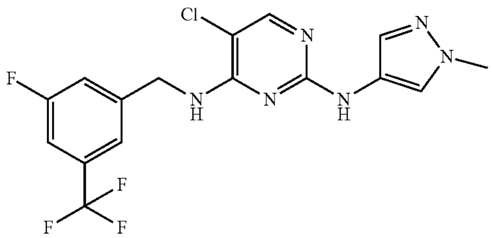 [SMILES: Cn1cc(Nc2ncc(Cl)c(NCc3cc(F)cc(C(F)(F)F)c3)n2)cn1] | A | 0.99 | 401 |
| I-167 | 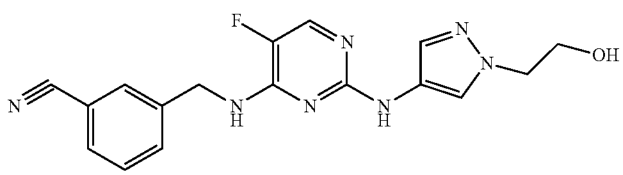 [SMILES: N#Cc1cccc(CNc2nc(Nc3cnn(CCO)c3)ncc2F)c1] | A | 0.74 | 354 |
| I-168 | 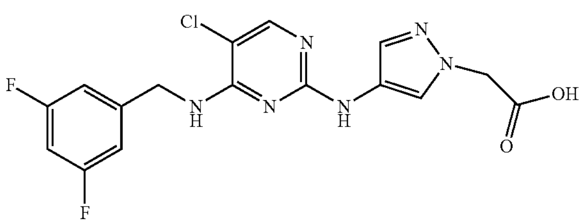 [SMILES: O=C(O)Cn1cc(Nc2ncc(Cl)c(NCc3cc(F)cc(F)c3)n2)cn1] | A | 0.83 | 395 |
| I-169 | 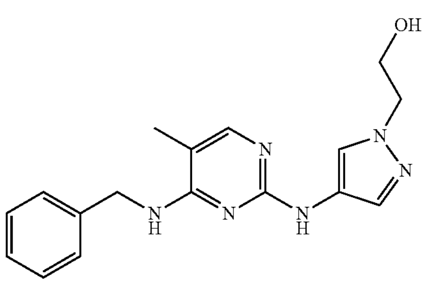 [SMILES: Cc1cnc(Nc2cnn(CCO)c2)nc1NCc1ccccc1] | C | 1.46 | 325 |

TABLE 11-continued

Table of Examples

| Example | Structure | Analytical Method | RT (min) | m/z ES+ |
|---|---|---|---|---|
| I-170 | 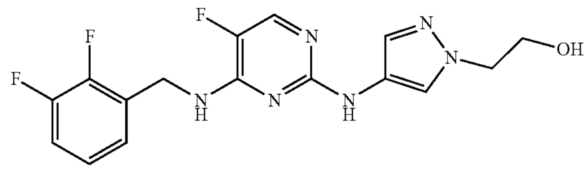 [SMILES: OCCn1cc(Nc2ncc(F)c(NCc3cccc(F)c3F)n2)cn1] | A | 0.82 | 365 |
| I-171 | 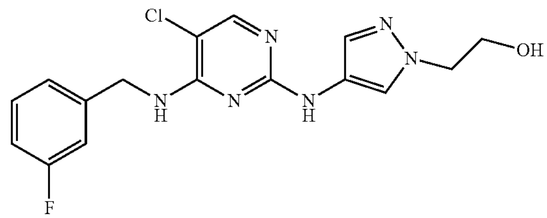 [SMILES: OCCn1cc(Nc2ncc(Cl)c(NCc3cccc(F)c3)n2)cn1] | A | 0.81 | 363 |
| I-172 | 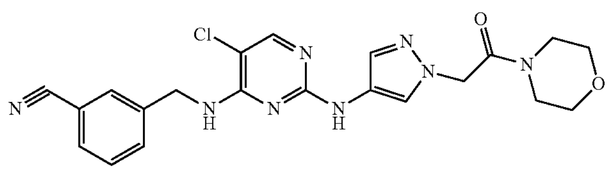 [SMILES: N#Cc1cccc(CNc2nc(Nc3cnn(CC(=O)N4CCOCC4)c3)ncc2Cl)c1] | A | 0.80 | 453 |
| I-173 | 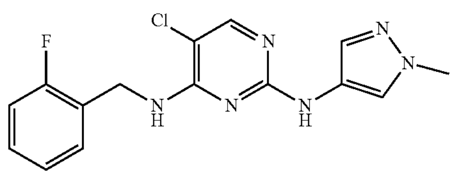 [SMILES: Cn1cc(Nc2ncc(Cl)c(NCc3ccccc3F)n2)cn1] | A | 0.80 | 333 |
| I-174 | 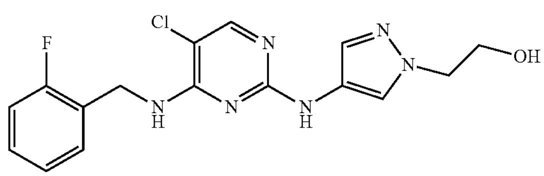 [SMILES: OCCn1cc(Nc2ncc(Cl)c(NCc3ccccc3F)n2)cn1] | A | 0.81 | 363 |
| I-175 | 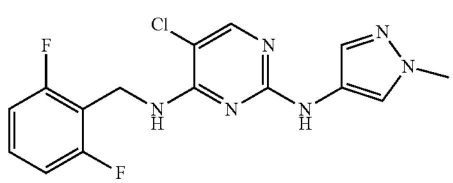 [SMILES: Cn1cc(Nc2ncc(Cl)c(NCc3c(F)cccc3F)n2)cn1] | D | 2.47 | 351 |
| I-176 | 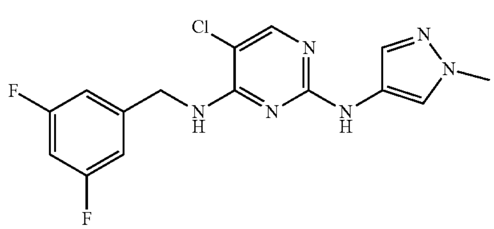 [SMILES: Cn1cc(Nc2ncc(Cl)c(NCc3cc(F)cc(F)c3)n2)cn1] | D | 2.47 | 351 |
| I-177 | 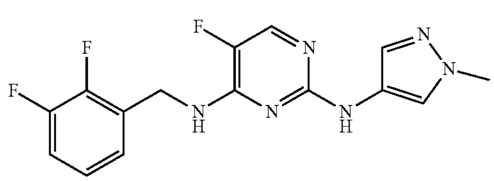 [SMILES: Cn1cc(Nc2ncc(F)c(NCc3cccc(F)c3F)n2)cn1] | A | 0.84 | 335 |

TABLE 11-continued

Table of Examples

| Example | Structure | Analytical Method | RT (min) | m/z ES+ |
|---------|-----------|-------------------|----------|---------|
| I-178 | 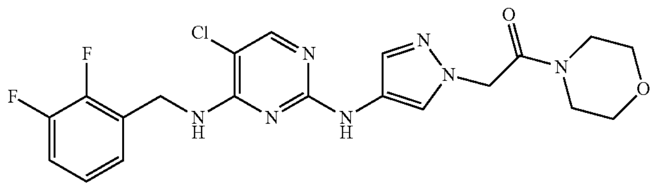 [SMILES: O=C(Cn1cc(Nc2ncc(Cl)c(NCc3cccc(F)c3F)n2)cn1)N1CCOCC1] | A | 0.85 | 464 |
| I-179 | 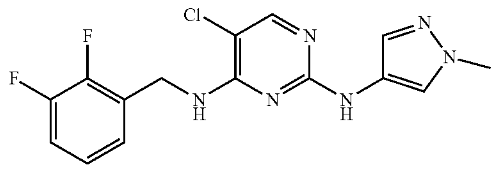 | A | 0.89 | 351 |
| I-180 | 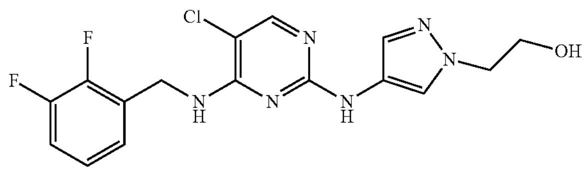 | A | 0.82 | 381 |
| I-181 | 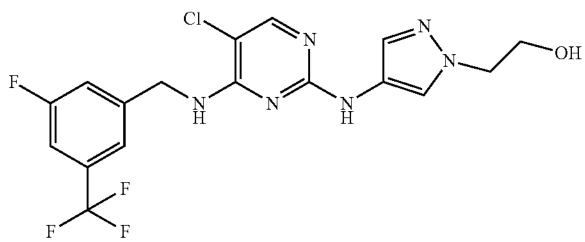 [SMILES: OCCn1cc(Nc2ncc(Cl)c(NCc3cc(F)cc(C(F)(F)F)c3)n2)cn1] | A | 0.99 | 431 |
| I-182 | 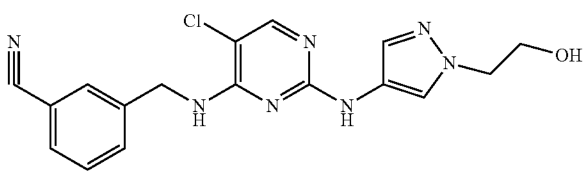 [SMILES: N#Cc1cccc(CNc2nc(Nc3cnn(CCO)c3)ncc2Cl)c1] | A | 0.82 | 370 |
| I-183 | 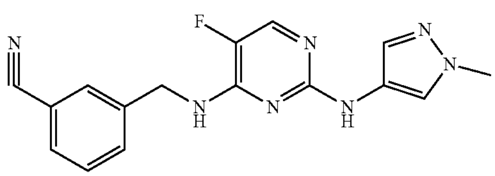 [SMILES: Cn1cc(Nc2ncc(F)c(NCc3cccc(C#N)c3)n2)cn1] | A | 0.81 | 324 |
| I-184 | 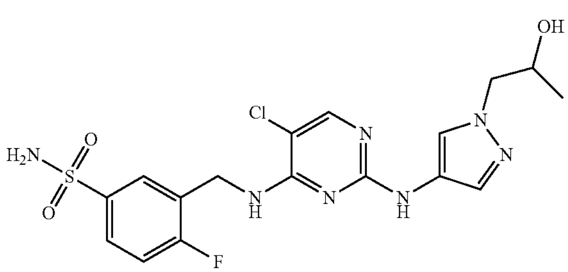 [SMILES: CC(O)Cn1cc(Nc2ncc(Cl)c(NCc3cc(S(N)(=O)=O)ccc3F)n2)cn1] | D | 4.55 | 442 |

TABLE 11-continued

Table of Examples

| Example | Structure | Analytical Method | RT (min) | m/z ES+ |
|---|---|---|---|---|
| I-185 | 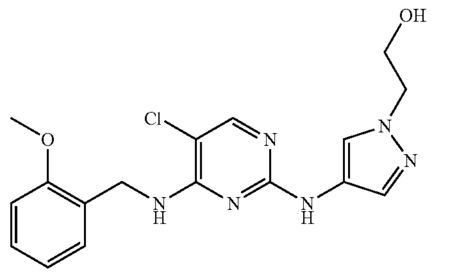 [SMILES: COc1ccccc1CNc1nc(Nc2cnn(CCO)c2)ncc1Cl] | A | 0.81 | 375 |
| I-186 | 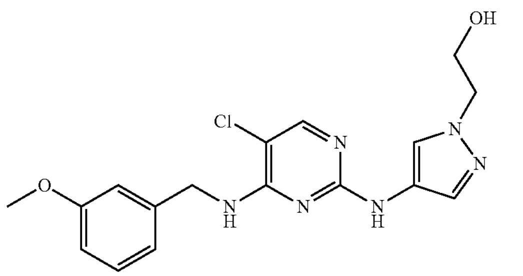 [SMILES: COc1cccc(CNc2nc(Nc3cnn(CCO)c3)ncc2Cl)c1] | A | 0.79 | 375 |
| I-187 | 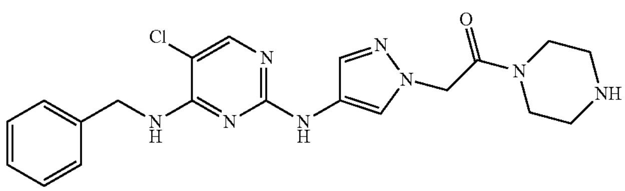 [SMILES: O=C(Cn1cc(Nc2ncc(Cl)c(NCc3ccccc3)n2)cn1)N1CCNCC1] | B | 0.91 | 427 |
| I-188 | 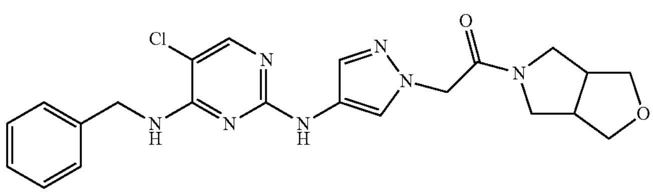 [SMILES: O=C(Cn1cc(Nc2ncc(Cl)c(NCc3ccccc3)n2)cn1)N1CC2COCC2C1] | B | 0.96 | 454 |
| I-189 | 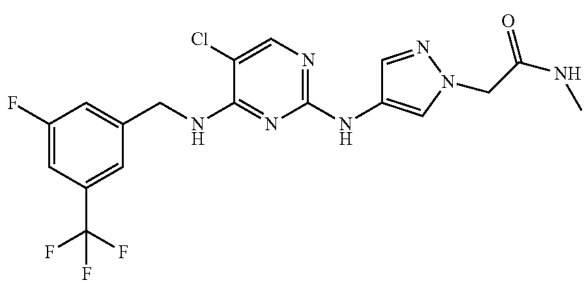 [SMILES: CNC(=O)Cn1cc(Nc2ncc(Cl)c(NCc3cc(F)cc(C(F)(F)F)c3)n2)cn1] | B | 1.03 | 458 |
| I-190 | 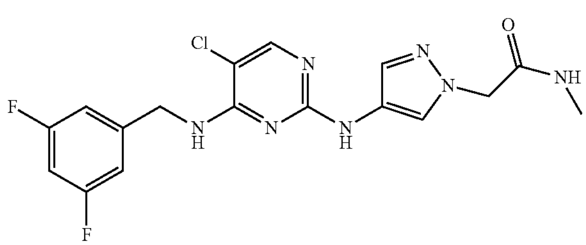 [SMILES: CNC(=O)Cn1cc(Nc2ncc(Cl)c(NCc3cc(F)cc(F)c3)n2)cn1] | B | 0.96 | 408 |

TABLE 11-continued

Table of Examples

| Example | Structure | Analytical Method | RT (min) | m/z ES+ |
|---|---|---|---|---|
| I-191 | 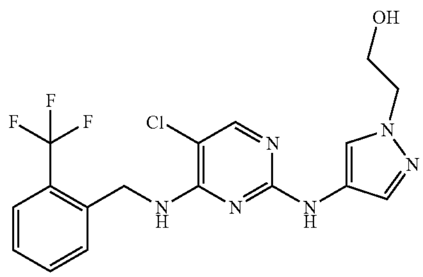 [SMILES: OCCn1cc(Nc2ncc(Cl)c(NCc3ccccc3C(F)(F)F)n2)cn1] | C | 1.86 | 413 |
| I-192 | 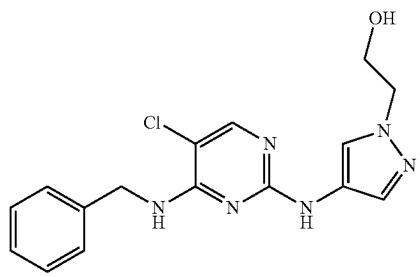 [SMILES: OCCn1cc(Nc2ncc(Cl)c(NCc3ccccc3)n2)cn1] | C | 1.56 | 345 |
| I-193 | 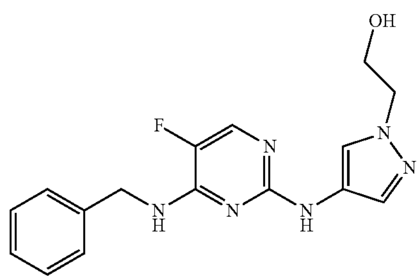 [SMILES: OCCn1cc(Nc2ncc(F)c(NCc3ccccc3)n2)cn1] | C | 1.44 | 329 |
| I-194 | 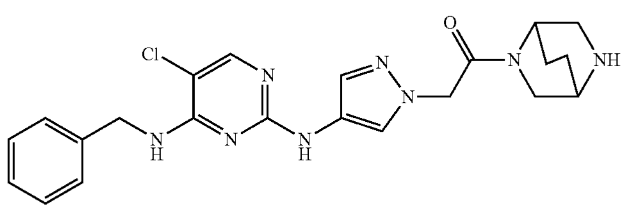 [SMILES: O=C(Cn1cc(Nc2ncc(Cl)c(NCc3ccccc3)n2)cn1)N1CC2CCC1CN2] | B | 0.92 | 453 |
| I-195 | 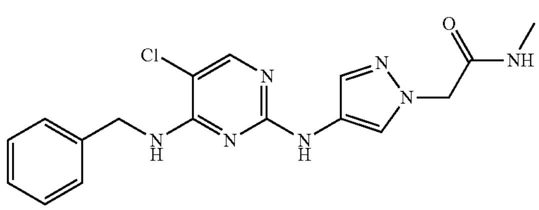 [SMILES: CNC(=O)Cn1cc(Nc2ncc(Cl)c(NCc3ccccc3)n2)cn1] | B | 0.94 | 371 |
| I-196 | 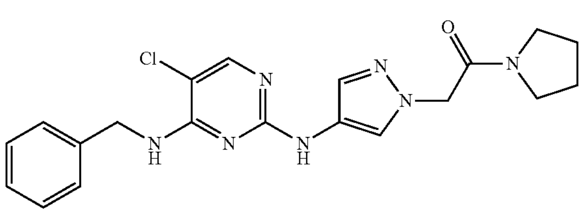 [SMILES: O=C(Cn1cc(Nc2ncc(Cl)c(NCc3ccccc3)n2)cn1)N1CCCC1] | B | 1.00 | 412 |

TABLE 11-continued

Table of Examples

| Example | Structure | Analytical Method | RT (min) | m/z ES+ |
|---------|-----------|-------------------|----------|---------|
| I-197 | 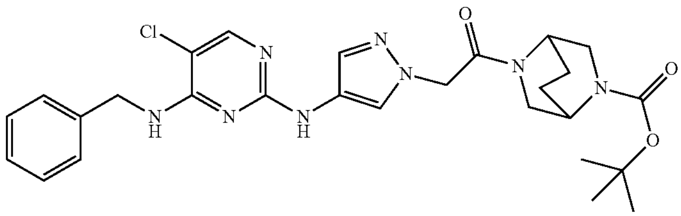 [SMILES: CC(C)(C)OC(=O)N1CC2CCC1CN2C(=O)Cn1cc(Nc2ncc(Cl)c(NCc3ccccc3)n2)cn1] | B | 1.11 | 553 |
| I-198 | 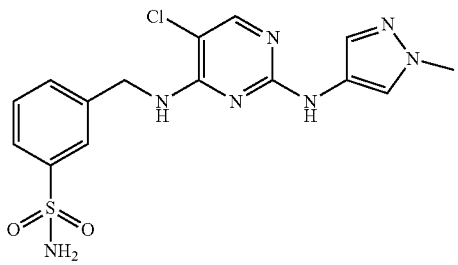 [SMILES: Cn1cc(Nc2ncc(Cl)c(NCc3cccc(S(N)(=O)=O)c3)n2)cn1] | A | 0.74 | 393 |
| I-199 | 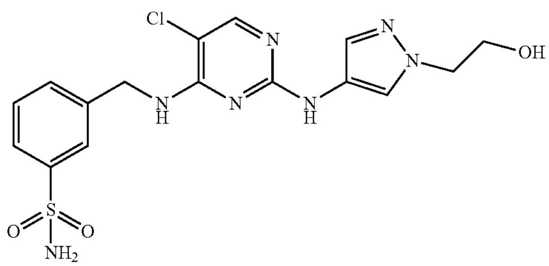 [SMILES: NS(=O)(=O)c1cccc(CNc2nc(Nc3cnn(CCO)c3)ncc2Cl)c1] | A | 0.71 | 423 |
| I-200 | 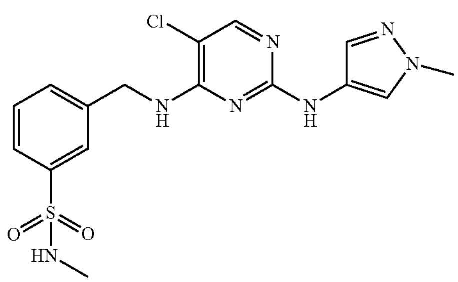 [SMILES: CNS(=O)(=O)c1cccc(CNc2nc(Nc3cnn(C)c3)ncc2Cl)c1] | A | 0.75 | 408 |
| I-201 | 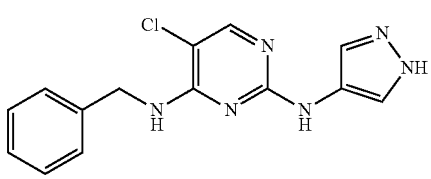 [SMILES: Clc1cnc(Nc2cn[nH]c2)nc1NCc1ccccc1] | A | 0.79 | 301 |
| I-202 | 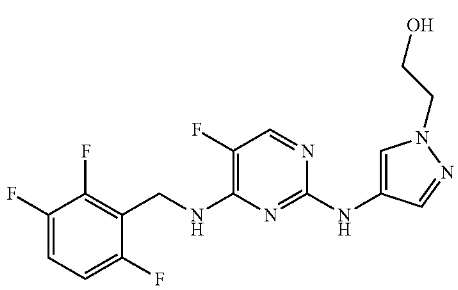 [SMILES: OCCn1cc(Nc2ncc(F)c(NCc3c(F)ccc(F)c3F)n2)cn1] | A | 0.94 | 383 |

TABLE 11-continued

Table of Examples

| Example | Structure | Analytical Method | RT (min) | m/z ES+ |
|---|---|---|---|---|
| I-203 | 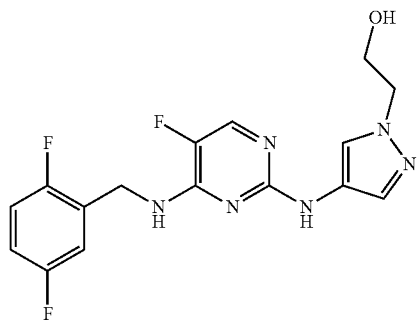 [SMILES: OCCn1cc(Nc2ncc(F)c(NCc3cc(F)ccc3F)n2)cn1] | B | 0.92 | 365 |
| I-204 | 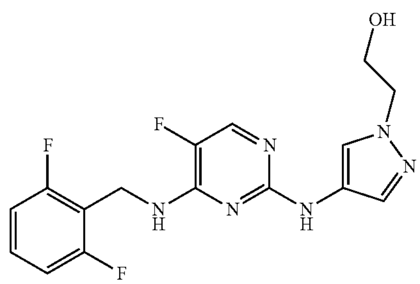 | B | 0.93 | 365 |
| I-205 | 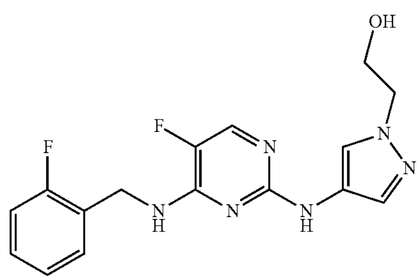 [SMILES: OCCn1cc(Nc2ncc(F)c(NCc3ccccc3F)n2)cn1] | B | 0.91 | 347 |
| I-206 | 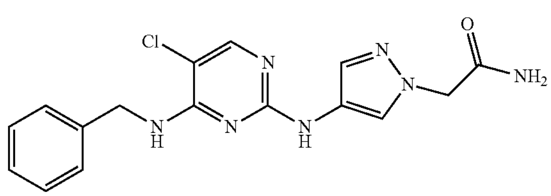 [SMILES: NC(=O)Cn1cc(Nc2ncc(Cl)c(NCc3ccccc3)n2)cn1] | B | 0.91 | 358 |
| I-207 | 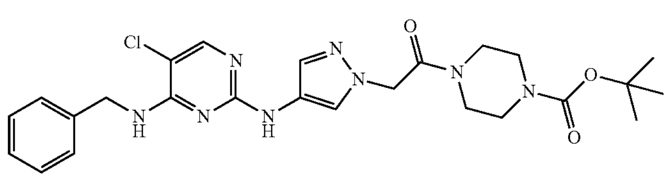 [SMILES: CC(C)(C)OC(=O)N1CCN(C(=O)Cn2cc(Nc3ncc(Cl)c(NCc4ccccc4)n3)cn2)CC1] | B | 1.10 | 527 |
| I-208 | 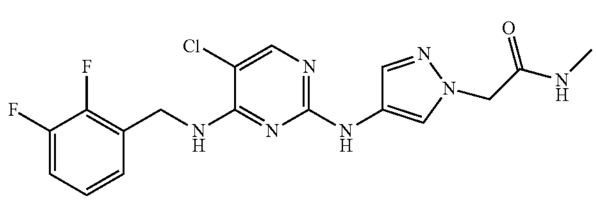 [SMILES: CNC(=O)Cn1cc(Nc2ncc(Cl)c(NCc3cccc(F)c3F)n2)cn1] | B | 0.96 | 408 |

TABLE 11-continued

Table of Examples

| Example | Structure | Analytical Method | RT (min) | m/z ES+ |
|---|---|---|---|---|
| I-209 | 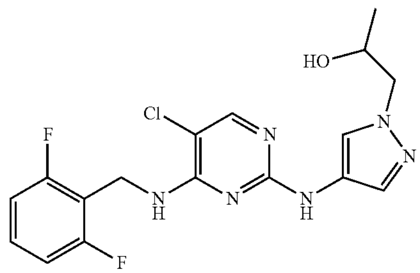 [SMILES: CC(O)Cn1cc(Nc2ncc(Cl)c(NCc3c(F)cccc3F)n2)cn1] | D | 5.86 | 395 |
| I-210 | 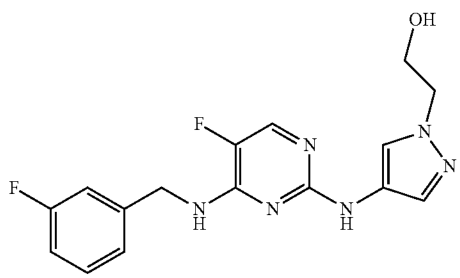 [SMILES: OCCn1cc(Nc2ncc(F)c(NCc3cccc(F)c3)n2)cn1] | A | 0.92 | 347 |
| I-211 | 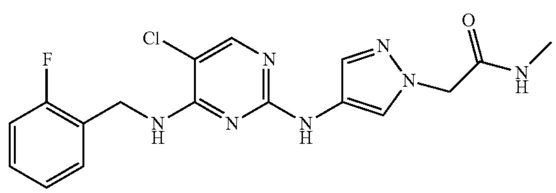 [SMILES: CNC(=O)Cn1cc(Nc2ncc(Cl)c(NCc3ccccc3F)n2)cn1] | B | 0.95 | 390 |
| I-212 | 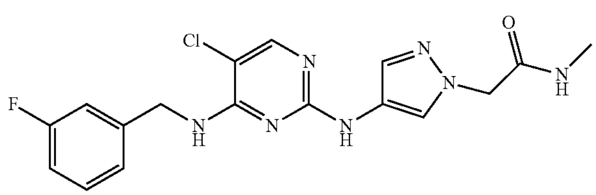 [SMILES: CNC(=O)Cn1cc(Nc2ncc(Cl)c(NCc3cccc(F)c3)n2)cn1] | B | 0.95 | 390 |
| I-213 | 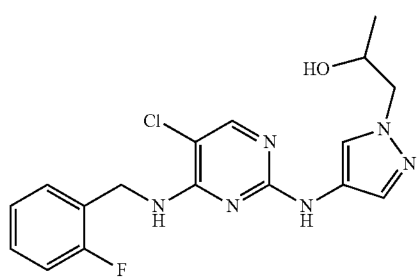 [SMILES: CC(O)Cn1cc(Nc2ncc(Cl)c(NCc3ccccc3F)n2)cn1] | D | 5.83 | 377 |
| I-214 | 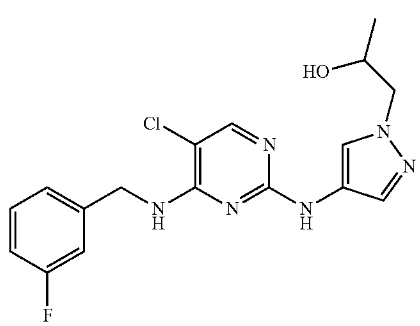 [SMILES: CC(O)Cn1cc(Nc2ncc(Cl)c(NCc3cccc(F)c3)n2)cn1] | D | 5.56 | 377 |

TABLE 11-continued

Table of Examples

| Example | Structure | Analytical Method | RT (min) | m/z ES+ |
|---|---|---|---|---|
| I-215 | 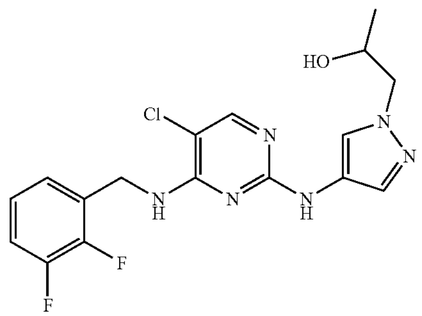 [SMILES: CC(O)Cn1cc(Nc2ncc(Cl)c(NCc3cccc(F)c3F)n2)cn1] | D | 6.08 | 395 |
| I-216 | 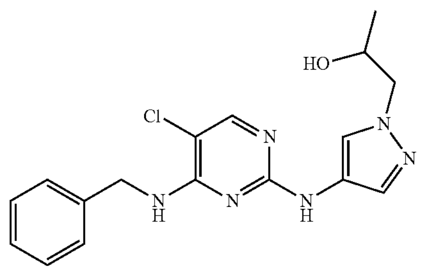 [SMILES: CC(O)Cn1cc(Nc2ncc(Cl)c(NCc3ccccc3)n2)cn1] | D | 5.41 | 359 |
| I-217 | 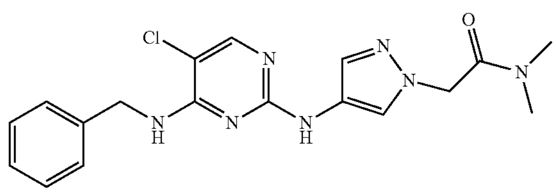 [SMILES: CN(C)C(=O)Cn1cc(Nc2ncc(Cl)c(NCc3ccccc3)n2)cn1] | B | 0.96 | 386 |
| I-218 | 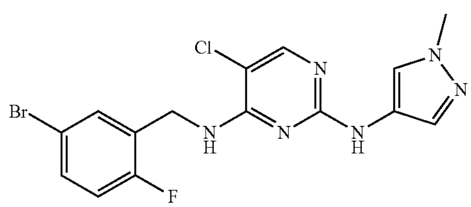 [SMILES: Cn1cc(Nc2ncc(Cl)c(NCc3cc(Br)ccc3F)n2)cn1] | C | 1.95 | 412 |
| I-219 | 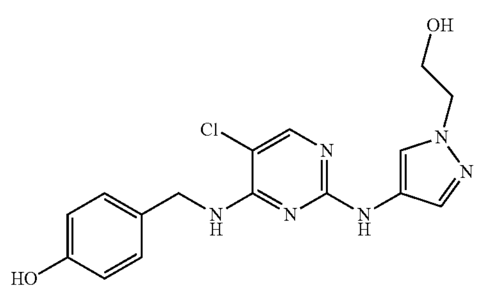 [SMILES: OCCn1cc(Nc2ncc(Cl)c(NCc3ccc(O)cc3)n2)cn1] | A | 0.72 | 361 |
| I-220 | 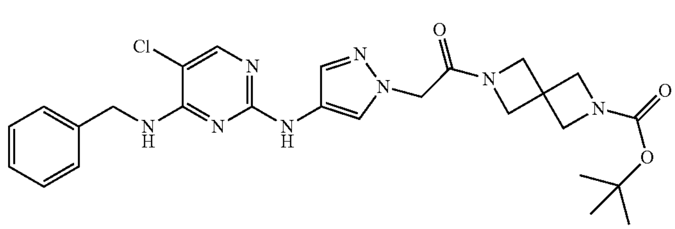 [SMILES: CC(C)(C)OC(=O)N1CC2(CN(C(=O)Cn3cc(Nc4ncc(Cl)c(NCc5ccccc5)n4)cn3)C2)C1] | B | 1.07 | 539 |

TABLE 11-continued

Table of Examples

| Example | Structure | Analytical Method | RT (min) | m/z ES+ |
|---|---|---|---|---|
| I-221 | 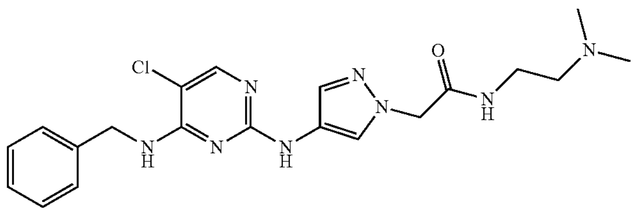 [SMILES: CN(C)CCNC(=O)Cn1cc(Nc2ncc(Cl)c(NCc3ccccc3)n2)cn1] | B | 0.96 | 429 |
| I-222 | 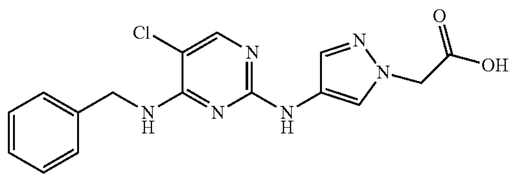 [SMILES: O=C(O)Cn1cc(Nc2ncc(Cl)c(NCc3ccccc3)n2)cn1] | B | 0.79 | 359 |
| I-223 | 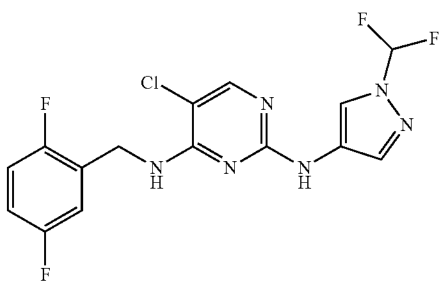 [SMILES: Fc1ccc(F)c(CNc2nc(Nc3cnn(C(F)F)c3)ncc2Cl)c1] | A | 1.05 | 387 |
| I-224 | 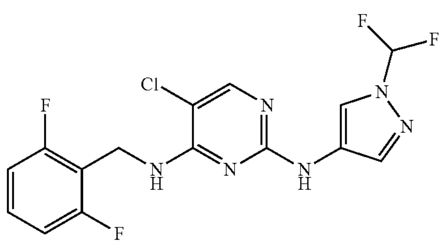 [SMILES: Fc1cccc(F)c1CNc1nc(Nc2cnn(C(F)F)c2)ncc1Cl] | C | 2.33 | 387 |
| I-225 | 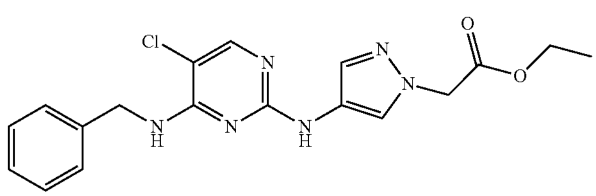 [SMILES: CCOC(=O)Cn1cc(Nc2ncc(Cl)c(NCc3ccccc3)n2)cn1] | B | 1.09 | 387 |
| I-226 | 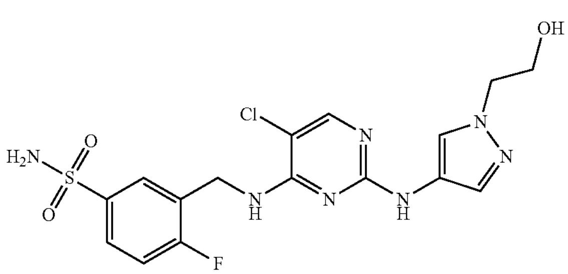 [SMILES: NS(=O)(=O)c1ccc(F)c(CNc2nc(Nc3cnn(CCO)c3)ncc2Cl)c1] | D | 4.55 | 442 |

TABLE 11-continued

Table of Examples

| Example | Structure | Analytical Method | RT (min) | m/z ES+ |
|---|---|---|---|---|
| I-227 | 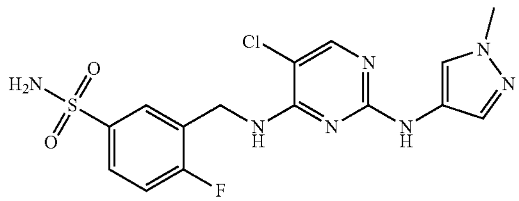 [SMILES: Cn1cc(Nc2ncc(Cl)c(NCc3cc(S(N)(=O)=O)ccc3F)n2)cn1] | D | 4.94 | 421 |
| I-228 | 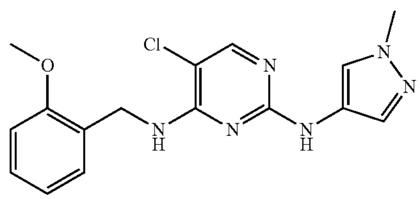 [SMILES: COc1ccccc1CNc1nc(Nc2cnn(C)c2)ncc1Cl] | B | 0.86 | 345 |
| I-229 | 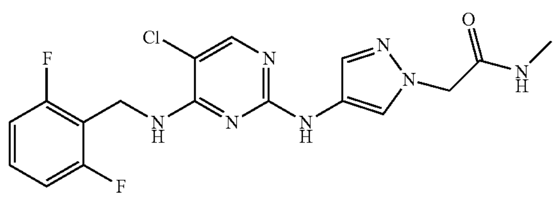 [SMILES: CNC(=O)Cn1cc(Nc2ncc(Cl)c(NCc3c(F)cccc3F)n2)cn1] | B | 0.97 | 408 |
| I-230 | 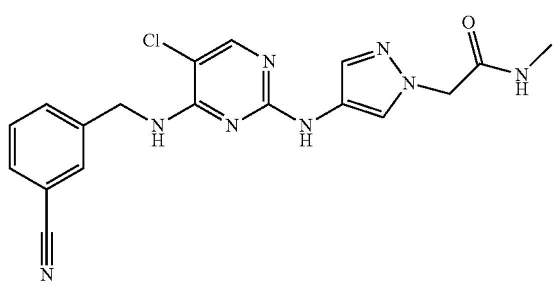 [SMILES: CNC(=O)Cn1cc(Nc2ncc(Cl)c(NCc3cccc(C#N)c3)n2)cn1] | B | 0.90 | 397 |
| I-231 | 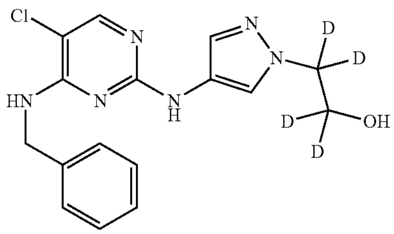 [SMILES: [2H]C([2H])(O)C([2H])([2H])n1cc(Nc2ncc(Cl)c(NCc3ccccc3)n2)cn1] | D | 5.04 | 349 |
| I-232 | 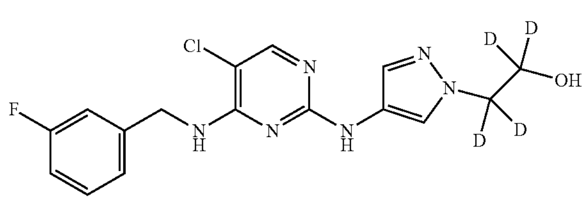 [SMILES: [2H]C([2H])(O)C([2H])([2H])n1cc(Nc2ncc(Cl)c(NCc3cccc(F)c3)n2)cn1] | D | 5.28 | 367 |

TABLE 11-continued

Table of Examples

| Example | Structure | Analytical Method | RT (min) | m/z ES+ |
|---|---|---|---|---|
| I-233 | 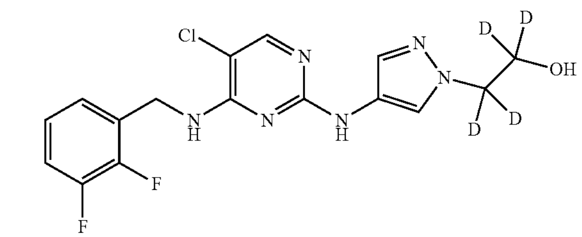 [SMILES: [2H]C([2H])(O)C([2H])([2H])n1cc(Nc2ncc(Cl)c(NCc3cccc(F)c3F)n2)cn1] | D | 5.55 | 385 |
| I-234 | 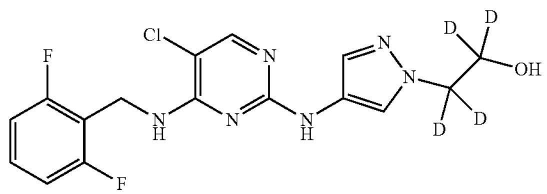 [SMILES: [2H]C([2H])(O)C([2H])([2H])n1cc(Nc2ncc(Cl)c(NCc3c(F)cccc3F)n2)cn1] | D | 5.42 | 385 |
| I-235 | 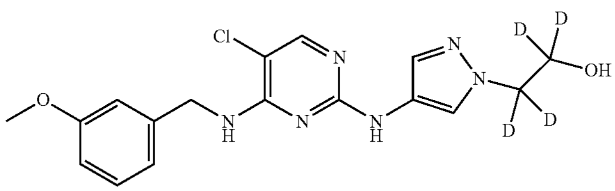 [SMILES: [2H]C([2H])(O)C([2H])([2H])n1cc(Nc2ncc(Cl)c(NCc3cccc(OC)c3)n2)cn1] | D | 5.21 | 379 |
| I-236 | 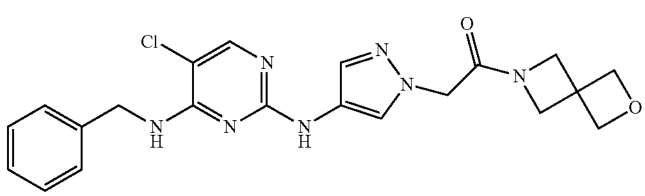 [SMILES: O=C(Cn1cc(Nc2ncc(Cl)c(NCc3ccccc3)n2)cn1)N1CC2(COC2)C1] | B | 0.93 | 440 |
| I-237 | 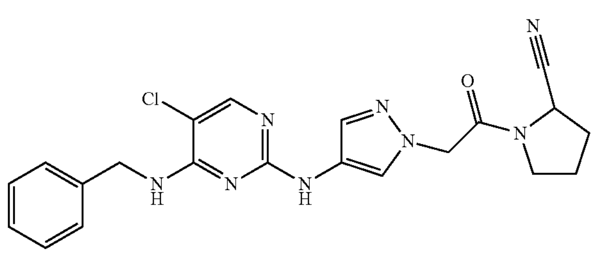 [SMILES: N#CC1CCCN1C(=O)Cn1cc(Nc2ncc(Cl)c(NCc3ccccc3)n2)cn1] | B | 0.97 | 437 |
| I-238 | 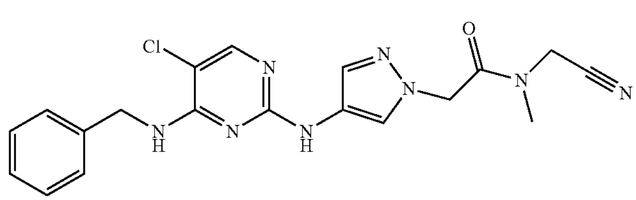 [SMILES: CN(CC#N)C(=O)Cn1cc(Nc2ncc(Cl)c(NCc3ccccc3)n2)cn1] | B | 0.98 | 411 |
| I-239 | 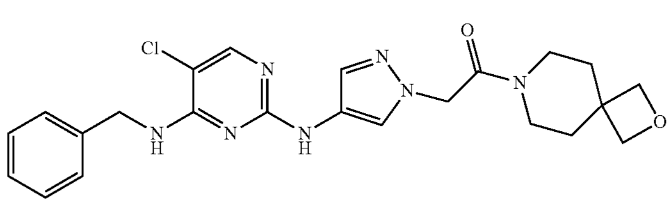 [SMILES: O=C(Cn1cc(Nc2ncc(Cl)c(NCc3ccccc3)n2)cn1)N1CCC2(CC1)COC2] | B | 0.97 | 468 |

TABLE 11-continued

Table of Examples

| Example | Structure | Analytical Method | RT (min) | m/z ES+ |
|---|---|---|---|---|
| I-240 | 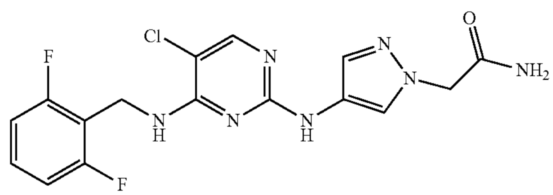 [SMILES: NC(=O)Cn1cc(Nc2ncc(Cl)c(NCc3c(F)cccc3F)n2)cn1] | B | 0.94 | 394 |
| I-241 | 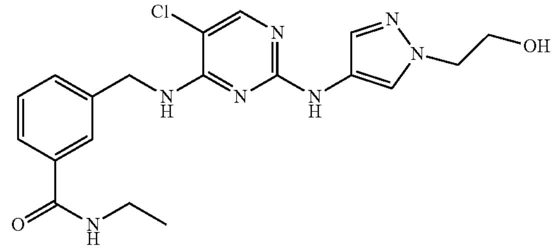 [SMILES: CCNC(=O)c1cccc(CNc2nc(Nc3cnn(CCO)c3)ncc2Cl)c1] | B | 0.86 | 416 |
| I-242 | 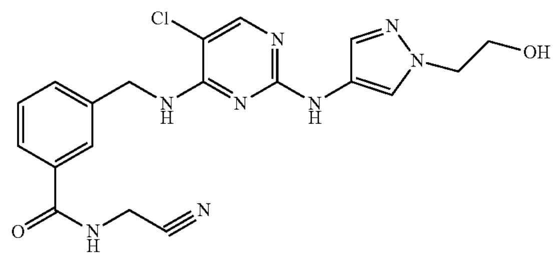 [SMILES: N#CCNC(=O)c1cccc(CNc2nc(Nc3cnn(CCO)c3)ncc2Cl)c1] | B | 0.85 | 427 |
| I-243 | 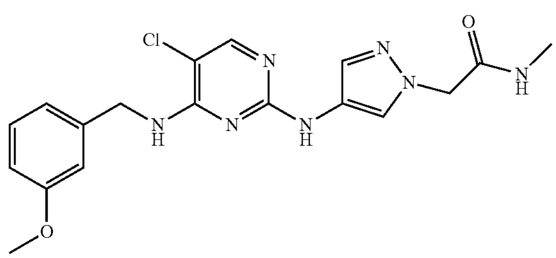 [SMILES: CNC(=O)Cn1cc(Nc2ncc(Cl)c(NCc3cccc(OC)c3)n2)cn1] | B | 0.94 | 402 |
| I-244 | 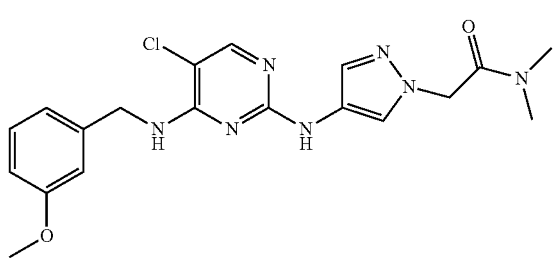 [SMILES: COc1cccc(CNc2nc(Nc3cnn(CC(=O)N(C)C)c3)ncc2Cl)c1] | B | 0.96 | 416 |
| I-245 | 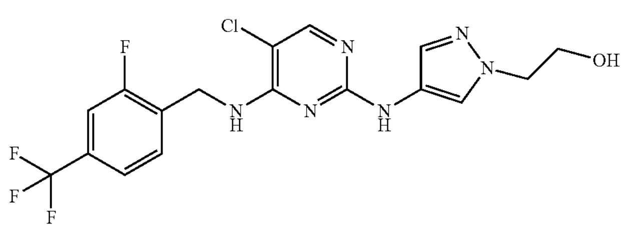 [SMILES: OCCn1cc(Nc2ncc(Cl)c(NCc3ccc(C(F)(F)F)cc3F)n2)cn1] | D | 0.89 | 429 |

TABLE 11-continued

Table of Examples

| Example | Structure | Analytical Method | RT (min) | m/z ES+ |
|---|---|---|---|---|
| I-246 | 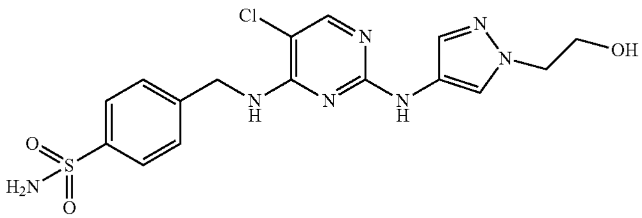 [SMILES: NS(=O)(=O)c1ccc(CNc2nc(Nc3cnn(CCO)c3)ncc2Cl)cc1] | D | 0.69 | 392 |
| I-247 | 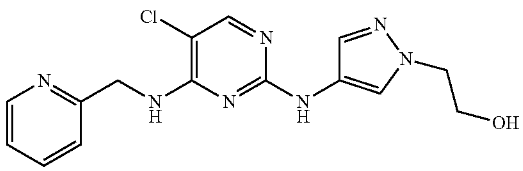 [SMILES: OCCn1cc(Nc2ncc(Cl)c(NCc3ccccn3)n2)cn1] | D | 0.76 | 346 |
| I-248 | 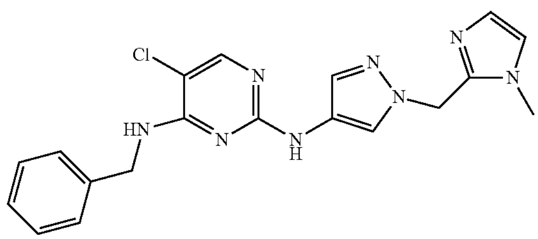 [SMILES: Cn1ccnc1Cn1cc(Nc2ncc(Cl)c(NCc3ccccc3)n2)cn1] | B | 4.16 | 395 |
| I-249 | 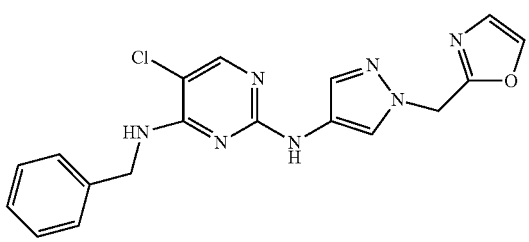 [SMILES: Clc1cnc(Nc2cnn(Cc3ncco3)c2)nc1NCc1ccccc1] | B | 5.86 | 382 |
| I-250 | 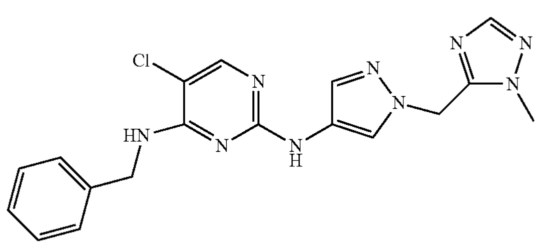 [SMILES: Cn1ncnc1Cn1cc(Nc2ncc(Cl)c(NCc3ccccc3)n2)cn1] | B | 5.5 | 396 |
| I-251 | 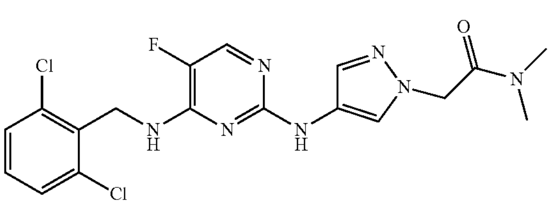 [SMILES: CN(C)C(=O)Cn1cc(Nc2ncc(F)c(NCc3c(Cl)cccc3Cl)n2)cn1] | D | 0.92 | 438 |

TABLE 11-continued

Table of Examples

| Example | Structure | Analytical Method | RT (min) | m/z ES+ |
|---|---|---|---|---|
| I-252 | 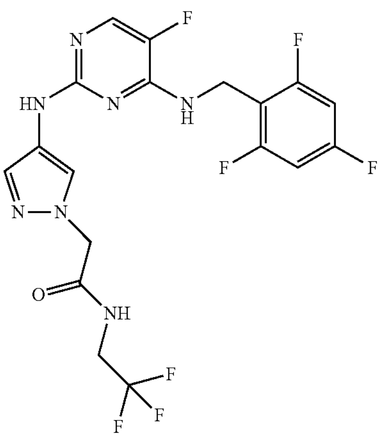 [SMILES: O=C(Cn1cc(Nc2ncc(F)c(NCc3c(F)cc(F)cc3F)n2)cn1)NCC(F)(F)F] | D | 1.01 | 478 |
| I-253 | 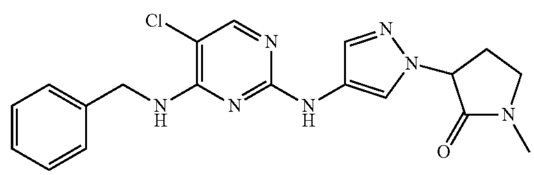 [SMILES: CN1CCC(n2cc(Nc3ncc(Cl)c(NCc4ccccc4)n3)cn2)C1=O] | B | 5.76 | 398 |
| I-254 | 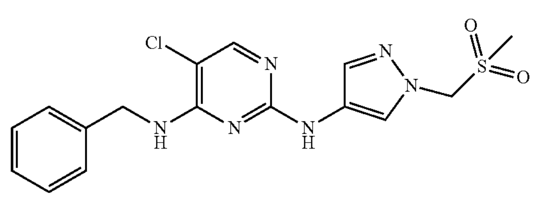 [SMILES: CS(=O)(=O)Cn1cc(Nc2ncc(Cl)c(NCc3ccccc3)n2)cn1] | B | 6.16 | 393 |
| I-255 | 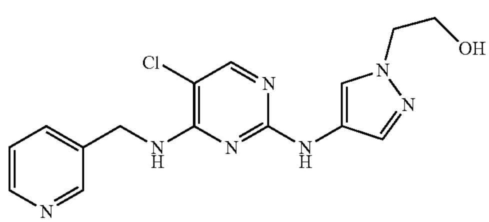 [SMILES: OCCn1cc(Nc2ncc(Cl)c(NCc3cccnc3)n2)cn1] | B | 6.55 | 346 |
| I-256 | 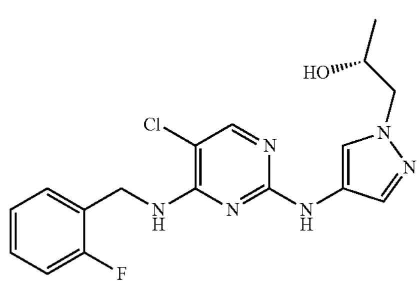 [SMILES: C[C@@H](O)Cn1cc(Nc2ncc(Cl)c(NCc3ccccc3F)n2)cn1] | D | 5.84 | 377 |

TABLE 11-continued

Table of Examples

| Example | Structure | Analytical Method | RT (min) | m/z ES+ |
|---------|-----------|-------------------|----------|---------|
| I-257 | 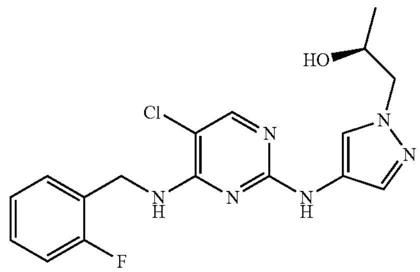 [SMILES: C[C@H](O)Cn1cc(Nc2ncc(Cl)c(NCc3ccccc3F)n2)cn1] | D | 5.87 | 377 |
| I-258 | 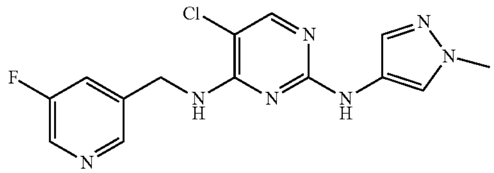 [SMILES: Cn1cc(Nc2ncc(Cl)c(NCc3cncc(F)c3)n2)cn1] | B | 4.92 | 334 |
| I-259 | 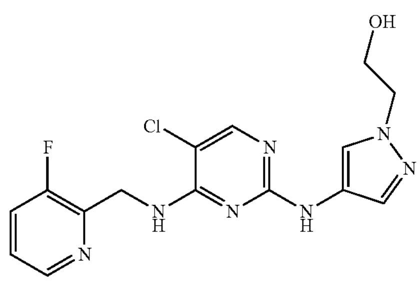 [SMILES: OCCn1cc(Nc2ncc(Cl)c(NCc3ncccc3F)n2)cn1] | B | 6.99 | 364 |
| I-260 | 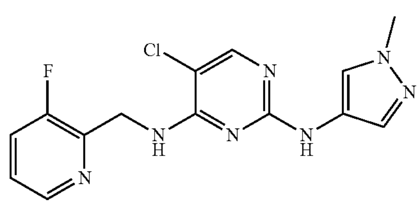 [SMILES: Cn1cc(Nc2ncc(Cl)c(NCc3ncccc3F)n2)cn1] | B | 7.92 | 334 |
| I-261 | 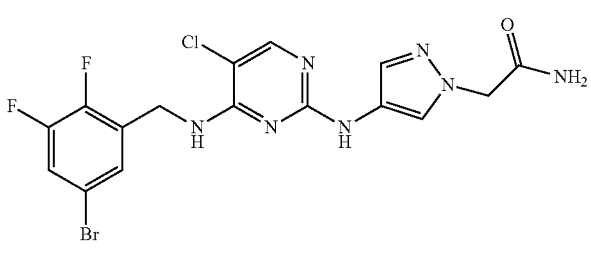 [SMILES: NC(=O)Cn1cc(Nc2ncc(Cl)c(NCc3cc(Br)cc(F)c3F)n2)cn1] | C | 1.00 | 472 |
| I-262 | 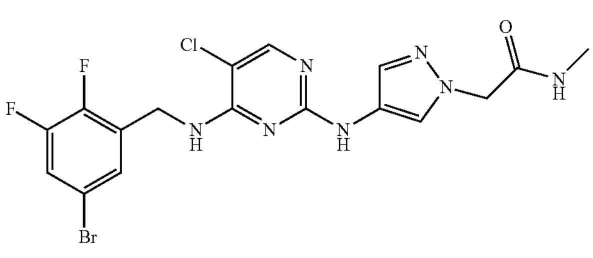 [SMILES: CNC(=O)Cn1cc(Nc2ncc(Cl)c(NCc3cc(Br)cc(F)c3F)n2)cn1] | C | 1.03 | 486 |

TABLE 11-continued

Table of Examples

| Example | Structure | Analytical Method | RT (min) | m/z ES+ |
|---|---|---|---|---|
| I-263 | 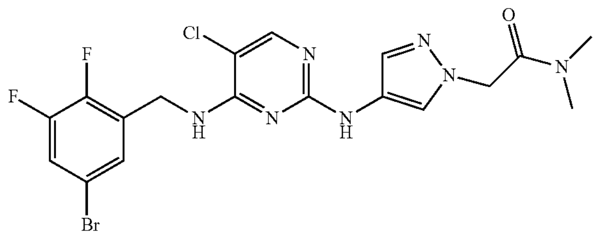 [SMILES: CN(C)C(=O)Cn1cc(Nc2ncc(Cl)c(NCc3cc(Br)cc(F)c3F)n2)cn1] | C | 1.04 | 500 |
| I-264 | 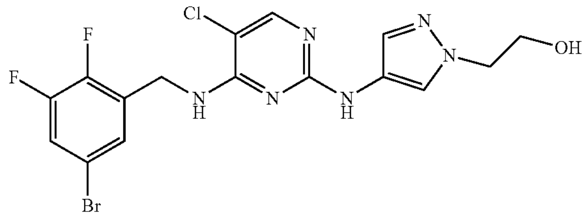 [SMILES: OCCn1cc(Nc2ncc(Cl)c(NCc3cc(Br)cc(F)c3F)n2)cn1] | C | 1.04 | 459 |
| I-265 | 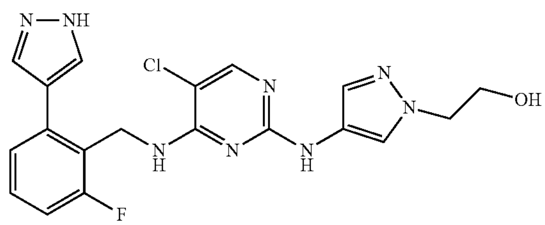 [SMILES: OCCn1cc(Nc2ncc(Cl)c(NCc3c(F)cccc3-c3cn[nH]c3)n2)cn1] | C | 0.94 | 429 |
| I-266 | 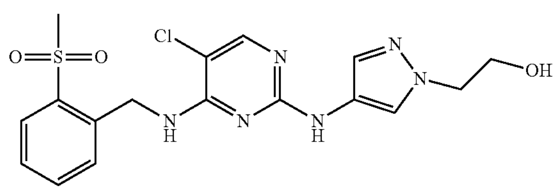 [SMILES: CS(=O)(=O)c1ccccc1CNc1nc(Nc2cnn(CCO)c2)ncc1Cl] | C | 0.89 | 423 |
| I-267 | 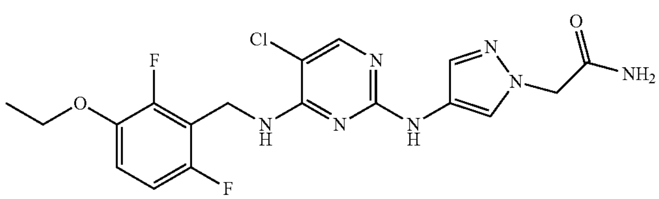 [SMILES: CCOc1ccc(F)c(CNc2nc(Nc3cnn(CC(N)=O)c3)ncc2Cl)c1F] | D | 0.99 | 438 |
| I-268 | 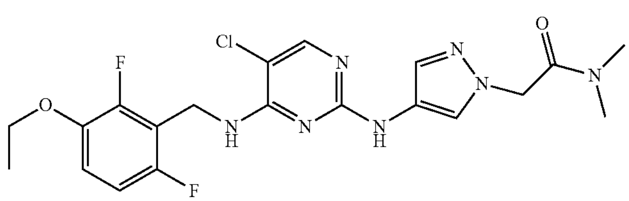 [SMILES: CCOc1ccc(F)c(CNc2nc(Nc3cnn(CC(=O)N(C)C)c3)ncc2Cl)c1F] | D | 1.04 | 466 |
| I-269 | 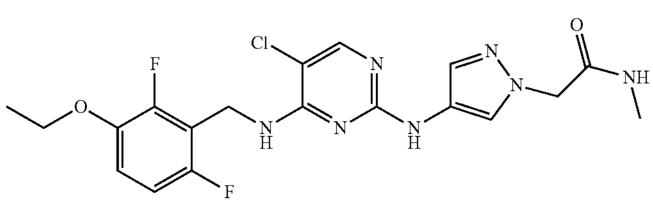 [SMILES: CCOc1ccc(F)c(CNc2nc(Nc3cnn(CC(=O)NC)c3)ncc2Cl)c1F] | D | 1.01 | 452 |

TABLE 11-continued

Table of Examples

| Example | Structure | Analytical Method | RT (min) | m/z ES+ |
|---|---|---|---|---|
| I-270 | 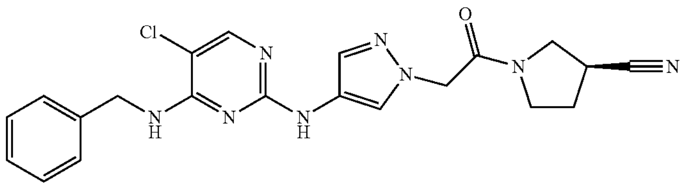 [SMILES: N#C[C@H]1CCN(C(=O)Cn2cc(Nc3ncc(Cl)c(NCc4ccccc4)n3)cn2)C1] | D | 1.05 | 437 |
| I-271 | 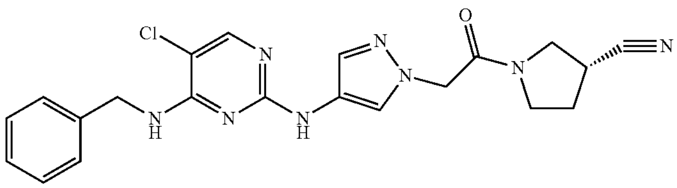 [SMILES: N#C[C@@H]1CCN(C(=O)Cn2cc(Nc3ncc(Cl)c(NCc4ccccc4)n3)cn2)C1] | D | 1.04 | 437 |
| I-272 | 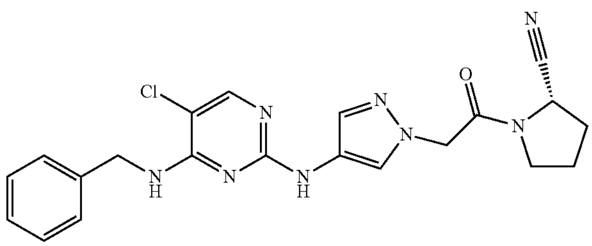 | D | 1.08 | 437 |
| I-273 | 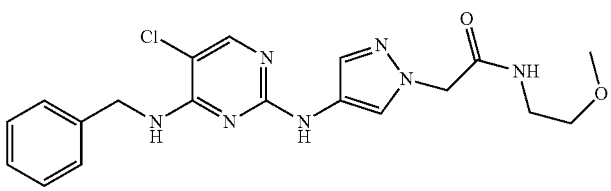 [SMILES: COCCNC(=O)Cn1cc(Nc2ncc(Cl)c(NCc3ccccc3)n2)cn1] | D | 0.96 | 416 |
| I-274 | 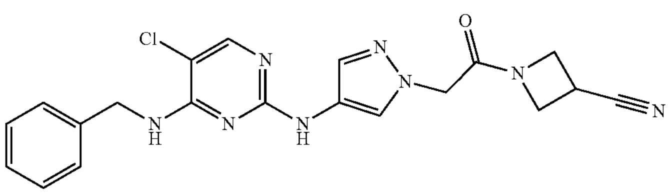 [SMILES: N#CC1CN(C(=O)Cn2cc(Nc3ncc(Cl)c(NCc4ccccc4)n3)cn2)C1] | D | 0.96 | 423 |
| I-275 | 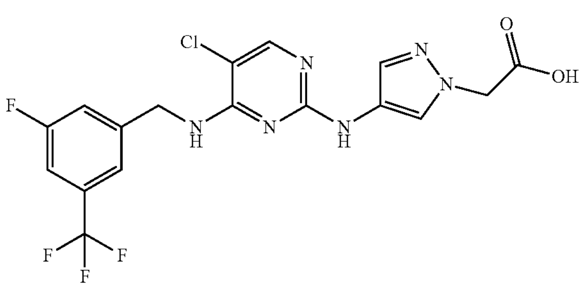 [SMILES: O=C(O)Cn1cc(Nc2ncc(Cl)c(NCc3cc(F)cc(C(F)(F)F)c3)n2)cn1] | D | 0.89 | 444 |
| I-276 | 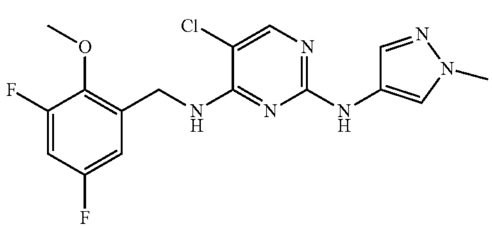 [SMILES: COc1c(F)cc(F)cc1CNc1nc(Nc2cnn(C)c2)ncc1Cl] | D | 1.04 | 381 |

TABLE 11-continued

Table of Examples

| Example | Structure | Analytical Method | RT (min) | m/z ES+ |
|---|---|---|---|---|
| I-277 | 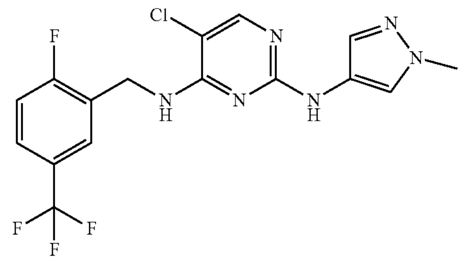 [SMILES: Cn1cc(Nc2ncc(Cl)c(NCc3cc(C(F)(F)F)ccc3F)n2)cn1] | D | 1.06 | 401 |
| I-278 | 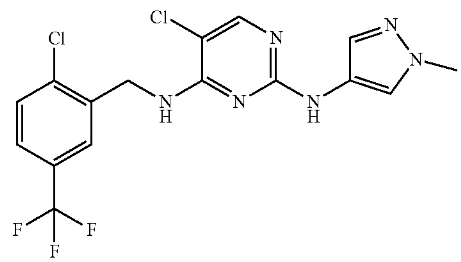 [SMILES: Cn1cc(Nc2ncc(Cl)c(NCc3cc(C(F)(F)F)ccc3Cl)n2)cn1] | D | 1.10 | 417 |
| I-279 | 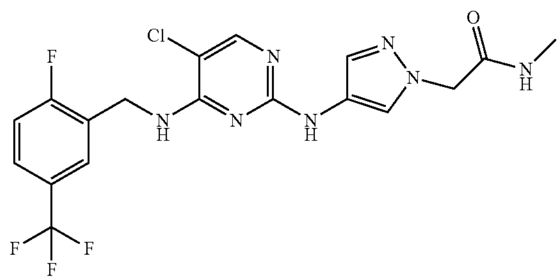 [SMILES: CNC(=O)Cn1cc(Nc2ncc(Cl)c(NCc3cc(C(F)(F)F)ccc3F)n2)cn1] | D | 1.00 | 458 |
| I-280 | 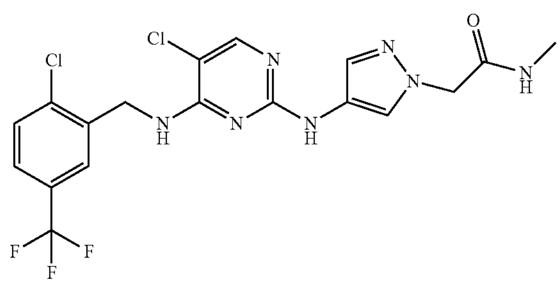 [SMILES: CNC(=O)Cn1cc(Nc2ncc(Cl)c(NCc3cc(C(F)(F)F)ccc3Cl)n2)cn1] | D | 1.02 | 474 |
| I-281 | 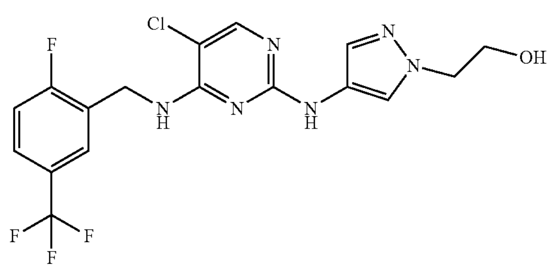 [SMILES: OCCn1cc(Nc2ncc(Cl)c(NCc3cc(C(F)(F)F)ccc3F)n2)cn1] | D | 1.01 | 431 |
| I-282 | 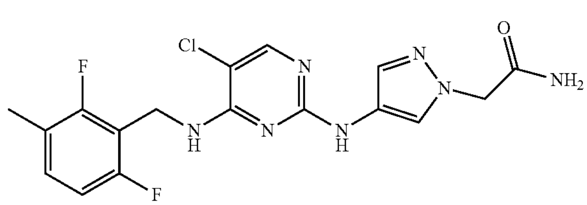 [SMILES: Cc1ccc(F)c(CNc2nc(Nc3cnn(CC(N)=O)c3)ncc2Cl)c1F] | D | 0.99 | 408 |

TABLE 11-continued
Table of Examples
| Example | Structure | Analytical Method | RT (min) | m/z ES+ |
|---|---|---|---|---|
| I-283 | 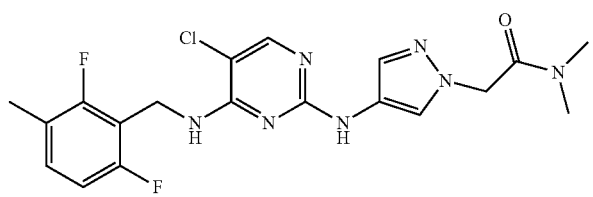 | D | 1.04 | 436 |
| I-284 | 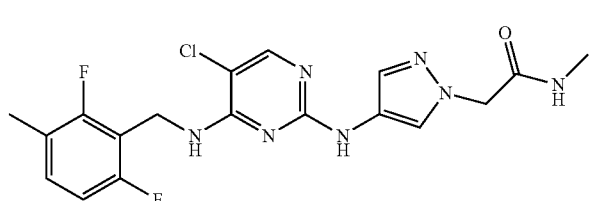 | D | 1.01 | 422 |
| I-285 | 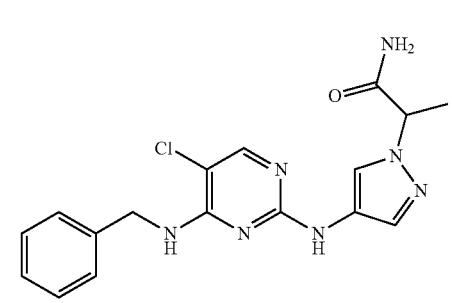 [SMILES: CC(C(N)=O)n1cc(Nc2ncc(Cl)c(NCc3ccccc3)n2)cn1] | B | 5.27 | 372 |
| I-286 | 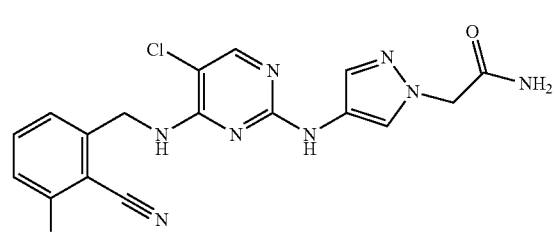 | B | 5.20 | 401 |
| I-287 | 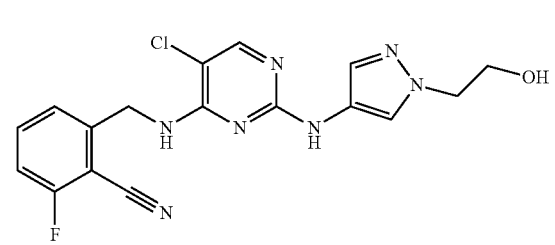 [SMILES: N#Cc1c(F)cccc1CNc1nc(Nc2cnn(CCO)c2)ncc1Cl] | B | 5.40 | 388 |
| I-288 | 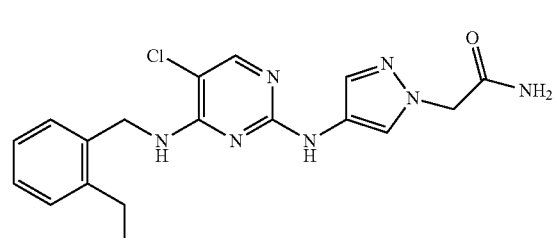 | C | 0.85 | 388 |

TABLE 11-continued

Table of Examples

| Example | Structure | Analytical Method | RT (min) | m/z ES+ |
|---|---|---|---|---|
| I-289 | 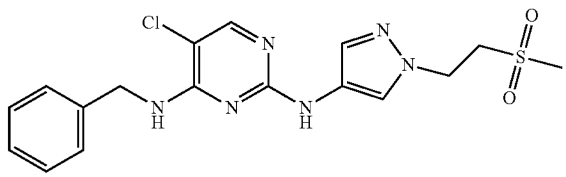 [SMILES: CS(=O)(=O)CCn1cc(Nc2ncc(Cl)c(NCc3ccccc3)n2)cn1] | B | 5.53 | 407 |
| I-290 | 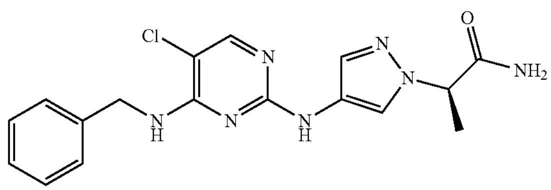 [SMILES: C[C@H](C(N)=O)n1cc(Nc2ncc(Cl)c(NCc3ccccc3)n2)cn1] | B | 5.27 | 372 |
| I-291 | 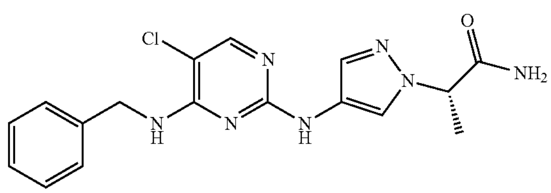 [SMILES: C[C@@H](C(N)=O)n1cc(Nc2ncc(Cl)c(NCc3ccccc3)n2)cn1] | B | 5.33 | 372 |
| I-292 | 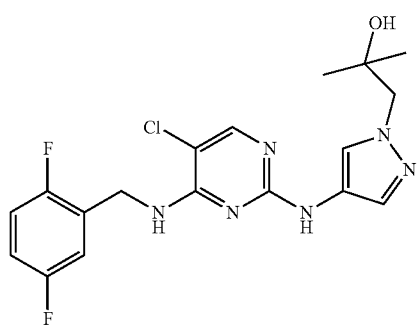 [SMILES: CC(C)(O)Cn1cc(Nc2ncc(Cl)c(NCc3cc(F)ccc3F)n2)cn1] | B | 6.11 | 409 |
| I-293 | 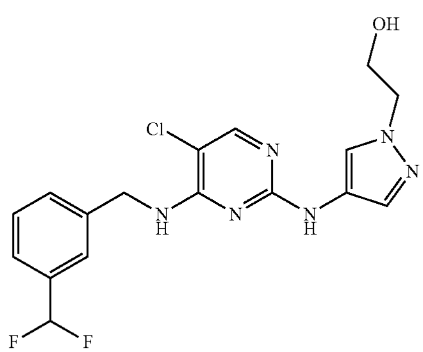 [SMILES: OCCn1cc(Nc2ncc(Cl)c(NCc3cccc(C(F)F)c3)n2)cn1] | D | 0.82 | 395 |

TABLE 11-continued

Table of Examples

| Example | Structure | Analytical Method | RT (min) | m/z ES+ |
|---------|-----------|-------------------|----------|---------|
| I-294 | 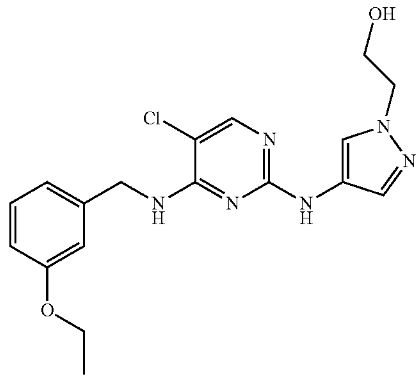 [SMILES: CCOc1cccc(CNc2nc(Nc3cnn(CCO)c3)ncc2Cl)c1] | D | 0.84 | 389 |
| I-295 | 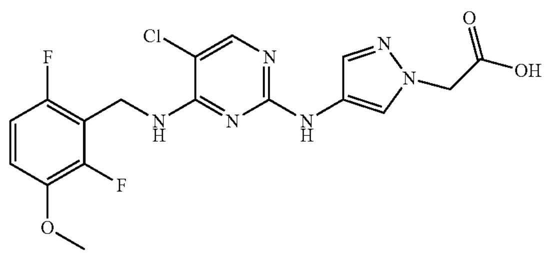 [SMILES: COc1ccc(F)c(CNc2nc(Nc3cnn(CC(=O)O)c3)ncc2Cl)c1F] | C | 0.82 | 424 |
| I-296 | 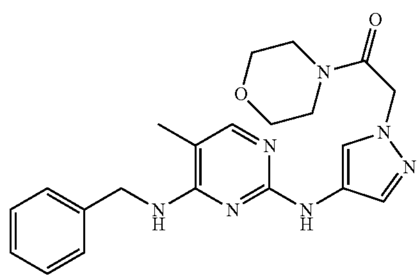 [SMILES: Cc1cnc(Nc2cnn(CC(=O)N3CCOCC3)c2)nc1NCc1ccccc1] | D | 0.92 | 408 |
| I-297 | 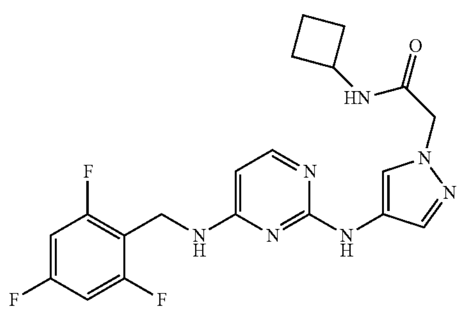 [SMILES: O=C(Cn1cc(Nc2nccc(NCc3c(F)cc(F)cc3F)n2)cn1)NC1CCC1] | D | 1.02 | 401 |
| I-298 | 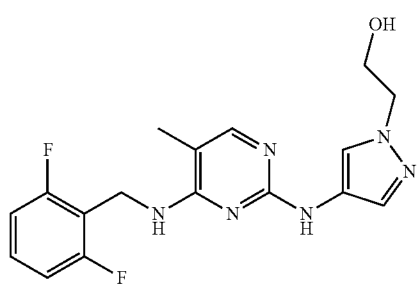 [SMILES: Cc1cnc(Nc2cnn(CCO)c2)nc1NCc1c(F)cccc1F] | D | 0.93 | 361 |

TABLE 11-continued

Table of Examples

| Example | Structure | Analytical Method | RT (min) | m/z ES+ |
|---------|-----------|-------------------|----------|---------|
| I-299 | 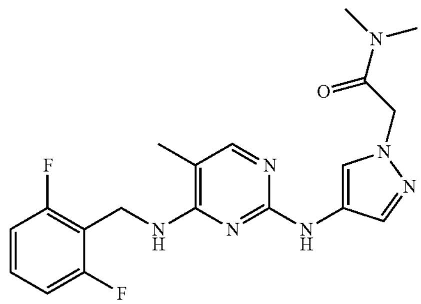 [SMILES: Cc1cnc(Nc2cnn(CC(=O)N(C)C)c2)nc1NCc1c(F)cccc1F] | D | 0.94 | 402 |
| I-300 | 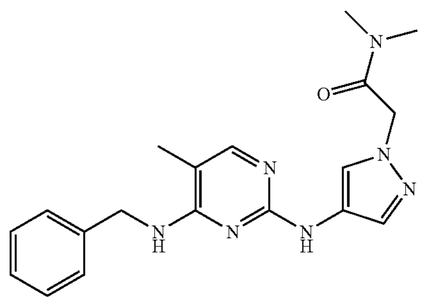 [SMILES: Cc1cnc(Nc2cnn(CC(=O)N(C)C)c2)nc1NCc1ccccc1] | D | 0.92 | 366 |
| I-301 | 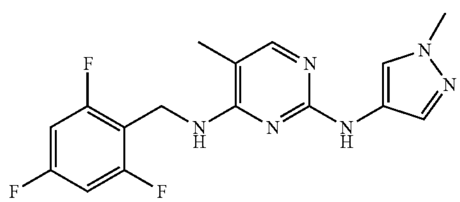 [SMILES: Cc1cnc(Nc2cnn(C)c2)nc1NCc1c(F)cc(F)cc1F] | C | 1.01 | 349 |
| I-302 | 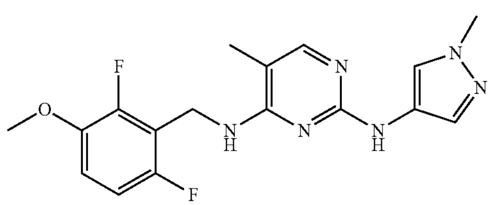 [SMILES: COc1ccc(F)c(CNc2nc(Nc3cnn(C)c3)ncc2C)c1F] | D | 0.99 | 361 |
| I-303 | 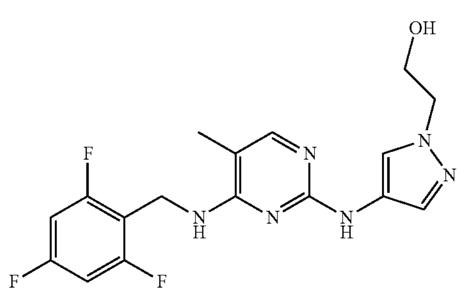 [SMILES: Cc1cnc(Nc2cnn(CCO)c2)nc1NCc1c(F)cc(F)cc1F] | D | 0.95 | 379 |

TABLE 11-continued

Table of Examples

| Example | Structure | Analytical Method | RT (min) | m/z ES+ |
|---|---|---|---|---|
| I-304 | 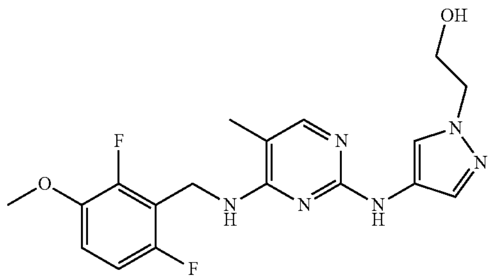 [SMILES: COc1ccc(F)c(CNc2nc(Nc3cnn(CCO)c3)ncc2C)c1F] | D | 0.93 | 391 |
| I-305 | 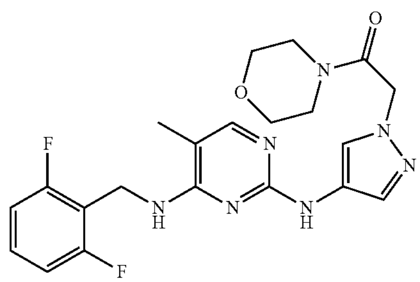 [SMILES: Cc1cnc(Nc2cnn(CC(=O)N3CCOCC3)c2)nc1NCc1c(F)cccc1F] | D | 0.94 | 444 |
| I-306 | 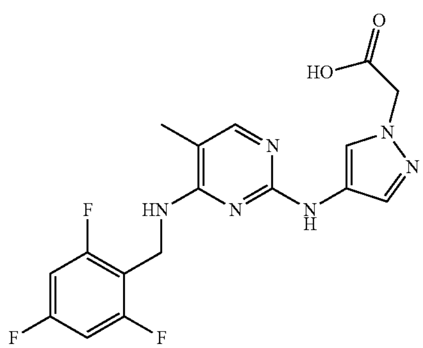 [SMILES: Cc1cnc(Nc2cnn(CC(=O)O)c2)nc1NCc1c(F)cc(F)cc1F] | C | 0.78 | 393 |
| I-307 | 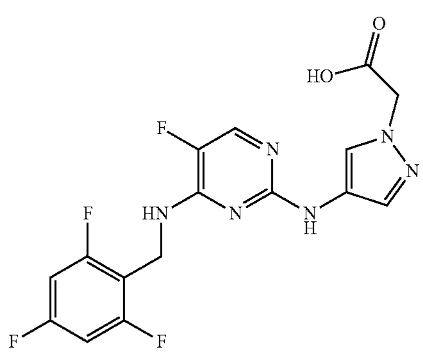 [SMILES: O=C(O)Cn1cc(Nc2ncc(F)c(NCc3c(F)cc(F)cc3F)n2)cn1] | C | 0.76 | 397 |

TABLE 11-continued

Table of Examples

| Example | Structure | Analytical Method | RT (min) | m/z ES+ |
|---|---|---|---|---|
| I-308 | 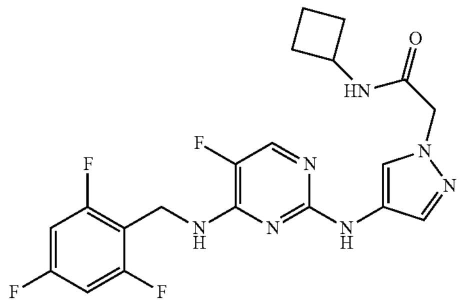 [SMILES: O=C(Cn1cc(Nc2ncc(F)c(NCc3c(F)cc(F)cc3F)n2)cn1)NC1CCC1] | D | 1.03 | 450 |
| I-309 | 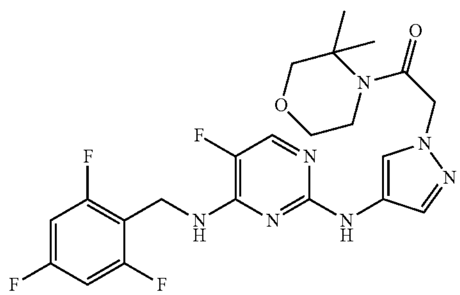 [SMILES: CC1(C)COCCN1C(=O)Cn1cc(Nc2ncc(F)c(NCc3c(F)cc(F)cc3F)n2)cn1] | D | 1.03 | 494 |
| I-310 | 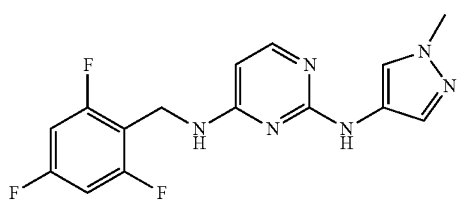 [SMILES: Cn1cc(Nc2nccc(NCc3c(F)cc(F)cc3F)n2)cn1] | D | 0.97 | 335 |
| I-311 | 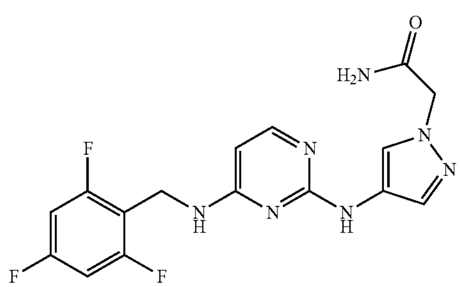 [SMILES: NC(=O)Cn1cc(Nc2nccc(NCc3c(F)cc(F)cc3F)n2)cn1] | D | 0.89 | 378 |
| I-312 | 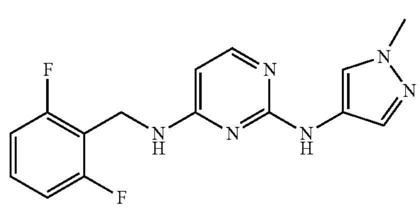 [SMILES: Cn1cc(Nc2nccc(NCc3c(F)cccc3F)n2)cn1] | D | 0.94 | 317 |

TABLE 11-continued
Table of Examples
| Example | Structure | Analytical Method | RT (min) | m/z ES+ |
|---------|-----------|-------------------|----------|---------|
| I-313 | 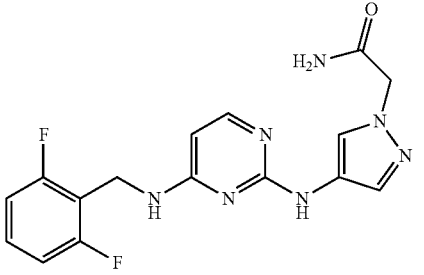 [SMILES: NC(=O)Cn1cc(Nc2nccc(NCc3c(F)cccc3F)n2)cn1] | D | 0.87 | 360 |
| I-314 | 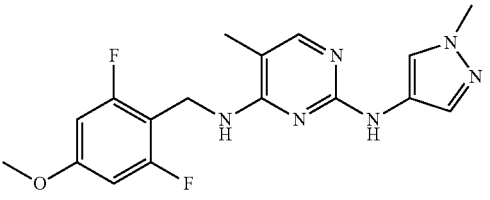 [SMILES: COc1cc(F)c(CNc2nc(Nc3cnn(C)c3)ncc2C)c(F)c1] | D | 1.01 | 361 |
| I-315 | 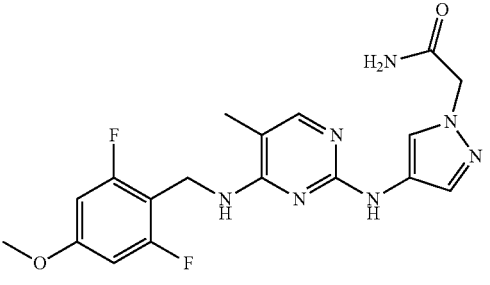 [SMILES: COc1cc(F)c(CNc2nc(Nc3cnn(CC(N)=O)c3)ncc2C)c(F)c1] | D | 0.93 | 404 |
| I-316 | 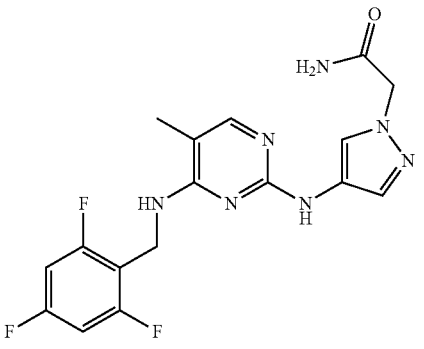 [SMILES: Cc1cnc(Nc2cnn(CC(N)=O)c2)nc1NCc1c(F)cc(F)cc1F] | D | 0.92 | 292 |
| I-317 | 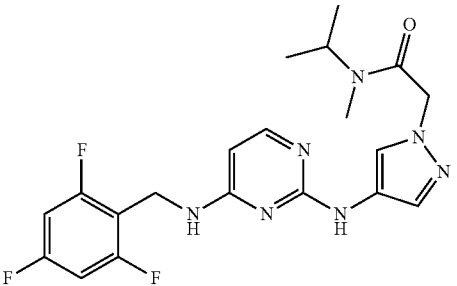 [SMILES: CC(C)N(C)C(=O)Cn1cc(Nc2nccc(NCc3c(F)cc(F)cc3F)n2)cn1] | D | 1.01 | 434 |

TABLE 11-continued

Table of Examples

| Example | Structure | Analytical Method | RT (min) | m/z ES+ |
|---------|-----------|-------------------|----------|---------|
| I-318 | 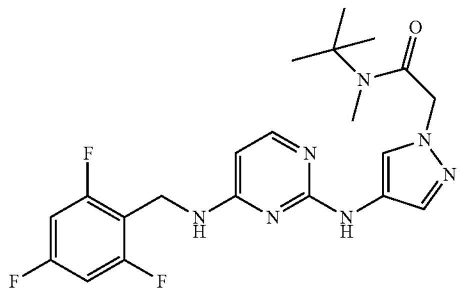 [SMILES: CN(C(=O)Cn1cc(Nc2nccc(NCc3c(F)cc(F)cc3F)n2)cn1)C(C)(C)C] | D | 1.03 | 434 |
| I-319 | 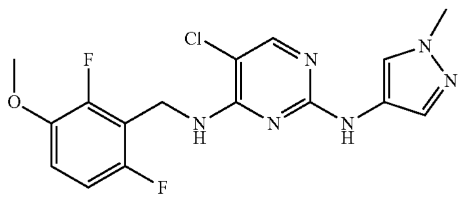 [SMILES: COc1ccc(F)c(CNc2nc(Nc3cnn(C)c3)ncc2Cl)c1F] | D | 0.86 | 381 |
| I-320 | 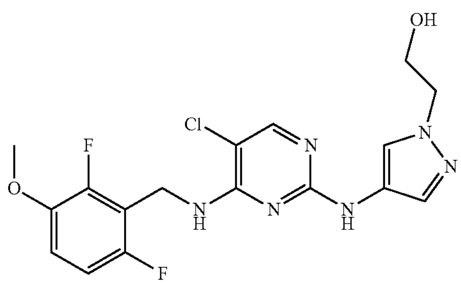 [SMILES: COc1ccc(F)c(CNc2nc(Nc3cnn(CCO)c3)ncc2Cl)c1F] | G | 1.68 | 410 |
| I-321 | 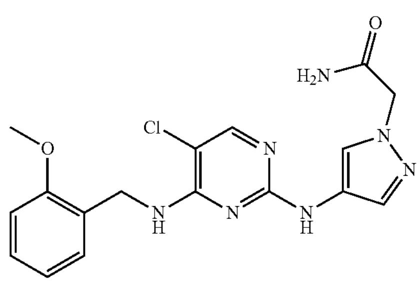 [SMILES: COc1ccccc1CNc1nc(Nc2cnn(CC(N)=O)c2)ncc1Cl] | D | 1.61 | 387 |
| I-322 | 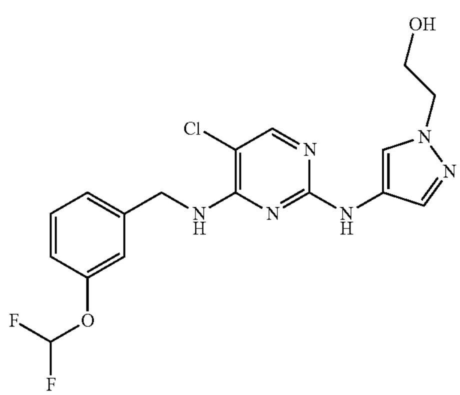 [SMILES: OCCn1cc(Nc2ncc(Cl)c(NCc3cccc(OC(F)F)c3)n2)cn1] | D | 0.99 | 411 |

TABLE 11-continued

Table of Examples

| Example | Structure | Analytical Method | RT (min) | m/z ES+ |
|---|---|---|---|---|
| I-323 | 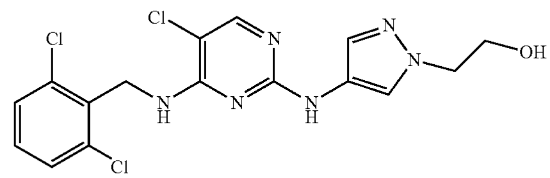 [SMILES: OCCn1cc(Nc2ncc(Cl)c(NCc3c(Cl)cccc3Cl)n2)cn1] | D | 1.04 | 411 |
| I-324 | 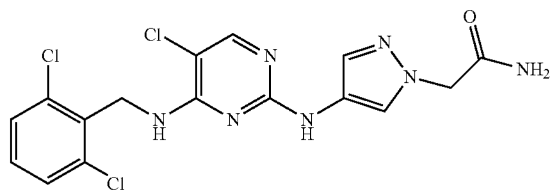 [SMILES: NC(=O)Cn1cc(Nc2ncc(Cl)c(NCc3c(Cl)cccc3Cl)n2)cn1] | D | 1.00 | 424 |
| I-325 | 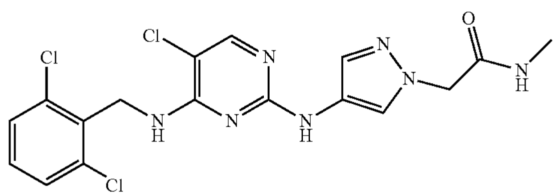 [SMILES: CNC(=O)Cn1cc(Nc2ncc(Cl)c(NCc3c(Cl)cccc3Cl)n2)cn1] | D | 1.04 | 438 |
| I-326 | 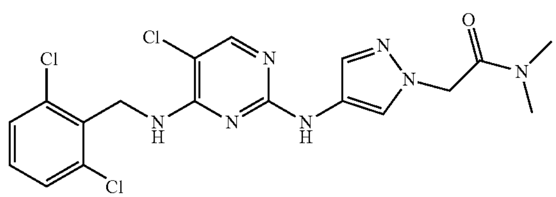 [SMILES: CN(C)C(=O)Cn1cc(Nc2ncc(Cl)c(NCc3c(Cl)cccc3Cl)n2)cn1] | D | 1.04 | 452 |
| I-327 | 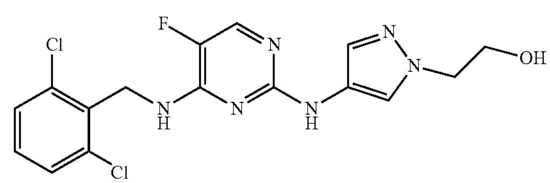 [SMILES: OCCn1cc(Nc2ncc(F)c(NCc3c(Cl)cccc3Cl)n2)cn1] | D | 0.98 | 393 |
| I-328 | 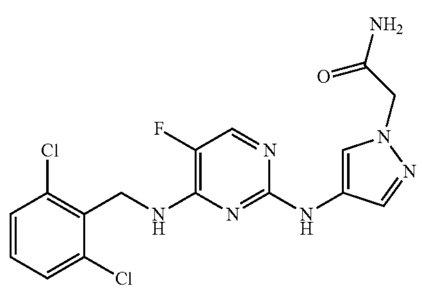 [SMILES: NC(=O)Cn1cc(Nc2ncc(F)c(NCc3c(Cl)cccc3Cl)n2)cn1] | D | 1.00 | 408 |
| I-329 | 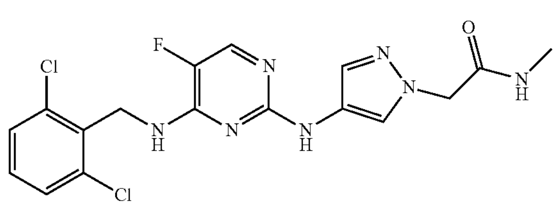 [SMILES: CNC(=O)Cn1cc(Nc2ncc(F)c(NCc3c(Cl)cccc3Cl)n2)cn1] | D | 0.97 | 422 |

TABLE 11-continued

Table of Examples

| Example | Structure | Analytical Method | RT (min) | m/z ES+ |
|---|---|---|---|---|
| I-330 | 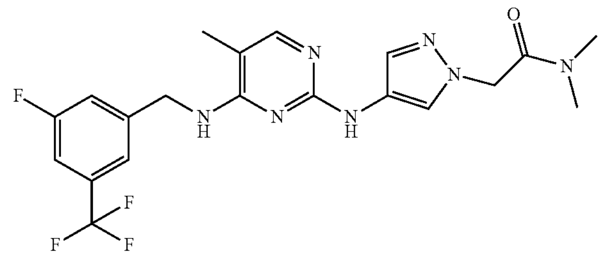 [SMILES: Cc1cnc(Nc2cnn(CC(=O)N(C)C)c2)nc1NCc1cc(F)cc(C(F)(F)F)c1] | D | 1.04 | 452 |
| I-331 | 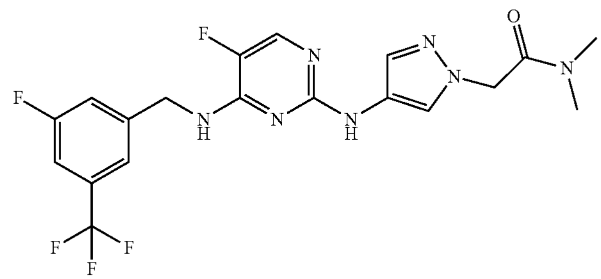 [SMILES: CN(C)C(=O)Cn1cc(Nc2ncc(F)c(NCc3cc(F)cc(C(F)(F)F)c3)n2)cn1] | D | 0.86 | 455 |
| I-332 | 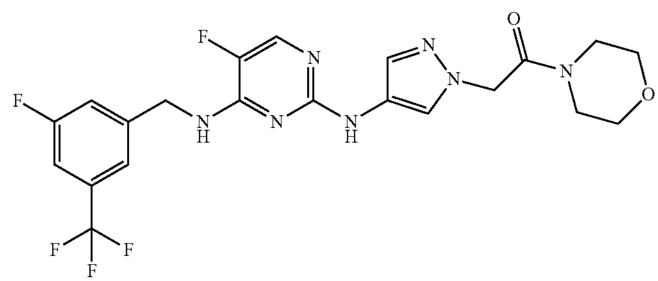 [SMILES: O=C(Cn1cc(Nc2ncc(F)c(NCc3cc(F)cc(C(F)(F)F)c3)n2)cn1)N1CCOCC1] | D | 0.86 | 497 |
| I-333 | 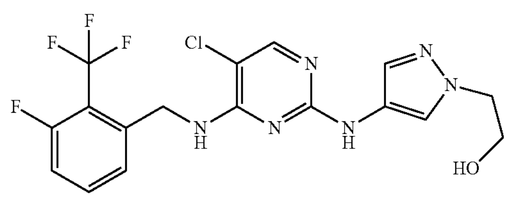 [SMILES: OCCn1cc(Nc2ncc(Cl)c(NCc3cccc(F)c3C(F)(F)F)n2)cn1] | D | 0.90 | 429 |
| I-334 | 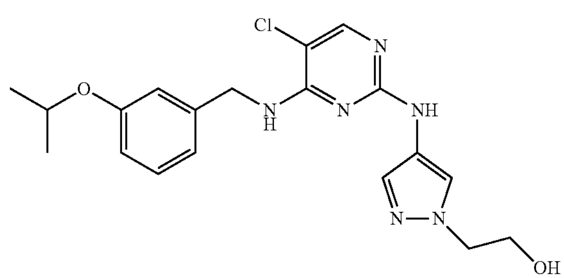 [SMILES: CC(C)Oc1cccc(CNc2nc(Nc3cnn(CCO)c3)ncc2Cl)c1] | G | 6.05 | 404 |
| I-335 | 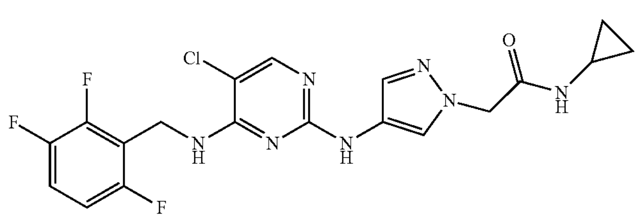 [SMILES: O=C(Cn1cc(Nc2ncc(Cl)c(NCc3c(F)ccc(F)c3F)n2)cn1)NC1CC1] | G | 6.61 | 453 |

TABLE 11-continued
Table of Examples
| Example | Structure | Analytical Method | RT (min) | m/z ES+ |
|---|---|---|---|---|
| I-336 | 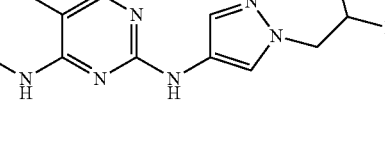 | G | 7.60 | 420 |
| I-337 | 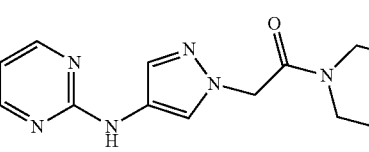 | G | 3.99 | 430 |
| I-338 | 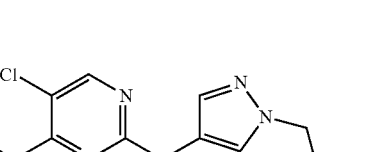 | G | 3.69 | 430 |
| I-339 | 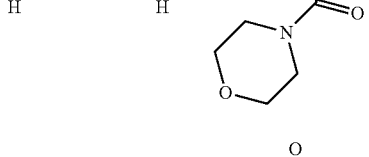 | G | 4.68 | 448 |
| I-340 | 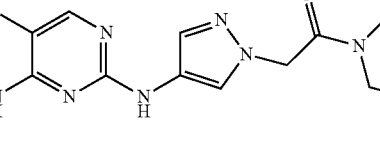 | G | 6.31 | 370 |
| I-341 | 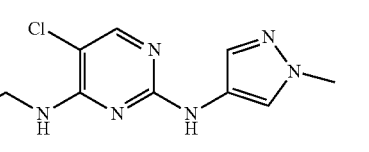 | G | 5.42 | 414 |
| I-342 | 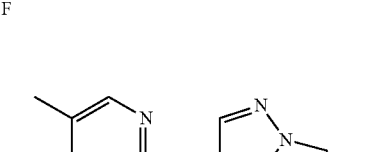 | G | 5.52 | 349 |

TABLE 11-continued

Table of Examples

| Example | Structure | Analytical Method | RT (min) | m/z ES+ |
|---------|-----------|-------------------|----------|---------|
| I-343 | 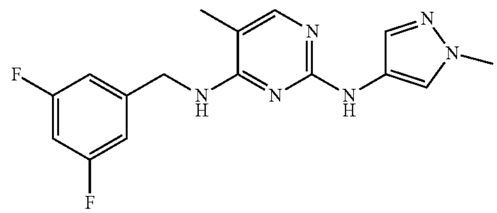 [SMILES: Cc1cnc(Nc2cnn(C)c2)nc1NCc1cc(F)cc(F)c1] | G | 5.59 | 331 |
| I-344 | 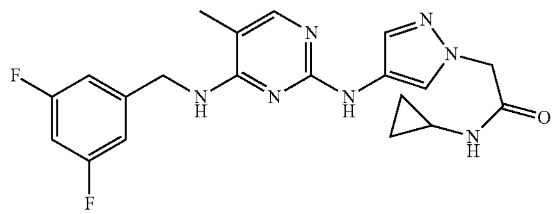 [SMILES: Cc1cnc(Nc2cnn(CC(=O)NC3CC3)c2)nc1NCc1cc(F)cc(F)c1] | G | 5.44 | 414 |
| I-345 | 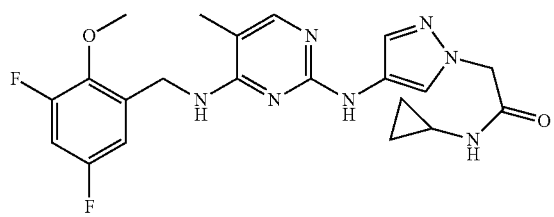 [SMILES: COc1c(F)cc(F)cc1CNc1nc(Nc2cnn(CC(=O)NC3CC3)c2)ncc1C] | G | 5.8 | 444 |
| I-346 | 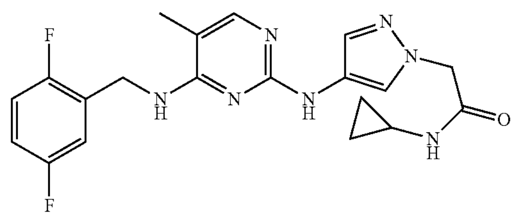 [SMILES: Cc1cnc(Nc2cnn(CC(=O)NC3CC3)c2)nc1NCc1cc(F)ccc1F] | G | 5.31 | 414 |
| I-347 | 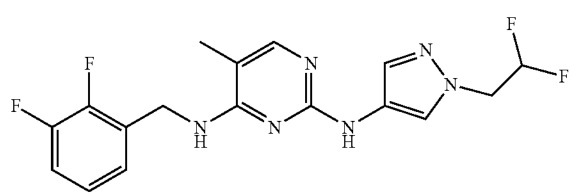 [SMILES: Cc1cnc(Nc2cnn(CC(F)F)c2)nc1NCc1cccc(F)c1F] | G | 5.93 | 381 |
| I-348 | 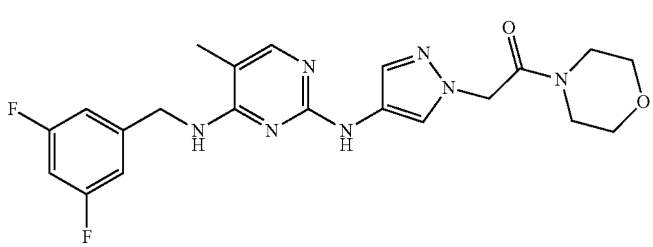 [SMILES: Cc1cnc(Nc2cnn(CC(=O)N3CCOCC3)c2)nc1NCc1cc(F)cc(F)c1] | G | 5.3 | 444 |
| I-349 | 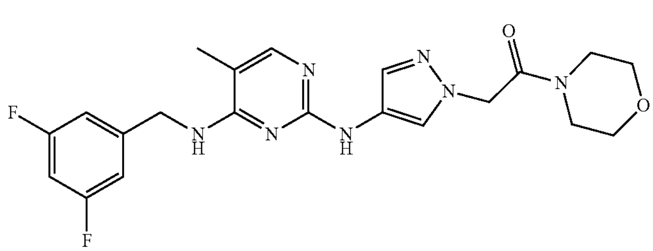 [SMILES: Cc1cnc(Nc2cnn(CC(=O)N3CCOCC3)c2)nc1NCc1cc(F)cc(F)c1] | G | 6.03 | 411 |

TABLE 11-continued

Table of Examples

| Example | Structure | Analytical Method | RT (min) | m/z ES+ |
|---------|-----------|-------------------|----------|---------|
| I-350 | 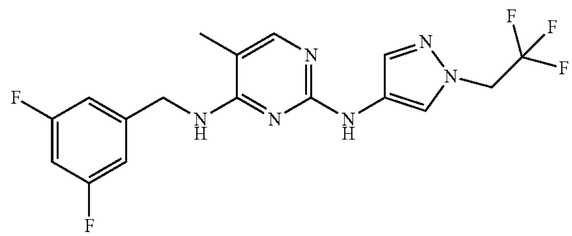 [SMILES: Cc1cnc(Nc2cnn(CC(F)(F)F)c2)nc1NCc1cc(F)cc(F)c1] | G | 6.41 | 399 |
| I-351 | 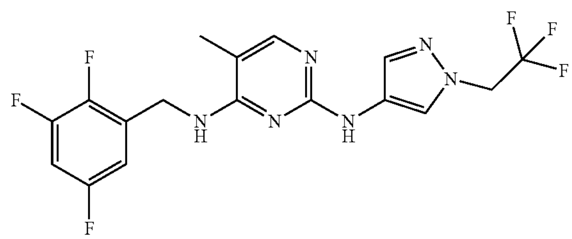 [SMILES: Cc1cnc(Nc2cnn(CC(F)(F)F)c2)nc1NCc1cc(F)cc(F)c1F] | G | 6.15 | 417 |
| I-352 | 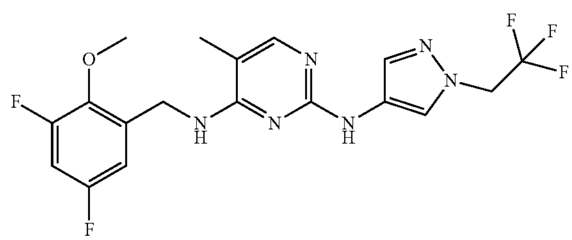 [SMILES: COc1c(F)cc(F)cc1CNc1nc(Nc2cnn(CC(F)(F)F)c2)ncc1C] | G | 6.51 | 429 |
| I-353 | 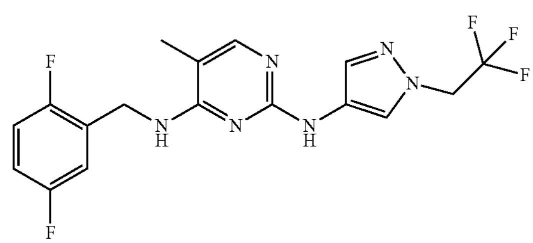 [SMILES: Cc1cnc(Nc2cnn(CC(F)(F)F)c2)nc1NCc1cc(F)ccc1F] | G | 6.22 | 399 |
| I-354 | 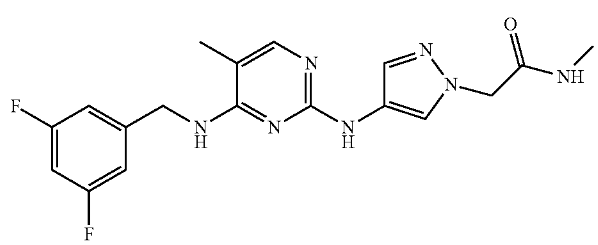 [SMILES: CNC(=O)Cn1cc(Nc2ncc(C)c(NCc3cc(F)cc(F)c3)n2)cn1] | G | 5.14 | 388 |
| I-355 | 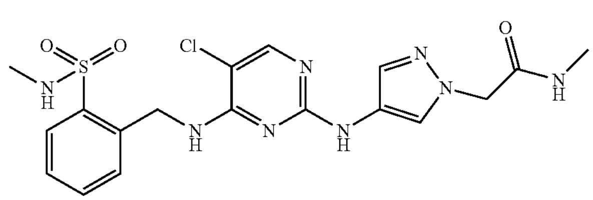 | F | 1.42 | 466 |

TABLE 11-continued

Table of Examples

| Example | Structure | Analytical Method | RT (min) | m/z ES+ |
|---------|-----------|-------------------|----------|---------|
| I-356 | 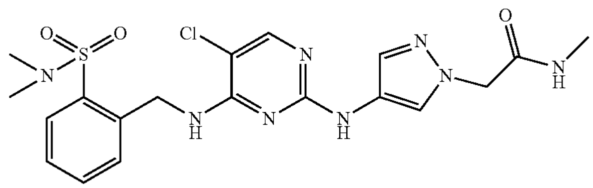 | F | 1.58 | 480 |
| I-357 | 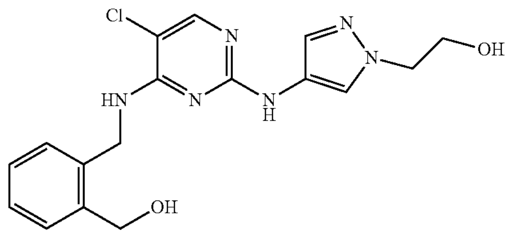 [SMILES: OCCn1cc(Nc2ncc(Cl)c(NCc3ccccc3CO)n2)cn1] | G | 4.58 | 376 |
| I-358 | 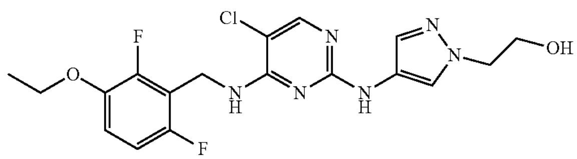 [SMILES: CCOc1ccc(F)c(CNc2nc(Nc3cnn(CCO)c3)ncc2Cl)c1F] | G | 6.03 | 426 |
| I-359 | 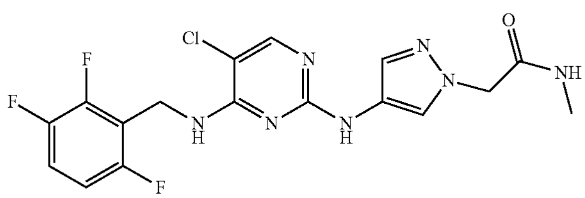 [SMILES: CNC(=O)Cn1cc(Nc2ncc(Cl)c(NCc3c(F)ccc(F)c3F)n2)cn1] | G | 5.70 | 413 |
| I-360 | 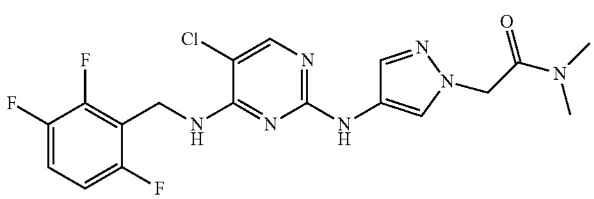 [SMILES: CN(C)C(=O)Cn1cc(Nc2ncc(Cl)c(NCc3c(F)ccc(F)c3F)n2)cn1] | G | 5.79 | 441 |
| I-361 | 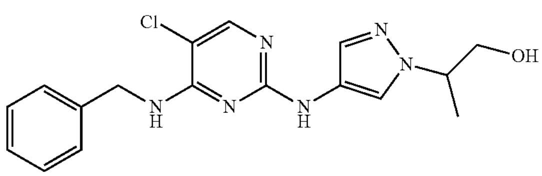 [SMILES: CC(CO)n1cc(Nc2ncc(Cl)c(NCc3ccccc3)n2)cn1] | G | 5.41 | 360 |
| I-362 | 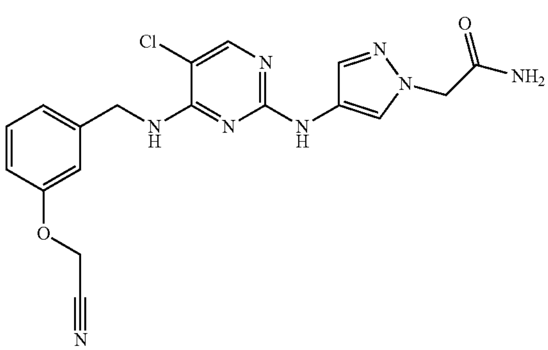 [SMILES: N#CCOc1cccc(CNc2nc(Nc3cnn(CC(N)=O)c3)ncc2Cl)c1] | G | 5.01 | 414 |

TABLE 11-continued

Table of Examples

| Example | Structure | Analytical Method | RT (min) | m/z ES+ |
|---|---|---|---|---|
| I-363 | 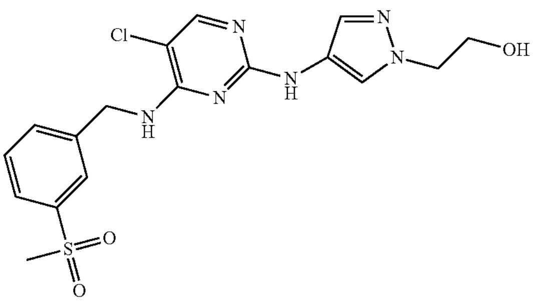 [SMILES: CS(=O)(=O)c1cccc(CNc2nc(Nc3cnn(CCO)c3)ncc2Cl)c1] | G | 4.54 | 424 |
| I-364 | 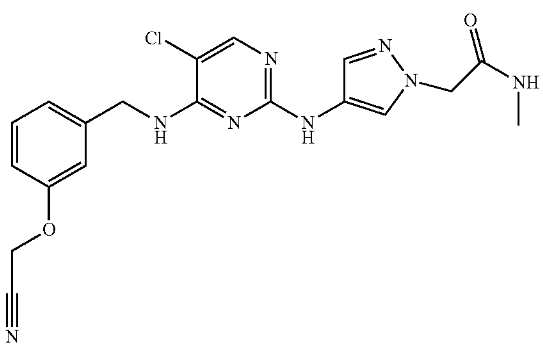 [SMILES: CNC(=O)Cn1cc(Nc2ncc(Cl)c(NCc3cccc(OCC#N)c3)n2)cn1] | G | 5.3 | 428 |
| I-365 | 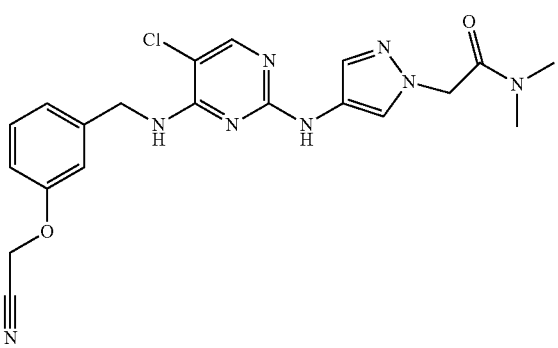 [SMILES: CN(C)C(=O)Cn1cc(Nc2ncc(Cl)c(NCc3cccc(OCC#N)c3)n2)cn1] | G | 4.29 | 442 |
| I-366 | 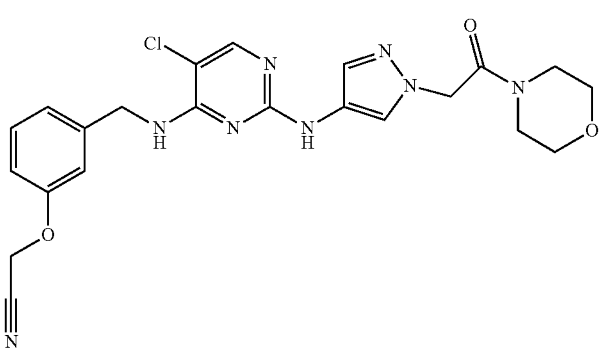 [SMILES: N#CCOc1cccc(CNc2nc(Nc3cnn(CC(=O)N4CCOCC4)c3)ncc2Cl)c1] | G | 5.42 | 484 |

TABLE 11-continued

Table of Examples

| Example | Structure | Analytical Method | RT (min) | m/z ES+ |
|---------|-----------|-------------------|----------|---------|
| I-367 | 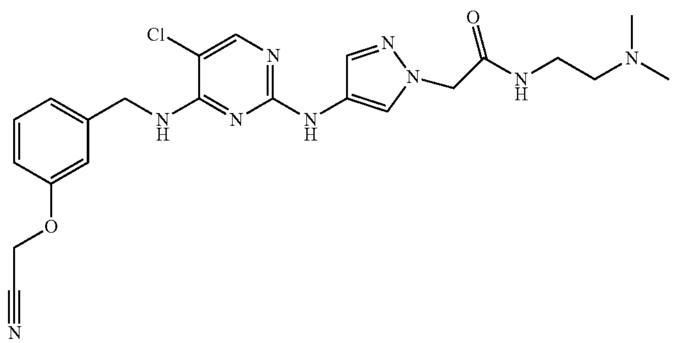 [SMILES: CN(C)CCNC(=O)Cn1cc(Nc2ncc(Cl)c(NCc3cccc(OCC#N)c3)n2)cn1] | G | 4.29 | 485 |
| I-368 | 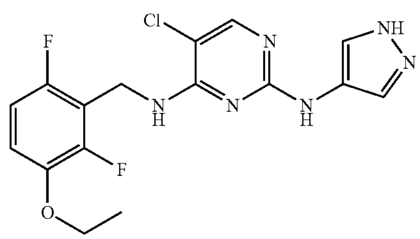 [SMILES: CCOc1ccc(F)c(CNc2nc(Nc3cn[nH]c3)ncc2Cl)c1F] | G | 5.06 | 382 |
| I-369 | 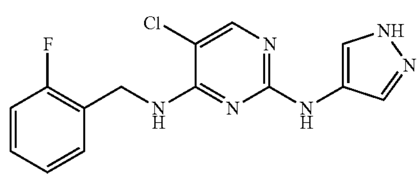 [SMILES: Fc1ccccc1CNc1nc(Nc2cn[nH]c2)ncc1Cl] | G | 4.26 | 320 |
| I-370 | 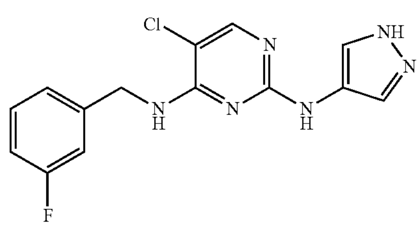 [SMILES: Fc1cccc(CNc2nc(Nc3cn[nH]c3)ncc2Cl)c1] | G | 4.28 | 320 |
| I-371 | 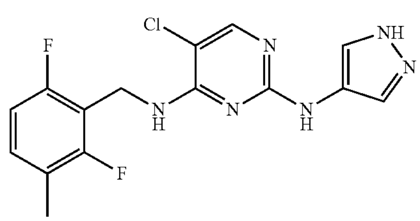 [SMILES: Cc1ccc(F)c(CNc2nc(Nc3cn[nH]c3)ncc2Cl)c1F] | G | 5.00 | 352 |
| I-372 | 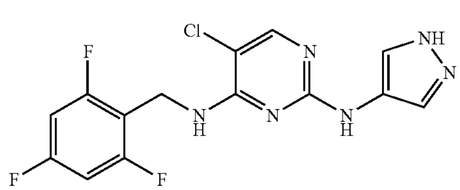 [SMILES: Fc1cc(F)c(CNc2nc(Nc3cn[nH]c3)ncc2Cl)c(F)c1] | G | 4.62 | 356 |

TABLE 11-continued

Table of Examples

| Example | Structure | Analytical Method | RT (min) | m/z ES+ |
|---|---|---|---|---|
| I-373 | 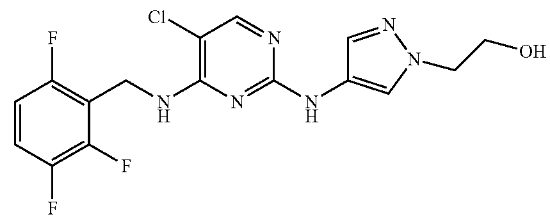 [SMILES: OCCn1cc(Nc2ncc(Cl)c(NCc3c(F)ccc(F)c3F)n2)cn1] | G | 5.64 | 400 |
| I-374 | 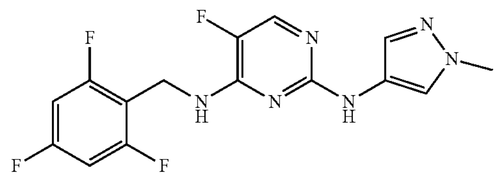 [SMILES: Cn1cc(Nc2ncc(F)c(NCc3c(F)cc(F)cc3F)n2)cn1] | G | 5.36 | 353 |
| I-375 | 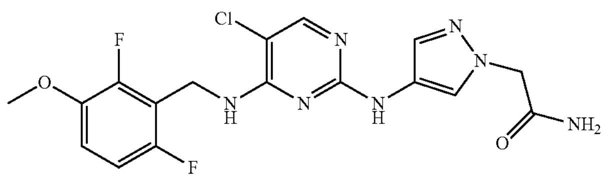 [SMILES: COc1ccc(F)c(CNc2nc(Nc3cnn(CC(N)=O)c3)ncc2Cl)c1F] | G | 5.33 | 424 |
| I-376 | 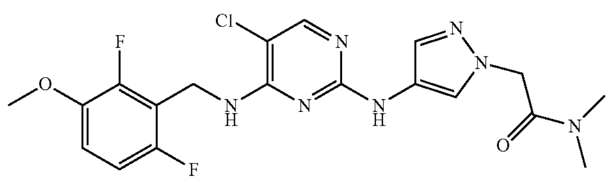 | G | 5.68 | 452 |
| I-377 | 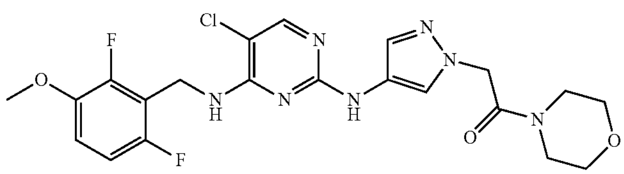 [SMILES: COc1ccc(F)c(CNc2nc(Nc3cnn(CC(=O)N4CCOCC4)c3)ncc2Cl)c1F] | G | 5.72 | 494 |
| I-378 | 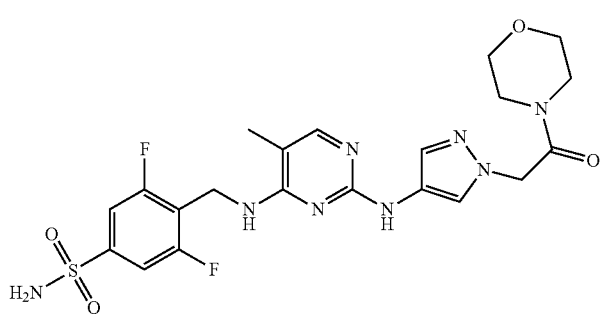 [SMILES: Cc1cnc(Nc2cnn(CC(=O)N3CCOCC3)c2)nc1NCc1c(F)cc(S(N)(=O)=O)cc1F] | G | 4.29 | 523 |
| I-379 | 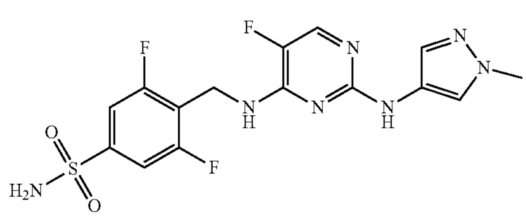 [SMILES: Cn1cc(Nc2ncc(F)c(NCc3c(F)cc(S(N)(=O)=O)cc3F)n2)cn1] | G | 4.25 | 414 |

TABLE 11-continued

Table of Examples

| Example | Structure | Analytical Method | RT (min) | m/z ES+ |
|---------|-----------|-------------------|----------|---------|
| I-380 | 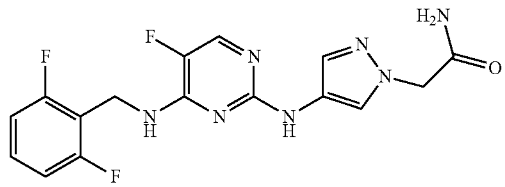 [SMILES: NC(=O)Cn1cc(Nc2ncc(F)c(NCc3c(F)cccc3F)n2)cn1] | G | 4.48 | 378 |
| I-381 | 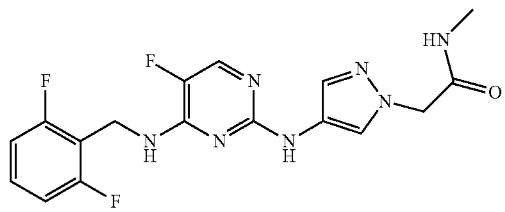 [SMILES: CNC(=O)Cn1cc(Nc2ncc(F)c(NCc3c(F)cccc3F)n2)cn1] | G | 4.74 | 392 |
| I-382 | 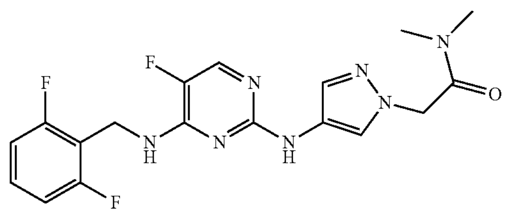 [SMILES: CN(C)C(=O)Cn1cc(Nc2ncc(F)c(NCc3c(F)cccc3F)n2)cn1] | G | 4.94 | 406 |
| I-383 | 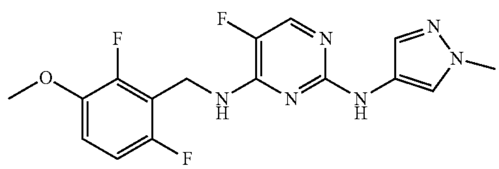 | G | 5.38 | 365 |
| I-384 | 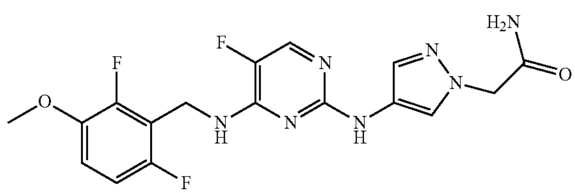 [SMILES: COc1ccc(F)c(CNc2nc(Nc3cnn(CC(N)=O)c3)ncc2F)c1F] | G | 4.81 | 408 |
| I-385 | 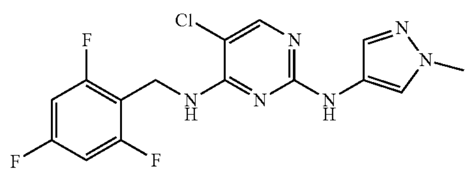 [SMILES: Cn1cc(Nc2ncc(Cl)c(NCc3c(F)cc(F)cc3F)n2)cn1] | G | 6.3 | 369 |
| I-386 | 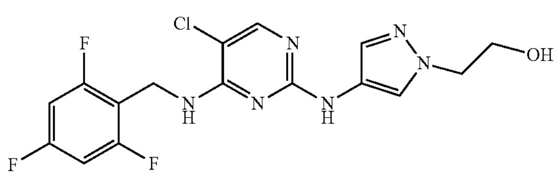 [SMILES: OCCn1cc(Nc2ncc(Cl)c(NCc3c(F)cc(F)cc3F)n2)cn1] | G | 5.63 | 399 |
| I-387 | 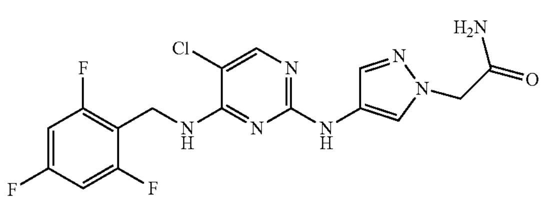 [SMILES: NC(=O)Cn1cc(Nc2ncc(Cl)c(NCc3c(F)cc(F)cc3F)n2)cn1] | G | 5.5 | 412 |

TABLE 11-continued
Table of Examples
| Example | Structure | Analytical Method | RT (min) | m/z ES+ |
|---------|-----------|-------------------|----------|---------|
| I-388 | 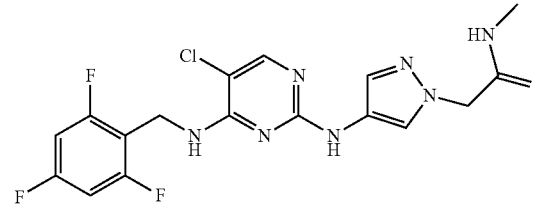 | G | 5.76 | 426 |
| I-389 | 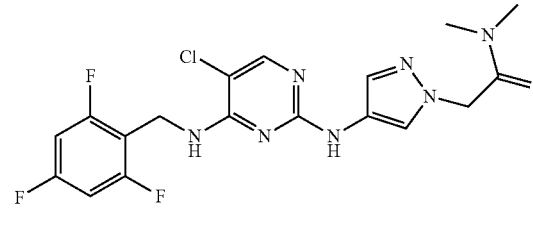 | G | 5.83 | 440 |
| I-390 | 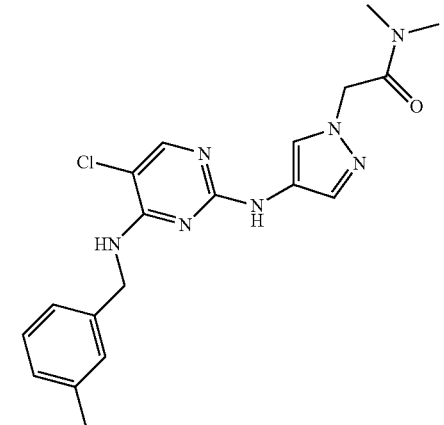 | G | 4.35 | 429 |
| I-391 | 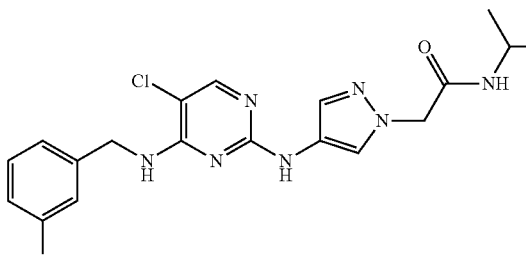 | G | 6.78 | 466 |

TABLE 11-continued

Table of Examples

| Example | Structure | Analytical Method | RT (min) | m/z ES+ |
|---|---|---|---|---|
| I-392 | 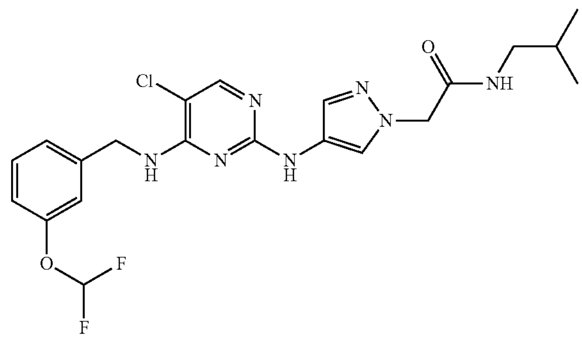 [SMILES: CC(C)CNC(=O)Cn1cc(Nc2ncc(Cl)c(NCc3cccc(OC(F)F)c3)n2)cn1] | G | 7.1 | 480 |
| I-393 | 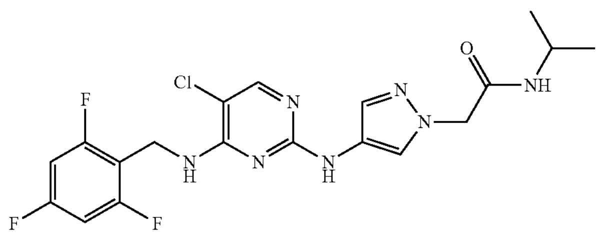 [SMILES: CC(C)NC(=O)Cn1cc(Nc2ncc(Cl)c(NCc3c(F)cc(F)cc3F)n2)cn1] | G | 6.65 | 454 |
| I-394 | 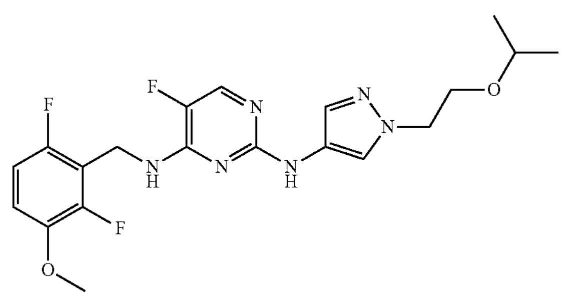 [SMILES: COc1ccc(F)c(CNc2nc(Nc3cnn(CCOC(C)C)c3)ncc2F)c1F] | G | 6.42 | 437 |
| I-395 | 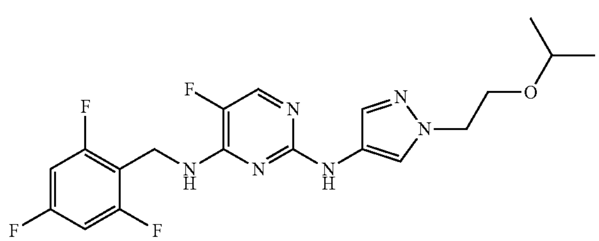 [SMILES: CC(C)OCCn1cc(Nc2ncc(F)c(NCc3c(F)cc(F)cc3F)n2)cn1] | G | 6.32 | 417 |
| I-396 | 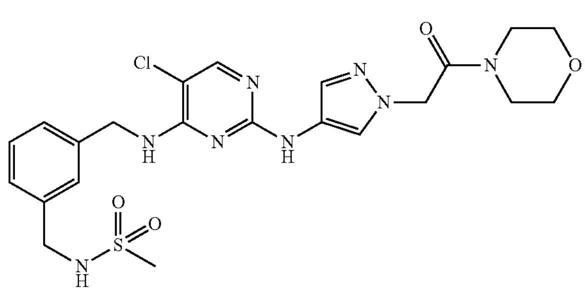 [SMILES: CS(=O)(=O)NCc1cccc(CNc2nc(Nc3cnn(CC(=O)N4CCOCC4)c3)ncc2Cl)c1] | G | 5.00 | 535 |

TABLE 11-continued

Table of Examples

| Example | Structure | Analytical Method | RT (min) | m/z ES+ |
|---------|-----------|-------------------|----------|---------|
| I-397 | 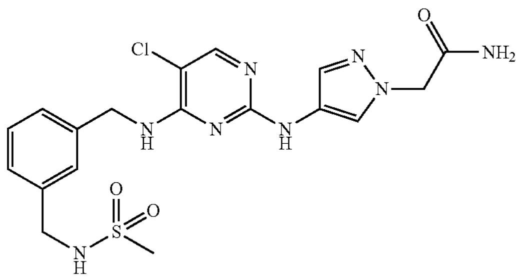 [SMILES: CS(=O)(=O)NCc1cccc(CNc2nc(Nc3cnn(CC(N)=O)c3)ncc2Cl)c1] | G | 4.66 | 465 |
| I-398 | 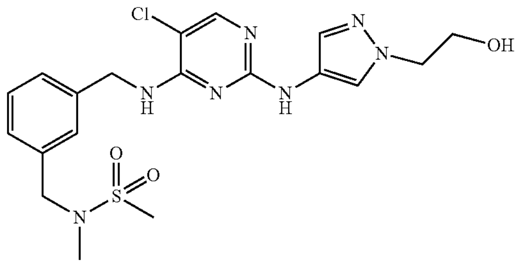 [SMILES: CN(Cc1cccc(CNc2nc(Nc3cnn(CCO)c3)ncc2Cl)c1)S(C)(=O)=O] | G | 5.14 | 466 |
| I-399 | 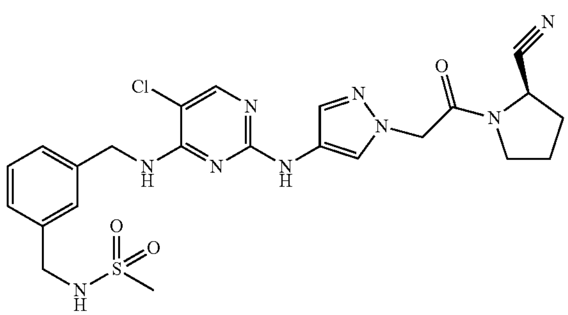 [SMILES: CS(=O)(=O)NCc1cccc(CNc2nc(Nc3cnn(CC(=O)N4CCC[C@@H]4C#N)c3)ncc2Cl)c1] | G | 5.56 | 544 |
| I-400 | 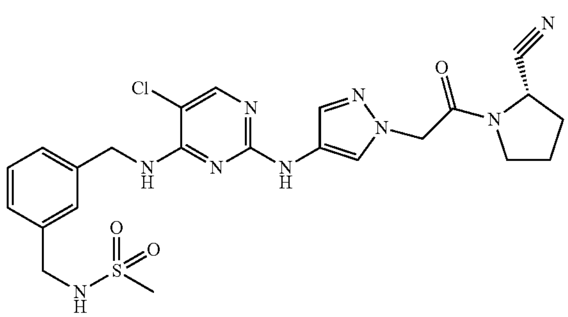 [SMILES: CS(=O)(=O)NCc1cccc(CNc2nc(Nc3cnn(CC(=O)N4CCC[C@H]4C#N)c3)ncc2Cl)c1] | G | 5.49 | 544 |
| I-401 | 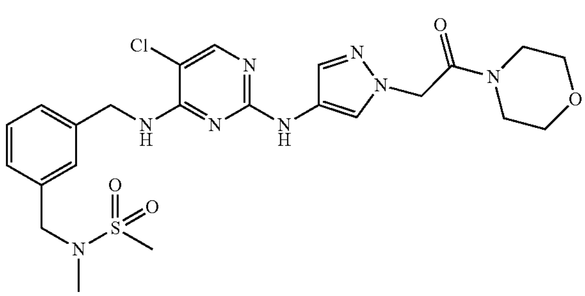 [SMILES: CN(Cc1cccc(CNc2nc(Nc3cnn(CC(=O)N4CCOCC4)c3)ncc2Cl)c1)S(C)(=O)=O] | G | 5.43 | 549 |

TABLE 11-continued

Table of Examples

| Example | Structure | Analytical Method | RT (min) | m/z ES+ |
|---|---|---|---|---|
| I-402 | 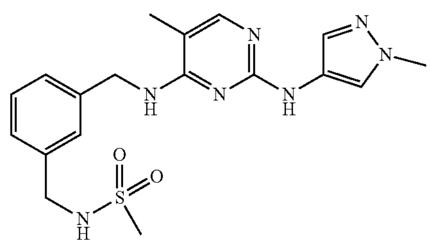 [SMILES: Cc1cnc(Nc2cnn(C)c2)nc1NCc1cccc(CNS(C)(=O)=O)c1] | G | 4.63 | 402 |
| I-403 | 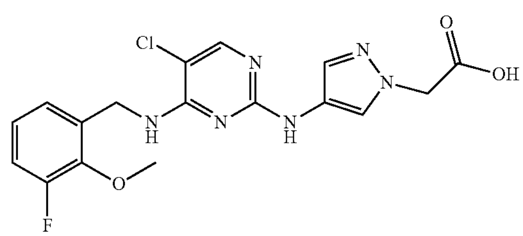 [SMILES: COc1c(F)cccc1CNc1nc(Nc2cnn(CC(=O)O)c2)ncc1Cl] | G | 5.95 | 407 |
| I-404 | 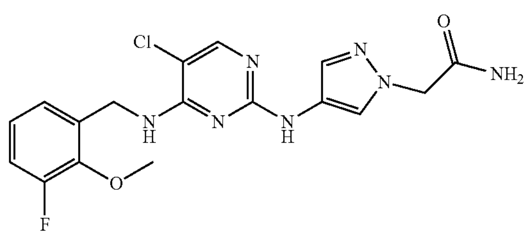 [SMILES: COc1c(F)cccc1CNc1nc(Nc2cnn(CC(N)=O)c2)ncc1Cl] | G | 5.50 | 406 |
| I-405 | 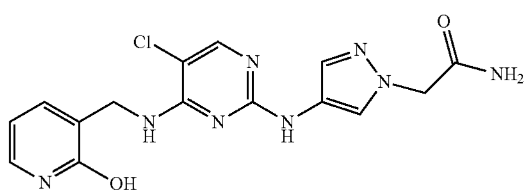 [SMILES: NC(=O)Cn1cc(Nc2ncc(Cl)c(NCc3cccnc3O)n2)cn1] | G | 3.91 | 376 |
| I-406 | 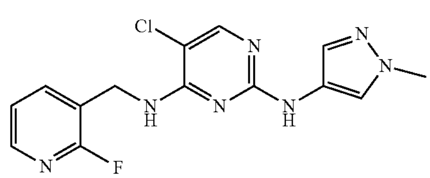 [SMILES: Cn1cc(Nc2ncc(Cl)c(NCc3cccnc3F)n2)cn1] | G | 5.09 | 334 |
| I-407 | 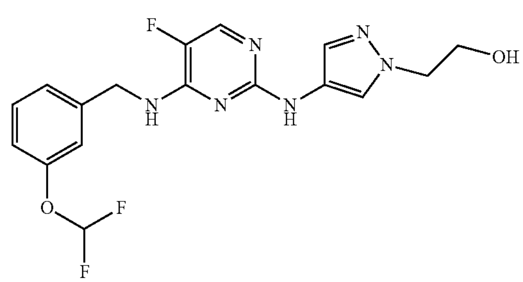 [SMILES: OCCn1cc(Nc2ncc(F)c(NCc3cccc(OC(F)F)c3)n2)cn1] | G | 5.51 | 365 |

TABLE 11-continued

Table of Examples

| Example | Structure | Analytical Method | RT (min) | m/z ES+ |
|---------|-----------|-------------------|----------|---------|
| I-408 | 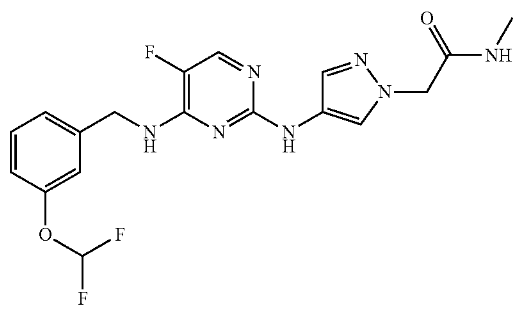 [SMILES: CNC(=O)Cn1cc(Nc2ncc(F)c(NCc3cccc(OC(F)F)c3)n2)cn1] | G | 5.39 | 422 |
| I-409 | 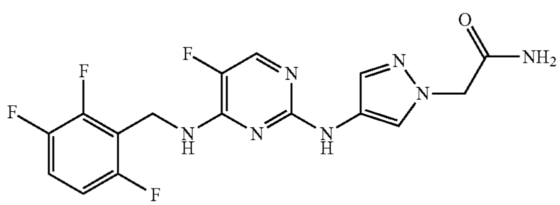 [SMILES: NC(=O)Cn1cc(Nc2ncc(F)c(NCc3c(F)ccc(F)c3F)n2)cn1] | G | 5.2 | 397 |
| I-410 | 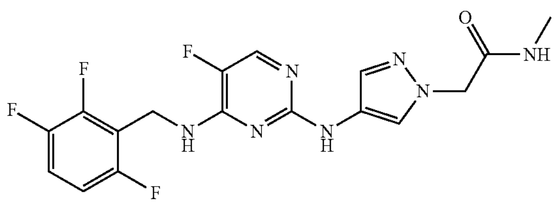 [SMILES: CNC(=O)Cn1cc(Nc2ncc(F)c(NCc3c(F)ccc(F)c3F)n2)cn1] | G | 5.08 | 410 |
| I-411 | 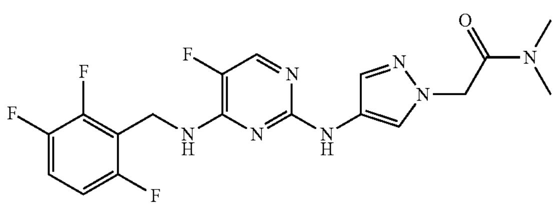 [SMILES: CN(C)C(=O)Cn1cc(Nc2ncc(F)c(NCc3c(F)ccc(F)c3F)n2)cn1] | G | 5.29 | 424 |
| I-412 | 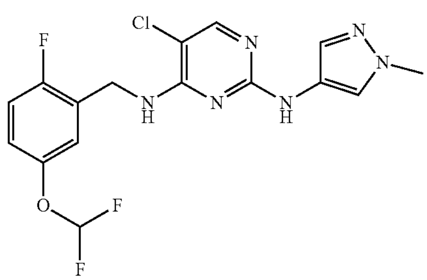 [SMILES: Cn1cc(Nc2ncc(Cl)c(NCc3cc(OC(F)F)ccc3F)n2)cn1] | G | 6.72 | 400 |
| I-413 | 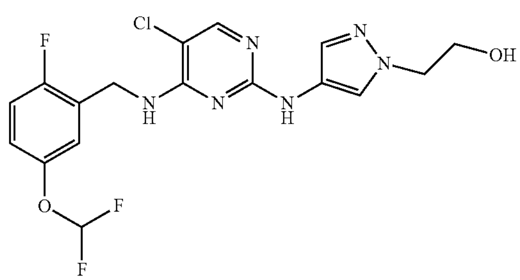 [SMILES: OCCn1cc(Nc2ncc(Cl)c(NCc3cc(OC(F)F)ccc3F)n2)cn1] | G | 6.08 | 429 |

TABLE 11-continued

Table of Examples

| Example | Structure | Analytical Method | RT (min) | m/z ES+ |
|---------|-----------|-------------------|----------|---------|
| I-414 | 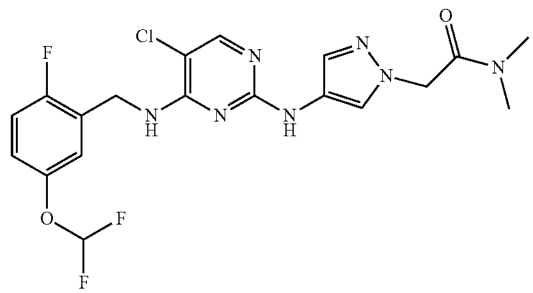 [SMILES: CN(C)C(=O)Cn1cc(Nc2ncc(Cl)c(NCc3cc(OC(F)F)ccc3F)n2)cn1] | G | 6.23 | 470 |
| I-415 | 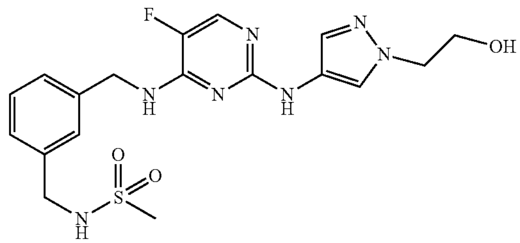 [SMILES: CS(=O)(=O)NCc1cccc(CNc2nc(Nc3cnn(CCO)c3)ncc2F)c1] | G | 4.47 | 436 |
| I-416 | 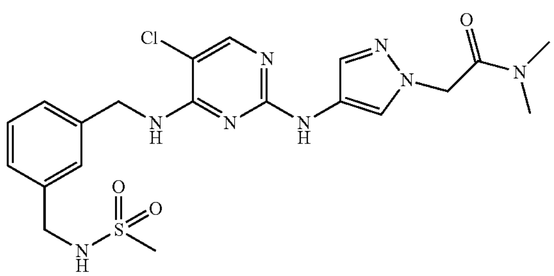 [SMILES: CN(C)C(=O)Cn1cc(Nc2ncc(Cl)c(NCc3cccc(CNS(C)(=O)=O)c3)n2)cn1] | E | 1.90 | 493 |
| I-417 | 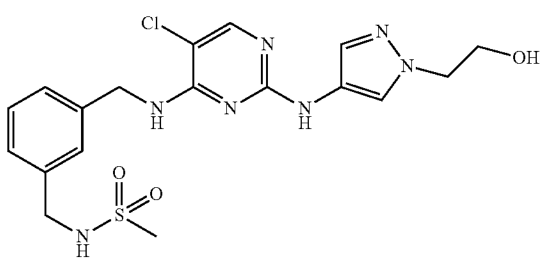 [SMILES: CS(=O)(=O)NCc1cccc(CNc2nc(Nc3cnn(CCO)c3)ncc2Cl)c1] | G | 4.74 | 452 |
| I-418 | 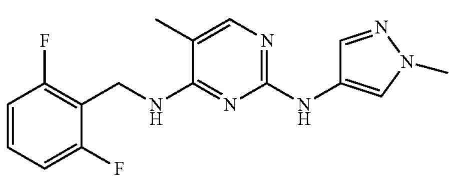 [SMILES: Cc1cnc(Nc2cnn(C)c2)nc1NCc1c(F)cccc1F] | G | 5.24 | 331 |
| I-419 | 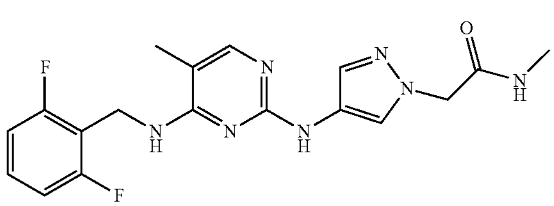 [SMILES: CNC(=O)Cn1cc(Nc2ncc(C)c(NCc3c(F)cccc3F)n2)cn1] | G | 4.83 | 388 |

TABLE 11-continued

Table of Examples

| Example | Structure | Analytical Method | RT (min) | m/z ES+ |
|---|---|---|---|---|
| I-420 | 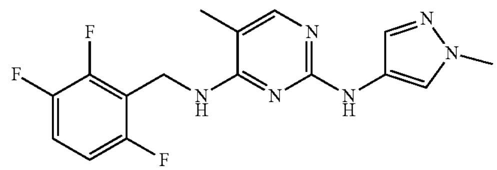 [SMILES: Cc1cnc(Nc2cnn(C)c2)nc1NCc1c(F)ccc(F)c1F] | G | 5.33 | 349 |
| I-421 | 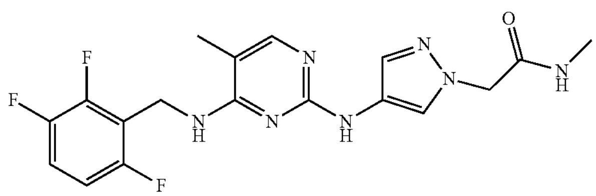 [SMILES: CNC(=O)Cn1cc(Nc2ncc(C)c(NCc3c(F)ccc(F)c3F)n2)cn1] | G | 5.04 | 406 |
| I-422 | 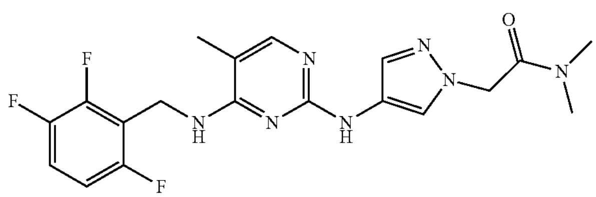 | G | 5.27 | 420 |
| I-423 | 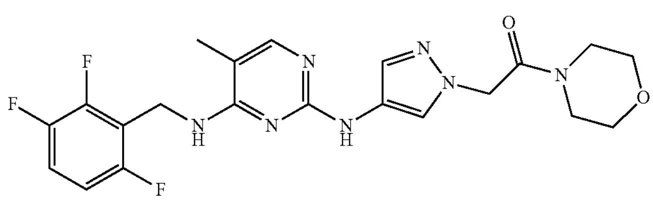 [SMILES: Cc1cnc(Nc2cnn(CC(=O)N3CCOCC3)c2)nc1NCc1c(F)ccc(F)c1F] | G | 5.12 | 462 |
| I-424 | 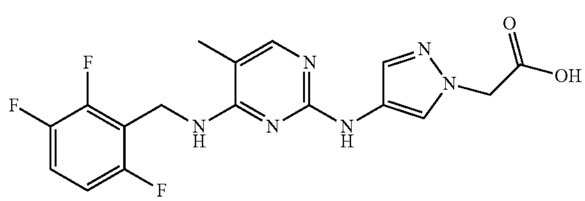 [SMILES: Cc1cnc(Nc2cnn(CC(=O)O)c2)nc1NCc1c(F)ccc(F)c1F] | E | 1.23 | 393 |
| I-425 | 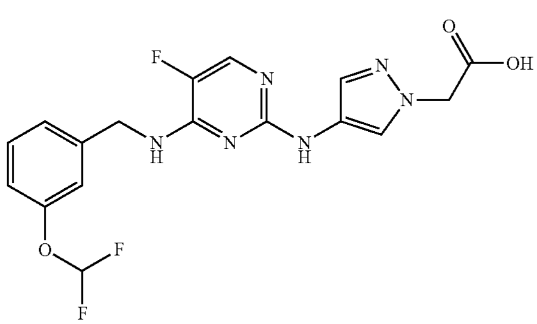 [SMILES: O=C(O)Cn1cc(Nc2ncc(F)c(NCc3cccc(OC(F)F)c3)n2)cn1] | E | 0.76 | 409 |

TABLE 11-continued

Table of Examples

| Example | Structure | Analytical Method | RT (min) | m/z ES+ |
|---|---|---|---|---|
| I-426 | 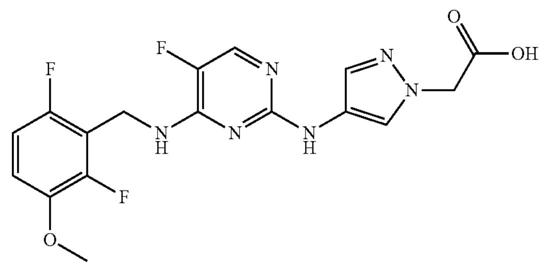 [SMILES: COc1ccc(F)c(CNc2nc(Nc3cnn(CC(=O)O)c3)ncc2F)c1F] | G | 5.22 | 409 |
| I-427 | 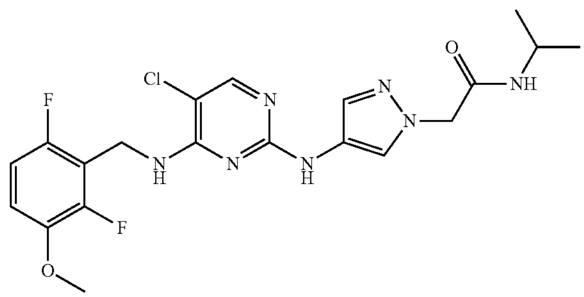 [SMILES: COc1ccc(F)c(CNc2nc(Nc3cnn(CC(=O)NC(C)C)c3)ncc2Cl)c1F] | G | 6.36 | 466 |
| I-428 | 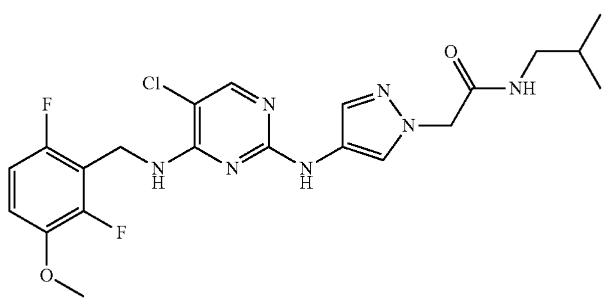 [SMILES: COc1ccc(F)c(CNc2nc(Nc3cnn(CC(=O)NCC(C)C)c3)ncc2Cl)c1F] | G | 7.1 | 480 |
| I-429 | 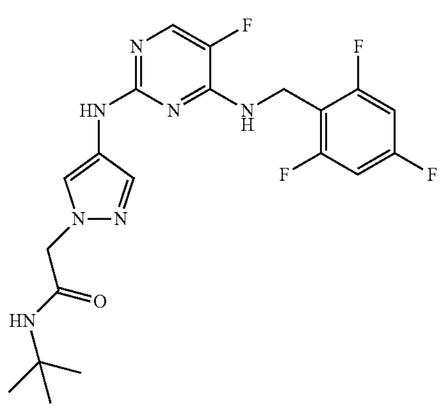 [SMILES: CC(C)(C)NC(=O)Cn1cc(Nc2ncc(F)c(NCc3c(F)cc(F)cc3F)n2)cn1] | G | 6.29 | 452 |

TABLE 11-continued

Table of Examples

| Example | Structure | Analytical Method | RT (min) | m/z ES+ |
|---|---|---|---|---|
| I-430 | 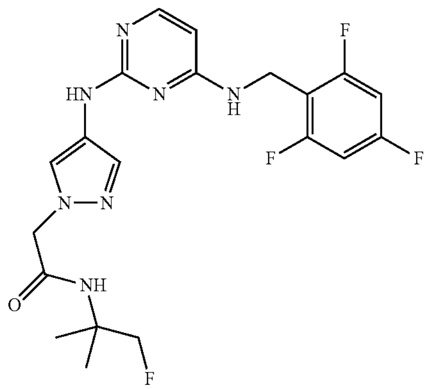 [SMILES: CC(C)(CF)NC(=O)Cn1cc(Nc2nccc(NCc3c(F)cc(F)cc3F)n2)cn1] | G | 5.70 | 452 |
| I-431 | 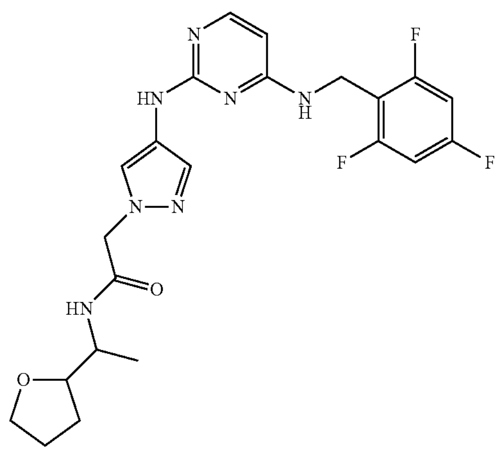 [SMILES: CC(NC(=O)Cn1cc(Nc2nccc(NCc3c(F)cc(F)cc3F)n2)cn1)C1CCCO1] | G | 5.58 | 476 |
| I-432 | 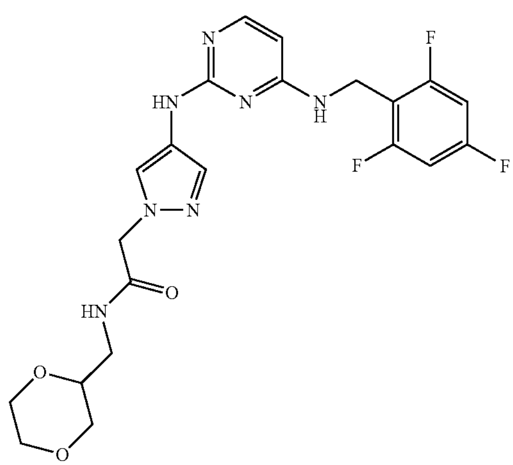 [SMILES: O=C(Cn1cc(Nc2nccc(NCc3c(F)cc(F)cc3F)n2)cn1)NCC1COCCO1] | G | 5.16 | 478 |
| I-433 | 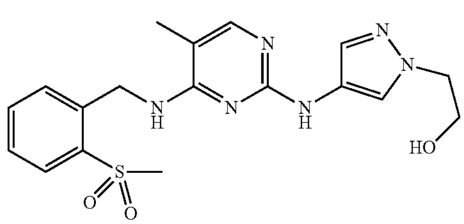 [SMILES: Cc1cnc(Nc2cnn(CCO)c2)nc1NCc1ccccc1S(C)(=O)=O] | E | 0.82 | 403 |

TABLE 11-continued

Table of Examples

| Example | Structure | Analytical Method | RT (min) | m/z ES+ |
|---|---|---|---|---|
| I-434 | 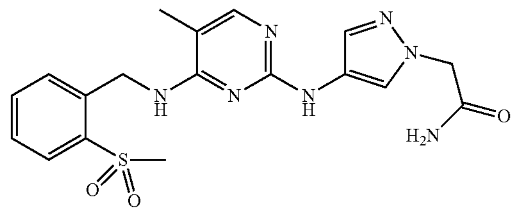 [SMILES: Cc1cnc(Nc2cnn(CC(N)=O)c2)nc1NCc1ccccc1S(C)(=O)=O] | E | 0.80 | 416 |
| I-435 | 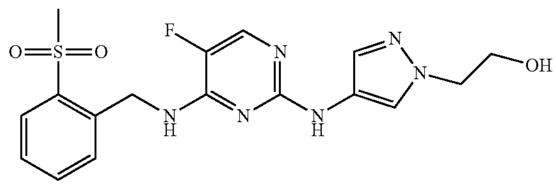 | E | 0.82 | 407 |
| I-436 | 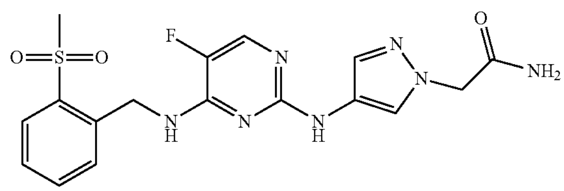 [SMILES: CS(=O)(=O)c1ccccc1CNc1nc(Nc2cnn(CC(N)=O)c2)ncc1F] | E | 0.80 | 420 |
| I-437 | 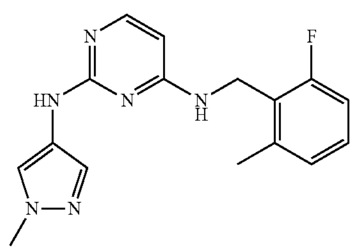 [SMILES: Cc1cccc(F)c1CNc1ccnc(Nc2cnn(C)c2)n1] | G | 5.28 | 313 |
| I-438 | 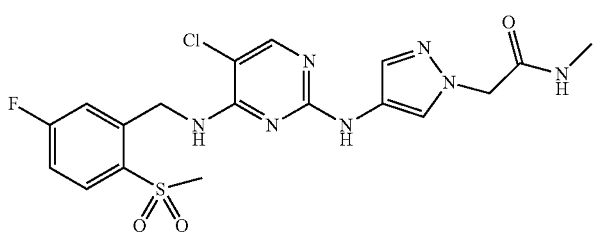 [SMILES: CNC(=O)Cn1cc(Nc2ncc(Cl)c(NCc3cc(F)ccc3S(C)(=O)=O)n2)cn1] | E | 0.88 | 468 |
| I-439 | 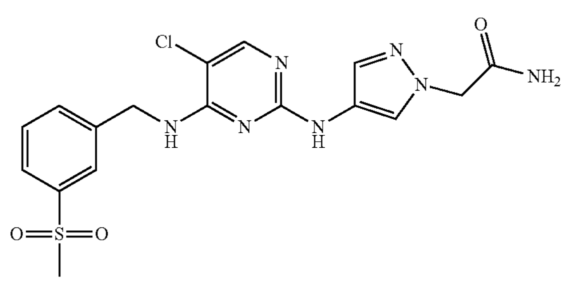 [SMILES: CS(=O)(=O)c1cccc(CNc2nc(Nc3cnn(CC(N)=O)c3)ncc2Cl)c1] | E | 0.82 | 436 |

TABLE 11-continued

Table of Examples

| Example | Structure | Analytical Method | RT (min) | m/z ES+ |
|---|---|---|---|---|
| I-440 | 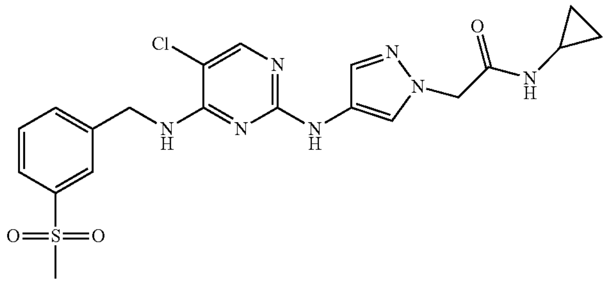 [SMILES: CS(=O)(=O)c1cccc(CNc2nc(Nc3cnn(CC(=O)NC4CC4)c3)ncc2Cl)c1] | E | 0.87 | 476 |
| I-441 | 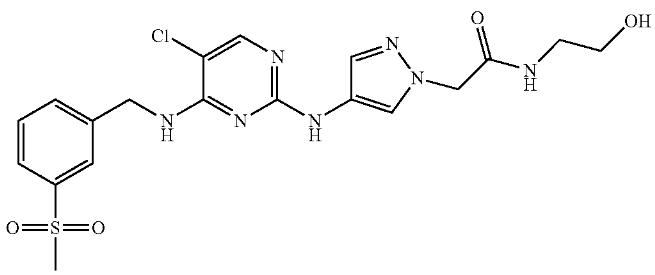 [SMILES: CS(=O)(=O)c1cccc(CNc2nc(Nc3cnn(CC(=O)NCCO)c3)ncc2Cl)c1] | E | 0.81 | 480 |
| I-442 | 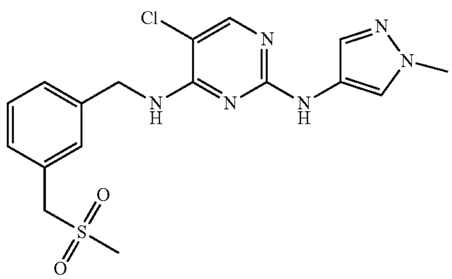 [SMILES: Cn1cc(Nc2ncc(Cl)c(NCc3cccc(CS(C)(=O)=O)c3)n2)cn1] | E | 0.89 | 407 |
| I-443 | 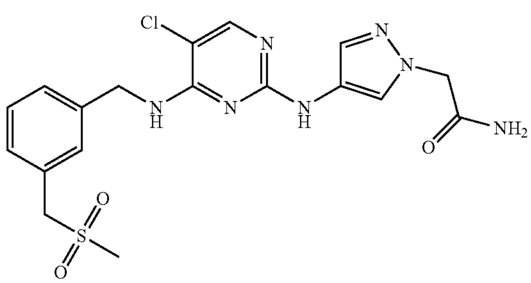 [SMILES: CS(=O)(=O)Cc1cccc(CNc2nc(Nc3cnn(CC(N)=O)c3)ncc2Cl)c1] | E | 0.82 | 450 |
| I-444 | 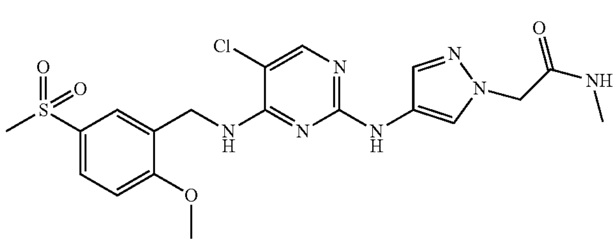 | E | 0.86 | 480 |

TABLE 11-continued

Table of Examples

| Example | Structure | Analytical Method | RT (min) | m/z ES+ |
|---------|-----------|-------------------|----------|---------|
| I-445 | 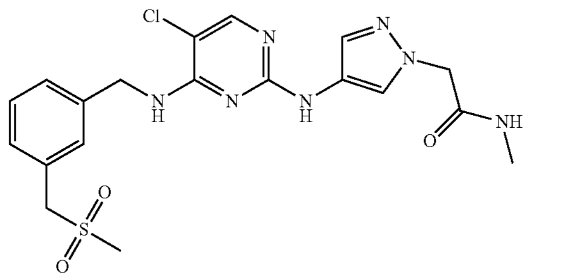 [SMILES: CNC(=O)Cn1cc(Nc2ncc(Cl)c(NCc3cccc(CS(C)(=O)=O)c3)n2)cn1] | E | 0.84 | 464 |
| I-446 | 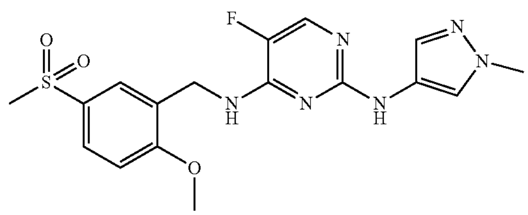 | E | 0.87 | 407 |
| I-447 | 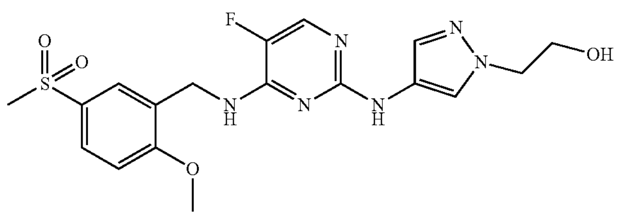 [SMILES: COc1ccc(S(C)(=O)=O)cc1CNc1nc(Nc2cnn(CCO)c2)ncc1F] | E | 0.82 | 407 |
| I-448 | 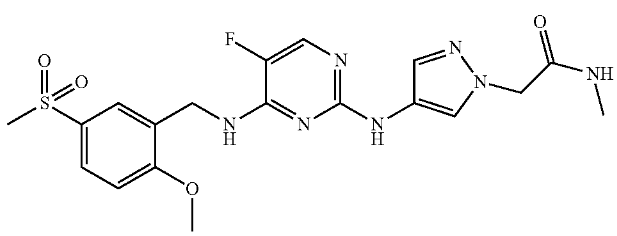 | E | 0.82 | 464 |
| I-449 | 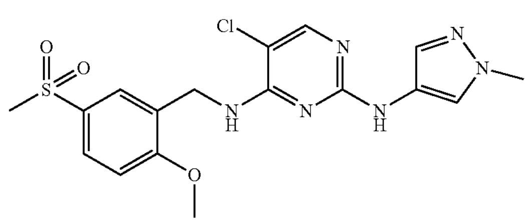 | E | 0.91 | 423 |
| I-450 | 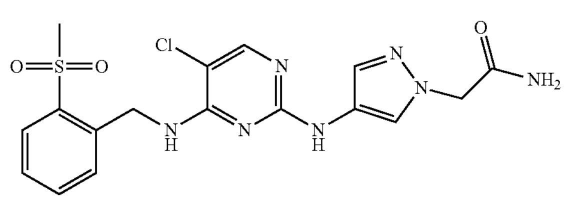 [SMILES: CS(=O)(=O)c1ccccc1CNc1nc(Nc2cnn(CC(N)=O)c2)ncc1Cl] | E | 0.89 | 436 |
| I-451 | 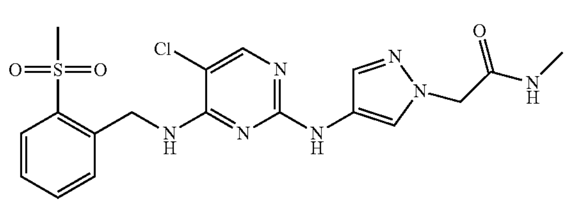 [SMILES: CNC(=O)Cn1cc(Nc2ncc(Cl)c(NCc3ccccc3S(C)(=O)=O)n2)cn1] | E | 0.86 | 450 |

TABLE 11-continued
Table of Examples
| Example | Structure | Analytical Method | RT (min) | m/z ES+ |
|---|---|---|---|---|
| I-452 | 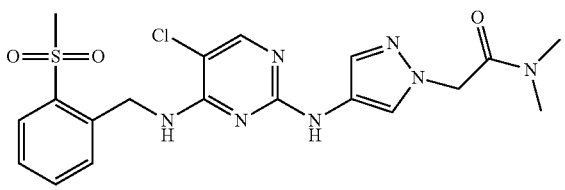 [SMILES: CN(C)C(=O)Cn1cc(Nc2ncc(Cl)c(NCc3ccccc3S(C)(=O)=O)n2)cn1] | E | 0.90 | 464 |
| I-453 | 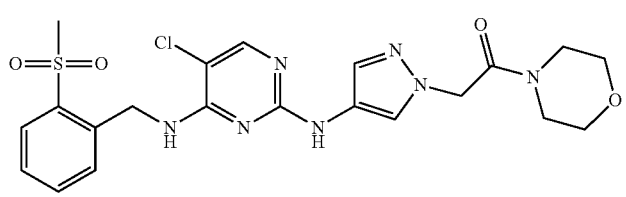 [SMILES: CS(=O)(=O)c1ccccc1CNc1nc(Nc2cnn(CC(=O)N3CCOCC3)c2)ncc1Cl] | E | 0.90 | 506 |
| I-454 | 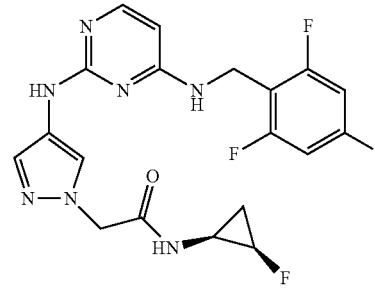 | G | 4.98 | 436 |
| I-455 | 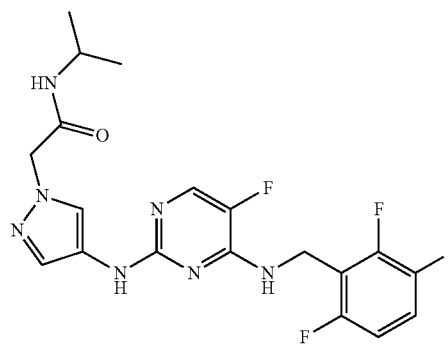 | G | 5.63 | 438 |
| I-456 | 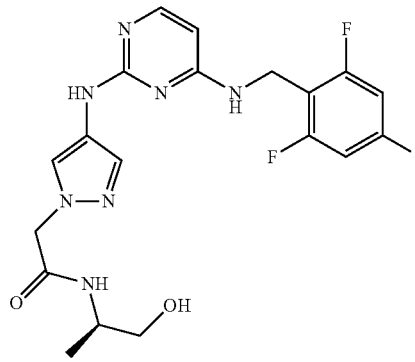 | G | 4.86 | 436 |

TABLE 11-continued

Table of Examples

| Example | Structure | Analytical Method | RT (min) | m/z ES+ |
|---------|-----------|-------------------|----------|---------|
| I-457 | 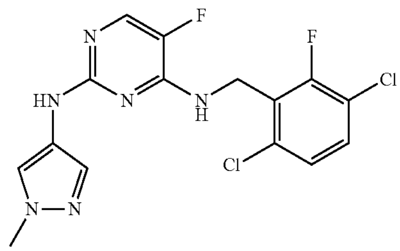 [SMILES: Cn1cc(Nc2ncc(F)c(NCc3c(Cl)ccc(Cl)c3F)n2)cn1] | G | 6.36 | 385 |
| I-458 | 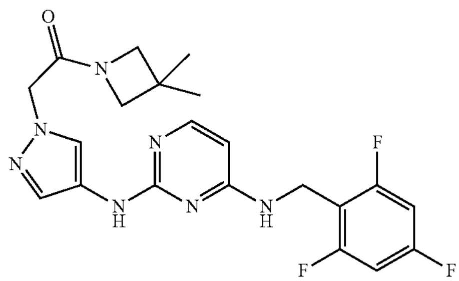 [SMILES: CC1(C)CN(C(=O)Cn2cc(Nc3nccc(NCc4c(F)cc(F)cc4F)n3)cn2)C1] | F | 1.8 | 446 |
| I-459 | 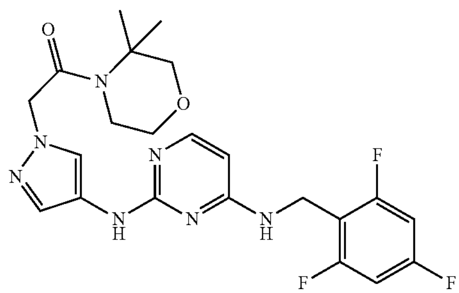 [SMILES: CC1(C)COCCN1C(=O)Cn1cc(Nc2nccc(NCc3c(F)cc(F)cc3F)n2)cn1] | F | 1.72 | 476 |
| I-460 | 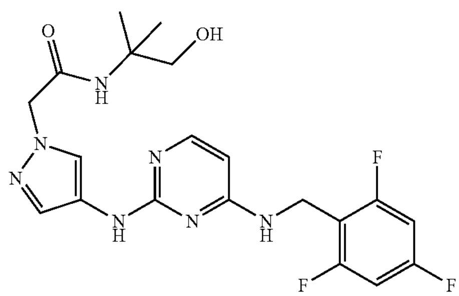 [SMILES: CC(C)(CO)NC(=O)Cn1cc(Nc2nccc(NCc3c(F)cc(F)cc3F)n2)cn1] | F | 1.51 | 450 |
| I-461 | 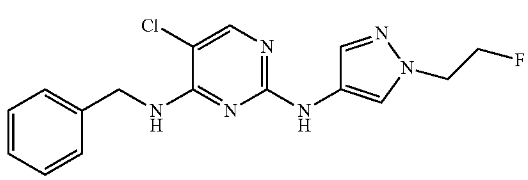 [SMILES: FCCn1cc(Nc2ncc(Cl)c(NCc3ccccc3)n2)cn1] | F | 2.45 | 347 |
| I-462 | 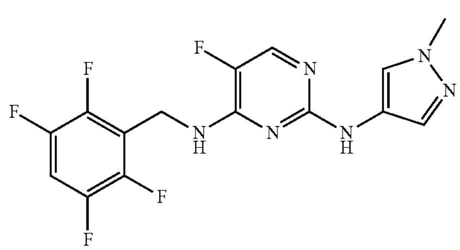 [SMILES: Cn1cc(Nc2ncc(F)c(NCc3c(F)c(F)cc(F)c3F)n2)cn1] | B | 0.99 | 371 |

TABLE 11-continued

Table of Examples

| Example | Structure | Analytical Method | RT (min) | m/z ES+ |
|---|---|---|---|---|
| I-463 | 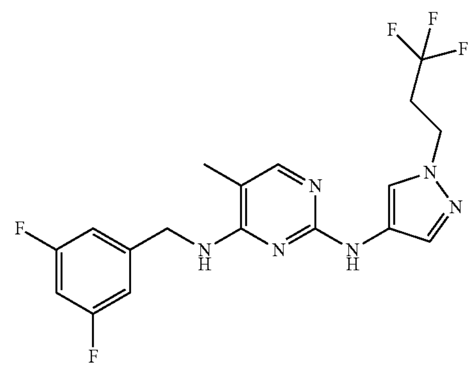 [SMILES: Cc1cnc(Nc2cnn(CCC(F)(F)F)c2)nc1NCc1cc(F)cc(F)c1] | B | 1.06 | 413 |
| I-464 | 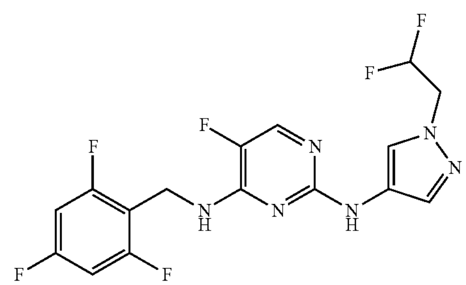 [SMILES: Fc1cc(F)c(CNc2nc(Nc3cnn(CC(F)F)c3)ncc2F)c(F)c1] | B | 1.04 | 403 |
| I-465 | 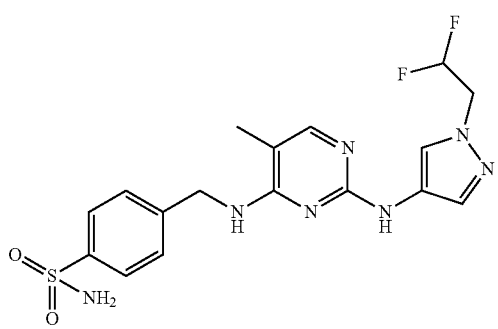 [SMILES: Cc1cnc(Nc2cnn(CC(F)F)c2)nc1NCc1ccc(S(N)(=O)=O)cc1] | B | 0.85 | 424 |
| I-466 | 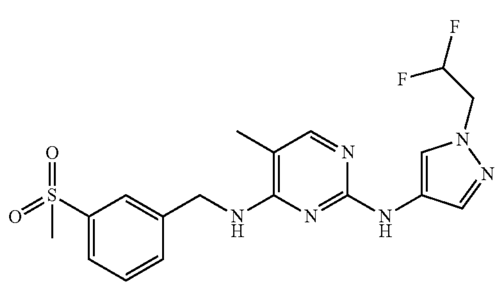 [SMILES: Cc1cnc(Nc2cnn(CC(F)F)c2)nc1NCc1cccc(S(C)(=O)=O)c1] | B | 0.90 | 423 |
| I-467 | 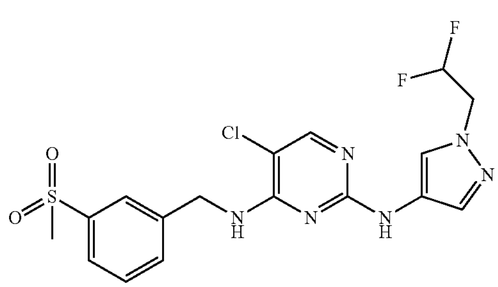 [SMILES: CS(=O)(=O)c1cccc(CNc2nc(Nc3cnn(CC(F)F)c3)ncc2Cl)c1] | B | 0.94 | 443 |

TABLE 11-continued

Table of Examples

| Example | Structure | Analytical Method | RT (min) | m/z ES+ |
|---|---|---|---|---|
| I-468 | 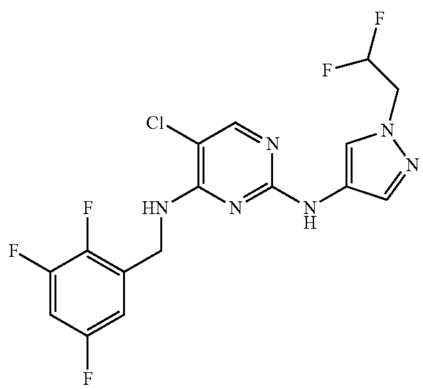 [SMILES: Fc1cc(F)c(F)c(CNc2nc(Nc3cnn(CC(F)F)c3)ncc2Cl)c1] | B | 1.08 | 419 |
| I-469 | 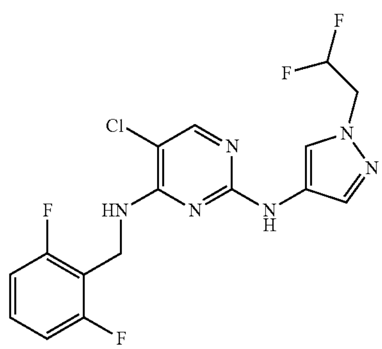 [SMILES: Fc1cccc(F)c1CNc1nc(Nc2cnn(CC(F)F)c2)ncc1Cl] | B | 1.06 | 401 |
| I-470 | 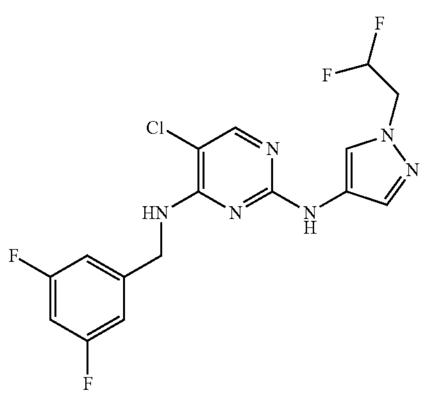 [SMILES: Fc1cc(F)cc(CNc2nc(Nc3cnn(CC(F)F)c3)ncc2Cl)c1] | B | 1.01 | 401 |
| I-471 | 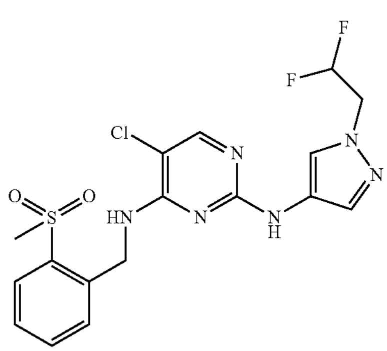 [SMILES: CS(=O)(=O)c1ccccc1CNc1nc(Nc2cnn(CC(F)F)c2)ncc1Cl] | B | 0.98 | 443 |

TABLE 11-continued

Table of Examples

| Example | Structure | Analytical Method | RT (min) | m/z ES+ |
|---------|-----------|-------------------|----------|---------|
| I-472 | 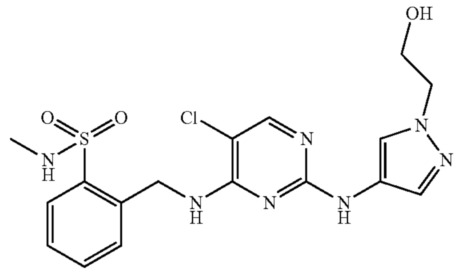 [SMILES: CNS(=O)(=O)c1ccccc1CNc1nc(Nc2cnn(CCO)c2)ncc1Cl] | B | 0.88 | 438 |
| I-473 | 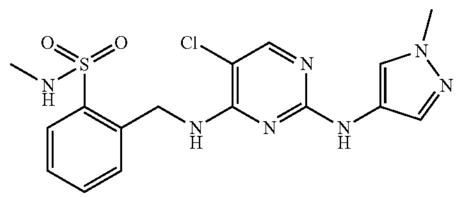 [SMILES: CNS(=O)(=O)c1ccccc1CNc1nc(Nc2cnn(C)c2)ncc1Cl] | B | 0.93 | 408 |
| I-474 | 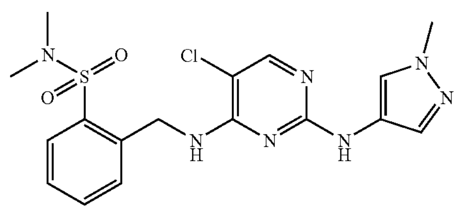 [SMILES: CN(C)S(=O)(=O)c1ccccc1CNc1nc(Nc2cnn(C)c2)ncc1Cl] | B | 0.99 | 422 |
| I-475 | 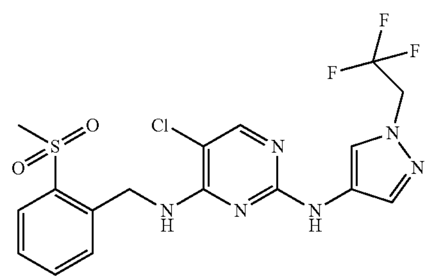 [SMILES: CS(=O)(=O)c1ccccc1CNc1nc(Nc2cnn(CC(F)(F)F)c2)ncc1Cl] | B | 1.06 | 461 |
| I-476 | 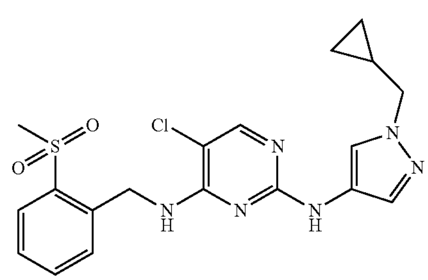 [SMILES: CS(=O)(=O)c1ccccc1CNc1nc(Nc2cnn(CC3CC3)c2)ncc1Cl] | B | 1.01 | 433 |
| I-477 | 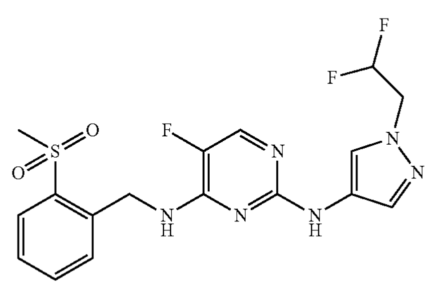 [SMILES: CS(=O)(=O)c1ccccc1CNc1nc(Nc2cnn(CC(F)F)c2)ncc1F] | B | 0.93 | 427 |

TABLE 11-continued

Table of Examples

| Example | Structure | Analytical Method | RT (min) | m/z ES+ |
|---|---|---|---|---|
| I-478 | 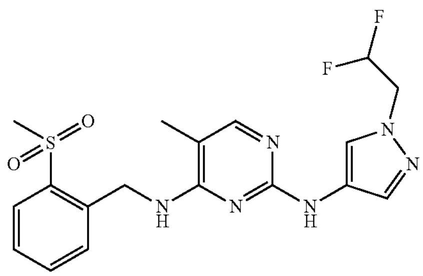 [SMILES: Cc1cnc(Nc2cnn(CC(F)F)c2)nc1NCc1ccccc1S(C)(=O)=O] | B | 0.92 | 423 |
| I-479 | 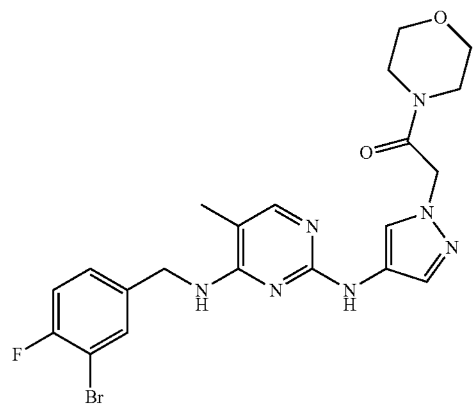 [SMILES: Cc1cnc(Nc2cnn(CC(=O)N3CCOCC3)c2)nc1NCc1ccc(F)c(Br)c1] | G | 4.97 | 474 |
| I-480 | 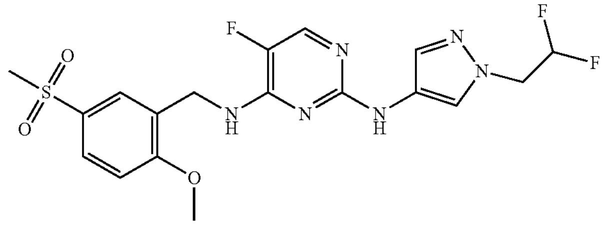 [SMILES: COc1ccc(S(C)(=O)=O)cc1CNc1nc(Nc2cnn(CC(F)F)c2)ncc1F] | G | 5.19 | 457 |
| I-481 | 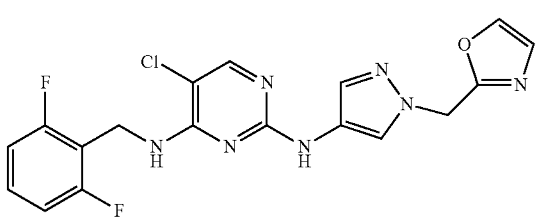 [SMILES: Fc1cccc(F)c1CNc1nc(Nc2cnn(Cc3ncco3)c2)ncc1Cl] | G | 6.35 | 418 |
| I-482 | 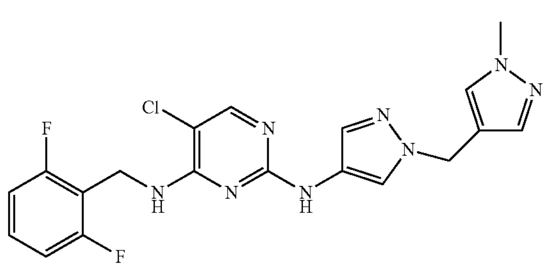 [SMILES: Cn1cc(Cn2cc(Nc3ncc(Cl)c(NCc4c(F)cccc4F)n3)cn2)cn1] | G | 6.19 | 431 |

TABLE 11-continued

Table of Examples

| Example | Structure | Analytical Method | RT (min) | m/z ES+ |
|---|---|---|---|---|
| I-483 | 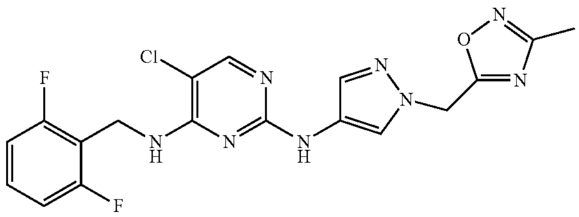 [SMILES: Cc1noc(Cn2cc(Nc3ncc(Cl)c(NCc4c(F)cccc4F)n3)cn2)n1] | G | 6.80 | 433 |
| I-484 | 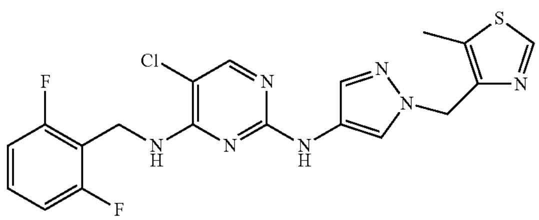 [SMILES: Cc1scnc1Cn1cc(Nc2ncc(Cl)c(NCc3c(F)cccc3F)n2)cn1] | G | 6.90 | 448 |
| I-485 | 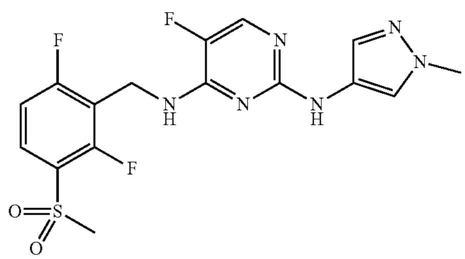 [SMILES: Cn1cc(Nc2ncc(F)c(NCc3c(F)ccc(S(C)(=O)=O)c3F)n2)cn1] | D | 0.86 | 395 |
| I-486 | 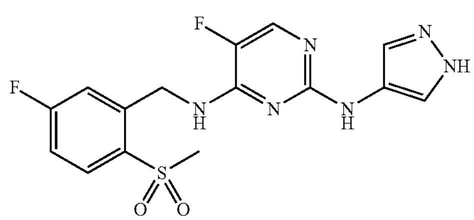 [SMILES: CS(=O)(=O)c1ccc(F)cc1CNc1nc(Nc2cn[nH]c2)ncc1F] | E | 0.86 | 381 |
| I-487 | 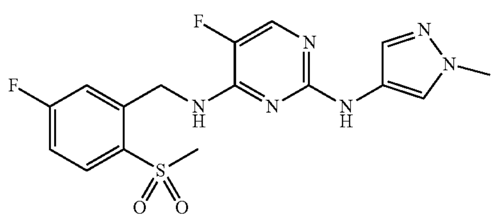 [SMILES: Cn1cc(Nc2ncc(F)c(NCc3cc(F)ccc3S(C)(=O)=O)n2)cn1] | E | 0.85 | 395 |
| I-488 | 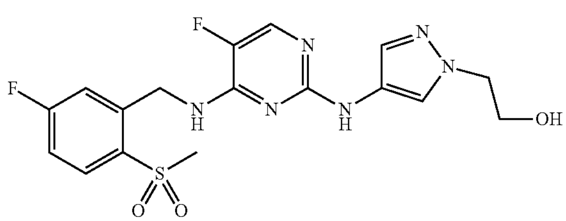 [SMILES: CS(=O)(=O)c1ccc(F)cc1CNc1nc(Nc2cnn(CCO)c2)ncc1F] | E | 0.85 | 425 |

TABLE 11-continued

Table of Examples

| Example | Structure | Analytical Method | RT (min) | m/z ES+ |
|---|---|---|---|---|
| I-489 | 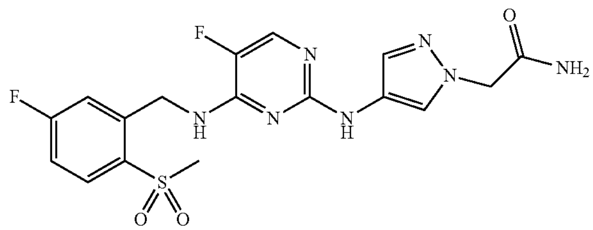 [SMILES: CS(=O)(=O)c1ccc(F)cc1CNc1nc(Nc2cnn(CC(N)=O)c2)ncc1F] | E | 0.82 | 438 |
| I-490 | 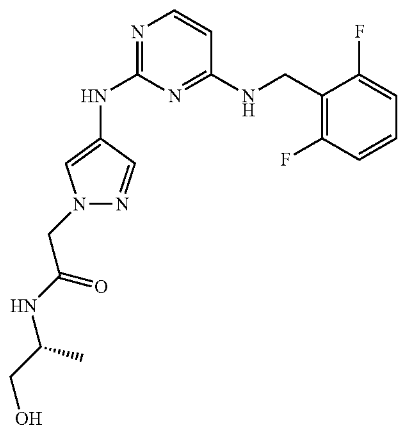 [SMILES: C[C@H](CO)NC(=O)Cn1cc(Nc2nccc(NCc3c(F)cccc3F)n2)cn1] | G | 4.64 | 418 |

Biology Assays
Determination of the Effect of the Compounds According to the Invention on TYK2

The compounds of the present invention as described in the previous examples were tested in a Kinobeads™ assay as described for ZAP-70 (WO-A 2007/137867). Briefly, test compounds (at various concentrations) and the affinity matrix with the immobilized aminopyrido-pyrimidine ligand 24 were added to cell lysate aliquots and allowed to bind to the proteins in 10 the lysate sample. After the incubation time the beads with captured proteins were separated from the lysate. Bound proteins were then eluted and the presence of TYK2 and JAK2 was detected and quantified using specific antibodies in a dot blot procedure and the Odyssey infrared detection system. Dose response curves for individual kinases were generated and $IC_{50}$ values calculated. Kinobeads™ assays have been previously described (WO-A 2007/137867; WO-A 2006/134056).

Protocols
Washing of Affinity Matrix

The affinity matrix was washed two times with 15 mL of 1×DP buffer containing 0.2% NP40 (IGEPAL® CA-630, Sigma, #13021) and then resuspended in 1×DP buffer containing 0.2% NP40 (3% beads slurry). 5×DP buffer: 250 mM Tris-HCl pH 7.4, 25% Glycerol, 7.5 mM $MgCl_2$, 750 mM NaCl, 5 mM $Na_3VO_4$; filter the 5×DP buffer through a 0.22 μm filter and store in aliquots at −80° C. The 5×DP buffer is diluted with $H_2O$ to 1×DP buffer containing 1 mM DTT and 25 mM NaF.

Preparation of Test Compounds

Stock solutions of test compounds were prepared in DMSO. In a 96 well plate 30 μL solution of diluted test compounds at 5 mM in DMSO were prepared. Starting with this solution a 1:3 dilution series (9 steps) was prepared. For control experiments (no test compound) a buffer containing 2% DMSO was used.

Cell Culture and Preparation of Cell Lysates

Molt4 cells (ATCC catalogue number CRL-1582) and Ramos cells (ATCC catalogue number CRL-1596) were grown in 1 L Spinner flasks (Integra Biosciences, #182101) in suspension in RPMI 1640 medium (Invitrogen, #21875-034) supplemented with 10% Fetal Bovine Serum (Invitrogen) at a density between $0.15 \times 10^6$ and $1.2 \times 10^6$ cells/mL. Cells were harvested by centrifugation, washed once with 1×PBS buffer (Invitrogen, #14190-094) and cell pellets were frozen in liquid nitrogen and subsequently stored at −80° C. Cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1873580) per 25 mL buffer was added. The material was dounced 10 times using a mechanized POTTER S, transferred to 50 mL falcon tubes, incubated for 30 minutes on ice and spun down for 10 minutes at 20,000 g at 4° C. (10,000 rpm in Sorvall SLA600, pre-cooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 mL falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Cell lysate (approximately 50 mg protein per plate) was thawed in a water bath at room temperature and then stored on ice. To the thawed cell lysate 1×DP 0.8% NP40 buffer containing protease inhibitors (1 tablet for 25 mL buffer; EDTA-free protease inhibitor cocktail; Roche Diagnostics 1873580) was added in order to reach a final protein concentration of 10 mg/mL total protein. The diluted cell lysate was stored on ice. Mixed Molt4/Ramos lysate was prepared by combining one volume of Molt4 lysate and two volumes of Ramos lysate (ratio 1:2).

Incubation of Lysate with Test Compound and Affinity Matrix

To a 96 well filter plate (Multiscreen HTS, BV Filter Plates, Millipore #MSBVN1250) were added per well: 100 µL affinity matrix (3% beads slurry), 3 µL of compound solution, and 50 µL of diluted lysate. Plates were sealed and incubated for 3 hours in a cold room on a plate shaker (Heidolph tiramax 1000) at 750 rpm. Afterwards the plate was washed 3 times with 230 µL washing buffer (1×DP 0.4% NP40). The filter plate was placed on top of a collection plate (Greiner bio-one, PP-microplate 96 well V-shape, 65120) and the beads were then eluted with 20 µL of sample buffer (100 mM Tris, pH 7.4, 4% SDS, 0.00025% bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on nitrocellulose membranes and using a first antibody directed against the kinase of interest and a fluorescently labelled secondary antibody (anti-rabbit IRDye™ antibody 800 (Licor, #926-32211). The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for 1 hour at room temperature. Blocked membranes were then incubated for 16 hours at the temperature shown in table 12 with the first antibody diluted in Odyssey blocking buffer (LICOR #927-40000). Afterwards the membrane was washed twice for 10 minutes with PBS buffer containing 0.2% Tween 20 at room temperature. The membrane was then incubated for 60 min at room temperature with the detection antibody (anti-rabbit IRDye™ antibody 800, Licor, #926-32211) diluted in Odyssey blocking buffer (LICOR #927-40000). Afterwards the membrane was washed twice for 10 min each with 1×PBS buffer containing 0.2% Tween 20 at room temperature. Then the membrane was rinsed once with PBS buffer to remove residual Tween 20. The membrane was kept in PBS buffer at 4° C. and then scanned with the Odyssey instrument. Fluorescence signals were recorded and analysed according to the instructions of the manufacturer.

TABLE 12

Sources and dilutions of antibodies

| Target kinase | Primary antibody (dilution) | Temperature of primary incubation | Secondary antibody (dilution) |
|---|---|---|---|
| JAK2 | Cell signaling #3230 (1:100) | Room temperature | Licor anti-rabbit 800 (1:15000) |
| TYK2 | Upstate #06-638 (1:1000) | Room temperature | Licor anti-rabbit 800 (1:5000) |

Results

In general, compounds of the invention inhibit TYK2 with $IC_{50} \leq 1$ µM and are selective for JAK2. Table 13 illustrates this technical feature. Inhibition values ($IC_{50}$ in µM) are banded according to the degree of potency: A≤0.01 µM; 0.01 µM<B≤0.1 µM; 0.1 µM<C≤1 µM; 1 µM<Kinobeads™ assay D≤10 µM; E>10 µM).

TABLE 13

Kinobeads™ assay potency

| Example | TYK2 Band | JAK2 Band |
|---|---|---|
| I-1 | B | D |
| I-3 | B | D |
| I-4 | B | D |
| I-5 | B | E |
| I-6 | B | D |
| I-8 | B | D |
| I-9 | B | E |
| I-10 | B | E |
| I-11 | B | E |
| I-12 | B | D |
| I-13 | A | D |
| I-14 | B | D |
| I-15 | B | C |
| I-16 | B | D |
| I-17 | B | D |
| I-18 | B | D |
| I-19 | B | C |
| I-20 | A | C |
| I-21 | A | D |
| I-22 | A | C |
| I-23 | A | D |
| I-24 | A | D |
| I-26 | A | D |
| I-27 | B | D |
| I-28 | A | D |
| I-29 | A | D |
| I-30 | B | E |
| I-31 | B | D |
| I-32 | A | D |
| I-33 | B | D |
| I-34 | A | D |
| I-35 | A | C |
| I-36 | A | C |
| I-37 | B | C |
| I-38 | A | D |
| I-39 | B | D |
| I-40 | B | D |
| I-41 | B | D |
| I-42 | A | D |
| I-43 | B | C |
| I-44 | A | D |
| I-45 | B | E |
| I-46 | B | E |
| I-47 | B | E |
| I-48 | A | D |
| I-49 | B | D |
| I-50 | B | D |
| I-51 | B | E |
| I-52 | B | D |
| I-53 | B | D |
| I-54 | B | D |
| I-55 | B | D |
| I-56 | B | E |
| I-57 | A | D |
| I-58 | B | E |
| I-59 | A | D |
| I-60 | B | C |
| I-61 | B | C |
| I-62 | B | E |
| I-63 | A | D |
| I-64 | B | E |
| I-65 | B | D |
| I-66 | A | D |
| I-67 | B | E |
| I-68 | B | C |
| I-70 | B | E |
| I-71 | B | E |

TABLE 13-continued

Kinobeads ™ assay potency

| Example | TYK2 Band | JAK2 Band |
|---|---|---|
| I-72 | B | C |
| I-73 | A | D |
| I-74 | B | C |
| I-75 | A | E |
| I-76 | B | E |
| I-77 | A | D |
| I-78 | A | C |
| I-79 | A | D |
| I-80 | B | D |
| I-81 | A | C |
| I-82 | B | C |
| I-83 | B | C |
| I-84 | A | C |
| I-85 | B | C |
| I-86 | B | E |
| I-87 | B | C |
| I-88 | B | C |
| I-89 | B | D |
| I-90 | B | D |
| I-91 | B | E |
| I-92 | B | D |
| I-93 | B | D |
| I-94 | B | D |
| I-95 | B | D |
| I-98 | B | C |
| I-99 | B | C |
| I-100 | B | C |
| I-101 | B | C |
| I-102 | A | D |
| I-105 | B | E |
| I-106 | A | D |
| I-107 | B | C |
| I-110 | B | E |
| I-112 | B | D |
| I-114 | B | D |
| I-115 | B | D |
| I-116 | B | D |
| I-117 | A | D |
| I-118 | B | D |
| I-119 | B | E |
| I-120 | A | D |
| I-121 | A | C |
| I-122 | A | C |
| I-123 | A | C |
| I-124 | B | D |
| I-125 | A | D |
| I-126 | B | D |
| I-127 | B | D |
| I-128 | B | D |
| I-129 | A | E |
| I-130 | B | D |
| I-131 | B | C |
| I-132 | A | D |
| I-133 | A | D |
| I-134 | A | D |
| I-135 | B | D |
| I-136 | B | C |
| I-137 | B | D |
| I-138 | B | D |
| I-139 | A | D |
| I-140 | B | D |
| I-141 | B | D |
| I-142 | B | D |
| I-143 | B | D |
| I-144 | A | D |
| I-145 | A | E |
| I-146 | B | E |
| I-147 | B | E |
| I-148 | B | D |
| I-149 | B | E |
| I-151 | B | D |
| I-152 | B | D |
| I-153 | A | D |
| I-154 | A | D |
| I-155 | A | D |
| I-156 | A | D |
| I-157 | B | D |
| I-158 | C | D |
| I-159 | B | D |
| I-160 | B | D |
| I-161 | A | C |
| I-162 | B | B |
| I-163 | C | D |
| I-164 | B | C |
| I-165 | B | D |
| I-166 | C | D |
| I-167 | B | D |
| I-168 | C | C |
| I-169 | C | D |
| I-170 | C | D |
| I-171 | B | C |
| I-172 | B | C |
| I-173 | C | C |
| I-174 | B | C |
| I-175 | B | D |
| I-176 | B | B |
| I-177 | C | D |
| I-178 | B | C |
| I-179 | C | C |
| I-180 | B | C |
| I-181 | C | D |
| I-182 | B | C |
| I-183 | B | D |
| I-184 | C | D |
| I-185 | C | D |
| I-186 | C | D |
| I-187 | B | C |
| I-188 | B | D |
| I-189 | C | D |
| I-190 | C | C |
| I-191 | C | D |
| I-192 | B | C |
| I-193 | C | D |
| I-194 | B | C |
| I-195 | C | D |
| I-196 | B | D |
| I-197 | C | D |
| I-198 | C | D |
| I-199 | C | D |
| I-200 | C | D |
| I-201 | C | D |
| I-202 | A | C |
| I-203 | A | B |
| I-204 | A | D |
| I-205 | B | D |
| I-206 | C | C |
| I-207 | C | E |
| I-208 | C | C |
| I-209 | B | D |
| I-210 | B | C |
| I-211 | C | C |
| I-212 | C | C |
| I-213 | C | C |
| I-214 | C | D |
| I-215 | C | C |
| I-216 | C | D |
| I-217 | C | D |
| I-218 | C | C |
| I-219 | B | C |
| I-220 | C | D |
| I-221 | C | C |
| I-222 | C | D |
| I-223 | C | C |
| I-224 | C | D |
| I-225 | C | D |
| I-226 | B | D |
| I-227 | C | D |
| I-228 | C | D |
| I-229 | B | D |
| I-230 | B | D |
| I-231 | C | D |
| I-232 | C | D |

TABLE 13-continued

Kinobeads ™ assay potency

| Example | TYK2 Band | JAK2 Band |
|---|---|---|
| I-233 | C | D |
| I-234 | B | C |
| I-235 | C | D |
| I-236 | C | D |
| I-237 | B | C |
| I-238 | C | D |
| I-239 | C | D |
| I-240 | B | D |
| I-241 | C | D |
| I-242 | C | D |
| I-243 | C | D |
| I-244 | C | D |
| I-245 | D | B |
| I-246 | D | B |
| I-247 | D | C |
| I-248 | C | D |
| I-249 | D | D |
| I-250 | D | D |
| I-251 | B | D |
| I-252 | B | E |
| I-253 | C | C |
| I-254 | C | D |
| I-255 | C | D |
| I-256 | C | D |
| I-257 | C | C |
| I-258 | C | C |
| I-259 | B | D |
| I-260 | C | D |
| I-261 | C | C |
| I-262 | C | C |
| I-263 | C | C |
| I-264 | C | C |
| I-265 | C | D |
| I-266 | C | D |
| I-267 | B | C |
| I-268 | B | D |
| I-269 | B | D |
| I-270 | B | D |
| I-271 | B | C |
| I-272 | C | D |
| I-273 | C | D |
| I-274 | B | D |
| I-275 | C | D |
| I-276 | C | B |
| I-277 | C | D |
| I-278 | C | D |
| I-279 | B | C |
| I-280 | B | C |
| I-281 | B | C |
| I-282 | B | D |
| I-283 | B | D |
| I-284 | B | D |
| I-285 | C | D |
| I-286 | C | C |
| I-287 | C | C |
| I-288 | C | D |
| I-289 | D | D |
| I-290 | C | D |
| I-291 | C | D |
| I-292 | C | C |
| I-293 | C | C |
| I-294 | C | D |
| I-295 | B | D |
| I-296 | B | D |
| I-297 | B | D |
| I-298 | A | C |
| I-299 | A | C |
| I-300 | C | D |
| I-301 | B | D |
| I-302 | B | C |
| I-303 | B | C |
| I-304 | A | B |
| I-305 | A | C |
| I-306 | B | D |
| I-307 | B | E |
| I-308 | B | E |
| I-309 | B | D |
| I-310 | C | E |
| I-311 | B | D |
| I-312 | C | E |
| I-313 | B | D |
| I-314 | B | D |
| I-315 | B | D |
| I-316 | B | D |
| I-317 | B | E |
| I-318 | B | E |
| I-319 | B | D |
| I-320 | B | C |
| I-321 | C | D |
| I-322 | B | D |
| I-323 | B | C |
| I-324 | B | C |
| I-325 | B | D |
| I-326 | B | C |
| I-327 | B | D |
| I-328 | B | D |
| I-329 | B | D |
| I-330 | C | D |
| I-331 | C | D |
| I-332 | C | D |
| I-333 | C | D |
| I-334 | C | D |
| I-335 | A | C |
| I-336 | B | C |
| I-337 | C | D |
| I-338 | C | D |
| I-339 | B | C |
| I-340 | B | C |
| I-341 | B | D |
| I-342 | B | B |
| I-343 | B | B |
| I-344 | B | C |
| I-345 | B | C |
| I-346 | B | C |
| I-347 | D | D |
| I-348 | B | B |
| I-349 | B | B |
| I-350 | D | D |
| I-351 | D | D |
| I-352 | D | D |
| I-353 | C | D |
| I-354 | C | C |
| I-355 | C | C |
| I-356 | C | C |
| I-357 | C | D |
| I-358 | B | C |
| I-359 | B | C |
| I-360 | A | C |
| I-361 | C | C |
| I-362 | C | D |
| I-363 | C | D |
| I-364 | C | D |
| I-365 | B | D |
| I-366 | B | D |
| I-367 | C | D |
| I-368 | B | D |
| I-369 | C | C |
| I-370 | C | C |
| I-371 | B | D |
| I-372 | B | D |
| I-373 | A | B |
| I-374 | B | D |
| I-375 | B | C |
| I-376 | B | C |
| I-377 | B | C |
| I-378 | A | C |
| I-379 | B | D |
| I-380 | B | D |
| I-381 | B | D |
| I-382 | B | D |
| I-383 | B | D |
| I-384 | B | D |

TABLE 13-continued

Kinobeads ™ assay potency

| Example | TYK2 Band | JAK2 Band |
|---|---|---|
| I-385 | B | D |
| I-386 | B | C |
| I-387 | B | D |
| I-388 | B | D |
| I-389 | B | D |
| I-390 | C | D |
| I-391 | B | D |
| I-392 | B | D |
| I-393 | B | E |
| I-394 | C | E |
| I-395 | C | E |
| I-396 | B | D |
| I-397 | C | D |
| I-398 | C | D |
| I-399 | C | D |
| I-400 | C | D |
| I-401 | C | D |
| I-402 | C | D |
| I-403 | C | D |
| I-404 | C | C |
| I-405 | D | D |
| I-406 | C | C |
| I-407 | B | D |
| I-408 | B | E |
| I-409 | B | D |
| I-410 | B | D |
| I-411 | B | D |
| I-412 | B | D |
| I-413 | B | C |
| I-414 | B | D |
| I-415 | C | D |
| I-416 | C | C |
| I-417 | C | C |
| I-418 | B | C |
| I-419 | B | C |
| I-420 | B | C |
| I-421 | A | C |
| I-422 | A | C |
| I-423 | A | C |
| I-424 | B | C |
| I-425 | B | E |
| I-426 | B | E |
| I-427 | B | D |
| I-428 | B | D |
| I-429 | B | D |
| I-430 | B | D |
| I-431 | B | E |
| I-432 | B | D |
| I-433 | C | D |
| I-434 | C | D |
| I-435 | C | D |
| I-436 | C | D |
| I-437 | B | D |
| I-438 | B | C |
| I-439 | C | C |
| I-440 | B | D |
| I-441 | C | D |
| I-442 | D | D |
| I-443 | C | D |
| I-444 | B | C |
| I-445 | C | D |
| I-446 | B | D |
| I-447 | B | C |
| I-448 | B | D |
| I-449 | B | C |
| I-450 | C | C |
| I-451 | D | D |
| I-452 | C | C |
| I-453 | C | C |
| I-454 | B | D |
| I-455 | A | D |
| I-456 | B | D |
| I-457 | B | C |
| I-458 | B | E |
| I-459 | B | E |
| I-460 | B | D |
| I-461 | D | D |
| I-462 | C | D |
| I-463 | D | D |
| I-464 | C | E |
| I-465 | C | D |
| I-466 | C | D |
| I-467 | D | D |
| I-468 | C | C |
| I-469 | C | C |
| I-470 | C | C |
| I-471 | D | D |
| I-472 | B | C |
| I-473 | C | C |
| I-474 | C | C |
| I-475 | D | E |
| I-476 | D | D |
| I-477 | D | D |
| I-478 | D | E |
| I-479 | C | E |
| I-480 | C | D |
| I-481 | C | D |
| I-482 | C | D |
| I-483 | C | D |
| I-484 | C | C |
| I-485 | B | D |
| I-486 | C | C |
| I-487 | C | C |
| I-488 | B | C |
| I-489 | B | C |
| I-490 | B | D |

Furthermore, examples I-3, I-38, I-50, I-62, I-65, I-67, I-112 and I-125 have TYK2 $IC_{50}$<0.1 µM and are >100-fold selective over all of JAK1, JAK2 and JAK3.

The invention claimed is:
1. A compound of formula (I)

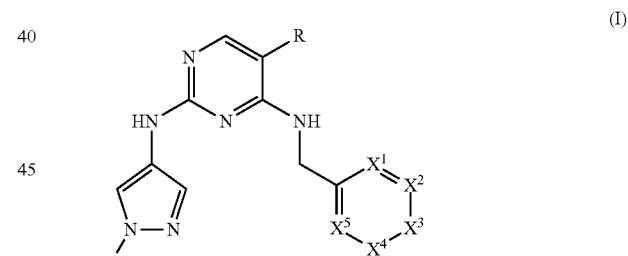

(I)

or a pharmaceutically acceptable salt derivative thereof, wherein

R is H; F; Cl; Br; or unsubstituted $C_{1-3}$ alkyl;

$R^1$ is H; $C(O)OR^2$; $C(O)R^2$; $C(O)N(R^2R^{2a})$; $S(O)_2N(R^2R^{2a})$; $S(O)N(R^2R^{2a})$; $S(O)_2R^2$; $S(O)R^2$; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^2$, $R^{2a}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $NO_2$; $OC(O)R^4$; $N(R^4)C(O)R^{4a}$; $N(R^4)$ S(O)$_2$R$^{4a}$; N(R$^4$)S(O)R$^{4a}$; N(R$^4$)C(O)N(R$^{4a}$R$^{4b}$); N(R$^4$)C(O)OR$^{4a}$; OC(O)N(R$^4$R$^{4a}$); or T$^1$;

R$^4$, R$^{4a}$, R$^{4b}$ are independently selected from the group consisting of H; T$^1$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^5$, which are the same or different;

R$^5$ is halogen; CN; C(O)OR$^6$; OR$^6$; C(O)R$^6$; C(O)N(R$^6$R$^{6a}$); S(O)$_2$N(R$^6$R$^{6a}$); S(O)N(R$^6$R$^{6a}$); S(O)$_2$R$^6$; S(O)R$^6$; N(R$^6$)S(O)$_2$N(R$^{6a}$R$^{6b}$); N(R$^6$)S(O)N(R$^{6a}$R$^{6b}$); SR$^6$; N(R$^6$R$^{6a}$); NO$_2$; OC(O)R$^6$; N(R$^6$)C(O)R$^{6a}$; N(R$^6$)S(O)$_2$R$^{6a}$; N(R$^6$)S(O)R$^{6a}$; N(R$^6$)C(O)N(R$^{6a}$R$^{6b}$); N(R$^6$)C(O)OR$^{6a}$; OC(O)N(R$^6$R$^{6a}$); or T$^1$;

R$^6$, R$^{6a}$, R$^{6b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;

T$^1$ is phenyl, C$_{3-7}$ cycloalkyl; 4 to 7 membered heterocyclyl; or 7 to 11 membered heterobicyclyl, wherein T$^1$ is optionally substituted with one or more R$^7$, which are the same or different;

R$^7$ is halogen; CN; C(O)OR$^8$; OR$^8$; oxo (=O), where the ring is at least partially saturated; C(O)R$^8$; C(O)N(R$^8$R$^{8a}$); S(O)$_2$N(R$^8$R$^{8a}$); S(O)N(R$^8$R$^{8a}$); S(O)$_2$R$^8$; S(O)R$^8$; N(R$^8$)S(O)$_2$N(R$^{8a}$R$^{8b}$); N(R$^8$)S(O)N(R$^{8a}$R$^{8b}$); SR$^8$; N(R$^8$R$^{8a}$); NO$_2$; OC(O)R$^8$; N(R$^8$)C(O)R$^{8a}$; N(R$^8$)S(O)$_2$R$^{8a}$; N(R$^8$)S(O)R$^{8a}$; N(R$^8$)C(O)N(R$^{8a}$R$^{8b}$); N(R$^8$)C(O)OR$^{8a}$; OC(O)N(R$^8$R$^{8a}$); C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more R$^9$, which are the same or different;

R$^8$, R$^{8a}$, R$^{8b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^9$, which are the same or different;

R$^9$ is halogen; CN; C(O)OR$^{10}$; OR$^{10}$; C(O)R$^{10}$; C(O)N(R$^{10}$R$^{10a}$); S(O)$_2$N(R$^{10}$R$^{10a}$); S(O)N(R$^{10}$R$^{10a}$); S(O)$_2$R$^{10}$; S(O)R$^{10}$; N(R$^{10}$)S(O)$_2$N(R$^{10a}$R$^{10b}$); N(R$^{10}$)S(O)N(R$^{10a}$R$^{10b}$); SR$^{10}$; N(R$^{10}$R$^{10a}$); NO$_2$; OC(O)R$^{10}$; N(R$^{10}$)C(O)R$^{10a}$; N(R$^{10}$)S(O)$_2$R$^{10a}$; N(R$^{10}$)S(O)R$^{10a}$; N(R$^{10}$)C(O)N(R$^{10a}$R$^{10b}$); N(R$^{10}$)C(O)OR$^{10a}$; or OC(O)N(R$^{10}$R$^{10a}$);

R$^{10}$, R$^{10a}$, R$^{10b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;

X$^1$ is C(R$^{11a}$) or N; X$^2$ is C(R$^{11b}$) or N; X$^3$ is C(R$^{11c}$) or N; X$^4$ is C(R$^{11d}$) or N; X$^5$ is C(R$^{11e}$) or N, provided that at most two of X$^1$, X$^2$, X$^3$, X$^4$, X$^5$ are N;

R$^{11a}$, R$^{11c}$, R$^{11e}$ are independently selected from the group consisting of H; halogen; CN; C(O)OR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); N(R$^{12}$)S(O)N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)C(O)N(R$^{12a}$R$^{12b}$); N(R$^{12}$)C(O)OR$^{12a}$; OC(O)N(R$^{12}$R$^{12a}$); T$^2$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^{13}$, which are the same or different;

R$^{11b}$, R$^{11d}$ are independently selected from the group consisting of H; halogen; CN; C(O)OR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); N(R$^{12}$)S(O)N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)C(O)N(R$^{12a}$R$^{12b}$); N(R$^{12}$)C(O)OR$^{12a}$; OC(O)N(R$^{12}$R$^{12a}$); C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^{13}$, which are the same or different;

R$^{12}$, R$^{12a}$, R$^{12b}$ are independently selected from the group consisting of H; T$^2$; and C$_{1-6}$ alkyl, wherein C$_{1-6}$ alkyl; is optionally substituted with one or more R$^{13}$, which are the same or different;

R$^{13}$ is halogen; CN; C(O)OR$^{14}$; OR$^{14}$; C(O)R$^{14}$; C(O)N(R$^{14}$R$^{14a}$); S(O)$_2$N(R$^{14}$R$^{14a}$); S(O)N(R$^{14}$R$^{14a}$); S(O)$_2$R$^{14}$; S(O)R$^{14}$; N(R$^{14}$)S(O)$_2$N(R$^{14a}$R$^{14b}$); N(R$^{14}$)S(O)N(R$^{14a}$R$^{14b}$); SR$^{14}$; N(R$^{14}$R$^{14a}$); NO$_2$; OC(O)R$^{14}$; N(R$^{14}$)C(O)R$^{14a}$; N(R$^{14}$)S(O)$_2$R$^{14a}$; N(R$^{14}$)S(O)R$^{14a}$; N(R$^{14}$)C(O)N(R$^{14a}$R$^{14b}$); N(R$^{14}$)C(O)OR$^{14a}$; OC(O)N(R$^{14}$R$^{14a}$); or T$^2$;

R$^{14}$, R$^{14a}$, R$^{14b}$ are independently selected from the group consisting of H; T$^2$; or C$_{1-6}$ alkyl, wherein C$_{1-6}$ alkyl is optionally substituted with one or more R$^{15}$, which are the same or different;

R$^{15}$ is halogen; CN; C(O)OR$^{16}$; OR$^{16}$; C(O)R$^{16}$; C(O)N(R$^{16}$R$^{16a}$); S(O)$_2$N(R$^{16}$R$^{16a}$); S(O)N(R$^{16}$R$^{16a}$); S(O)$_2$R$^{16}$; S(O)R$^{16}$; N(R$^{16}$)S(O)$_2$N(R$^{16a}$R$^{16b}$); N(R$^{16}$)S(O)N(R$^{16a}$R$^{16b}$); SR$^{16}$; N(R$^{16}$R$^{16a}$); NO$_2$; OC(O)R$^{16}$; N(R$^{16}$)C(O)R$^{16a}$; N(R$^{16}$)S(O)$_2$R$^{16a}$; N(R$^{16}$)S(O)R$^{16a}$; N(R$^{16}$)C(O)N(R$^{16a}$R$^{16b}$); N(R$^{16}$)C(O)OR$^{16a}$; OC(O)N(R$^{16}$R$^{16a}$); or T$^2$;

R$^{16}$, R$^{16a}$, R$^{16b}$ are independently selected from the group consisting of H; T$^2$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;

T$^2$ is phenyl; naphthyl; indenyl; indanyl; C$_3$-7 cycloalkyl; 4 to 7 membered heterocyclyl; or 7 to 11 membered heterobicyclyl, wherein T$^2$ is optionally substituted with one or more R$^{17}$, which are the same or different;

R$^{17}$ is halogen; CN; C(O)OR$^{18}$; OR$^{18}$; oxo (=O), where the ring is at least partially saturated; C(O)R$^{18}$; C(O)N(R$^{18}$R$^{18a}$); S(O)$_2$N(R$^{18}$R$^{18a}$); S(O)N(R$^{18}$R$^{18a}$); S(O)$_2$R$^{18}$; S(O)R$^{18}$; N(R$^{18}$)S(O)$_2$N(R$^{18a}$R$^{18b}$); N(R$^{18}$)S(O)N(R$^{18a}$R$^{18b}$); SR$^{18}$; N(R$^{18}$R$^{18a}$); NO$_2$; OC(O)R$^{18}$; N(R$^{18}$)C(O)R$^{18a}$; N(R$^{18}$)S(O)$_2$R$^{18a}$; N(R$^{18}$)S(O)R$^{18a}$; N(R$^{18}$)C(O)N(R$^{18a}$R$^{18b}$); N(R$^{18}$)C(O)OR$^{18a}$; OC(O)N(R$^{18}$R$^{18a}$); C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more R$^{19}$, which are the same or different;

R$^{18}$, R$^{18a}$, R$^{18b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^{19}$, which are the same or different;

R$^{19}$ is halogen; CN; C(O)OR$^{20}$; OR$^{20}$; C(O)R$^{20}$; C(O)N(R$^{20}$R$^{20a}$); S(O)$_2$N(R$^{20}$R$^{20a}$); S(O)N(R$^{20}$R$^{20a}$); S(O)$_2$R$^{20}$; S(O)R$^{20}$; N(R$^{20}$)S(O)$_2$N(R$^{20a}$R$^{20b}$); N(R$^{20}$)S(O)N(R$^{2a}$R$^{20b}$); SR$^{20}$; N(R$^{20}$R$^{20a}$); NO$_2$; OC(O)R$^{20}$; N(R$^{20}$)C(O)R$^{20a}$; N(R$^{20}$)S(O)$_2$R$^{20a}$; N(R$^{20}$)S(O)R$^{20a}$; N(R$^{20}$)C(O)N(R$^{2a}$R$^{20b}$); N(R$^{20}$)C(O)OR$^{20a}$; or OC(O)N(R$^{20}$R$^{20a}$);

R$^{20}$, R$^{20a}$, R$^{20b}$ are independently selected from the group consisting of H; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different.

2. The compound of claim 1, wherein $R^1$ is $C_{1-4}$ alkyl, substituted with one or two $R^3$, which are the same or different.

3. The compound of claim 1, wherein $R^3$ is halogen; $OR^4$; $C(O)T^1$; $C(O)N(R^4R^{4a})$; or $T^1$.

4. The compound of claim 1, wherein $R^3$ is $C(O)N(R^4R^{4a})$; $C(O)T^1$; or $T^1$.

5. The compound of claim 1, wherein $R^4$ and $R^{4a}$ are independently selected from the group consisting of H; $T^1$; and $C_1$-4 alkyl, optionally substituted with $OR^6$.

6. The compound of claim 1, wherein $T^1$ is morpholinyl; pyrrolidinyl; piperidinyl; tetrahydrofuranyl; cyclobutyl; or cyclopropyl.

7. The compound of claim 1, wherein $R^1$ is H or $CH_3$.

8. The compound of claim 1, wherein R is H; F; Cl; or $CH_3$.

9. The compound of claim 1, wherein $R^{11a}$, $R^{11b}$, $R^{11c}$, $R^{11d}$, $R^{11e}$ are independently selected from the group consisting of H; halogen; CN; $OR^{12}$; $C(O)R^{12}$; $C(O)N(R^{12}R^{12a})$; $S(O)_2N(R^{12}R^{12a})$; $S(O)_2R^{12}$; or $C_{1-6}$ alkyl optionally substituted with one or more halogen.

10. The compound of claim 1, wherein $R^{11a}$ and $R^{11b}$ are independently F; or Cl.

11. The compounds of claim 1 with formula (Ia)

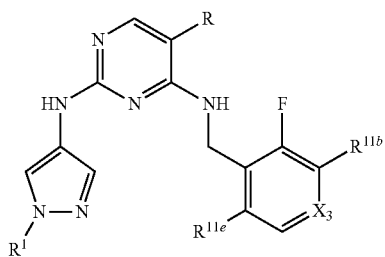

(Ia)

wherein, R is H; or F;
$X^3$ is N; or $C(R^{11c})$;
$R^{11b}$ is H; F; Cl; $CH_3$; CN; or $OCH_3$;
$R^{11c}$ is H; F; Cl; $CH_3$; CN; $OCH_3$; $SO_2NH_2$; or $C(O)N(R^{12}R^{12a})$;
$R^{11e}$ is F; Cl; or $CH_3$;
and wherein $R^1$, $R^{12}$, $R^{12a}$ have the meanings as indicated in any one of claims 1 to 7;
provided that at least one or both of $R^{11b}$, $R^{11c}$ are H.

12. The compound of claim 1, wherein $X^1$, $X^2$, $X^4$, $X^5$ are other than N.

13. The compound of claim 1, wherein R is H.

14. The compound of claim 1 or a pharmaceutically acceptable salt, selected from the group consisting of:
2-(4-((4-((4-cyano-2,6-difluorobenzyl)amino)pyrimidin-2-yl)amino)-1H-pyrazol-1-yl)-N-isopropylacetamide;
(S)-2-(4-((4-((2,6-dichlorobenzyl)amino)pyrimidin-2-yl)amino)-1H-pyrazol-1-yl)-N-(1-hydroxypropan-2-yl)acetamide;
N-cyclopropyl-2-(4-((5-fluoro-4-((2,4,6-trifluorobenzyl)amino)pyrimidin-2-yl)amino)-1H-pyrazol-1-yl)acetamide;
N-(1-cyanoethyl)-2-(4-((4-((2,4,6-trifluorobenzyl)amino)pyrimidin-2-yl)amino)-1H-pyrazol-1-yl)acetamide;
N-ethyl-2-(4-((4-((2,4,6-trifluorobenzyl)amino)pyrimidin-2-yl)amino)-1H-pyrazol-1-yl)acetamide;
3,5-difluoro-N,N-dimethyl-4-(((2-((1-methyl-1H-pyrazol-4-yl)amino)pyrimidin-4-yl)amino)methyl)benzamide;
4-(((2-((1-(2-hydroxyethyl)-1H-pyrazol-4-yl)amino)-5-methylpyrimidin-4-yl)amino)methyl)benzenesulfonamide;
4-(((5-fluoro-2-((1-(2-hydroxyethyl)-1H-pyrazol-4-yl)amino)pyrimidin-4-yl)amino)methyl)benzenesulfonamide;
2-(4-((5-chloro-4-((4-sulfamoylbenzyl)amino)pyrimidin-2-yl)amino)-1H-pyrazol-1-yl)-N-cyclopropylacetamide;
4-(((5-fluoro-2-((1-(2-morpholino-2-oxoethyl)-1H-pyrazol-4-yl)amino)pyrimidin-4-yl)amino)methyl)benzenesulfonamide;
2-(4-((4-((2,6-difluoro-3-methoxybenzyl)amino)-5-fluoropyrimidin-2-yl)amino)-1H-pyrazol-1-yl)-N-methylacetamide;
2-(4-((4-((2,6-difluoro-3-methoxybenzyl)amino)-5-fluoropyrimidin-2-yl)amino)-1H-pyrazol-1-yl)-N,N-dimethylacetamide;
2-(4-((4-((3-(difluoromethoxy)benzyl)amino)-5-fluoropyrimidin-2-yl)amino)-1H-pyrazol-1-yl)-N,N-dimethylacetamide;
2-(4-((5-chloro-4-((2,4,6-trifluorobenzyl)amino)pyrimidin-2-yl)amino)-1H-pyrazol-1-yl)ethanol;
2-(4-((5-chloro-4-((2,4,6-trifluorobenzyl)amino)pyrimidin-2-yl)amino)-1H-pyrazol-1-yl)-N,N-dimethylacetamide;
2-(4-((5-fluoro-4-((2,4,6-trifluorobenzyl)amino)pyrimidin-2-yl)amino)-1H-pyrazol-1-yl)ethanol;
2-(4-((5-fluoro-4-((2,4,6-trifluorobenzyl)amino)pyrimidin-2-yl)amino)-1H-pyrazol-1-yl)-N,N-dimethylacetamide;
N,N-dimethyl-2-(4-((5-methyl-4-((2,4,6-trifluorobenzyl)amino)pyrimidin-2-yl)amino)-1H-pyrazol-1-yl)acetamide;
2-(4-((4-((2,6-difluoro-3-methoxybenzyl)amino)-5-methylpyrimidin-2-yl)amino)-1H-pyrazol-1-yl)-N,N-dimethylacetamide;
2-(4-((5-methyl-4-((2,4,6-trifluorobenzyl)amino)pyrimidin-2-yl)amino)-1H-pyrazol-1-yl)-1-morpholinoethanone;
2-(4-((4-((2,6-difluoro-3-methoxybenzyl)amino)-5-methylpyrimidin-2-yl)amino)-1H-pyrazol-1-yl)-1-morpholinoethanone;
2-(4-((4-((3-(difluoromethoxy)benzyl)amino)-5-methylpyrimidin-2-yl)amino)-1H-pyrazol-1-yl)-1-morpholinoethanone;
2-(4-((4-((2,6-difluoro-3-methoxybenzyl)amino)-5-fluoropyrimidin-2-yl)amino)-1H-pyrazol-1-yl)-1-morpholinoethanone;
2-(4-((4-((3-bromo-2-fluorobenzyl)amino)-5-chloropyrimidin-2-yl)amino)-1H-pyrazol-1-yl)ethanol;
2-(4-((5-fluoro-4-((2,4,6-trifluorobenzyl)amino)pyrimidin-2-yl)amino)-1H-pyrazol-1-yl)-1-morpholinoethanone;
1-morpholino-2-(4-((4-((2,4,6-trifluorobenzyl)amino)pyrimidin-2-yl)amino)-1H-pyrazol-1-yl)ethanone;
2-(4-((4-((2,6-difluorobenzyl)amino)pyrimidin-2-yl)amino)-1H-pyrazol-1-yl)-1-morpholinoethanone;
2-(4-((4-((2,6-difluoro-4-methoxybenzyl)amino)-5-methylpyrimidin-2-yl)amino)-1H-pyrazol-1-yl)-1-morpholinoethanone;
4-(((5-fluoro-2-((1-(2-oxo-2-(piperidin-1-yl)ethyl)-1H-pyrazol-4-yl)amino)pyrimidin-4-yl)amino)methyl)benzenesulfonamide;
3,5-difluoro-4-(((5-fluoro-2-((1-(2-oxo-2-(piperidin-1-yl)ethyl)-1H-pyrazol-4-yl)amino)pyrimidin-4-yl)amino)methyl)benzenesulfonamide;

N-isopropyl-2-(4-((5-methyl-4-((2,4,6-trifluorobenzyl)amino)pyrimidin-2-yl)amino)-1H-pyrazol-1-yl)acetamide;
N-cyclobutyl-2-(4-((5-methyl-4-((2,4,6-trifluorobenzyl)amino)pyrimidin-2-yl)amino)-1H-pyrazol-1-yl)acetamide;
1-(2,2-dimethylmorpholino)-2-(4-((5-methyl-4-((2,4,6-trifluorobenzyl)amino)pyrimidin-2-yl)amino)-1H-pyrazol-1-yl)ethanone;
(R)—N-(1-hydroxypropan-2-yl)-2-(4-((5-methyl-4-((2,4,6-trifluorobenzyl)amino)pyrimidin-2-yl)amino)-1H-pyrazol-1-yl)acetamide;
(S)—N-(1-hydroxypropan-2-yl)-2-(4-((5-methyl-4-((2,4,6-trifluorobenzyl)amino)pyrimidin-2-yl)amino)-1H-pyrazol-1-yl)acetamide;
2-(4-((5-methyl-4-((2,4,6-trifluorobenzyl)amino)pyrimidin-2-yl)amino)-1H-pyrazol-1-yl)-N-(tetrahydrofuran-3-yl)acetamide;
2-(4-((5-fluoro-4-((2,4,6-trifluorobenzyl)amino)pyrimidin-2-yl)amino)-1H-pyrazol-1-yl)-N-isopropylacetamide;
1-(2,2-dimethylmorpholino)-2-(4-((5-fluoro-4-((2,4,6-trifluorobenzyl)amino)pyrimidin-2-yl)amino)-1H-pyrazol-1-yl)ethanone;
(R)-2-(4-((5-fluoro-4-((2,4,6-trifluorobenzyl)amino)pyrimidin-2-yl)amino)-1H-pyrazol-1-yl)-1-(3-methylmorpholino)ethanone;
(R)-2-(4-((5-fluoro-4-((2,4,6-trifluorobenzyl)amino)pyrimidin-2-yl)amino)-1H-pyrazol-1-yl)-N-(1-hydroxypropan-2-yl)acetamide;
(S)-2-(4-((5-fluoro-4-((2,4,6-trifluorobenzyl)amino)pyrimidin-2-yl)amino)-1H-pyrazol-1-yl)-N-(1-hydroxypropan-2-yl)acetamide;
3,5-difluoro-4-(((5-methyl-2-((1-methyl-1H-pyrazol-4-yl)amino)pyrimidin-4-yl)amino)methyl)benzenesulfonamide;
2-(4-((4-((3-(difluoromethoxy)benzyl)amino)-5-fluoropyrimidin-2-yl)amino)-1H-pyrazol-1-yl)-1-morpholinoethanone;
2-(4-((4-((3-(difluoromethoxy)benzyl)amino)-5-fluoropyrimidin-2-yl)amino)-1H-pyrazol-1-yl)-N-isopropylacetamide;
N-cyclopropyl-2-(4-((4-((3-(difluoromethoxy)benzyl)amino)-5-fluoropyrimidin-2-yl)amino)-1H-pyrazol-1-yl)acetamide;
isopropyl 2-(4-((4-((2,6-difluoro-3-methoxybenzyl)amino)-5-fluoropyrimidin-2-yl)amino)-1H-pyrazol-1-yl)acetate;
2-(4-((4-((2,6-difluoro-3-methoxybenzyl)amino)-5-fluoropyrimidin-2-yl)amino)-1H-pyrazol-1-yl)-N-isopropylacetamide;
2-(4-((4-((2,6-dichlorobenzyl)amino)-5-fluoropyrimidin-2-yl)amino)-1H-pyrazol-1-yl)-1-morpholinoethanone;
N-isopropyl-2-(4-((4-((2,4,6-trifluorobenzyl)amino)pyrimidin-2-yl)amino)-1H-pyrazol-1-yl)acetamide;
N-(tert-butyl)-2-(4-((4-((2,4,6-trifluorobenzyl)amino)pyrimidin-2-yl)amino)-1H-pyrazol-1-yl)acetamide;
(S)-1-(3-methylmorpholino)-2-(4-((4-((2,4,6-trifluorobenzyl)amino)pyrimidin-2-yl)amino)-1H-pyrazol-1-yl)ethanone;
ethyl 2-(4-((4-((2,6-difluoro-3-methoxybenzyl)amino)-5-fluoropyrimidin-2-yl)amino)-1H-pyrazol-1-yl)acetate;
ethyl 2-(4-((5-fluoro-4-((2,4,6-trifluorobenzyl)amino)pyrimidin-2-yl)amino)-1H-pyrazol-1-yl)acetate;
N4-(2-chloro-6-fluorobenzyl)-N2-(1-methyl-1H-pyrazol-4-yl)pyrimidine-2,4-diamine;
2-(4-((4-((3-(difluoromethoxy)benzyl)amino)-5-fluoropyrimidin-2-yl)amino)-1H-pyrazol-1-yl)-N-isopropyl-N-methylacetamide;
2-(4-((4-((2,6-difluoro-3-methoxybenzyl)amino)-5-fluoropyrimidin-2-yl)amino)-1H-pyrazol-1-yl)-N-isopropyl-N-methylacetamide;
2-(4-((5-fluoro-4-((2,4,6-trifluorobenzyl)amino)pyrimidin-2-yl)amino)-1H-pyrazol-1-yl)-N-(pentan-3-yl)acetamide;
2-(4-((5-fluoro-4-((2,4,6-trifluorobenzyl)amino)pyrimidin-2-yl)amino)-1H-pyrazol-1-yl)-N-isopropyl-N-methylacetamide;
N4-(3,6-dichloro-2-fluorobenzyl)-N2-(1-methyl-1H-pyrazol-4-yl)pyrimidine-2,4-diamine;
N4-(6-chloro-2-fluoro-3-methoxybenzyl)-N2-(1-methyl-1H-pyrazol-4-yl)pyrimidine-2,4-diamine;
2-(4-((4-((2,6-difluorobenzyl)amino)pyrimidin-2-yl)amino)-1H-pyrazol-1-yl)-N-isopropylacetamide;
N-isopropyl-2-(4-((4-((2,3,6-trifluorobenzyl)amino)pyrimidin-2-yl)amino)-1H-pyrazol-1-yl)acetamide;
2-(4-((4-((2,6-difluoro-4-methoxybenzyl)amino)pyrimidin-2-yl)amino)-1H-pyrazol-1-yl)-N-isopropylacetamide;
2-(4-((4-((2,6-difluoro-3-methoxybenzyl)amino)pyrimidin-2-yl)amino)-1H-pyrazol-1-yl)-N-isopropylacetamide;
2-(4-((4-((2,6-difluorobenzyl)amino)-5-fluoropyrimidin-2-yl)amino)-1H-pyrazol-1-yl)-N-isopropylacetamide;
2-(4-((4-((3-(difluoromethoxy)benzyl)amino)pyrimidin-2-yl)amino)-1H-pyrazol-1-yl)-N-isopropylacetamide;
N4-(6-chloro-2,3-difluorobenzyl)-N2-(1-methyl-1H-pyrazol-4-yl)pyrimidine-2,4-diamine;
3,5-difluoro-4-(((2-((1-methyl-1H-pyrazol-4-yl)amino)pyrimidin-4-yl)amino)methyl)benzamide;
2-(4-((4-((2,6-difluoro-4-methoxybenzyl)amino)-5-fluoropyrimidin-2-yl)amino)-1H-pyrazol-1-yl)-N-isopropylacetamide;
(S)-2-(4-((5-fluoro-4-((2,4,6-trifluorobenzyl)amino)pyrimidin-2-yl)amino)-1H-pyrazol-1-yl)-N-(1-methoxypropan-2-yl)acetamide;
5-chloro-N4-(5-fluoro-2-(methylsulfonyl)benzyl)-N2-(1H-pyrazol-4-yl)pyrimidine-2,4-diamine;
(S)-2-(4-((5-fluoro-4-((2,4,6-trifluorobenzyl)amino)pyrimidin-2-yl)amino)-1H-pyrazol-1-yl)-1-(3-methylmorpholino)ethanone;
2-(4-((5-chloro-4-((5-fluoro-2-(methylsulfonyl)benzyl)amino)pyrimidin-2-yl)amino)-1H-pyrazol-1-yl)-N-cyclopropylacetamide;
(S)—N-(1-hydroxypropan-2-yl)-2-(4-((4-((2,4,6-trifluorobenzyl)amino)pyrimidin-2-yl)amino)-1H-pyrazol-1-yl)acetamide;
2-(4-((4-((2,6-dichlorobenzyl)amino)pyrimidin-2-yl)amino)-1H-pyrazol-1-yl)-N-isopropylacetamide;
2-(4-((4-((2-chloro-6-fluorobenzyl)amino)pyrimidin-2-yl)amino)-1H-pyrazol-1-yl)-N-isopropylacetamide;
2-(4-((4-((3,6-dichloro-2-fluorobenzyl)amino)pyrimidin-2-yl)amino)-1H-pyrazol-1-yl)-N-isopropylacetamide;
2-(4-((4-((6-chloro-2-fluoro-3-methoxybenzyl)amino)pyrimidin-2-yl)amino)-1H-pyrazol-1-yl)-N-isopropylacetamide;
N-cyclopropyl-2-(4-((4-((2,4,6-trifluorobenzyl)amino)pyrimidin-2-yl)amino)-1H-pyrazol-1-yl)acetamide;
2-(4-((4-((6-chloro-2-fluoro-3-methoxybenzyl)amino)-5-fluoropyrimidin-2-yl)amino)-1H-pyrazol-1-yl)-1-morpholinoethanone;

2-(4-((4-((3,6-dichloro-2-fluorobenzyl)amino)-5-fluoropyrimidin-2-yl)amino)-1H-pyrazol-1-yl)-N-isopropylacetamide;

2-(4-((4-((3,6-dichloro-2-fluorobenzyl)amino)-5-fluoropyrimidin-2-yl)amino)-1H-pyrazol-1-yl)-1-morpholinoethanone;

2-(4-((4-((6-chloro-2-fluoro-3-methoxybenzyl)amino)-5-fluoropyrimidin-2-yl)amino)-1H-pyrazol-1-yl)-N-isopropylacetamide;

N4-(6-chloro-2-fluoro-3-methoxybenzyl)-5-fluoro-N2-(1-methyl-1H-pyrazol-4-yl)pyrimidine-2,4-diamine;

2-(4-((4-((2,4,6-trifluorobenzyl)amino)pyrimidin-2-yl)amino)-1H-pyrazol-1-yl)-N-(2,2,2-trifluoroethyl)acetamide;

N2-(1-(2,2-difluoroethyl)-1H-pyrazol-4-yl)-5-methyl-N4-(2,3,6-trifluorobenzyl)pyrimidine-2,4-diamine;

2-(4-((5-fluoro-4-((2-methoxy-5-(methylsulfonyl)benzyl)amino)pyrimidin-2-yl)amino)-1H-pyrazol-1-yl)ethanol;

N-(2-hydroxyethyl)-2-(4-((4-((2,4,6-trifluorobenzyl)amino)pyrimidin-2-yl)amino)-1H-pyrazol-1-yl)acetamide;

N-(2-fluoroethyl)-2-(4-((4-((2,4,6-trifluorobenzyl)amino)pyrimidin-2-yl)amino)-1H-pyrazol-1-yl)acetamide;

N-(2,2-difluorocyclopropyl)-2-(4-((4-((2,4,6-trifluorobenzyl)amino)pyrimidin-2-yl)amino)-1H-pyrazol-1-yl)acetamide;

N-(2,2-difluoroethyl)-2-(4-((4-((2,4,6-trifluorobenzyl)amino)pyrimidin-2-yl)amino)-1H-pyrazol-1-yl)acetamide;

2-(4-((4-((6-chloro-2,3-difluorobenzyl)amino)pyrimidin-2-yl)amino)-1H-pyrazol-1-yl)-N-isopropylacetamide;

2-(4-((4-((2-chloro-4,6-difluorobenzyl)amino)pyrimidin-2-yl)amino)-1H-pyrazol-1-yl)-N-isopropylacetamide;

N-(tetrahydrofuran-3-yl)-2-(4-((4-((2,4,6-trifluorobenzyl)amino)pyrimidin-2-yl)amino)-1H-pyrazol-1-yl)acetamide;

N4-(3,5-difluoro-2-methoxybenzyl)-5-methyl-N2-(1-methyl-1H-pyrazol-4-yl)pyrimidine-2,4-diamine;

2-(4-((5-fluoro-4-((5-fluoro-2-(methylsulfonyl)benzyl)amino)pyrimidin-2-yl)amino)-1H-pyrazol-1-yl)-N-methylacetamide;

5-chloro-N4-(2-fluoro-5-(methylsulfonyl)benzyl)-N2-(1H-pyrazol-4-yl)pyrimidine-2,4-diamine;

5-chloro-N4-(2-fluoro-5-(methylsulfonyl)benzyl)-N2-(1-methyl-1H-pyrazol-4-yl)pyrimidine-2,4-diamine;

2-(4-((5-chloro-4-((2-fluoro-5-(methylsulfonyl)benzyl)amino)pyrimidin-2-yl)amino)-1H-pyrazol-1-yl)acetamide;

N-cyclopropyl-2-(4-((5-methyl-4-((2,3,5-trifluorobenzyl)amino)pyrimidin-2-yl)amino)-1H-pyrazol-1-yl)acetamide;

N-((1R,2S)-2-fluorocyclopropyl)-2-(4-((4-((2,4,6-trifluorobenzyl)amino)pyrimidin-2-yl)amino)-1H-pyrazol-1-yl)acetamide;

N2-(1-(2,2-difluoroethyl)-1H-pyrazol-4-yl)-5-methyl-N4-(2,3,5-trifluorobenzyl)pyrimidine-2,4-diamine;

N4-(2,5-difluorobenzyl)-N2-(1-(2,2-difluoroethyl)-1H-pyrazol-4-yl)-5-methylpyrimidine-2,4-diamine;

N-(1-(tetrahydrofuran-3-yl)ethyl)-2-(4-((4-((2,4,6-trifluorobenzyl)amino)pyrimidin-2-yl)amino)-1H-pyrazol-1-yl)acetamide;

(R)-2-(4-((4-((2-chloro-6-fluorobenzyl)amino)pyrimidin-2-yl)amino)-1H-pyrazol-1-yl)-N-(1-hydroxypropan-2-yl)acetamide;

N2-(1-(2,2-difluoroethyl)-1H-pyrazol-4-yl)-N4-(2-methoxy-5-(methylsulfonyl)benzyl)-5-methylpyrimidine-2,4-diamine;

2-(((5-chloro-2-((1-(2,2-difluoroethyl)-1H-pyrazol-4-yl)amino)pyrimidin-4-yl)amino)methyl)-N-methylbenzenesulfonamide;

2-(((5-chloro-2-((1-(2,2-difluoroethyl)-1H-pyrazol-4-yl)amino)pyrimidin-4-yl)amino)methyl)-N,N-dimethylbenzenesulfonamide;

N-(cyanomethyl)-2-(4-((4-((2,4,6-trifluorobenzyl)amino)pyrimidin-2-yl)amino)-1H-pyrazol-1-yl)acetamide;

1-(2-(4-((4-((2,4,6-trifluorobenzyl)amino)pyrimidin-2-yl)amino)-1H-pyrazol-1-yl)ethyl)pyrrolidin-2-one;

N2-(1-(2-morpholinoethyl)-1H-pyrazol-4-yl)-N4-(2,4,6-trifluorobenzyl)pyrimidine-2,4-diamine;

2-(4-((4-((3,5-difluoro-2-methoxybenzyl)amino)-5-methylpyrimidin-2-yl)amino)-1H-pyrazol-1-yl)-N-methylacetamide;

5-fluoro-N4-(2-fluoro-5-(methylsulfonyl)benzyl)-N2-(1H-pyrazol-4-yl)pyrimidine-2,4-diamine;

2-(4-((5-fluoro-4-((2-fluoro-5-(methylsulfonyl)benzyl)amino)pyrimidin-2-yl)amino)-1H-pyrazol-1-yl)ethanol;

2-(4-((5-fluoro-4-((2-fluoro-5-(methylsulfonyl)benzyl)amino)pyrimidin-2-yl)amino)-1H-pyrazol-1-yl)acetamide;

2-(4-((4-((2,6-difluoro-3-methoxybenzyl)amino)pyrimidin-2-yl)amino)-1H-pyrazol-1-yl)-1-morpholinoethanone;

5-chloro-N4-(2-fluoro-6-(trifluoromethyl)benzyl)-N2-(1-methyl-1H-pyrazol-4-yl)pyrimidine-2,4-diamine;

2-(4-((4-((2,6-dichloro-3-fluorobenzyl)amino)pyrimidin-2-yl)amino)-1H-pyrazol-1-yl)-N-isopropylacetamide;

(S)-2-(4-((4-((2-chloro-6-fluorobenzyl)amino)pyrimidin-2-yl)amino)-1H-pyrazol-1-yl)-N-(1-hydroxypropan-2-yl)acetamide;

(S)-2-(4-((4-((3,6-dichloro-2-fluorobenzyl)amino)pyrimidin-2-yl)amino)-1H-pyrazol-1-yl)-N-(1-hydroxypropan-2-yl)acetamide;

(S)-2-(4-((4-((6-chloro-2-fluoro-3-methoxybenzyl)amino)pyrimidin-2-yl)amino)-1H-pyrazol-1-yl)-N-(1-hydroxypropan-2-yl)acetamide;

(R)-2-(4-((4-((6-chloro-2-fluoro-3-methoxybenzyl)amino)pyrimidin-2-yl)amino)-1H-pyrazol-1-yl)-N-(1-hydroxypropan-2-yl)acetamide;

(R)-2-(4-((4-((2,6-difluoro-3-methoxybenzyl)amino)pyrimidin-2-yl)amino)-1H-pyrazol-1-yl)-N-(1-hydroxypropan-2-yl)acetamide;

N-cyclopropyl-2-(4-((4-((2,6-difluoro-3-methoxybenzyl)amino)pyrimidin-2-yl)amino)-1H-pyrazol-1-yl)acetamide;

2-(4-((4-((2,6-difluoro-3-methoxybenzyl)amino)pyrimidin-2-yl)amino)-1H-pyrazol-1-yl)-N-(2-fluoroethyl)acetamide;

2-(4-((4-((2,6-difluoro-3-methoxybenzyl)amino)pyrimidin-2-yl)amino)-1H-pyrazol-1-yl)-N-(2,2-difluoroethyl)acetamide;

2-(4-((4-((2,6-difluoro-3-methoxybenzyl)amino)pyrimidin-2-yl)amino)-1H-pyrazol-1-yl)-N-((1R,2S)-2-fluorocyclopropyl)acetamide;

2-(4-((4-((2-chloro-6-fluorobenzyl)amino)pyrimidin-2-yl)amino)-1H-pyrazol-1-yl)-1-morpholinoethanone;

(S)-2-(4-((4-((2,6-difluoro-3-methylbenzyl)amino)pyrimidin-2-yl)amino)-1H-pyrazol-1-yl)-N-(1-hydroxypropan-2-yl)acetamide;

(R)-2-(4-((4-((3,6-dichloro-2-fluorobenzyl)amino)pyrimidin-2-yl)amino)-1H-pyrazol-1-yl)-N-(1-hydroxypropan-2-yl)acetamide;
(S)-2-(4-((4-((2-chloro-4,6-difluorobenzyl)amino)pyrimidin-2-yl)amino)-1H-pyrazol-1-yl)-N-(1-hydroxypropan-2-yl)acetamide;
(S)-2-(4-((4-((2,6-difluoro-3-methoxybenzyl)amino)pyrimidin-2-yl)amino)-1H-pyrazol-1-yl)-N-(1-hydroxypropan-2-yl)acetamide;
2-(4-((4-((3-cyano-2,6-difluorobenzyl)amino)pyrimidin-2-yl)amino)-1H-pyrazol-1-yl)-N-isopropylacetamide;
2,4-difluoro-3-(((2-((1-methyl-1H-pyrazol-4-yl)amino)pyrimidin-4-yl)amino)methyl)benzonitrile;
5-chloro-N4-(3-fluoro-2-(trifluoromethyl)benzyl)-N2-(1H-pyrazol-4-yl)pyrimidine-2,4-diamine;
(R)—N-(tetrahydrofuran-3-yl)-2-(4-((4-((2,4,6-trifluorobenzyl)amino)pyrimidin-2-yl)amino)-1H-pyrazol-1-yl)acetamide;
(S)—N-(tetrahydrofuran-3-yl)-2-(4-((4-((2,4,6-trifluorobenzyl)amino)pyrimidin-2-yl)amino)-1H-pyrazol-1-yl)acetamide;
2-(4-((4-((2-chloro-6-fluorobenzyl)amino)pyrimidin-2-yl)amino)-1H-pyrazol-1-yl)-N-cyclopropylacetamide;
2-(4-((4-((2-chloro-6-fluorobenzyl)amino)pyrimidin-2-yl)amino)-1H-pyrazol-1-yl)-N-(2-fluoroethyl)acetamide;
2-(4-((4-((2-chloro-6-fluorobenzyl)amino)pyrimidin-2-yl)amino)-1H-pyrazol-1-yl)-N-(2,2-difluoroethyl)acetamide;
2-(4-((4-((2-chloro-6-fluorobenzyl)amino)pyrimidin-2-yl)amino)-1H-pyrazol-1-yl)-N-((1R,2S)-2-fluorocyclopropyl)acetamide;
(R)—N-(1-hydroxypropan-2-yl)-2-(4-((4-((2,3,6-trifluorobenzyl)amino)pyrimidin-2-yl)amino)-1H-pyrazol-1-yl)acetamide;
N-cyclopropyl-2-(4-((4-((2,3,6-trifluorobenzyl)amino)pyrimidin-2-yl)amino)-1H-pyrazol-1-yl)acetamide;
2-(4-((4-(((3,5-difluoropyridin-4-yl)methyl)amino)pyrimidin-2-yl)amino)-1H-pyrazol-1-yl)-N-isopropylacetamide;
(S)-2-(4-((4-(((3,5-difluoropyridin-4-yl)methyl)amino)pyrimidin-2-yl)amino)-1H-pyrazol-1-yl)-N-(1-hydroxypropan-2-yl)acetamide;
(R)-2-(4-((4-(((3,5-difluoropyridin-4-yl)methyl)amino)pyrimidin-2-yl)amino)-1H-pyrazol-1-yl)-N-(1-hydroxypropan-2-yl)acetamide;
N4-((3,5-difluoropyridin-4-yl)methyl)-N2-(1-methyl-1H-pyrazol-4-yl)pyrimidine-2,4-diamine;
N-(1,1-difluoropropan-2-yl)-2-(4-((4-((2,4,6-trifluorobenzyl)amino)pyrimidin-2-yl)amino)-1H-pyrazol-1-yl)acetamide;
N-(2-(4-((5-fluoro-4-((2,4,6-trifluorobenzyl)amino)pyrimidin-2-yl)amino)-1H-pyrazol-1-yl)ethyl)acetamide;
(S)-2-(4-((4-((2,6-difluorobenzyl)amino)pyrimidin-2-yl)amino)-1H-pyrazol-1-yl)-N-(1-hydroxypropan-2-yl)acetamide;
N-cyclopropyl-2-(4-((4-((2,6-difluorobenzyl)amino)pyrimidin-2-yl)amino)-1H-pyrazol-1-yl)acetamide;
(S)-2-(4-((4-((3-cyano-2,6-difluorobenzyl)amino)pyrimidin-2-yl)amino)-1H-pyrazol-1-yl)-N-(1-hydroxypropan-2-yl)acetamide;
(R)-2-(4-((4-((3-cyano-2,6-difluorobenzyl)amino)pyrimidin-2-yl)amino)-1H-pyrazol-1-yl)-N-(1-hydroxypropan-2-yl)acetamide;
2-(4-((4-((2-fluoro-6-methylbenzyl)amino)pyrimidin-2-yl)amino)-1H-pyrazol-1-yl)-N-isopropylacetamide;
(S)-2-(4-((4-((2-fluoro-6-methylbenzyl)amino)pyrimidin-2-yl)amino)-1H-pyrazol-1-yl)-N-(1-hydroxypropan-2-yl)acetamide;
2-(4-((5-fluoro-4-((2,4,6-trifluorobenzyl)amino)pyrimidin-2-yl)amino)-1H-pyrazol-1-yl)acetamide;
1N$^4$-benzyl-5-chloro-N$^2$-(1-methyl-1H-pyrazol-4-yl)pyrimidine-2,4-diamine;
3-(((5-chloro-2-((1-methyl-1H-pyrazol-4-yl)amino)pyrimidin-4-yl)amino)methyl)benzonitrile;
2-(4-((4-(benzylamino)-5-chloropyrimidin-2-yl)amino)-1H-pyrazol-1-yl)-1-morpholinoethanone;
2-(4-((5-chloro-4-((2,6-difluorobenzyl)amino)pyrimidin-2-yl)amino)-1H-pyrazol-1-yl)-1-morpholinoethanone;
2-(4-((5-chloro-4-((3,5-difluorobenzyl)amino)pyrimidin-2-yl)amino)-1H-pyrazol-1-yl)-1-morpholinoethanone;
N$^4$-(3-bromobenzyl)-5-chloro-N$^2$-(1-methyl-1H-pyrazol-4-yl)pyrimidine-2,4-diamine;
2-(4-((4-((5-bromo-2-fluorobenzyl)amino)-5-chloropyrimidin-2-yl)amino)-1H-pyrazol-1-yl)ethanol;
2-(4-((5-chloro-4-((2,6-difluorobenzyl)amino)pyrimidin-2-yl)amino)-1H-pyrazol-1-yl)acetic acid;
5-chloro-N$^4$-(3-fluoro-5-(trifluoromethyl)benzyl)-N$^2$-(1-methyl-1H-pyrazol-4-yl)pyrimidine-2,4-diamine;
3-(((5-fluoro-2-((1-(2-hydroxyethyl)-1H-pyrazol-4-yl)amino)pyrimidin-4-yl)amino)methyl)benzonitrile;
2-(4-((5-chloro-4-((3,5-difluorobenzyl)amino)pyrimidin-2-yl)amino)-1H-pyrazol-1-yl)acetic acid;
2-(4-((4-(benzylamino)-5-methylpyrimidin-2-yl)amino)-1H-pyrazol-1-yl)ethanol;
2-(4-((4-((2,3-difluorobenzyl)amino)-5-fluoropyrimidin-2-yl)amino)-1H-pyrazol-1-yl)ethanol;
2-(4-((5-chloro-4-((3-fluorobenzyl)amino)pyrimidin-2-yl)amino)-1H-pyrazol-1-yl)ethanol;
3-(((5-chloro-2-((1-(2-morpholino-2-oxoethyl)-1H-pyrazol-4-yl)amino)pyrimidin-4-yl)amino)methyl)benzonitrile;
5-chloro-N$^4$-(2-fluorobenzyl)-N$^2$-(1-methyl-1H-pyrazol-4-yl)pyrimidine-2,4-diamine;
2-(4-((5-chloro-4-((2-fluorobenzyl)amino)pyrimidin-2-yl)amino)-1H-pyrazol-1-yl)ethanol;
5-chloro-N$^4$-(2,6-difluorobenzyl)-N$^2$-(1-methyl-1H-pyrazol-4-yl)pyrimidine-2,4-diamine;
5-chloro-N$^4$-(3,5-difluorobenzyl)-N$^2$-(1-methyl-1H-pyrazol-4-yl)pyrimidine-2,4-diamine;
N$^4$-(2,3-difluorobenzyl)-5-fluoro-N$^2$-(1-methyl-1H-pyrazol-4-yl)pyrimidine-2,4-diamine;
2-(4-((5-chloro-4-((2,3-difluorobenzyl)amino)pyrimidin-2-yl)amino)-1H-pyrazol-1-yl)-1-morpholinoethanone;
5-chloro-N$^4$-(2,3-difluorobenzyl)-N$^2$-(1-methyl-1H-pyrazol-4-yl)pyrimidine-2,4-diamine;
2-(4-((5-chloro-4-((2,3-difluorobenzyl)amino)pyrimidin-2-yl)amino)-1H-pyrazol-1-yl)ethanol;
2-(4-((5-chloro-4-((3-fluoro-5-(trifluoromethyl)benzyl)amino)pyrimidin-2-yl)amino)-1H-pyrazol-1-yl)ethanol;
3-(((5-chloro-2-((1-(2-hydroxyethyl)-1H-pyrazol-4-yl)amino)pyrimidin-4-yl)amino)methyl)benzonitrile;
3-(((5-fluoro-2-((1-methyl-1H-pyrazol-4-yl)amino)pyrimidin-4-yl)amino)methyl)benzonitrile;
3-(((5-chloro-2-((1-(2-hydroxypropyl)-1H-pyrazol-4-yl)amino)pyrimidin-4-yl)amino)methyl)-4-fluorobenzenesulfonamide;
2-(4-((5-chloro-4-((2-methoxybenzyl)amino)pyrimidin-2-yl)amino)-1H-pyrazol-1-yl)ethanol;
2-(4-((5-chloro-4-((3-methoxybenzyl)amino)pyrimidin-2-yl)amino)-1H-pyrazol-1-yl)ethanol;

2-(4-((4-(benzylamino)-5-chloropyrimidin-2-yl)amino)-1H-pyrazol-1-yl)-1-(piperazin-1-yl)ethanone;
2-(4-((4-(benzylamino)-5-chloropyrimidin-2-yl)amino)-1H-pyrazol-1-yl)-1-(tetrahydro-1H-furo[3,4-c]pyrrol-5(3H)-yl)ethanone;
2-(4-((5-chloro-4-((3-fluoro-5-(trifluoromethyl)benzyl)amino)pyrimidin-2-yl)amino)-1H-pyrazol-1-yl)-N-methylacetamide;
2-(4-((5-chloro-4-((3,5-difluorobenzyl)amino)pyrimidin-2-yl)amino)-1H-pyrazol-1-yl)-N-methylacetamide;
2-(4-((5-chloro-4-((2-(trifluoromethyl)benzyl)amino)pyrimidin-2-yl)amino)-1H-pyrazol-1-yl)ethanol;
2-(4-((4-(benzylamino)-5-chloropyrimidin-2-yl)amino)-1H-pyrazol-1-yl)ethanol;
2-(4-((4-(benzylamino)-5-fluoropyrimidin-2-yl)amino)-1H-pyrazol-1-yl)ethanol;
2-(4-((4-(benzylamino)-5-chloropyrimidin-2-yl)amino)-1H-pyrazol-1-yl)-1-(2,5-diazabicyclo[2.2.2]octan-2-yl)ethanone;
2-(4-((4-(benzylamino)-5-chloropyrimidin-2-yl)amino)-1H-pyrazol-1-yl)-N-methylacetamide;
2-(3-((4-(benzylamino)-5-chloropyrimidin-2-yl)amino)-1H-pyrazol-1-yl)ethanol;
tert-butyl 5-(2-(4-((4-(benzylamino)-5-chloropyrimidin-2-yl)amino)-1H-pyrazol-1-yl)acetyl)-2,5-diazabicyclo[2.2.2]octane-2-carboxylate;
3-(((5-chloro-2-((1-methyl-1H-pyrazol-4-yl)amino)pyrimidin-4-yl)amino)methyl)benzenesulfonamide;
3-(((5-chloro-2-((1-(2-hydroxyethyl)-1H-pyrazol-4-yl)amino)pyrimidin-4-yl)amino)methyl)benzenesulfonamide;
3-(((5-chloro-2-((1-methyl-1H-pyrazol-4-yl)amino)pyrimidin-4-yl)amino)methyl)-N-methylbenzenesulfonamide;
1N$^4$-benzyl-5-chloro-N$^2$-(1H-pyrazol-4-yl)pyrimidine-2,4-diamine;
2-(4-((5-fluoro-4-((2,3,6-trifluorobenzyl)amino)pyrimidin-2-yl)amino)-1H-pyrazol-1-yl)ethanol;
2-(4-((4-((2,5-difluorobenzyl)amino)-5-fluoropyrimidin-2-yl)amino)-1H-pyrazol-1-yl)ethanol;
2-(4-((4-((2,6-difluorobenzyl)amino)-5-fluoropyrimidin-2-yl)amino)-1H-pyrazol-1-yl)ethanol;
2-(4-((5-fluoro-4-((2-fluorobenzyl)amino)pyrimidin-2-yl)amino)-1H-pyrazol-1-yl)ethanol;
2-(4-((4-(benzylamino)-5-chloropyrimidin-2-yl)amino)-1H-pyrazol-1-yl)acetamide;
tert-butyl 4-(2-(4-((4-(benzylamino)-5-chloropyrimidin-2-yl)amino)-1H-pyrazol-1-yl)acetyl)piperazine-1-carboxylate;
2-(4-((5-chloro-4-((2,3-difluorobenzyl)amino)pyrimidin-2-yl)amino)-1H-pyrazol-1-yl)-N-methylacetamide;
1-(4-((5-chloro-4-((2,6-difluorobenzyl)amino)pyrimidin-2-yl)amino)-1H-pyrazol-1-yl)propan-2-ol;
2-(4-((5-fluoro-4-((3-fluorobenzyl)amino)pyrimidin-2-yl)amino)-1H-pyrazol-1-yl)ethanol;
2-(4-((5-chloro-4-((2-fluorobenzyl)amino)pyrimidin-2-yl)amino)-1H-pyrazol-1-yl)-N-methylacetamide;
2-(4-((5-chloro-4-((3-fluorobenzyl)amino)pyrimidin-2-yl)amino)-1H-pyrazol-1-yl)-N-methylacetamide;
1-(4-((5-chloro-4-((2-fluorobenzyl)amino)pyrimidin-2-yl)amino)-1H-pyrazol-1-yl)propan-2-ol;
1-(4-((5-chloro-4-((3-fluorobenzyl)amino)pyrimidin-2-yl)amino)-1H-pyrazol-1-yl)propan-2-ol;
1-(4-((5-chloro-4-((2,3-difluorobenzyl)amino)pyrimidin-2-yl)amino)-1H-pyrazol-1-yl)propan-2-ol;
1-(4-((4-(benzylamino)-5-chloropyrimidin-2-yl)amino)-1H-pyrazol-1-yl)propan-2-ol;
2-(4-((4-(benzylamino)-5-chloropyrimidin-2-yl)amino)-1H-pyrazol-1-yl)-N,N-dimethylacetamide;
N$^4$-(5-bromo-2-fluorobenzyl)-5-chloro-N$^2$-(1-methyl-1H-pyrazol-4-yl)pyrimidine-2,4-diamine;
4-(((5-chloro-2-((1-(2-hydroxyethyl)-1H-pyrazol-4-yl)amino)pyrimidin-4-yl)amino)methyl)phenol;
tert-butyl 6-(2-(4-((4-(benzylamino)-5-chloropyrimidin-2-yl)amino)-1H-pyrazol-1-yl)acetyl)-2,6-diazaspiro[3.3]heptane-2-carboxylate;
2-(4-((4-(benzylamino)-5-chloropyrimidin-2-yl)amino)-1H-pyrazol-1-yl)-N-(2-(dimethylamino)ethyl)acetamide;
2-(4-((4-(benzylamino)-5-chloropyrimidin-2-yl)amino)-1H-pyrazol-1-yl)acetic acid;
5-chloro-N$^4$-(2,5-difluorobenzyl)-N$^2$-(1-(difluoromethyl)-1H-pyrazol-4-yl)pyrimidine-2,4-diamine;
5-chloro-N$^4$-(2,6-difluorobenzyl)-N$^2$-(1-(difluoromethyl)-1H-pyrazol-4-yl)pyrimidine-2,4-diamine;
ethyl 2-(4-((4-(benzylamino)-5-chloropyrimidin-2-yl)amino)-1H-pyrazol-1-yl)acetate;
3-(((5-chloro-2-((1-(2-hydroxyethyl)-1H-pyrazol-4-yl)amino)pyrimidin-4-yl)amino)methyl)-4-fluorobenzenesulfonamide;
3-(((5-chloro-2-((1-methyl-1H-pyrazol-4-yl)amino)pyrimidin-4-yl)amino)methyl)-4-fluorobenzenesulfonamide;
5-chloro-N$^4$-(2-methoxybenzyl)-N$^2$-(1-methyl-1H-pyrazol-4-yl)pyrimidine-2,4-diamine;
2-(4-((5-chloro-4-((2,6-difluorobenzyl)amino)pyrimidin-2-yl)amino)-1H-pyrazol-1-yl)-N-methylacetamide;
2-(4-((5-chloro-4-((3-cyanobenzyl)amino)pyrimidin-2-yl)amino)-1H-pyrazol-1-yl)-N-methylacetamide;
2-(4-((4-(benzylamino)-5-chloropyrimidin-2-yl)amino)-1H-pyrazol-1-yl)1,1,2,2-d4-ethanol;
2-(4-((5-chloro-4-((3-fluorobenzyl)amino)pyrimidin-2-yl)amino)-1H-pyrazol-1-yl)1,1,2,2-d4-ethanol;
2-(4-((5-chloro-4-((2,3-difluorobenzyl)amino)pyrimidin-2-yl)amino)-1H-pyrazol-1-yl)1,1,2,2-d4-ethanol;
2-(4-((5-chloro-4-((2,6-difluorobenzyl)amino)pyrimidin-2-yl)amino)-1H-pyrazol-1-yl)1,1,2,2-d4-ethanol;
2-(4-((5-chloro-4-((3-methoxybenzyl)amino)pyrimidin-2-yl)amino)-1H-pyrazol-1-yl)1,1,2,2-d4-ethanol;
2-(4-((4-(benzylamino)-5-chloropyrimidin-2-yl)amino)-1H-pyrazol-1-yl)-1-(2-oxa-6-azaspiro[3.3]heptan-6-yl)ethanone;
1-(2-(4-((4-(benzylamino)-5-chloropyrimidin-2-yl)amino)-1H-pyrazol-1-yl)acetyl)pyrrolidine-2-carbonitrile;
2-(4-((4-(benzylamino)-5-chloropyrimidin-2-yl)amino)-1H-pyrazol-1-yl)-N-(cyanomethyl)-N-methylacetamide;
2-(4-((4-(benzylamino)-5-chloropyrimidin-2-yl)amino)-1H-pyrazol-1-yl)-1-(2-oxa-7-azaspiro[3.5]nonan-7-yl)ethanone;
2-(4-((5-chloro-4-((2,6-difluorobenzyl)amino)pyrimidin-2-yl)amino)-1H-pyrazol-1-yl)acetamide;
3-(((5-chloro-2-((1-(2-hydroxyethyl)-1H-pyrazol-4-yl)amino)pyrimidin-4-yl)amino)methyl)-N-ethylbenzamide;
3-(((5-chloro-2-((1-(2-hydroxyethyl)-1H-pyrazol-4-yl)amino)pyrimidin-4-yl)amino)methyl)-N-(cyanomethyl)benzamide;
2-(4-((5-chloro-4-((3-methoxybenzyl)amino)pyrimidin-2-yl)amino)-1H-pyrazol-1-yl)-N-methylacetamide;
2-(4-((5-chloro-4-((3-methoxybenzyl)amino)pyrimidin-2-yl)amino)-1H-pyrazol-1-yl)-N,N-dimethylacetamide;

2-(4-((5-chloro-4-((2-fluoro-4-(trifluoromethyl)benzyl) amino)pyrimidin-2-yl)amino)-1H-pyrazol-1-yl)ethanol;

4-(((5-chloro-2-((1-(2-hydroxyethyl)-1H-pyrazol-4-yl) amino)pyrimidin-4-yl)amino)methyl)benzenesulfonamide;

2-(4-((5-chloro-4-((pyridin-2-ylmethyl)amino)pyrimidin-2-yl)amino)-1H-pyrazol-1-yl)ethanol;

$N^4$-benzyl-5-chloro-$N^2$-(1-((1-methyl-1H-imidazol-2-yl) methyl)-1H-pyrazol-4-yl)pyrimidine-2,4-diamine;

1$N^4$-benzyl-5-chloro-$N^2$-(1-(oxazol-2-ylmethyl)-1H-pyrazol-4-yl)pyrimidine-2,4-diamine;

1$N^4$-benzyl-5-chloro-$N^2$-(1-((1-methyl-1H-1,2,4-triazol-5-yl)methyl)-1H-pyrazol-4-yl)pyrimidine-2,4-diamine;

2-(4-((4-((2,6-dichlorobenzyl)amino)-5-fluoropyrimidin-2-yl)amino)-1H-pyrazol-1-yl)-N,N-dimethylacetamide;

2-(4-((5-fluoro-4-((2,4,6-trifluorobenzyl)amino)pyrimidin-2-yl)amino)-1H-pyrazol-1-yl)-N-(2,2,2-trifluoroethyl)acetamide;

3-(4-((4-(benzylamino)-5-chloropyrimidin-2-yl)amino)-1H-pyrazol-1-yl)-1-methylpyrrolidin-2-one;

1$N^4$-benzyl-5-chloro-$N^2$-(1-((methylsulfonyl)methyl)-1H-pyrazol-4-yl)pyrimidine-2,4-diamine;

2-(4-((5-chloro-4-((pyridin-3-ylmethyl)amino)pyrimidin-2-yl)amino)-1H-pyrazol-1-yl)ethanol;

(R)-1-(4-((5-chloro-4-((2-fluorobenzyl)amino)pyrimidin-2-yl)amino)-1H-pyrazol-1-yl)propan-2-ol;

(S)-1-(4-((5-chloro-4-((2-fluorobenzyl)amino)pyrimidin-2-yl)amino)-1H-pyrazol-1-yl)propan-2-ol;

5-chloro-$N^4$-((5-fluoropyridin-3-yl)methyl)-$N^2$-(1-methyl-1H-pyrazol-4-yl)pyrimidine-2,4-diamine;

2-(4-((5-chloro-4-(((3-fluoropyridin-2-yl)methyl)amino) pyrimidin-2-yl)amino)-1H-pyrazol-1-yl)ethanol;

5-chloro-$N^4$-((3-fluoropyridin-2-yl)methyl)-$N^2$-(1-methyl-1H-pyrazol-4-yl)pyrimidine-2,4-diamine;

2-(4-((4-((5-bromo-2,3-difluorobenzyl)amino)-5-chloropyrimidin-2-yl)amino)-1H-pyrazol-1-yl)acetamide;

2-(4-((4-((5-bromo-2,3-difluorobenzyl)amino)-5-chloropyrimidin-2-yl)amino)-1H-pyrazol-1-yl)-N-methylacetamide;

2-(4-((4-((5-bromo-2,3-difluorobenzyl)amino)-5-chloropyrimidin-2-yl)amino)-1H-pyrazol-1-yl)-N,N-dimethylacetamide;

2-(4-((4-((5-bromo-2,3-difluorobenzyl)amino)-5-chloropyrimidin-2-yl)amino)-1H-pyrazol-1-yl)ethanol;

2-(4-((5-chloro-4-((2-fluoro-6-(1H-pyrazol-4-yl)benzyl) amino)pyrimidin-2-yl)amino)-1H-pyrazol-1-yl)ethanol;

2-(4-((5-chloro-4-((2-(methylsulfonyl)benzyl)amino)pyrimidin-2-yl)amino)-1H-pyrazol-1-yl)ethanol;

2-(4-((5-chloro-4-((3-ethoxy-2,6-difluorobenzyl)amino) pyrimidin-2-yl)amino)-1H-pyrazol-1-yl)acetamide;

2-(4-((5-chloro-4-((3-ethoxy-2,6-difluorobenzyl)amino) pyrimidin-2-yl)amino)-1H-pyrazol-1-yl)-N,N-dimethylacetamide;

2-(4-((5-chloro-4-((3-ethoxy-2,6-difluorobenzyl)amino) pyrimidin-2-yl)amino)-1H-pyrazol-1-yl)-N-methylacetamide;

(S)-1-(2-(4-((4-(benzylamino)-5-chloropyrimidin-2-yl) amino)-1H-pyrazol-1-yl)acetyl)pyrrolidine-3-carbonitrile;

(R)-1-(2-(4-((4-(benzylamino)-5-chloropyrimidin-2-yl) amino)-1H-pyrazol-1-yl)acetyl)pyrrolidine-3-carbonitrile;

(S)-1-(2-(4-((4-(benzylamino)-5-chloropyrimidin-2-yl) amino)-1H-pyrazol-1-yl)acetyl)pyrrolidine-2-carbonitrile;

2-(4-((4-(benzylamino)-5-chloropyrimidin-2-yl)amino)-1H-pyrazol-1-yl)-N-(2-methoxyethyl)acetamide;

1-(2-(4-((4-(benzylamino)-5-chloropyrimidin-2-yl) amino)-1H-pyrazol-1-yl)acetyl)azetidine-3-carbonitrile;

2-(4-((5-chloro-4-((3-fluoro-5-(trifluoromethyl)benzyl) amino)pyrimidin-2-yl)amino)-1H-pyrazol-1-yl)acetic acid;

5-chloro-$N^4$-(3,5-difluoro-2-methoxybenzyl)-$N^2$-(1-methyl-1H-pyrazol-4-yl)pyrimidine-2,4-diamine;

5-chloro-$N^4$-(2-fluoro-5-(trifluoromethyl)benzyl)-$N^2$-(1-methyl-1H-pyrazol-4-yl)pyrimidine-2,4-diamine;

5-chloro-$N^4$-(2-chloro-5-(trifluoromethyl)benzyl)-$N^2$-(1-methyl-1H-pyrazol-4-yl)pyrimidine-2,4-diamine;

2-(4-((5-chloro-4-((2-fluoro-5-(trifluoromethyl)benzyl) amino)pyrimidin-2-yl)amino)-1H-pyrazol-1-yl)-N-methylacetamide;

2-(4-((5-chloro-4-((2-chloro-5-(trifluoromethyl)benzyl) amino)pyrimidin-2-yl)amino)-1H-pyrazol-1-yl)-N-methylacetamide;

2-(4-((5-chloro-4-((2-fluoro-5-(trifluoromethyl)benzyl) amino)pyrimidin-2-yl)amino)-1H-pyrazol-1-yl)ethanol;

2-(4-((5-chloro-4-((2,6-difluoro-3-methylbenzyl)amino) pyrimidin-2-yl)amino)-1H-pyrazol-1-yl)acetamide;

2-(4-((5-chloro-4-((2,6-difluoro-3-methylbenzyl)amino) pyrimidin-2-yl)amino)-1H-pyrazol-1-yl)-N,N-dimethylacetamide;

2-(4-((5-chloro-4-((2,6-difluoro-3-methylbenzyl)amino) pyrimidin-2-yl)amino)-1H-pyrazol-1-yl)-N-methylacetamide;

2-(4-((4-(benzylamino)-5-chloropyrimidin-2-yl)amino)-1H-pyrazol-1-yl)propanamide;

2-(4-((5-chloro-4-((2-cyano-3-fluorobenzyl)amino)pyrimidin-2-yl)amino)-1H-pyrazol-1-yl)acetamide;

2-(((5-chloro-2-((1-(2-hydroxyethyl)-1H-pyrazol-4-yl) amino)pyrimidin-4-yl)amino)methyl)-6-fluorobenzonitrile;

2-(4-((5-chloro-4-((2-(hydroxymethyl)benzyl)amino)pyrimidin-2-yl)amino)-1H-pyrazol-1-yl)acetamide;

1$N^4$-benzyl-5-chloro-$N^2$-(1-(2-(methylsulfonyl)ethyl)-1H-pyrazol-4-yl)pyrimidine-2,4-diamine;

(R)-2-(4-((4-(benzylamino)-5-chloropyrimidin-2-yl) amino)-1H-pyrazol-1-yl)propanamide;

(S)-2-(4-((4-(benzylamino)-5-chloropyrimidin-2-yl) amino)-1H-pyrazol-1-yl)propanamide;

1-(4-((5-chloro-4-((2,5-difluorobenzyl)amino)pyrimidin-2-yl)amino)-1H-pyrazol-1-yl)-2-methyl propan-2-ol;

2-(4-((5-chloro-4-((3-(difluoromethyl)benzyl)amino)pyrimidin-2-yl)amino)-1H-pyrazol-1-yl)ethanol;

2-(4-((5-chloro-4-((3-ethoxybenzyl)amino)pyrimidin-2-yl)amino)-1H-pyrazol-1-yl)ethanol;

2-(4-((5-chloro-4-((2,6-difluoro-3-methoxybenzyl) amino)pyrimidin-2-yl)amino)-1H-pyrazol-1-yl)acetic acid;

2-(4-((4-(benzylamino)-5-methylpyrimidin-2-yl)amino)-1H-pyrazol-1-yl)-1-morpholinoethanone;

N-cyclobutyl-2-(4-((4-((2,4,6-trifluorobenzyl)amino)pyrimidin-2-yl)amino)-1H-pyrazol-1-yl)acetamide;

2-(4-((4-((2,6-difluorobenzyl)amino)-5-methylpyrimidin-2-yl)amino)-1H-pyrazol-1-yl)ethanol;

2-(4-((4-((2,6-difluorobenzyl)amino)-5-methylpyrimidin-2-yl)amino)-1H-pyrazol-1-yl)-N,N-dimethylacetamide;

2-(4-((4-(benzylamino)-5-methylpyrimidin-2-yl)amino)-1H-pyrazol-1-yl)-N,N-dimethylacetamide;
5-methyl-$N^2$-(1-methyl-1H-pyrazol-4-yl)-$N^4$-(2,4,6-trifluorobenzyl)pyrimidine-2,4-diamine;
$N^4$-(2,6-difluoro-3-methoxybenzyl)-5-methyl-$N^2$-(1-methyl-1H-pyrazol-4-yl)pyrimidine-2,4-diamine;
2-(4-((5-methyl-4-((2,4,6-trifluorobenzyl)amino)pyrimidin-2-yl)amino)-1H-pyrazol-1-yl)ethanol;
2-(4-((4-((2,6-difluoro-3-methoxybenzyl)amino)-5-methylpyrimidin-2-yl)amino)-1H-pyrazol-1-yl)ethanol;
2-(4-((4-((2,6-difluorobenzyl)amino)-5-methylpyrimidin-2-yl)amino)-1H-pyrazol-1-yl)-1-morpholinoethanone;
2-(4-((5-methyl-4-((2,4,6-trifluorobenzyl)amino)pyrimidin-2-yl)amino)-1H-pyrazol-1-yl)acetic acid;
2-(4-((5-fluoro-4-((2,4,6-trifluorobenzyl)amino)pyrimidin-2-yl)amino)-1H-pyrazol-1-yl)acetic acid;
N-cyclobutyl-2-(4-((5-fluoro-4-((2,4,6-trifluorobenzyl)amino)pyrimidin-2-yl)amino)-1H-pyrazol-1-yl)acetamide;
1-(3,3-dimethylmorpholino)-2-(4-((5-fluoro-4-((2,4,6-trifluorobenzyl)amino)pyrimidin-2-yl)amino)-1H-pyrazol-1-yl)ethanone;
$N^2$-(1-methyl-1H-pyrazol-4-yl)-$N^4$-(2,4,6-trifluorobenzyl)pyrimidine-2,4-diamine;
2-(4-((4-((2,4,6-trifluorobenzyl)amino)pyrimidin-2-yl)amino)-1H-pyrazol-1-yl)acetamide;
$N^4$-(2,6-difluorobenzyl)-$N^2$-(1-methyl-1H-pyrazol-4-yl)pyrimidine-2,4-diamine;
2-(4-((4-((2,6-difluorobenzyl)amino)pyrimidin-2-yl)amino)-1H-pyrazol-1-yl)acetamide;
$N^4$-(2,6-difluoro-4-methoxybenzyl)-5-methyl-$N^2$-(1-methyl-1H-pyrazol-4-yl)pyrimidine-2,4-diamine;
2-(4-((4-((2,6-difluoro-4-methoxybenzyl)amino)-5-methylpyrimidin-2-yl)amino)-1H-pyrazol-1-yl)acetamide;
2-(4-((5-methyl-4-((2,4,6-trifluorobenzyl)amino)pyrimidin-2-yl)amino)-1H-pyrazol-1-yl)acetamide;
N-isopropyl-N-methyl-2-(4-((4-((2,4,6-trifluorobenzyl)amino)pyrimidin-2-yl)amino)-1H-pyrazol-1-yl)acetamide;
N-(tert-butyl)-N-methyl-2-(4-((4-((2,4,6-trifluorobenzyl)amino)pyrimidin-2-yl)amino)-1H-pyrazol-1-yl)acetamide;
5-chloro-$N^4$-(2,6-difluoro-3-methoxybenzyl)-$N^2$-(1-methyl-1H-pyrazol-4-yl)pyrimidine-2,4-diamine;
2-(4-((5-chloro-4-((2,6-difluoro-3-methoxybenzyl)amino)pyrimidin-2-yl)amino)-1H-pyrazol-1-yl)ethanol;
2-(4-((5-chloro-4-((2-methoxybenzyl)amino)pyrimidin-2-yl)amino)-1H-pyrazol-1-yl)acetamide;
2-(4-((5-chloro-4-((3-(difluoromethoxy)benzyl)amino)pyrimidin-2-yl)amino)-1H-pyrazol-1-yl)ethanol;
2-(4-((5-chloro-4-((2,6-dichlorobenzyl)amino)pyrimidin-2-yl)amino)-1H-pyrazol-1-yl)ethanol;
2-(4-((5-chloro-4-((2,6-dichlorobenzyl)amino)pyrimidin-2-yl)amino)-1H-pyrazol-1-yl)acetamide;
2-(4-((5-chloro-4-((2,6-dichlorobenzyl)amino)pyrimidin-2-yl)amino)-1H-pyrazol-1-yl)-N-methylacetamide;
2-(4-((5-chloro-4-((2,6-dichlorobenzyl)amino)pyrimidin-2-yl)amino)-1H-pyrazol-1-yl)-N,N-dimethylacetamide;
2-(4-((4-((2,6-dichlorobenzyl)amino)-5-fluoropyrimidin-2-yl)amino)-1H-pyrazol-1-yl)ethanol;
2-(4-((4-((2,6-dichlorobenzyl)amino)-5-fluoropyrimidin-2-yl)amino)-1H-pyrazol-1-yl)acetamide;
2-(4-((4-((2,6-dichlorobenzyl)amino)-5-fluoropyrimidin-2-yl)amino)-1H-pyrazol-1-yl)-N-methylacetamide;
2-(4-((4-((3-fluoro-5-(trifluoromethyl)benzyl)amino)-5-methylpyrimidin-2-yl)amino)-1H-pyrazol-1-yl)-N,N-dimethylacetamide;
2-(4-((5-fluoro-4-((3-fluoro-5-(trifluoromethyl)benzyl)amino)pyrimidin-2-yl)amino)-1H-pyrazol-1-yl)-N,N-dimethylacetamide;
2-(4-((5-fluoro-4-((3-fluoro-5-(trifluoromethyl)benzyl)amino)pyrimidin-2-yl)amino)-1H-pyrazol-1-yl)-1-morpholinoethanone;
2-(4-((5-chloro-4-((3-fluoro-2-(trifluoromethyl)benzyl)amino)pyrimidin-2-yl)amino)-1H-pyrazol-1-yl)ethanol;
2-(4-((5-chloro-4-((3-isopropoxybenzyl)amino)pyrimidin-2-yl)amino)-1H-pyrazol-1-yl)ethanol;
2-(4-((5-chloro-4-((2,3,6-trifluorobenzyl)amino)pyrimidin-2-yl)amino)-1H-pyrazol-1-yl)-N-cyclopropylacetamide;
5-chloro-$N^2$-(1-(2,2-difluoroethyl)-1H-pyrazol-4-yl)-$N^4$-(2,3,6-trifluorobenzyl)pyrimidine-2,4-diamine;
2-(4-((5-chloro-4-((pyridin-3-ylmethyl)amino)pyrimidin-2-yl)amino)-1H-pyrazol-1-yl)-1-morpholinoethanone;
2-(4-((5-chloro-4-((pyridin-2-ylmethyl)amino)pyrimidin-2-yl)amino)-1H-pyrazol-1-yl)-1-morpholinoethanone;
2-(4-((5-chloro-4-(((5-fluoropyridin-3-yl)methyl)amino)pyrimidin-2-yl)amino)-1H-pyrazol-1-yl)-1-morpholinoethanone;
5-chloro-$N^2$-(1-methyl-1H-pyrazol-4-yl)-$N^4$-(2,3,6-trifluorobenzyl)pyrimidine-2,4-diamine;
N-cyclopropyl-2-(4-((4-((2,3-difluorobenzyl)amino)-5-methylpyrimidin-2-yl)amino)-1H-pyrazol-1-yl)acetamide;
5-methyl-$N^2$-(1-methyl-1H-pyrazol-4-yl)-$N^4$-(2,3,5-trifluorobenzyl)pyrimidine-2,4-diamine;
$N^4$-(3,5-difluorobenzyl)-5-methyl-$N^2$-(1-methyl-1H-pyrazol-4-yl)pyrimidine-2,4-diamine;
N-cyclopropyl-2-(4-((4-((3,5-difluorobenzyl)amino)-5-methylpyrimidin-2-yl)amino)-1H-pyrazol-1-yl)acetamide;
N-cyclopropyl-2-(4-((4-((3,5-difluoro-2-methoxybenzyl)amino)-5-methylpyrimidin-2-yl)amino)-1H-pyrazol-1-yl)acetamide;
N-cyclopropyl-2-(4-((4-((2,5-difluorobenzyl)amino)-5-methylpyrimidin-2-yl)amino)-1H-pyrazol-1-yl)acetamide;
$N^4$-(2,3-difluorobenzyl)-$N^2$-(1-(2,2-difluoroethyl)-1H-pyrazol-4-yl)-5-methylpyrimidine-2,4-diamine;
2-(4-((4-((3,5-difluorobenzyl)amino)-5-methylpyrimidin-2-yl)amino)-1H-pyrazol-1-yl)-1-morpholinoethanone;
$N^4$-(3,5-difluoro-2-methoxybenzyl)-$N^2$-(1-(2,2-difluoroethyl)-1H-pyrazol-4-yl)-5-methylpyrimidine-2,4-diamine;
$N^4$-(3,5-difluorobenzyl)-5-methyl-$N^2$-(1-(2,2,2-trifluoroethyl)-1H-pyrazol-4-yl)pyrimidine-2,4-diamine;
5-methyl-$N^4$-(2,3,5-trifluorobenzyl)-$N^2$-(1-(2,2,2-trifluoroethyl)-1H-pyrazol-4-yl)pyrimidine-2,4-diamine;
$N^4$-(3,5-difluoro-2-methoxybenzyl)-5-methyl-$N^2$-(1-(2,2,2-trifluoroethyl)-1H-pyrazol-4-yl)pyrimidine-2,4-diamine;
$N^4$-(2,5-difluorobenzyl)-5-methyl-$N^2$-(1-(2,2,2-trifluoroethyl)-1H-pyrazol-4-yl)pyrimidine-2,4-diamine;
2-(4-((4-((3,5-difluorobenzyl)amino)-5-methylpyrimidin-2-yl)amino)-1H-pyrazol-1-yl)-N-methylacetamide;
2-(4-((5-chloro-4-((2-(N-methylsulfamoyl)benzyl)amino)pyrimidin-2-yl)amino)-1H-pyrazol-1-yl)-N-methylacetamide;

2-(4-((5-chloro-4-((2-(N,N-dimethylsulfamoyl)benzyl) amino)pyrimidin-2-yl)amino)-1H-pyrazol-1-yl)-N-methylacetamide;
2-(4-((5-chloro-4-((2-(hydroxymethyl)benzyl)amino)pyrimidin-2-yl)amino)-1H-pyrazol-1-yl)ethanol;
2-(4-((5-chloro-4-((3-ethoxy-2,6-difluorobenzyl)amino) pyrimidin-2-yl)amino)-1H-pyrazol-1-yl)ethanol;
2-(4-((5-chloro-4-((2,3,6-trifluorobenzyl)amino)pyrimidin-2-yl)amino)-1H-pyrazol-1-yl)-N-methylacetamide
2-(4-((5-chloro-4-((2,3,6-trifluorobenzyl)amino)pyrimidin-2-yl)amino)-1H-pyrazol-1-yl)-N,N-dimethylacetamide;
2-(4-((4-(benzylamino)-5-chloropyrimidin-2-yl)amino)-1H-pyrazol-1-yl)propan-1-ol;
2-(4-((5-chloro-4-((3-(cyanomethoxy)benzyl)amino)pyrimidin-2-yl)amino)-1H-pyrazol-1-yl)acetamide;
2-(4-((5-chloro-4-((3-(methylsulfonyl)benzyl)amino)pyrimidin-2-yl)amino)-1H-pyrazol-1-yl)ethanol;
2-(4-((5-chloro-4-((3-(cyanomethoxy)benzyl)amino)pyrimidin-2-yl)amino)-1H-pyrazol-1-yl)-N-methylacetamide;
2-(4-((5-chloro-4-((3-(cyanomethoxy)benzyl)amino)pyrimidin-2-yl)amino)-1H-pyrazol-1-yl)-N,N-dimethylacetamide;
2-(3-(((5-chloro-2-((1-(2-morpholino-2-oxoethyl)-1H-pyrazol-4-yl)amino)pyrimidin-4-yl)amino)methyl) phenoxy)acetonitrile;
2-(4-((5-chloro-4-((3-(cyanomethoxy)benzyl)amino)pyrimidin-2-yl)amino)-1H-pyrazol-1-yl)-N-(2-(dimethylamino)ethyl)acetamide;
5-chloro-$N^4$-(3-ethoxy-2,6-difluorobenzyl)-$N^2$-(1H-pyrazol-4-yl)pyrimidine-2,4-diamine;
5-chloro-$N^4$-(2-fluorobenzyl)-$N^2$-(1H-pyrazol-4-yl)pyrimidine-2,4-diamine;
5-chloro-$N^4$-(3-fluorobenzyl)-$N^2$-(1H-pyrazol-4-yl)pyrimidine-2,4-diamine;
5-chloro-$N^4$-(2,6-difluoro-3-methylbenzyl)-$N^2$-(1H-pyrazol-4-yl)pyrimidine-2,4-diamine;
5-chloro-$N^2$-(1H-pyrazol-4-yl)-$N^4$-(2,4,6-trifluorobenzyl)pyrimidine-2,4-diamine;
2-(4-((5-chloro-4-((2,3,6-trifluorobenzyl)amino)pyrimidin-2-yl)amino)-1H-pyrazol-1-yl)ethanol;
5-fluoro-$N^2$-(1-methyl-1H-pyrazol-4-yl)-$N^4$-(2,4,6-trifluorobenzyl)pyrimidine-2,4-diamine;
2-(4-((5-chloro-4-((2,6-difluoro-3-methoxybenzyl) amino)pyrimidin-2-yl)amino)-1H-pyrazol-1-yl)acetamide;
2-(4-((5-chloro-4-((2,6-difluoro-3-methoxybenzyl) amino)pyrimidin-2-yl)amino)-1H-pyrazol-1-yl)-N,N-dimethylacetamide;
2-(4-((5-chloro-4-((2,6-difluoro-3-methoxybenzyl) amino)pyrimidin-2-yl)amino)-1H-pyrazol-1-yl)-1-morpholinoethanone;
3,5-difluoro-4-(((5-methyl-2-((1-(2-morpholino-2-oxoethyl)-1H-pyrazol-4-yl)amino)pyrimidin-4-yl)amino) methyl)benzenesulfonamide;
3,5-difluoro-4-(((5-fluoro-2-((1-methyl-1H-pyrazol-4-yl) amino)pyrimidin-4-yl)amino)methyl)benzenesulfonamide;
2-(4-((4-((2,6-difluorobenzyl)amino)-5-fluoropyrimidin-2-yl)amino)-1H-pyrazol-1-yl)acetamide;
2-(4-((4-((2,6-difluorobenzyl)amino)-5-fluoropyrimidin-2-yl)amino)-1H-pyrazol-1-yl)-N-methylacetamide;
2-(4-((4-((2,6-difluorobenzyl)amino)-5-fluoropyrimidin-2-yl)amino)-1H-pyrazol-1-yl)-N,N-dimethylacetamide;

$N^4$-(2,6-difluoro-3-methoxybenzyl)-5-fluoro-$N^2$-(1-methyl-1H-pyrazol-4-yl)pyrimidine-2,4-diamine;
2-(4-((4-((2,6-difluoro-3-methoxybenzyl)amino)-5-fluoropyrimidin-2-yl)amino)-1H-pyrazol-1-yl)acetamide;
5-chloro-$N^2$-(1-methyl-1H-pyrazol-4-yl)-$N^4$-(2,4,6-trifluorobenzyl)pyrimidine-2,4-diamine;
2-(4-((5-chloro-4-((2,4,6-trifluorobenzyl)amino)pyrimidin-2-yl)amino)-1H-pyrazol-1-yl)ethanol;
2-(4-((5-chloro-4-((2,4,6-trifluorobenzyl)amino)pyrimidin-2-yl)amino)-1H-pyrazol-1-yl)acetamide;
2-(4-((5-chloro-4-((2,4,6-trifluorobenzyl)amino)pyrimidin-2-yl)amino)-1H-pyrazol-1-yl)-N-methylacetamide;
2-(4-((5-chloro-4-((2,4,6-trifluorobenzyl)amino)pyrimidin-2-yl)amino)-1H-pyrazol-1-yl)-N,N-dimethylacetamide;
3-(((5-chloro-2-((1-(2-(dimethylamino)-2-oxoethyl)-1H-pyrazol-4-yl)amino)pyrimidin-4-yl)amino)methyl) benzamide;
2-(4-((5-chloro-4-((3-(difluoromethoxy)benzyl)amino) pyrimidin-2-yl)amino)-1H-pyrazol-1-yl)-N-isopropylacetamide;
2-(4-((5-chloro-4-((3-(difluoromethoxy)benzyl)amino) pyrimidin-2-yl)amino)-1H-pyrazol-1-yl)-N-isobutylacetamide;
2-(4-((5-chloro-4-((2,4,6-trifluorobenzyl)amino)pyrimidin-2-yl)amino)-1H-pyrazol-1-yl)-N-isopropylacetamide;
$N^4$-(2,6-difluoro-3-methoxybenzyl)-5-fluoro-$N^2$-(1-(2-isopropoxyethyl)-1H-pyrazol-4-yl)pyrimidine-2,4-diamine;
5-fluoro-$N^2$-(1-(2-isopropoxyethyl)-1H-pyrazol-4-yl)-$N^4$-(2,4,6-trifluorobenzyl)pyrimidine-2,4-diamine;
N-(3-(((5-chloro-2-((1-(2-morpholino-2-oxoethyl)-1H-pyrazol-4-yl)amino)pyrimidin-4-yl)amino)methyl) benzyl)methanesulfonamide;
2-(4-((5-chloro-4-((3-(methylsulfonamidomethyl)benzyl) amino)pyrimidin-2-yl)amino)-1H-pyrazol-1-yl)acetamide;
N-(3-(((5-chloro-2-((1-(2-hydroxyethyl)-1H-pyrazol-4-yl)amino)pyrimidin-4-yl)amino)methyl)benzyl)-N-methylmethanesulfonamide;
(R)—N-(3-(((5-chloro-2-((1-(2-(2-cyanopyrrolidin-1-yl)-2-oxoethyl)-1H-pyrazol-4-yl)amino)pyrimidin-4-yl) amino)methyl)benzyl)methanesulfonamide;
(S)—N-(3-(((5-chloro-2-((1-(2-(2-cyanopyrrolidin-1-yl)-2-oxoethyl)-1H-pyrazol-4-yl)amino)pyrimidin-4-yl) amino)methyl)benzyl)methanesulfonamide;
N-(3-(((5-chloro-2-((1-(2-morpholino-2-oxoethyl)-1H-pyrazol-4-yl)amino)pyrimidin-4-yl)amino)methyl) benzyl)-N-methylmethanesulfonamide;
N-(3-(((5-methyl-2-((1-methyl-1H-pyrazol-4-yl)amino) pyrimidin-4-yl)amino)methyl)benzyl)methanesulfonamide;
2-(4-((5-chloro-4-((3-fluoro-2-methoxybenzyl)amino)pyrimidin-2-yl)amino)-1H-pyrazol-1-yl)acetic acid;
2-(4-((5-chloro-4-((3-fluoro-2-methoxybenzyl)amino)pyrimidin-2-yl)amino)-1H-pyrazol-1-yl)acetamide;
2-(4-((5-chloro-4-(((2-hydroxypyridin-3-yl)methyl) amino)pyrimidin-2-yl)amino)-1H-pyrazol-1-yl)acetamide;
5-chloro-$N^4$-((2-fluoropyridin-3-yl)methyl)-$N^2$-(1-methyl-1H-pyrazol-4-yl)pyrimidine-2,4-diamine;
2-(4-((4-((3-(difluoromethoxy)benzyl)amino)-5-fluoropyrimidin-2-yl)amino)-1H-pyrazol-1-yl)ethanol;

2-(4-((4-((3-(difluoromethoxy)benzyl)amino)-5-fluoropyrimidin-2-yl)amino)-1H-pyrazol-1-yl)-N-methylacetamide;
2-(4-((5-fluoro-4-((2,3,6-trifluorobenzyl)amino)pyrimidin-2-yl)amino)-1H-pyrazol-1-yl)acetamide;
2-(4-((5-fluoro-4-((2,3,6-trifluorobenzyl)amino)pyrimidin-2-yl)amino)-1H-pyrazol-1-yl)-N-methylacetamide;
2-(4-((5-fluoro-4-((2,3,6-trifluorobenzyl)amino)pyrimidin-2-yl)amino)-1H-pyrazol-1-yl)-N,N-dimethylacetamide;
5-chloro-N$^4$-(5-(difluoromethoxy)-2-fluorobenzyl)-N$^2$-(1-methyl-1H-pyrazol-4-yl)pyrimidine-2,4-diamine;
2-(4-((5-chloro-4-((5-(difluoromethoxy)-2-fluorobenzyl)amino)pyrimidin-2-yl)amino)-1H-pyrazol-1-yl)ethanol;
2-(4-((5-chloro-4-((5-(difluoromethoxy)-2-fluorobenzyl)amino)pyrimidin-2-yl)amino)-1H-pyrazol-1-yl)-N,N-dimethylacetamide;
N-(3-(((5-fluoro-2-((1-(2-hydroxyethyl)-1H-pyrazol-4-yl)amino)pyrimidin-4-yl)amino)methyl)benzyl)methanesulfonamide;
2-(4-((5-chloro-4-((3-(methylsulfonamidomethyl)benzyl)amino)pyrimidin-2-yl)amino)-1H-pyrazol-1-yl)-N,N-dimethylacetamide;
N-(3-(((5-chloro-2-((1-(2-hydroxyethyl)-1H-pyrazol-4-yl)amino)pyrimidin-4-yl)amino)methyl)benzyl)methanesulfonamide;
N$^4$-(2,6-difluorobenzyl)-5-methyl-N$^2$-(1-methyl-1H-pyrazol-4-yl)pyrimidine-2,4-diamine;
2-(4-((4-((2,6-difluorobenzyl)amino)-5-methylpyrimidin-2-yl)amino)-1H-pyrazol-1-yl)-N-methylacetamide;
5-methyl-N$^2$-(1-methyl-1H-pyrazol-4-yl)-N$^4$-(2,3,6-trifluorobenzyl)pyrimidine-2,4-diamine;
N-methyl-2-(4-((5-methyl-4-((2,3,6-trifluorobenzyl)amino)pyrimidin-2-yl)amino)-1H-pyrazol-1-yl)acetamide;
N,N-dimethyl-2-(4-((5-methyl-4-((2,3,6-trifluorobenzyl)amino)pyrimidin-2-yl)amino)-1H-pyrazol-1-yl)acetamide;
2-(4-((5-methyl-4-((2,3,6-trifluorobenzyl)amino)pyrimidin-2-yl)amino)-1H-pyrazol-1-yl)-1-morpholinoethanone;
2-(4-((5-methyl-4-((2,3,6-trifluorobenzyl)amino)pyrimidin-2-yl)amino)-1H-pyrazol-1-yl)acetic acid;
2-(4-((4-((3-(difluoromethoxy)benzyl)amino)-5-fluoropyrimidin-2-yl)amino)-1H-pyrazol-1-yl)acetic acid;
2-(4-((4-((2,6-difluoro-3-methoxybenzyl)amino)-5-fluoropyrimidin-2-yl)amino)-1H-pyrazol-1-yl)acetic acid;
2-(4-((5-chloro-4-((2,6-difluoro-3-methoxybenzyl)amino)pyrimidin-2-yl)amino)-1H-pyrazol-1-yl)-N-isopropylacetamide;
2-(4-((5-chloro-4-((2,6-difluoro-3-methoxybenzyl)amino)pyrimidin-2-yl)amino)-1H-pyrazol-1-yl)-N-isobutylacetamide;
N-(tert-butyl)-2-(4-((5-fluoro-4-((2,4,6-trifluorobenzyl)amino)pyrimidin-2-yl)amino)-1H-pyrazol-1-yl)acetamide;
N-(1-fluoro-2-methylpropan-2-yl)-2-(4-((4-((2,4,6-trifluorobenzyl)amino)pyrimidin-2-yl)amino)-1H-pyrazol-1-yl)acetamide;
N-(1-(tetrahydrofuran-2-yl)ethyl)-2-(4-((4-((2,4,6-trifluorobenzyl)amino)pyrimidin-2-yl)amino)-1H-pyrazol-1-yl)acetamide;
N-((1,4-dioxan-2-yl)methyl)-2-(4-((4-((2,4,6-trifluorobenzyl)amino)pyrimidin-2-yl)amino)-1H-pyrazol-1-yl)acetamide;
2-(4-((5-methyl-4-((2-(methylsulfonyl)benzyl)amino)pyrimidin-2-yl)amino)-1H-pyrazol-1-yl)ethanol;
2-(4-((5-methyl-4-((2-(methylsulfonyl)benzyl)amino)pyrimidin-2-yl)amino)-1H-pyrazol-1-yl)acetamide;
2-(4-((5-fluoro-4-((2-(methylsulfonyl)benzyl)amino)pyrimidin-2-yl)amino)-1H-pyrazol-1-yl)ethanol;
2-(4-((5-fluoro-4-((2-(methylsulfonyl)benzyl)amino)pyrimidin-2-yl)amino)-1H-pyrazol-1-yl)acetamide;
N$^4$-(2-fluoro-6-methylbenzyl)-N$^2$-(1-methyl-1H-pyrazol-4-yl)pyrimidine-2,4-diamine;
2-(4-((5-chloro-4-((5-fluoro-2-(methylsulfonyl)benzyl)amino)pyrimidin-2-yl)amino)-1H-pyrazol-1-yl)-N-methylacetamide;
2-(4-((5-chloro-4-((3-(methylsulfonyl)benzyl)amino)pyrimidin-2-yl)amino)-1H-pyrazol-1-yl)acetamide;
2-(4-((5-chloro-4-((3-(methylsulfonyl)benzyl)amino)pyrimidin-2-yl)amino)-1H-pyrazol-1-yl)-N-cyclopropylacetamide;
2-(4-((5-chloro-4-((3-(methylsulfonyl)benzyl)amino)pyrimidin-2-yl)amino)-1H-pyrazol-1-yl)-N-(2-hydroxyethyl)acetamide;
5-chloro-N$^2$-(1-methyl-1H-pyrazol-4-yl)-N$^4$-(3-((methylsulfonyl)methyl)benzyl)pyrimidine-2,4-diamine;
2-(4-((5-chloro-4-((3-((methylsulfonyl)methyl)benzyl)amino)pyrimidin-2-yl)amino)-1H-pyrazol-1-yl)acetamide;
2-(4-((5-chloro-4-((2-methoxy-5-(methylsulfonyl)benzyl)amino)pyrimidin-2-yl)amino)-1H-pyrazol-1-yl)-N-methylacetamide;
2-(4-((5-chloro-4-((3-((methylsulfonyl)methyl)benzyl)amino)pyrimidin-2-yl)amino)-1H-pyrazol-1-yl)-N-methylacetamide;
5-fluoro-N$^4$-(2-methoxy-5-(methylsulfonyl)benzyl)-N$^2$-(1-methyl-1H-pyrazol-4-yl)pyrimidine-2,4-diamine;
2-(4-((5-fluoro-4-((2-methoxy-5-(methylsulfonyl)benzyl)amino)pyrimidin-2-yl)amino)-1H-pyrazol-1-yl)ethanol;
2-(4-((5-fluoro-4-((2-methoxy-5-(methylsulfonyl)benzyl)amino)pyrimidin-2-yl)amino)-1H-pyrazol-1-yl)-N-methylacetamide;
5-chloro-N$^4$-(2-methoxy-5-(methylsulfonyl)benzyl)-N$^2$-(1-methyl-1H-pyrazol-4-yl)pyrimidine-2,4-diamine;
2-(4-((5-chloro-4-((2-(methylsulfonyl)benzyl)amino)pyrimidin-2-yl)amino)-1H-pyrazol-1-yl)acetamide;
2-(4-((5-chloro-4-((2-(methylsulfonyl)benzyl)amino)pyrimidin-2-yl)amino)-1H-pyrazol-1-yl)-N-methylacetamide;
2-(4-((5-chloro-4-((2-(methylsulfonyl)benzyl)amino)pyrimidin-2-yl)amino)-1H-pyrazol-1-yl)-N,N-dimethylacetamide;
2-(4-((5-chloro-4-((2-(methylsulfonyl)benzyl)amino)pyrimidin-2-yl)amino)-1H-pyrazol-1-yl)-1-morpholinoethanone;
N-((1S,2R)-2-fluorocyclopropyl)-2-(4-((4-((2,4,6-trifluorobenzyl)amino)pyrimidin-2-yl)amino)-1H-pyrazol-1-yl)acetamide;
2-(4-((5-fluoro-4-((2,3,6-trifluorobenzyl)amino)pyrimidin-2-yl)amino)-1H-pyrazol-1-yl)-N-isopropylacetamide;
(R)—N-(1-hydroxypropan-2-yl)-2-(4-((4-((2,4,6-trifluorobenzyl)amino)pyrimidin-2-yl)amino)-1H-pyrazol-1-yl)acetamide;
N$^4$-(3,6-dichloro-2-fluorobenzyl)-5-fluoro-N$^2$-(1-methyl-1H-pyrazol-4-yl)pyrimidine-2,4-diamine;
1-(3,3-dimethylazetidin-1-yl)-2-(4-((4-((2,4,6-trifluorobenzyl)amino)pyrimidin-2-yl)amino)-1H-pyrazol-1-yl)ethanone;

1-(3,3-dimethylmorpholino)-2-(4-((4-((2,4,6-trifluorobenzyl)amino)pyrimidin-2-yl)amino)-1H-pyrazol-1-yl)ethanone;

N-(1-hydroxy-2-methylpropan-2-yl)-2-(4-((4-((2,4,6-trifluorobenzyl)amino)pyrimidin-2-yl)amino)-1H-pyrazol-1-yl)acetamide;

$N^4$-benzyl-5-chloro-$N^2$-(1-(2-fluoroethyl)-1H-pyrazol-4-yl)pyrimidine-2,4-diamine;

5-fluoro-$N^2$-(1-methyl-1H-pyrazol-4-yl)-$N^4$-(2,3,5,6-tetrafluorobenzyl)pyrimidine-2,4-diamine;

$N^4$-(3,5-difluorobenzyl)-5-methyl-$N^2$-(1-(3,3,3-trifluoropropyl)-1H-pyrazol-4-yl)pyrimidine-2,4-diamine;

$N^2$-(1-(2,2-difluoroethyl)-1H-pyrazol-4-yl)-5-fluoro-$N^4$-(2,4,6-trifluorobenzyl)pyrimidine-2,4-diamine;

4-(((2-((1-(2,2-difluoroethyl)-1H-pyrazol-4-yl)amino)-5-methylpyrimidin-4-yl)amino)methyl)benzenesulfonamide;

$N^2$-(1-(2,2-difluoroethyl)-1H-pyrazol-4-yl)-5-methyl-$N^4$-(3-(methylsulfonyl)benzyl)pyrimidine-2,4-diamine;

5-chloro-$N^2$-(1-(2,2-difluoroethyl)-1H-pyrazol-4-yl)-$N^4$-(3-(methylsulfonyl)benzyl)pyrimidine-2,4-diamine;

5-chloro-$N^2$-(1-(2,2-difluoroethyl)-1H-pyrazol-4-yl)-$N^4$-(2,3,5-trifluorobenzyl)pyrimidine-2,4-diamine;

5-chloro-$N^4$-(2,6-difluorobenzyl)-$N^2$-(1-(2,2-difluoroethyl)-1H-pyrazol-4-yl)pyrimidine-2,4-diamine;

5-chloro-$N^4$-(3,5-difluorobenzyl)-$N^2$-(1-(2,2-difluoroethyl)-1H-pyrazol-4-yl)pyrimidine-2,4-diamine;

5-chloro-$N^2$-(1-(2,2-difluoroethyl)-1H-pyrazol-4-yl)-$N^4$-(2-(methylsulfonyl)benzyl)pyrimidine-2,4-diamine;

2-(((5-chloro-2-((1-(2-hydroxyethyl)-1H-pyrazol-4-yl)amino)pyrimidin-4-yl)amino)methyl)-N-methylbenzenesulfonamide;

2-(((5-chloro-2-((1-methyl-1H-pyrazol-4-yl)amino)pyrimidin-4-yl)amino)methyl)-N-methylbenzenesulfonamide;

2-(((5-chloro-2-((1-methyl-1H-pyrazol-4-yl)amino)pyrimidin-4-yl)amino)methyl)-N,N-dimethylbenzenesulfonamide;

5-chloro-$N^4$-(2-(methylsulfonyl)benzyl)-$N^2$-(1-(2,2,2-trifluoroethyl)-1H-pyrazol-4-yl)pyrimidine-2,4-diamine;

5-chloro-$N^2$-(1-(cyclopropylmethyl)-1H-pyrazol-4-yl)-$N^4$-(2-(methylsulfonyl)benzyl)pyrimidine-2,4-diamine;

$N^2$-(1-(2,2-difluoroethyl)-1H-pyrazol-4-yl)-5-fluoro-$N^4$-(2-(methylsulfonyl)benzyl)pyrimidine-2,4-diamine;

$N^2$-(1-(2,2-difluoroethyl)-1H-pyrazol-4-yl)-5-methyl-$N^4$-(2-(methylsulfonyl)benzyl)pyrimidine-2,4-diamine;

2-(4-((4-((3-bromo-4-fluorobenzyl)amino)-5-methylpyrimidin-2-yl)amino)-1H-pyrazol-1-yl)-1-morpholinoethanone;

$N^2$-(1-(2,2-difluoroethyl)-1H-pyrazol-4-yl)-5-fluoro-$N^4$-(2-methoxy-5-(methylsulfonyl)benzyl)pyrimidine-2,4-diamine;

5-chloro-$N^4$-(2,6-difluorobenzyl)-$N^2$-(1-(oxazol-2-ylmethyl)-1H-pyrazol-4-yl)pyrimidine-2,4-diamine;

5-chloro-$N^4$-(2,6-difluorobenzyl)-$N^2$-(1-((1-methyl-1H-pyrazol-4-yl)methyl)-1H-pyrazol-4-yl)pyrimidine-2,4-diamine;

5-chloro-$N^4$-(2,6-difluorobenzyl)-$N^2$-(1-((3-methyl-1,2,4-oxadiazol-5-yl)methyl)-1H-pyrazol-4-yl)pyrimidine-2,4-diamine;

5-chloro-$N^4$-(2,6-difluorobenzyl)-$N^2$-(1-((5-methylthiazol-4-yl)methyl)-1H-pyrazol-4-yl)pyrimidine-2,4-diamine;

5-fluoro-$N^4$-(2-fluoro-5-(methylsulfonyl)benzyl)-$N^2$-(1-methyl-1H-pyrazol-4-yl)pyrimidine-2,4-diamine;

5-fluoro-$N^4$-(5-fluoro-2-(methylsulfonyl)benzyl)-$N^2$-(1H-pyrazol-4-yl)pyrimidine-2,4-diamine;

5-fluoro-$N^4$-(5-fluoro-2-(methylsulfonyl)benzyl)-$N^2$-(1-methyl-1H-pyrazol-4-yl)pyrimidine-2,4-diamine;

2-(4-((5-fluoro-4-((5-fluoro-2-(methylsulfonyl)benzyl)amino)pyrimidin-2-yl)amino)-1H-pyrazol-1-yl)ethanol;

2-(4-((5-fluoro-4-((5-fluoro-2-(methylsulfonyl)benzyl)amino)pyrimidin-2-yl)amino)-1H-pyrazol-1-yl)acetamide; and (R)-2-(4-((4-((2,6-difluorobenzyl)amino)pyrimidin-2-yl)amino)-1H-pyrazol-1-yl)-N-(1-hydroxypropan-2-yl)acetamide.

15. A pharmaceutical composition comprising a compound or a pharmaceutically acceptable salt or isotopic derivative thereof of claim 1 together with a pharmaceutically acceptable carrier, optionally in combination with one or more other pharmaceutical compositions.

16. A compound or a pharmaceutically acceptable salt or isotopic derivative thereof of claim 1 for use as a medicament.

* * * * *